United States Patent
Lin et al.

(10) Patent No.: US 12,059,251 B2
(45) Date of Patent: Aug. 13, 2024

(54) GRAPHENE-BASED NANOSENSOR FOR IDENTIFYING TARGET ANALYTES

(71) Applicant: THE TRUSTEES OF COLUMBIA UNIVERSITY IN THE CITY OF NEW YORK, New York, NY (US)

(72) Inventors: Qiao Lin, New York, NY (US); Yibo Zhu, New York, NY (US); Junyi Shang, New York, NY (US); Zhixing Zhang, New York, NY (US); Xuejun Wang, New York, NY (US); Jaeyoung Yang, New York, NY (US); Cheng Wang, New York, NY (US); Zhuang Hao, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 16/810,183

(22) Filed: Mar. 5, 2020

(65) Prior Publication Data
US 2020/0196925 A1    Jun. 25, 2020

Related U.S. Application Data

(63) Continuation of application No. 16/012,527, filed on Jun. 19, 2018, now abandoned, which is a
(Continued)

(51) Int. Cl.
*A61B 5/145* (2006.01)
*A61B 5/00* (2006.01)
(Continued)

(52) U.S. Cl.
CPC ...... *A61B 5/14532* (2013.01); *A61B 5/14507* (2013.01); *A61B 5/14539* (2013.01);
(Continued)

(58) Field of Classification Search
CPC .............. A61B 5/14532; A61B 5/6821; A61B 5/14507; A61B 5/1477; A61B 5/14539;
(Continued)

(56) References Cited

U.S. PATENT DOCUMENTS 8,050,731 B2    11/2011   Tapsak et al.
8,241,567 B2    8/2012    Cai et al.
(Continued)

FOREIGN PATENT DOCUMENTS

EP          1 951 116 B1     2/2014
WO     WO 2015/192064 A1    12/2015

OTHER PUBLICATIONS

Xu, K. (2012). "Graphene-based FET structure: Modeling FET Characteristics for an Aptamer-based Analyte Sensor." IEEE. 2012 15th International Workshop on Computational Electronics. (Year: 2012).*

(Continued)

*Primary Examiner* — Benjamin R Whatley
*Assistant Examiner* — Jacqueline Brazin
(74) *Attorney, Agent, or Firm* — Baker Botts L.L.P.

(57) ABSTRACT

A microdevice for monitoring a target analyte is provided. The microdevice can include a field effect transistor comprising a substrate, a gate electrode, and a microfluidic channel including graphene. The microfluidic channel can be formed between drain electrodes and source electrodes on the substrate. The microdevice can also include at least one aptamer functionalized on a surface of the graphene. The at least one aptamer can be adapted for binding to the target analyte. Binding of the target analyte to the at least one aptamer can alter the conductance of the graphene.

22 Claims, 100 Drawing Sheets
Specification includes a Sequence Listing.

Related U.S. Application Data continuation-in-part of application No. 15/374,375, filed on Dec. 9, 2016, now abandoned, which is a continuation of application No. PCT/US2016/037362, filed on Jun. 14, 2016, and a continuation of application No. PCT/US2016/012297, filed on Jan. 6, 2016, and a continuation of application No. PCT/US2015/035640, filed on Jan. 12, 2015.

(60) Provisional application No. 62/523,516, filed on Jun. 22, 2017, provisional application No. 62/188,281, filed on Jul. 2, 2015, provisional application No. 62/180,484, filed on Jun. 16, 2015, provisional application No. 62/100,379, filed on Jan. 6, 2015, provisional application No. 62/100,366, filed on Jan. 6, 2015.

(51) Int. Cl.
*A61B 5/1477* (2006.01)
*A61B 5/1491* (2006.01)
*G01N 27/414* (2006.01)
*G01N 33/74* (2006.01)
*H01L 21/02* (2006.01)
*H01L 23/38* (2006.01)
*H01L 29/16* (2006.01)
*H10K 10/46* (2023.01)
*H10K 85/20* (2023.01)

(52) U.S. Cl.
CPC ........ *A61B 5/14546* (2013.01); *A61B 5/1477* (2013.01); *A61B 5/1491* (2013.01); *A61B 5/6821* (2013.01); *G01N 27/4145* (2013.01); *G01N 27/4146* (2013.01); *G01N 33/74* (2013.01); *H01L 21/02425* (2013.01); *H01L 21/02527* (2013.01); *H01L 21/0262* (2013.01); *H01L 21/02664* (2013.01); *H01L 23/38* (2013.01); *H01L 29/1606* (2013.01); *H10K 10/484* (2023.02); *G01N 2333/62* (2013.01); *H10K 85/20* (2023.02)

(58) Field of Classification Search
CPC .............. A61B 5/14546; A61B 5/1491; H01L 51/0558; H01L 21/02664; H01L 21/02425; H01L 23/38; H01L 29/1606; H01L 21/0262; H01L 21/02527; H01L 51/0045; G01N 27/4145; G01N 27/4146; G01N 33/74; G01N 2333/62
USPC ....................................................... 600/347
See application file for complete search history.

(56) References Cited

U.S. PATENT DOCUMENTS

| | | | |
|---|---|---|---|
| 8,562,815 B2 | 10/2013 | Jang et al. | |
| 2005/0265914 A1* | 12/2005 | Gu | G01N 33/66 423/445 B |
| 2008/0108164 A1* | 5/2008 | Oleynik | G01N 27/4145 438/49 |
| 2008/0185498 A1* | 8/2008 | Purdy | G01N 21/77 250/201.1 |
| 2008/0290941 A1* | 11/2008 | Ludwig | H03F 3/45076 330/253 |
| 2009/0060528 A1 | 3/2009 | Takashima et al. | |
| 2010/0173306 A1* | 7/2010 | Yaku | G01N 33/5308 435/6.18 |
| 2012/0043203 A1 | 2/2012 | Lin et al. | |
| 2012/0058350 A1* | 3/2012 | Long | H01L 51/0045 428/688 |
| 2012/0095200 A1* | 4/2012 | Brown | C12N 15/111 536/23.1 |
| 2012/0118751 A1* | 5/2012 | Cai | G01N 33/54346 977/773 |
| 2012/0134880 A1* | 5/2012 | Kurkina | G01N 33/487 422/82.01 |
| 2013/0018599 A1* | 1/2013 | Peng | H01L 29/778 702/30 |
| 2013/0078622 A1* | 3/2013 | Collins | G01N 27/26 977/750 |
| 2013/0143769 A1 | 6/2013 | Afzali-ardakani et al. | |
| 2013/0248380 A1* | 9/2013 | Cui | C12Q 1/001 205/777.5 |
| 2014/0015548 A1 | 1/2014 | Naughton et al. | |
| 2014/0134607 A1* | 5/2014 | Lin | G01N 33/5438 435/5 |
| 2014/0145735 A1 | 5/2014 | Koester | |
| 2014/0162893 A1 | 6/2014 | Cash et al. | |
| 2014/0335629 A1 | 11/2014 | Ahn et al. | |
| 2014/0363808 A1* | 12/2014 | Gu | G01N 33/57488 435/5 |

OTHER PUBLICATIONS

Orava, E.W. et al. "A Short DNA Aptamer that Recognizes TNFa and Blocks ITs Acitivty in vitro." ACS chem biol. 8:170-178. (Year: 2013).*

Okamoto, S. (2012). "Immunosensors Based on Graphene Field-Effect Transistors Fabricated Using Antigen-Binding Fragment." Jpn. J. Appl. Phys. 51: 06FD08. (Year: 2012).*

U.S. Appl. No. 16/012,527 (US 2018/0368743), filed Jun. 19, 2018 (Dec. 27, 2018).

U.S. Appl. No. 15/374,375 (US 2017/0181669), filed Dec. 9, 2016 (Jun. 29, 2017) Abandoned.

U.S. Appl. No. 16/012,527, filed Dec. 5, 2019 Non-Final Office Action.

U.S. Appl. No. 16/012,527, filed Sep. 12, 2019 Response to Requirement Restriction/Election.

U.S. Appl. No. 16/012,527, filed Jul. 12, 2019 Requirement for Restriction/Election.

U.S. Appl. No. 15/374,375, filed Feb. 13, 2019 Abandonment.

U.S. Appl. No. 15/374,375, filed Jul. 25, 2018 Final Office Action.

U.S. Appl. No. 15/374,375, filed Jun. 12, 2018 Response to Non-Final Office Action.

U.S. Appl. No. 15/374,375, filed Mar. 22, 2018 Non-Final Office Action.

U.S. Appl. No. 15/374,375, filed Feb. 7, 2018 Response to Requirement Restriction/Election.

U.S. Appl. No. 15/374,375, filed Dec. 21, 2017 Requirement for Restriction/Election.

Abbott Diabetes Care, FreeStyle Navigator® Continuous Glucose Monitoring System. https://www.diabetescare.abbott/products.html (Accessed on Jul. 25, 2017).

Alexeev et al., "Photonic Crystal Glucose-Sensing Material for Noninvasive Monitoring of Glucose in Tear Fluid," Clinical Chemistry 50(12):2353-2360 (2004).

Asher et al., "Photonic Crystal Carbohydrate Sensors: Low Ionic Strength Sugar Sensing," J. Am. Chem. Soc. 125:3322-3329 (2003).

Auer, "Hypoglycemic Brain Damage," Metabolic Brain Disease 19(3/4):169-175 (2004).

Baca et al., "Tear Glucose Analysis for the Noninvasive Detection and Monitoring of Diabetes Mellitus," The Ocular Surface 5(4):280-293 (2007).

Badugu et al., "Ophthalmic Glucose Monitoring Using Disposable Contact Lenses—A Review," Journal Fluoresc. 14(5):617-633 (2004).

Balcioglu et al., "Smart-Polymer-Functionalized Graphene Nanodevices for Thermo-Switch-Controlled Biodetection," ACS Biomaterials Science & Engineering 1:27-36 (2015).

Behlau et al., "Microbial Biofilms in Ophthalmology and Infectious Disease," Arch Ophthalmol. 126(11):1572-1581 (2008).

Bode et al., "Alarms Based on Real-time Sensor Glucose Values Alert Patients to Hypo- and Hyperglycemia: The Guardian Continuous Monitoring System," Diabetes Technology & Therapeutics 6(2):105-113 (2004).

(56) References Cited

OTHER PUBLICATIONS

Chang et al., "Graphene Fluorescence Resonance Energy Transfer Aptasensor for the Thrombin Detection," Analytical Chemistry 82:2341-2346 (2010).
Chen et al., "Boron Nitride Nanotubes Are Noncytotoxic and Can Be Functionalized for Interaction with Proteins and Cells," J. Am. Chem. Soc. 131:890-891 (2009).
Chen et al., "Noncovalent Sidewall Functionalization of Single-Walled Carbon Nanotubes for Protein Immobilization," J. Am. Chem. Soc. 123:3838-3839 (2001).
Chhabra et al., "A single-lens polarographic measurement of oxygen permeability (Dk) for hypertransmissible soft contact lenses," Biomaterials 28:4331-4342 (2007).
Chiefari et al., "Living Free-Radical Polymerization by Reversible Addition-Fragmentation Chain Transfer: The RAFT Process," Macromolecules 31:5559-5562 (1998).
Chu et al., "Soft contact lens biosensor for in situ monitoring of tear glucose as non-invasive blood sugar assessment," Talanta 83:960-965 (2011).
Ciofani et al., "Assessing cytotoxicity of boron nitride nanotubes: Interference with the MTT assay," Biochemical and Biophysical Research Communications 394:405-411 (2010).
Clarke et al., "Evaluating Clinical Accuracy of Continuous Glucose Monitoring Systems: Continuous Glucose-Error Grid Analysis (CG-EGA)," Current Diabetes Reviews 4:193-199 (2008).
Cong et al., "Allosteric Aptamers: Targeted Reversibly Attenuated Probes," Biochemistry 44:7945-7954 (2005).
Daum et al., "Human tear glucose," Investigative Ophthalmology & Visual Science 22:509-514 (1982).
Dean et al., "Boron nitride substrates for high-quality graphene electronics," Nature Nanotechnology 5:722-726 (2010).
DexCom, Inc., DexCom™ Seven® Plus System. http://www.dexcom.com/. (Accessed on Jul. 25, 2017).
Domschke et al., "Continuous Non-Invasive Ophthalmic Glucose Sensor for Diabetics," Chimia 64(1/2):43-44 (2010).
Dong et al., "Electrical Detection of DNA Hybridization with Single-Base Specificity Using Transistors Based on CVD-Grown Graphene Sheets," Advanced Materials 22:1649-1653 (2010).
Eastman et al., "Clinical review 51: Implications of the Diabetes Control and Complications Trial," J Clin Endocrinol Metab 77(5):1105-1107 (1993).
Eastman et al., "Model of Complications of NIDDM: I. Model construction and assumptions," Diabetes Care 20(5): 725-734 (1997).
Eastman et al., "Model of Complications of NIDDM: II. Analysis of the health benefits and cost-effectiveness of treating NIDDM with the goal of normoglycemia," Diabetes Care 20(5): 735-744 (1997).
El-Kady et al., "Laser Scribing of High-Performance and Flexible Graphene-Based Electrochemical Capacitors," Science 335:1326-1330 (2012).
Fang et al., "Progress in Boronic Acid-Based Fluorescent Glucose Sensors," Journal of Fluorescence 14(5):481-489 (2004).
Forbat et al., "Glucose-concentrations in parotid fluid and venous blood of patients attending a diabetic clinic," Journal of the Royal Society of Medicine 74:725-728 (1981).
Galas et al., "Humidity-Conditioned Gravimetric Method to Measure the Water Content of Hydrogel Contact Lens Materials," Optometry & Vision Science 70(7):577-586 (1993).
Galluzzi et al., "Guidelines for the use and interpretation of assays for monitoring cell death in higher eukaryotes," Cell Death and Differentiation 16(8): 1093-1107 (2009).
Gao et al., "Systematic review and evaluation of physiological track and trigger warning systems for identifying at-risk patients on the ward," Intensive Care Medicine 33:667-679 (2007).
Gong et al., "DNA surface hybridization regimes," PNAS 105(14):5301-5306 (2008).
Goto et al., "Mechanism and Kinetics of RAFT-Based Living Radical Polymerizations of Styrene and Methyl Methacrylate," Macromolecules 34:402-408 (2001).
Gough et al., "Advances and prospects in glucose assay technology," Diabetologia 40:S102-S107 (1997).
Groenendaal et al., "Quantifying the Composition of Human Skin for Glucose Sensor Development," J Diabetes Sci Technol 4(5):1032-1040 (2010).
Guariguata et al., "Global estimates of diabetes prevalence for 2013 and projections for 2035," Diabetes Research and Clinical Practice 103:137-149 (2014).
Holden et al., "Critical Oxygen Levels to Avoid Corneal Edema for Daily and Extended Wear Contact-Lenses," Investigative Ophthalmology & Visual Science 25:1161-1167 (1984).
Huang et al., "A Differential Dielectric Affinity Glucose Sensor," Lab Chip 14(2):294-301 (2014).
Huang et al., "A MEMS Dielectric Affinity Glucose Biosensor," J Microelectromech Syst 23(1):14-20 (2014).
Huang et al., "Continuous Monitoring of Glucose in Subcutaneous Tissue Using Microfabricated Differential Affinity Sensors," Journal of Diabetes Science and Technology 6(6):1436-1444 (2012).
Huang et al., "Thermally Tunable Polymer Microlenses for Biological Imaging," Journal of Microelectromechanical Systems 19(6):1444-1449 (2010).
Huang et al., "A Capacitive MEMS Viscometric Sensor for Affinity Detection of Glucose," Journal of Microelectromechanical Systems 18(6):1246-1254 (2009).
Huang et al., "A dielectric affinity microbiosensor," Applied Physics Letters 96:033701 (2010).
Huang et al., "A MEMS affinity glucose sensor using a biocompatible glucose-responsive polymer," Sensors and Actuators B: Chemical 140:603-609 (2009).
Huang et al., "Nanoelectronic biosensors based on CVD grown graphene," Nanoscale 2:1485-1488 (2010).
Huang, "Miniaturized Implantable Affinity Sensors for Continuous Glucose Monitoring," (Columbia University, United States—New York, 2011).
Iguchi et al., "A flexible and wearable biosensor for tear glucose measurement," Biomedical Microdevices 9:603-609 (2007).
International Search Report dated May 6, 2016 in International Application No. PCT/US16/12297.
International Search Report dated Nov. 23, 2015 in International Application No. PCT/US15/35640.
International Search Report dated Oct. 26, 2016 in International Application No. PCT/US16/37362.
Jenkinson H.F., "Genetic-analysis of adherence by oral streptococci," Journal of Industrial Microbiology 15:186-192 (1995).
Jungheim et al., "Subcutaneous Continuous Glucose Monitoring—Feasibility of a New Microdialysis-Based Glucose Sensor System," Diabetes Care 24(9):1696-1697 (2001).
Jurysta et al., "Salivary Glucose Concentration and Excretion in Normal and Diabetic Subjects," Journal of Biomedicine and Biotechnology, Article ID 430426, 6 pages (2009).
Justin et al., "Biomimetic hydrogels for biosensor implant biocompatibility: Electrochemical characterization using micro-disc electrode arrays (MDEAs)," Biomed Microdevices 11:103-115 (2009).
Keenan et al., "Delays in Minimally Invasive Continuous Glucose Monitoring Devices: A Review of Current Technology," Journal of Diabetes Science and Technology 3(5):1207-1214 (2009).
Ketelson et al., "Dynamic wettability properties of a soft contact lens hydrogel," Colloids and Surfaces B:Biointerfaces 40:1-9 (2005).
Kim et al., "Synthesis and Characterization of Hexagonal Boron Nitride Film As A Dielectric Layer For Graphene Devices," ACS Nano 6(10):8583-8590 (2012).
Kim et al., "Enhancement of sensitivity and specificity by surface modification of carbon nanotubes in diagnosis of prostate cancer based on carbon nanotube field effect transistors," Biosensors and Bioelectronics 24:3372-3378 (2009).
Kitano et al., "Accumulation of phenyl boronic acid-carrying telomers on a gold surface," Journal of Colloid and Interface Science 273:106-114 (2004).
Kwak et al., "Flexible glucose sensor using CVD-grown graphene-based field effect transistor," Biosensors and Bioelectronics 37:82-87 (2012).
Kwon et al., "Flexible FET-type VEGF Aptasensor Based on Nitrogen-Doped Graphene Converted from Conducting Polymer," ACS Nano 6(2):1486-1493 (2012).

(56) References Cited

OTHER PUBLICATIONS

Lacerda et al., "Carbon nanotubes as nanomedicines: From toxicology to pharmacology," Advanced Drug Delivery Reviews 58:1460-1470 (2006).
Lai et al., "Synthesis, characterization and ocular biocompatibility of potential keratoprosthetic hydrogels based on photopolymerized poly(2-hydroxyethyl methacrylate)-co-poly(acrylic acid)," Journal of Materials Chemistry 22:1812-1823 (2012).
Lane et al., "Tear Glucose Dynamics in Diabetes Mellitus," Current Eye Research 31: 895-901 (2006).
Lee et al., "Aptamers as molecular recognition elements for electrical nanobiosensors," Analytical and Bioanalytical Chemistry 390:1023-1032 (2008).
Lei et al., "A Hydrogel-Based Implantable Micromachined Transponder for Wireless Glucose Measurement," Diabetes Technology & Therapeutics 8(1):112-122 (2006).
Lerner et al., "Scalable, Non-Invasive Glucose Sensor Based on Boronic Acid Functionalized Carbon Nanotube Transistors," Applied Physics Letters 102:183113 (2013).
Lewis et al., "Tear Glucose In Diabetics," Br. J. Ophthal. 42:754-758 (1958).
Li et al., "Development of Novel Glucose Sensing Fluids with Potential Application to Microelectromechanical Systems-Based Continuous Glucose Monitoring," J Diabetes Sci Technol 2(6):1066-1074 (2008).
Li et al., "Development of Boronic Acid Grafted Random Copolymer Sensing Fluid for Continuous Glucose Monitoring," Biomacromolecules 10:113-118 (2009).
Li et al., "Synthesis and Development of Poly(N-Hydroxyethyl Acrylamide)-Ran-3-Acrylamidophenylboronic Acid Polymer Fluid for Potential Application in Affinity Sensing of Glucose," Journal of Diabetes Science and Technology 5(5):1060-1067 (2011).
Li et al., "The promotion of neurite sprouting and outgrowth of mouse hippocampal cells in culture by graphene substrates," Biomaterials 32:9374-9382 (2011).
Liao et al., "A 3-µW CMOS Glucose Sensor for Wireless Contact-Lens Tear Glucose Monitoring," IEEE Journal of Solid-State Circuits 47(1):335-344 (2012).
Liu et al., "Strategies for chemical modification of graphene and applications of chemically modified graphene," Journal of Materials Chemistry 22:12435-12452 (2012).
Liu et al., "Thermosensitive Graphene Nanocomposites Formed Using Pyrene-Terminal Polymers Made by RAFT Polymerization," Journal of Polymer Science Part A: Polymer Chemistry 48:425-433 (2010).
Lorand et al., "Polyol Complexes and Structure of the Benzeneboronate Ion," J. Org. Chem. 24:769-774 (1959).
Luo et al., "A novel non-enzymatic glucose sensor based on Cu nanoparticle modified graphene sheets electrode," Analytica Chimica Acta 709:47-53 (2012).
Magrez et al., "Cellular Toxicity of Carbon-Based Nanomaterials," Nano Letters 6(6):1121-1125 (2006).
March et al., "Clinical Trial of a Noninvasive Contact Lens Glucose Sensor," Diabetes Technology & Therapeutics 6(6):782-789 (2004).
McLaughlin-Borlace et al., "Bacterial biofilm on contact lenses and lens storage cases in wearers with microbial keratitis," Journal of Applied Microbiology 84:827-838 (1998).
Mohanty et al., "Graphene-Based Single-Bacterium Resolution Biodevice and DNA Transistor: Interfacing Graphene Derivatives with Nanoscale and Microscale Biocomponents," Nano Lett 8(12):4469-4476 (2008).
Möller, "Contact-Induced Cytotoxicity by Lymphoid Cells Containing Foreign Isoantigens," Science 147:873-879 (1965).
Morris et al., "Correlation Between Plasma and Urine Glucose in Diabetics," Annals of Internal Medicine 94(Part 1):469-471 (1981).
Najafi, "Packaging of Implantable Microsystems," IEEE Sensors 58-63 (2007).
New Standards for Biological Evaluation Of Medical Devices—Instrumentation Group Pondering ISO Standards. Biotechnology Law Report 14(3):408-409 (1995).
Novoselov et al., "Two-dimensional gas of massless Dirac fermions in graphene," Nature 438:197-200 (2005).
OEC-C Group. "Effect of Intensive Diabetes Treatment on Carotid Artery Wall Thickness in the Epidemiology of Diabetes Interventions and Complications," Diabetes 48(2):383-390 (1999).
Ohkubo et al., "Intensive insulin therapy prevents the progression of diabetic microvascular complications in Japanese patients with non-insulin-dependent diabetes-mellitus: a randomized prospective 6-year study," Diabetes Research and Clinical Practice 28:103-117 (1995).
Ohno et al., "Label-Free Biosensors Based on Aptamer-Modified Graphene Field-Effect Transistors," Journal of the American Chemical Society 132:18012-18013 (2010).
Oliver et al., "Glucose sensors: a review of current and emerging technology," Diabetic Medicine 26:197-210 (2009).
Orava et al., "A short DNA Aptamer that Recognizes TNFa and Blocks its Activity in Vitro," ACS Chem Biol 8:170-178 (2013).
Papas, "On the Relationship Between Soft Contact Lens Oxygen Transmissibility and Induced Limbal Hyperaemia," Experimental Eye Research 67:125-131 (1998).
Petrone et al., "Chemical Vapor Deposition-Derived Graphene with Electrical Performance of Exfoliated Graphene," Nano Letters 12:2751-2756 (2012).
Piao et al., "Highly conductive graphite nanoparticle-based enzyme biosensor for electrochemical glucose detection," Sensors and Actuators B: Chemical 194:454-459 (2014).
Quinn et al., "Photo-crosslinked copolymers of 2-hydroxyethyl methacrylate, poly(ethylene glycol) tetra-acrylate and ethylene dimethacrylate for improving biocompatibility of biosensors," Biomaterials 16:389-396 (1995).
Quinn et al., "Ambient temperature reversible addition-fragmentation chain transfer polymerisation," Chem. Commun., 1044-1045 (2001).
Rouillat et al., "Characterization of DNA chips on the molecular scale before and after hybridization with an atomic force microscope," Applied Surface Science 252:1765-1771 (2005).
Roy et al., "Glucose-Sensitivity of Boronic Acid Block Copolymers at Physiological pH," ACS Macro Lett. 1:529-532 (2012).
Roy et al., "Sugar-responsive block copolymers by direct RAFT polymerization of unprotected boronic acid monomers," Chem. Commun., (Camb), 2477-2479 (2008).
Roy et al., "Triply-responsive boronic acid block copolymers: solution self-assembly induced by changes in temperature, pH, or sugar concentration," Chem. Commun. 2106-2108 (2009).
Salvatore et al., "Wafer-Scale Design of Lightweight And Transparent Electronics That Wraps Around Hairs," Nature Communications 5:2982 (2014).
Satjapipat et al., "Selective Desorption of Alkanethiols in Mixed Self-Assembled Monolayers for Subsequent Oligonucleotide Attachment and DNA Hybridization," Langmuir 17:7637-7644 (2001).
Schedin et al., "Detection of individual gas molecules adsorbed on graphene," Nature Materials 6:652-655 (2007).
Scheiner et al., "Imbalanced Biphasic Electrical Stimulation: Muscle-Tissue Damage," Annals of Biomedical Engineering 18:407-425 (1990).
Schultz et al., "Affinity Sensors for Individual Metabolites," Biotechnol. Bioeng. Symp. 9:65-71 (1979).
Sen et al., "Tear glucose levels in normal people and in diabetic patients," British Journal of Ophthalmology 64:693-695 (1980).
Shin et al., "Surface-Energy Engineering of Graphene," Langmuir 26(6):3798-3802 (2010).
Singh, "Prospects of Nanobiomaterials for Biosensing," International Journal of Electrochemistry, Article ID 125487, 30 pages (2011).
Squires et al., "Making it stick: convection, reaction and diffusion in surface-based biosensors," Nature Biotechnology 26(4):417-426 (2008).
Stapleton et al., "Silicone Hydrogel Contact Lenses and the Ocular Surface," The Ocular Surface 4(1):24-43 (2006).
Stine et al., "Real-Time DNA Detection Using Reduced Graphene Oxide Field Effect Transistors," Advanced Materials 22:5297-5300 (2010).

(56) References Cited

OTHER PUBLICATIONS

Su et al., "Colorimetric Detection of Urine Glucose Based ZnFe2O4 Magnetic Nanoparticles," Analytical Chemistry 84:5753-5758 (2012).
Suarez, L. Tailoring Surfaces to Improve Biomaterials Performance: piCVD & iCVD Approaches. Doctoral Thesis. Sep. 6, 2012 (with English translation).
Thomas et al., "Conditions for Facile, Controlled RAFT Polymerization of Acrylamide in Water," Macromolecules 36:1436-1439 (2003).
Thomas et al., "A contact lens with an integrated lactate sensor," Sensors and Actuators B: Chemical 162:128-134 (2012).
Timko et al., "Electrical Recording from Hearts with Flexible Nanowire Device Arrays," Nano Letters 9(2):914-918 (2009).
Vermeltfoort et al., "Influence of Day and Night Wear on Surface Properties of Silicone Hydrogel Contact Lenses and Bacterial Adhesion," Cornea 25:516-523 (2006).
Vlandas et al., "Enzyme-Free Sugar Sensing in Microfluidic Channels with an Affinity-Based Single-Wall Carbon Nanotube Sensor," Analytical Chemistry 82:6090-6097 (2010).
Walker et al., "Preclinical assessment of the distribution of maraviroc to potential human immunodeficiency virus (HIV) sanctuary sites in the central nervous system (CNS) and gut-associated lymphoid tissue (GALT)," Xenobiotica 38(10):1330-1339 (2008).
Wang et al., "A Graphene Nanosensor for Detection of Small Molecules," IEEE, MEMS 1075-1078 (2014).
Wang et al., "Nonfouling Polypeptide Brushes via Surface-initiated Polymerization of Nξ-oligo(ethylene glycol)succinate-L-lysine N-carboxyanhydride-a," Macromolecular Rapid Communications 30:845-850 (2009).
Wang, "Electrochemical Glucose Biosensors," Chemical Reviews 108:814-825 (2008).
Ward et al., "An Implantable Subcutaneous Glucose Sensor Array in Ketosis-prone Rats: Closed Loop Glycemic Control," Artificial Organs 29(2):131-143 (2005).
Willis et al., "A novel phosphorylcholine-coated contact lens for extended wear use," Biomaterials 22:3261-3272 (2001).
Winterton et al., "Coulometric Method for Measuring Oxygen Flux and Dk of Contact Lenses and Lens Materials," Cornea 6(2):160 (1987).
Wisniewski et al., "Methods for reducing biosensor membrane biofouling," Colloids and Surfaces B: Biointerfaces 18:197-219 (2000).
Xu, "Graphene-based FET structure: Modeling FET Characteristics for an Aptamer-based Analyte Sensor," IEEE. 2012 15th International Workshop on Computational Electronics. DOI: 10.1109/IWCE.2012.6242868 (2012).
Yamaguchi et al., "Noninvasively Measuring Blood Glucose Using Saliva," IEEE Engineering in Medicine and Biology 17:59-63 (1998).
Yan et al., "Boronolectins and Fluorescent Boronolectins: An Examination of the Detailed Chemistry Issues Important for the Design," Medicinal Research Reviews 25(5):490-520 (2005).
Yang et al., "Graphene and its derivatives for cell biotechnology," Analyst 138:72-86 (2013).
Yao et al. "A contact lens with embedded sensor for monitoring tear glucose level," Biosensors and Bioelectronics 26:3290-3296 (2011).
Ye et al., "A novel nonenzymatic sensor based on CuO nanoneedle/graphene/carbon nanofiber modified electrode for probing glucose in saliva," Talanta 116:223-230 (2013).
Zhang et al., "Noninvasive Diagnostic Devices for Diabetes through Measuring Tear Glucose," Journal of Diabetes Science and Technology 5(1):166-172 (2011).
Zhang et al., "Experimental observation of the quantum Hall effect and Berry's phase in graphene," Nature 438:201-204 (2005).
Zhu et al., "A Critical Review of Glucose Biosensors Based on Carbon Nanomaterials: Carbon Nanotubes and Graphene," Sensors 12:5996-6022 (2012).

\* cited by examiner

FIG. 5A
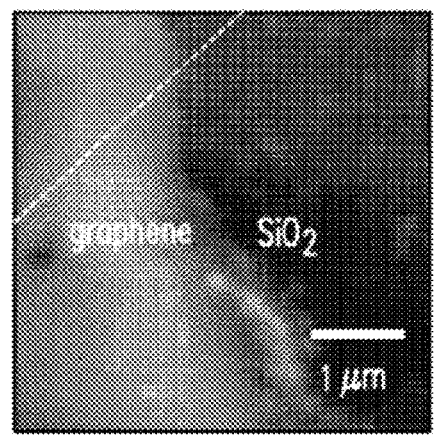
FIG. 5B
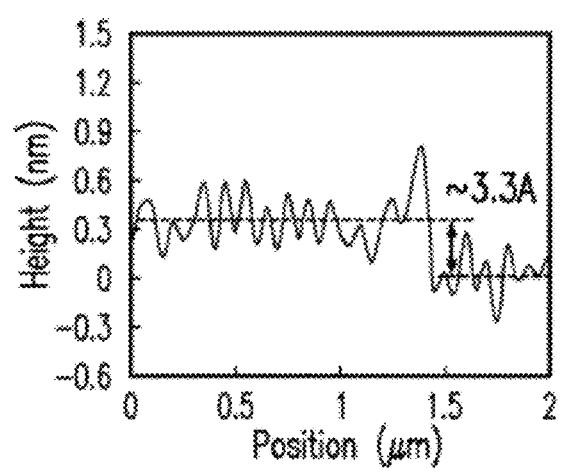
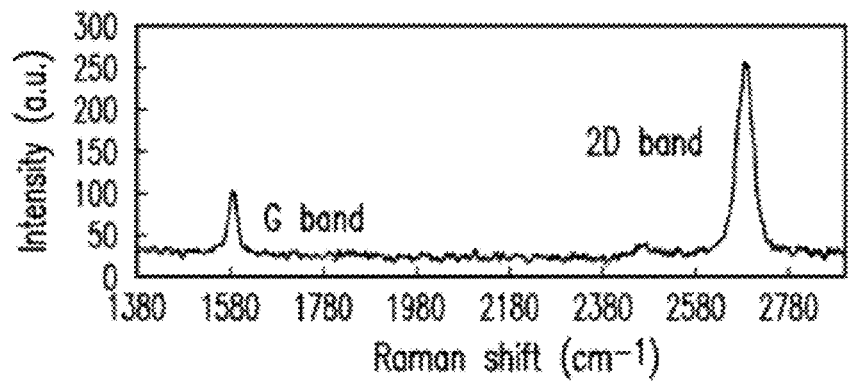
FIG. 5C

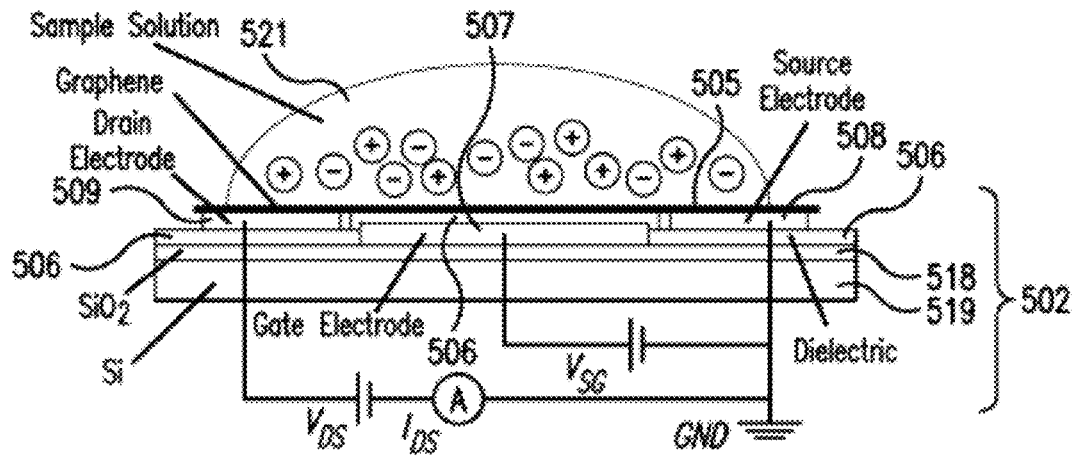
FIG. 8
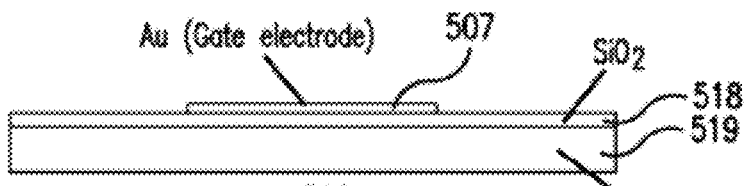
FIG. 9A
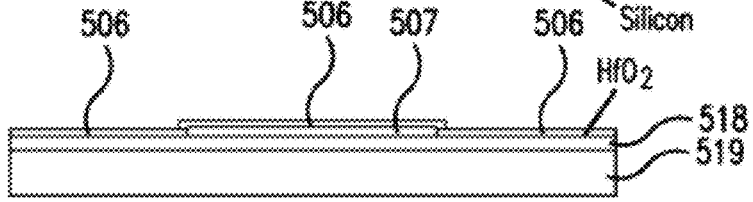
FIG. 9B
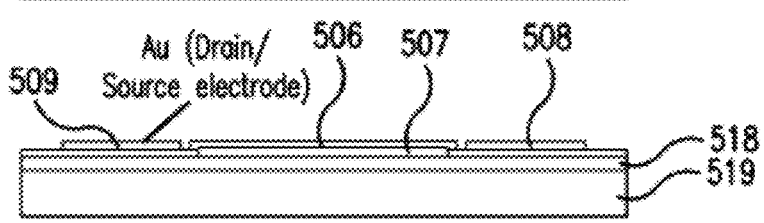
FIG. 9C
FIG. 9D

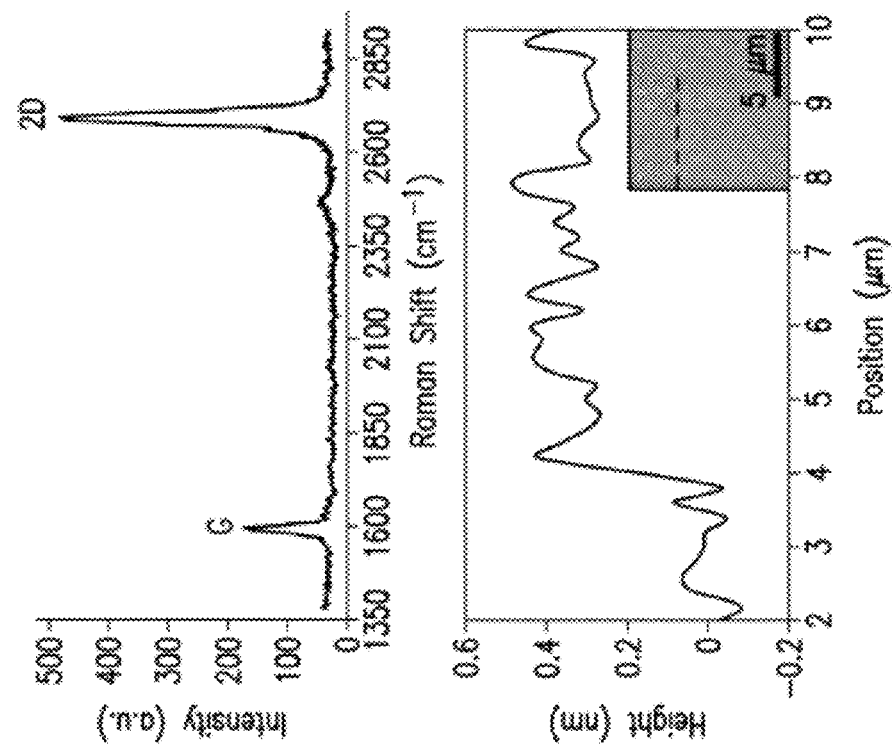
FIG. 10C
FIG. 10D
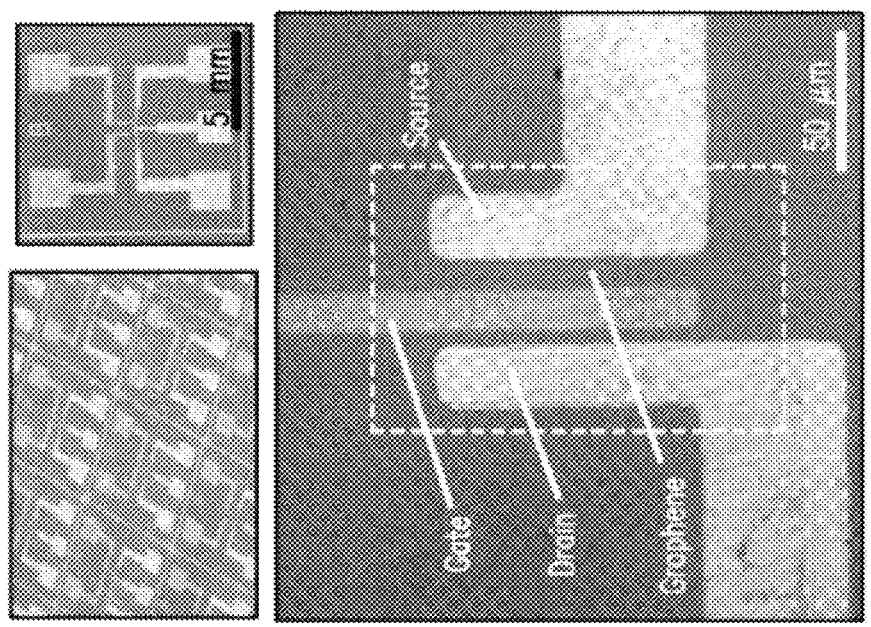
FIG. 10A
FIG. 10B

FIG. 16A
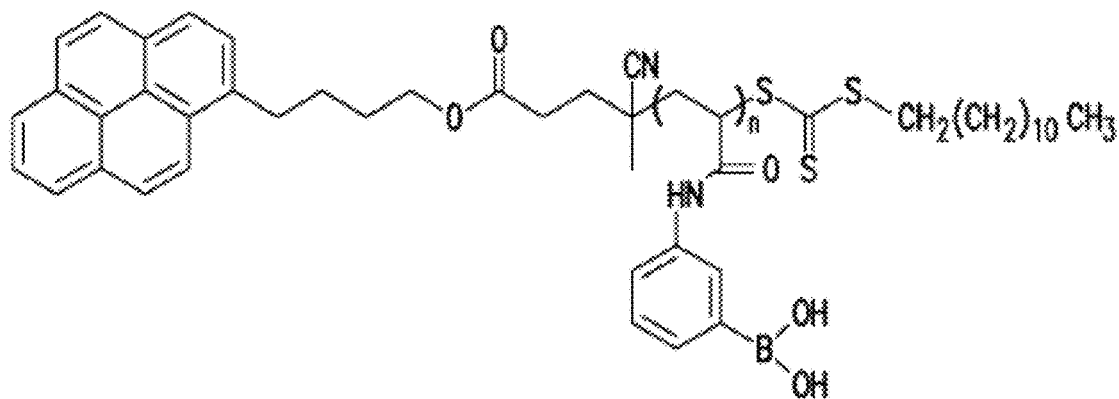
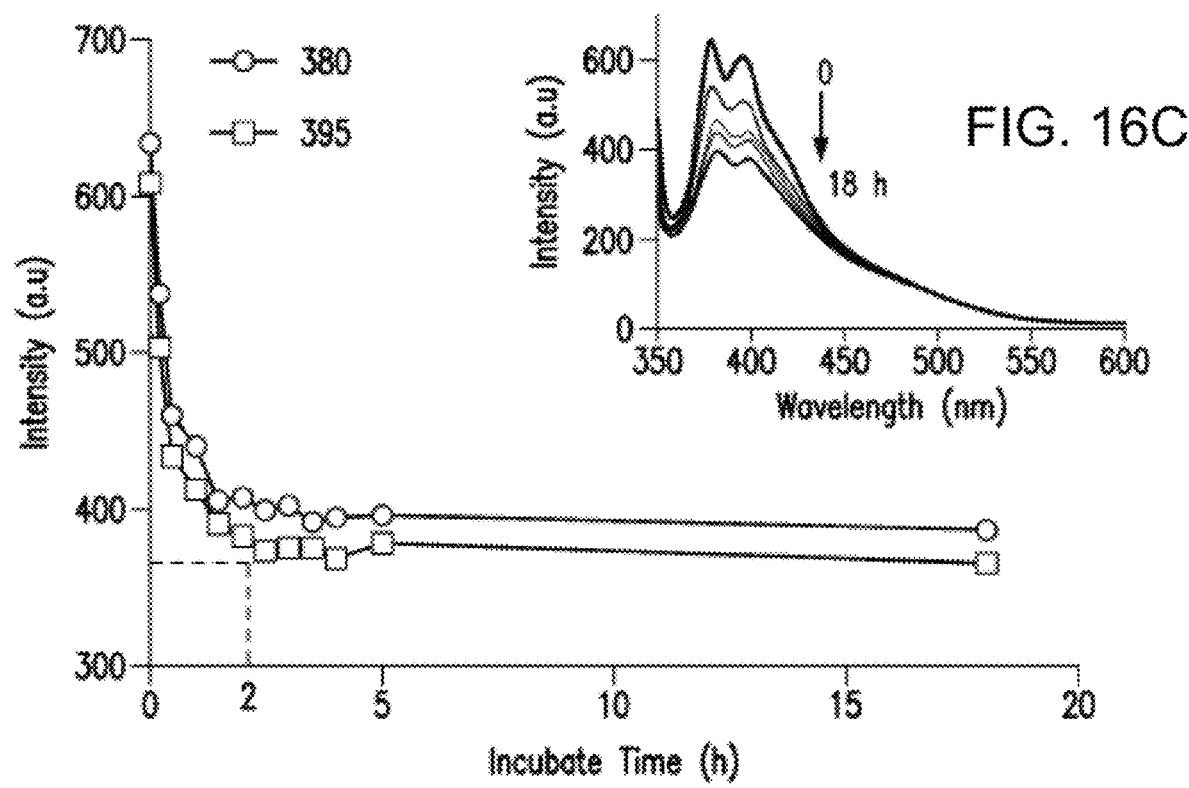
FIG. 16B
FIG. 16C

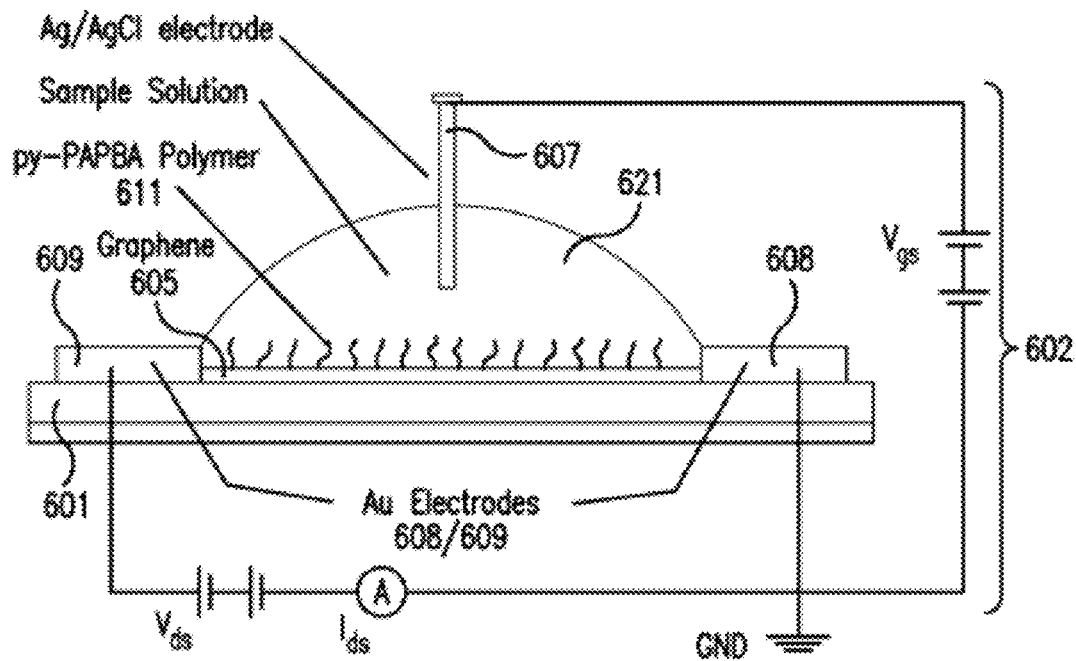
FIG. 18
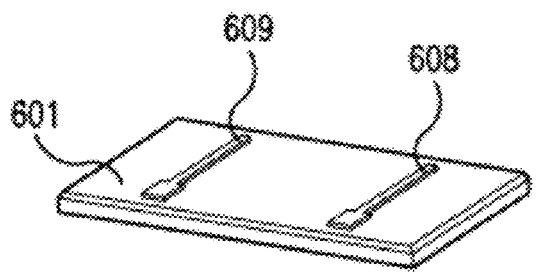
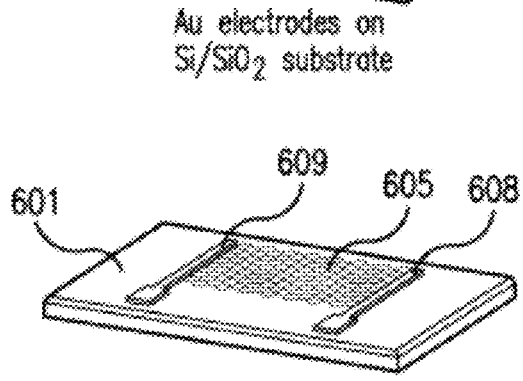
FIG. 19B
FIG. 19A
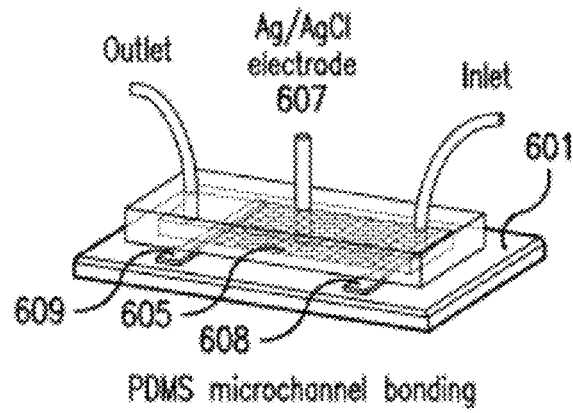
FIG. 19C

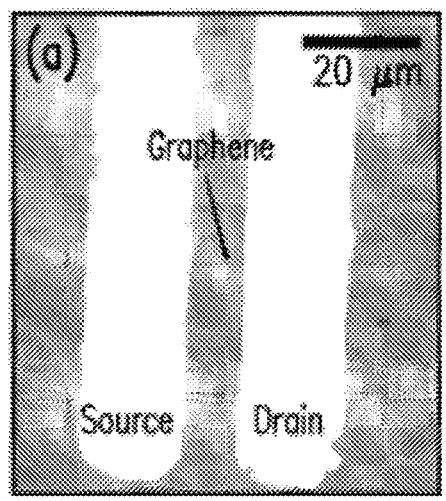
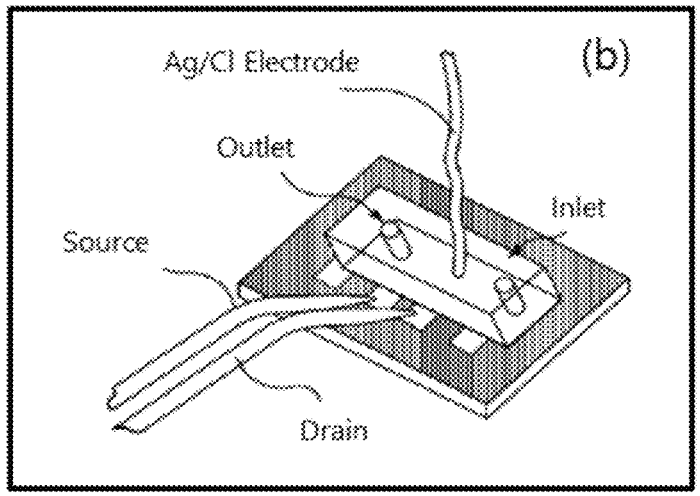
FIG. 20A    FIG. 20B
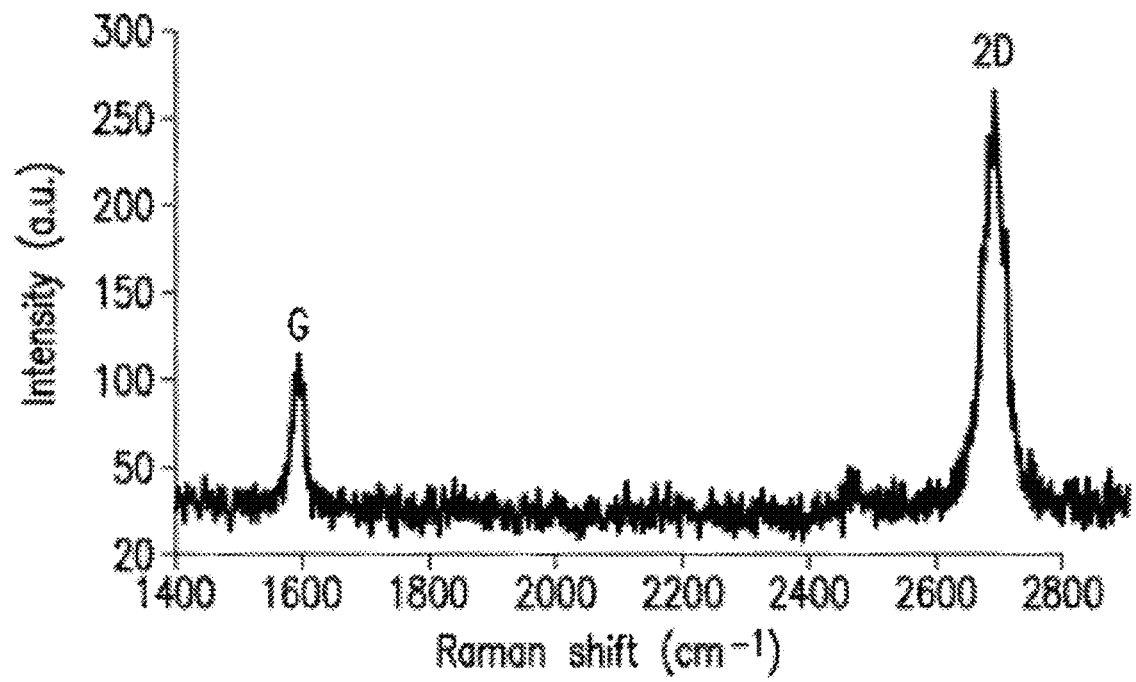
FIG. 21

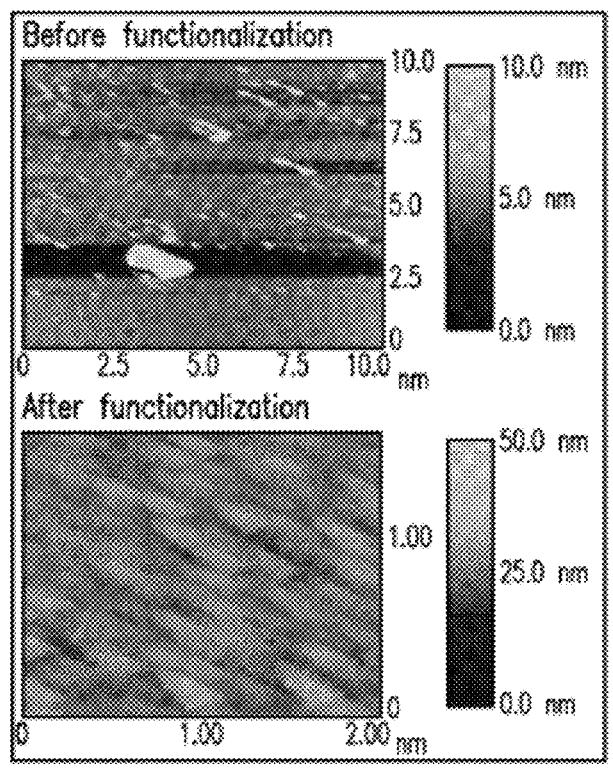
FIG. 22A
FIG. 22B
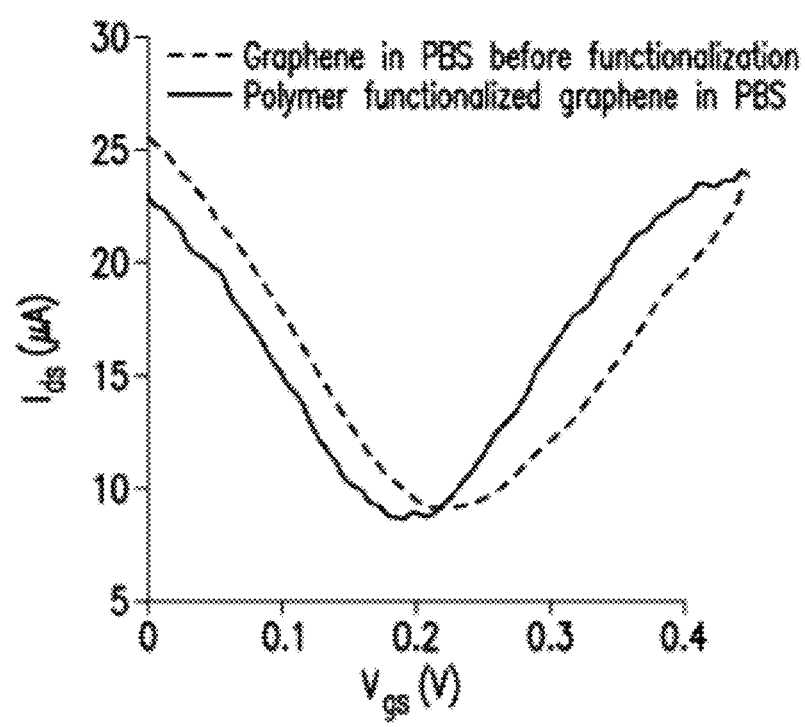
FIG. 23

FIG. 28A
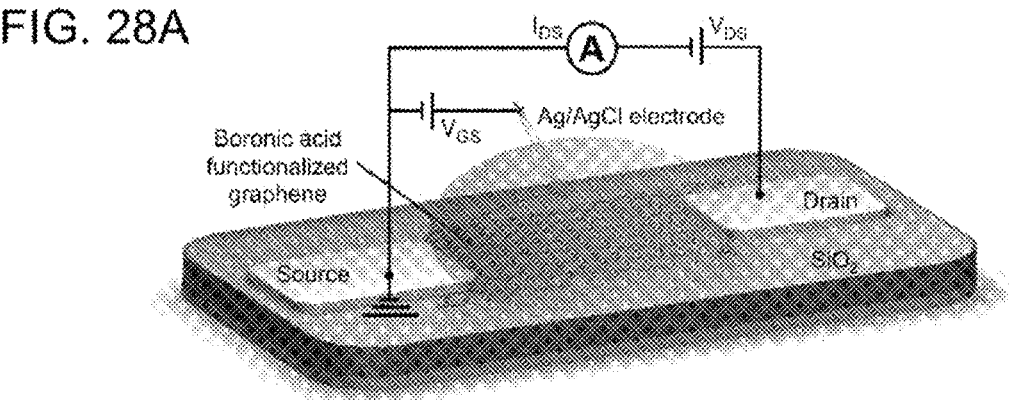
FIG. 28B
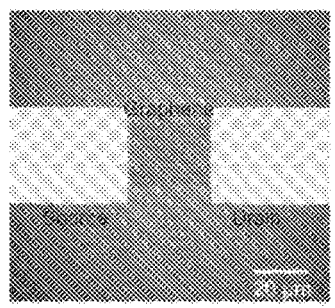
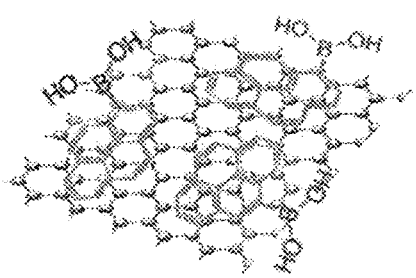
FIG. 28C
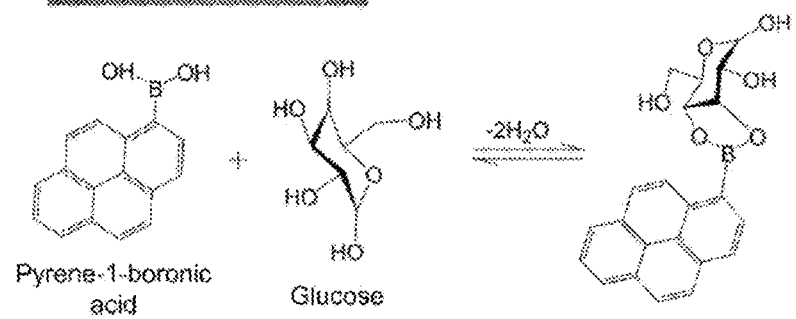
FIG. 28D

FIG. 32Bi
FIG. 32Bii
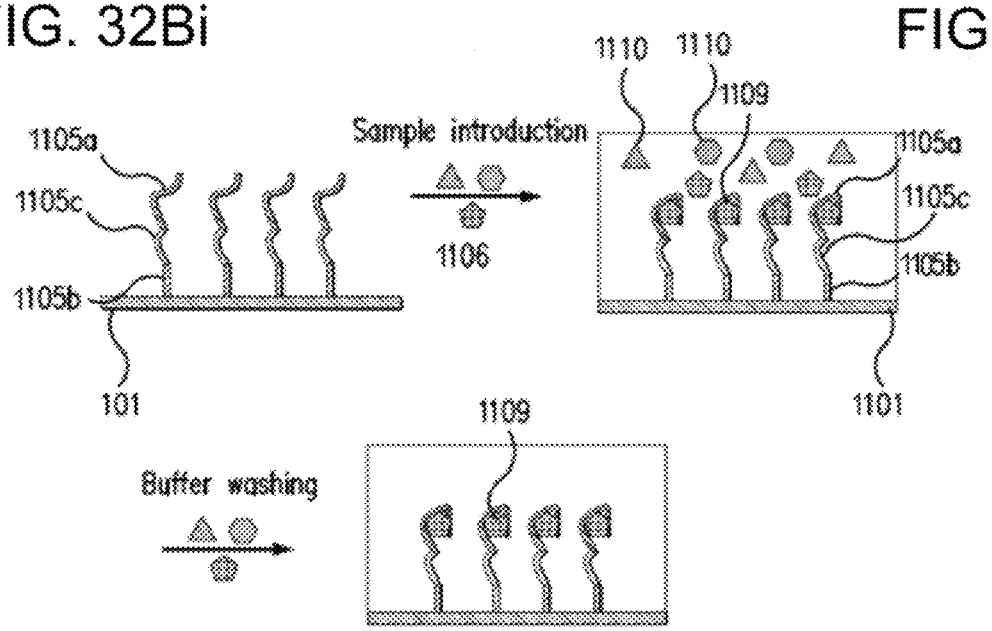
FIG. 32Biii
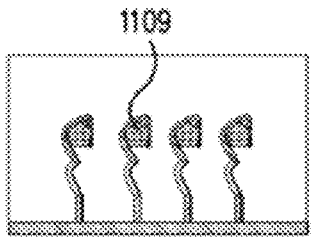
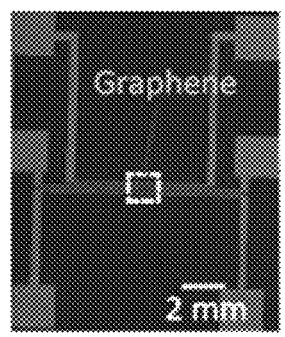
FIG. 33

3400

| Step | # |
|---|---|
| Place a layer of the material for the source and drain electrodes on a clean support (*e.g.* by thermal evaporation) | 1301 |
| Add a layer of photoresist on top of the electrode material (*e.g.*, spin-coat) | 1302 |
| Bake | 1303 |
| Pattern the source and drain electrodes | 1304 |
| Develop the device | 1305 |
| Etch in Gold | 1306 |
| Etch in chrome etchant | 1307 |
| Transfer layer of graphene to cover the source and drain electrodes | 1308 |
| Place polymeric well above the graphene | 1309 |

| Step | |
|---|---|
| Immerse the device with graphene with a solution of the linker | 1401 |
| Rinse with ethanol and PBS | 1402 |
| Optionally immerse the device in a solution of the polymer | 1403 |
| Optionally Add EDC•HCl and NHS to activate the carboxylic group at the end of the polymer | 1404 |
| Add a solution of aptamer | 1405 |

| | |
|---|---|
| Place a layer of the material for the source and drain electrodes on a clean support | 1601 |
| Transfer layer of graphene to cover the source and drain electrodes | 1602 |
| Functionalize the graphene surface with control target analyte | 1603 |
| Fabricate the microchambers and channels with soft lithography in the polymeric material | 1604 |
| Punch holes in the polymeric material to create inlet and outlets for the buffer and sample | 1605 |
| Bond the polymeric material onto the support containing microheater and temperature sensors (patterned by lithography) | 1606 |
| Stack and bind the graphene sensor chip over the sensor chamber | 1607 |

FIG. 37

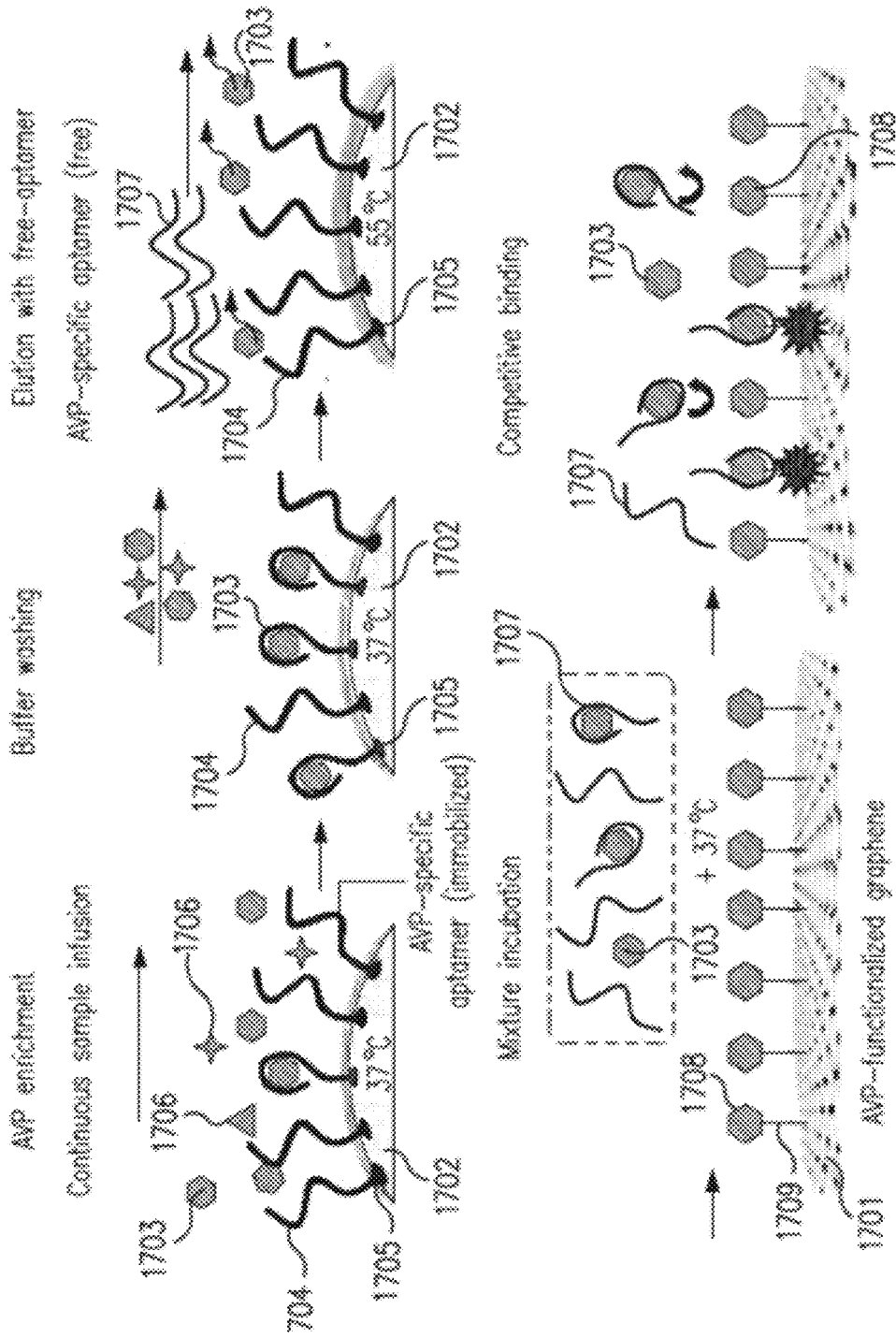

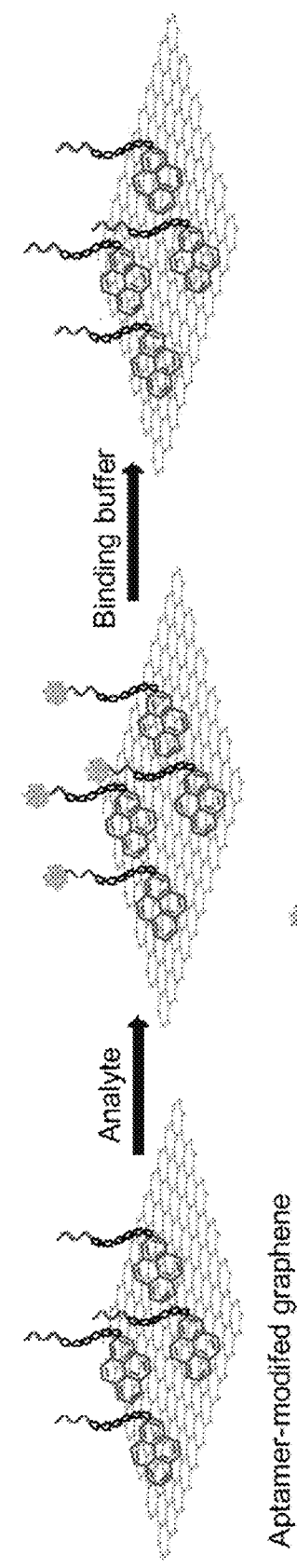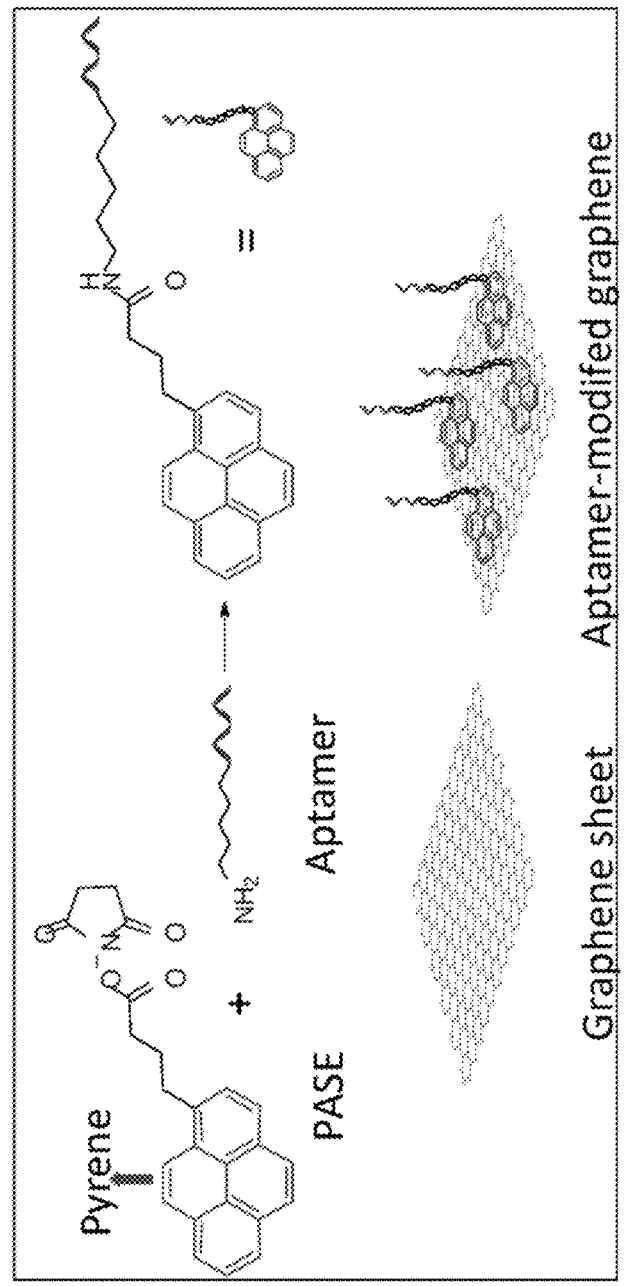
FIG. 85A  FIG. 85B  FIG. 85C  FIG. 85D

GRAPHENE-BASED NANOSENSOR FOR IDENTIFYING TARGET ANALYTES

CROSS REFERENCE TO RELATED APPLICATIONS

This application is continuation of U.S. Non-Provisional application Ser. No. 16/012,527, filed Jun. 19, 2018, which is a continuation in part of U.S. Non-Provisional application Ser. No. 15/374,375, filed Dec. 9, 2016, which is a continuation of International Application No. PCT/US15/035640, filed Jan. 12, 2015, which claims priority from U.S. Provisional Application No. 62/011,481, filed Jun. 12, 2014, Provisional Application No. 62/100,366, filed Jan. 6, 2015, and Provisional Application No. 62/100,379, filed Jan. 6, 2015, each of which is incorporated by reference herein in its entirety, and priority to each of which is claimed.

This application is continuation of U.S. Non-Provisional application Ser. No. 16/012,527, filed Jun. 19, 2018, which is a continuation in part of U.S. Non-Provisional application Ser. No. 15/374,375, filed Dec. 9, 2016, which is a continuation of International Application No. PCT/US16/012297, filed Jan. 6, 2016, which claims priority from U.S. Provisional Application No. 62/100,412, filed Jan. 6, 2015, each of which is incorporated by reference herein in its entirety, and priority to each of which is claimed.

This application is continuation of U.S. Non-Provisional application Ser. No. 16/012,527, filed Jun. 19, 2018, which is a continuation in part of U.S. Non-Provisional application Ser. No. 15/374,375, filed Dec. 9, 2016, which is a continuation of International Application No. PCT/US16/037362, filed Jun. 14, 2016, which claims priority to U.S. Provisional Application Ser. No. 62/180,484, filed on Jun. 16, 2015, and U.S. Provisional Application Ser. No. 62/188,281, filed on Jul. 2, 2015, each of which is hereby incorporated by reference in its entirety, and priority to each of which is claimed.

This application is continuation of U.S. Non-Provisional application Ser. No. 16/012,527, filed Jun. 19, 2018, which claims priority to U.S. Provisional Application Ser. No. 62/523,516, filed on Jun. 22, 2017, which is incorporated by reference herein in its entirety.

STATEMENT REGARDING FEDERALLY FUNDED RESEARCH

This invention was made with government support under 1509760 awarded by National Science Foundation. The government has certain rights in this invention.

SEQUENCE LISTING

The instant application contains a Sequence Listing which has been submitted electronically in ASCII format and is hereby incorporated by reference in its entirety. Said ASCII copy, created on Mar. 5, 2020, is named 070050 6357 SL.txt and is 1,755 bytes in size.

BACKGROUND

Several hundred million people in the world have diabetes, making it a leading cause of death. In addition, complications induced by diabetes, such as heart disease, stroke, hypertension, blindness, kidney failure, and amputation, impact many others. Tight control of glycemia can reduce certain diabetes-related complications by 50% or more among Type I diabetics, with similar results for Type II diabetes patients. Thus, it is important to closely monitor abnormal blood sugar levels in diabetes patients so timely treatments (e.g., insulin injection, exercise, and diabetic diet, intake of carbohydrates) can be administered.

Certain glucometers with sparsely discrete measurements, however, do not allow tight blood sugar control. In contrast, continuous glucose monitoring (CGM) can effectively detect hypo- and hyperglycemic (i.e., low and high blood sugar, respectively) events. CGM can achieve this by taking repetitive measurements of physiological glucose concentrations to enable close monitoring and timely correction of problematic blood sugar patterns of patients with diabetes mellitus. CGM can reduce the risk of diabetes-related complications, but certain CGM devices are not adequate because of limited stability, insufficient accuracy, and slow time.

CGM can be achieved via minimally invasive or noninvasive methods, such as those which use subcutaneously implanted devices that determine glucose concentration in interstitial fluid (ISF) via measurement of electrochemical enzymatic reactions or equilibrium-based affinity binding. Electrochemistry, however, can involve irreversible consumption of glucose and depends on the rate at which glucose reaches the electrodes, which often makes electrochemical CGM sensors susceptible to influences of reactant supply rates, electroactive interferences, and biofouling (deposition of biological material such as proteins and cell debris on sensor surfaces). As a result, certain sensors can exhibit drifts, have delays, require frequent calibration, and have limited accuracy (especially at low glucose concentrations), not have adequate accuracy in the hypoglycemic realm (blood glucose concentration below 70 mg/dL), and exhibit significant delays.

Nonreactive methods that use equilibrium affinity binding of glucose to a specific receptor and do not involve irreversible consumption of glucose and can offer improved stability. Affinity glucose sensing can use concanavalin A (Con A), a glucose-binding protein, which unfortunately lacks stability and whose toxicity generates safety concerns.

Glucose sensors using stable, nontoxic glucose-binding can be limited by issues in accuracy, time response or miniaturization. Micro/nanoscale glucose affinity sensors, using microelectromechanical systems (MEMS), as well as using nanoscale materials such as carbon nanotubes, offer improvement in accuracy and stability, but can suffer from slow time response, rigid construction, and poor sensitivity. Moreover, they can be invasive by requiring subcutaneous implantation.

Noninvasive devices can attempt detection of interstitial fluid (ISF) glucose across the skin use optical spectroscopy or transdermal ISF sampling, which can be susceptible to variations in skin conditions. Others can use a measurement of glucose in urine, saliva, and tears. Unfortunately, glucose concentration in urine does not necessarily accurately reflect that in plasma, in particular in the hypoglycemic regime. Electrochemical methods to detect saliva glucose levels can suffer from the presences of residual food in saliva which can cause interferences.

Certain correlations have been found between tear and blood glucose concentrations, with deviations attributable to artifacts such as inconsistent tear collection methods. For example, the absorption and emission spectra of boronic acid containing fluorophores for glucose sensing can cumbersome and prevent CGM. Contact lens-based electrochemical sensors using glucose oxidase can be error-prone because of the irreversible nature of the reaction which consumes glucose during the measurement process.

There is a need to develop noninvasive glucose monitoring systems that offer improved long-term accuracy and stability, biocompatibility, resistance to biofouling, resistance to environmental parameter fluctuations, easier calibration, as well as the capability of providing real-time report of a subject's glucose level via wireless telemetry. Certain approaches to blood-based glucose monitoring can involve extracting blood such as by intermittent finger-stick testing, or continuous glucose monitoring, and can have drawbacks. For example, apart from the invasive and sometime painful extraction of blood, finger-stick glucose monitoring can miss abnormal blood excursions. Continuous glucose monitoring, while able to monitor glucose levels throughout the day via electrochemical detection, can suffer from interferences from electroactive chemicals.

MEMS (micro-electro-mechanical systems) technology can enable innovative subcutaneously implanted sensors to measure concentrations of certain molecules, such as glucose, in interstitial fluid (ISF). Such sensors can employ affinity binding between the target molecules and a sensing material to achieve high accuracy and stability. Affinity sensors based on dielectric measurements can be used in applications such as detecting or quantifying biochemical targets under excitations at various frequencies. However, such microsensors utilizing dielectric measurements can lack sufficient sensitivity for the detection of certain low-charged and low-molecular-weight molecules.

Additionally, MEMS devices can be limited by complicated and inefficient designs or slow time responses. For example, affinity glucose sensing has been implemented using optical, mechanical, and electrical methods on conventional or microscale platforms typically requiring complex sensor structures such as moving mechanical components or physical barriers. Semi-permeable membranes or other physical barriers or mechanically movable structures can increase complexity of the devices and limit the reliability of the devices.

Graphene is a single atom thick two-dimensional nanomaterial with honeycomb lattice of carbon. While graphene can be attractive functional nanomaterial in sensors that allow highly sensitive detection of chemical and biological analytes, analytes and like molecules detectable by such graphene-based sensors can be highly charged or strong electron donors or acceptors that can induce carrier doping in graphene for field effect transistor (FET)-based measurements. Graphene can form a conducting channel in field effect transistors (FETs), allowing sensitive electrically based detection of gas molecules, physiological parameters of liquids (e.g., pH level) and biological molecules (e.g., proteins) in solution. Glucose, however, is an uncharged, low-molecular-weight molecule. Sensitive detection of glucose has been accomplished within graphene FET-based enzymatic sensors. Unfortunately, due to the irreversible, consumptive nature of the enzyme-catalyzed electrochemical reactions of glucose, as well as undesirable byproducts (e.g., hydrogen peroxide) generated in the reactions of enzymes and glucose, certain enzyme-based sensors can suffer from limitations in stability and accuracy when operating in physiological environments.

Subcutaneous detection of certain low-charged molecules, low-molecular weight molecules, which can be important for applications such as glucose monitoring, thus still remains a challenge. Accordingly, a need exists for an accurate, subcutaneous sensor reliable for continuous monitoring of low-charged molecules in a physiological environment.

Furthermore, although graphene nanosensors configured as FETs can provide a sensitive, label-free biomarker detection platform because of the ability of surface-based binding to cause changes in the bulk properties of graphene, certain existing aptameric graphene nanosensors have been limited to well-conditioned buffers, while analyte detection in physiological samples such as human serum has remained a challenge. One difficulty involves the hydrophobic nature of pristine graphene, as background molecules in serum tend to nonspecifically adsorb to the graphene surface, thus interfering with the detection of the target analyte. Another difficulty is their application to the detection of small biomolecules is still limited, as the binding of low charged small molecules does not directly induce detectable changes in graphene conductance, hence suffering low sensitivity.

Furthermore, understanding binding properties of biomolecules and their dependence on environmental conditions such as temperature and ionic strength can be of great interest to basic science studies and applied pharmacology. While successful characterization of biomolecular binding properties can be performed with traditional methods (e.g., optical, electrochemical, and electromechanical characterization), the traditional approaches for binding studies commonly either require molecular labeling groups and/or involve complex sensor structure and instrumentation.

There is a need to develop graphene nanosensors that offer improved specificity and sensitivity, including for diagnostic testing. Furthermore, there is a need for nanosensors that can be used to characterize biomolecular interactions under different levels of ionic strength and temperature.

SUMMARY

The disclosed subject matter provides microdevices and techniques for monitoring a target analyte.

In one aspect, the disclosed subject matter provides a microdevice and techniques for monitoring a target analyte in a sample using a receptor capable of binding to the target analyte. In one aspect, the microdevice does not require a receptor that binds the target analyte.

In certain embodiments, a microdevice includes a nanosensor, on a substrate platform, including a pair of conductance sensors functionalized with a receptor. One receptor (sensing receptor) binds specifically to the target analyte, and the other (reference receptor) is insensitive to the target analyte. Target analyte binding of the sensing receptor changes the charge density on the sensor surface, inducing changes in the carrier concentration of the sensor. Meanwhile, the reference receptor does not bind to the target analyte and its associated sensor conductance would change due to fluctuations in environmental parameters. Thus, differential measurement of the target analyte conductance allows determination of the target analyte concentration in, for example, a sample or bodily fluid. In certain embodiments, the receptors bind reversibly with essentially all analytes. In certain embodiments, the sensing receptor binds reversibly with the target analyte. In certain embodiments, the receptor is a synthetic polymer. In certain embodiments, the sensor includes graphene.

In certain embodiments, a microdevice includes a nanosensor, on a substrate platform, including a single conductance sensor functionalized with synthetic receptors (sensing receptors), which bind specifically to the target analyte, on a substrate platform. Target analyte binding of the sensing receptor changes the charge density on the sensor surface, inducing changes in the carrier concentration of the sensor allowing for the determination of the target analyte concentration in, for example, a sample or bodily fluid. In certain embodiments, the sensing receptor binds reversibly with the target analyte. In certain embodiments, the receptor is a synthetic polymer. In certain embodiments, the sensor includes graphene.

The disclosed subject matter also provides microdevices for monitoring a target analyte in a bodily fluid using a polymer capable of binding to the target analyte. In certain embodiments, the microdevice includes a substrate platform and a nanosensor including a first conductance element functionalized with a sensing polymer for detecting the target analyte and a second conductance element functionalized with a reference polymer that is insensitive to the target analyte. Detecting a difference, if any, in the conductance of the first and second conductance elements can be used to determine the presence and/or concentration of the target analyte in the sample. In some embodiments, the differential measurement of the conductance of the first and second conductance elements can reject or minimize environmental effects on the disclosed microdevices. In non-limiting embodiments, the target analyte can be at physiologically relevant concentration in the sample.

In certain embodiments, the microdevice includes a graphene nanosensor on a contact lens platform. A noninvasive contact lens-based nanosensor, which is miniaturized and mechanically flexible, can include graphene functionalized with a glucose-binding polymer and enable noninvasive CGM. By differential measurement of glucose binding-induced changes in graphene conductance as compared to measurements from a sensor insensitive to glucose, the device can allow specific, sensitive, and rapid detection of glucose concentration in tear fluid. In certain embodiments, the nanosensor includes a pair of graphene conductance sensors on a flexible, contact lens-based substrate respectively functionalized with synthetic polymers. In certain embodiments, synthetic glucose-specific polymers and reference polymers can be grafted on graphene surfaces for differential measurements. In certain embodiments, the polymer includes a PAAPBA based polymer. In certain embodiments, the polymer includes a plurality of boronic acid moieties.

In certain embodiments, the nanosensor can be coated with a biocompatible glucose-permeable hydrogel thin layer. Glucose binding of the sensing polymer changes the charge density on the graphene surface, inducing changes in the carrier concentration within the bulk of the atomically thin graphene and hence in the graphene electric conductance.

In certain embodiments, the microdevice can be adapted to be disposed on or coupled to a contact lens-based substrate, a dermal patch, an eye patch, a tattoo, jewelry, a watch, bandages, clothing, or a wireless body sensor.

In certain embodiments, the bodily fluid is tears, blood, saliva, mucus, interstitial fluid, spinal fluid, intestinal fluid, amniotic fluid, lymphatic fluid, pericardial fluid, peritoneal fluid, pleural fluid, semen, vaginal secretions, sweat, or synovial fluid of a subject.

The disclosed subject matter also provides synthetic polymer-functionalized affinity-based nanosensors for detection of low-charge, low-molecular-weight molecules, such as, for example and without limitation, glucose. The disclosed subject matter can utilize a material functionalized with a synthetic polymer monolayer derivatized with a boronic acid group whose reversible complexation with the target low-charge, low-molecular-weight molecule (e.g., glucose) generates a detectable signal.

In one aspect of the disclosed subject matter, a graphene-based affinity nanosensor is provided. The binding of the polymer monolayer with glucose on the graphene surface of the device can induce changes in the carrier density and mobility in the graphene, which can cause an increase in charge on the graphene. Thus, the binding can offer a high detection sensitivity of the target molecule and/or analyte.

For example and without limitation, an affinity nanosensor for detection of low-charge, low-molecular-weight molecules includes a solution-gated field effect transistor, which can enable reliable monitoring of a target molecules in a sample solution. The solution-gated field effect transistor can include a silicon substrate, a source electrode disposed on the silicon substrate, and a drain electrode disposed on the silicon substrate. The graphene can be a graphene sheet, which can be disposed between the source electrode and drain electrode and can connect the source and drain electrodes. The solution-gated field effect transistor can further include graphene functionalized with a synthetic polymer monolayer, which is disposed between the source electrode and drain electrode on the silicon substrate. The functionalized graphene forming a conducting channel of the solution-gated field effect transistor, and the synthetic polymer monolayer being responsive to a first analyte. The affinity nanosensor can also include a reference electrode disposed between the source and drain electrodes, and an electrical double layer at the interface of the graphene and solution comprising a gate capacitor.

Additionally, or alternatively, the silicon substrate can be an oxidized silicon substrate wafer. The source electrode and drain electrode can be gold electrodes. The synthetic polymer monomer can include a boronic acid. The graphene can be functionalized with the synthetic polymer monolayer via π-π stacking interactions. The first analyte can be glucose. The reference electrode can include silver chloride. Furthermore, the gate capacitor can be affected by varying concentrations of the first analyte in the sample solution.

The graphene-based affinity nanosensor can include any or all of the features described herein.

According to another aspect of the disclosed subject matter, methods of fabricating an affinity nanosensor for detecting low-charge, low-molecular-weight molecules are provided. An example method includes providing a silicon substrate wafer having a uniform thickness throughout, the wafer having oppositely disposed top and bottom faces; and providing a first gold portion on the top face of the first material, and a second gold portion separated from the first gold portion by a channel region. The method can further include transferring graphene onto the top face of the wafer in the channel region to connect the first and second gold portions, and functionalizing the graphene with a synthetic polymer monolayer, the synthetic polymer monolayer being sensitive to a first analyte. The method can also include mounting a conductive wire within the channel region.

Additionally, or alternatively, the providing the first and second gold portions can include etching the first gold portion and the second gold portion to the top face of the wafer. The transferring the graphene can include coupling graphene to the top face of the wafer via chemical vapor deposition. Furthermore, the functionalizing can include immersing at least the graphene transferred onto the wafer in a solution comprising boronic acid for at least four hours at room temperature, and washing the graphene transferred onto the wafer using methanol. The immersing can include coupling a pyrene-1-boronic acid to the graphene via π-π stacking interactions. The mounting the conductive wire within the channel region can include providing a silver wire mounted on a positioner to serve as a gate electrode.

In another aspect of the disclosed subject matter, hydrogel-based affinity nanosensors are provided. For example, an affinity nanosensor can include a parallel plate transducer, a synthetic hydrogel disposed between a first plate and a second plate of the parallel plate transducer, the hydrogel being responsive to a first analyte, and a temperature sensor located below the first and second plates.

Additionally, or alternatively, the first and second plates of the parallel plate transducer each further include a sensing electrode. The sensing electrode can be formed of gold. At least one of the first plate and second plate of the parallel plate transducer can be perforated and passivated within a perforated diaphragm. The at least one perforated plate and at least one perforated diaphragm can be supported by at least one micropost.

The synthetic hydrogel of the affinity nanosensor can further include a synthetic copolymer including boronic acid. The first analyte can be glucose.

The hydrogel-based affinity nanosensor can include any or all of the features described herein.

According to yet aspect of the disclosed subject matter, an example method for fabricating an affinity nanosensor for detecting low-charge, low-molecular-weight molecules includes providing a silicon substrate wafer having a uniform thickness throughout and having oppositely disposed top and bottom faces, providing a first electrode on the top face of the wafer, and providing a second electrode, spaced a first distance over the first electrode, above the top face of the wafer, the second electrode being supported above the top face of the wafer by at least one micropost. The method can also include preparing a hydrogel functionalized with a polymer responsive to a first analyte and filling the hydrogel between the first and second electrodes.

The method can also include providing the second electrode with one or more perforations and separating the second electrode from the hydrogel by a perforated diaphragm. The first analyte can be glucose. Furthermore, the preparing the functionalized hydrogel can include synthesizing the hydrogel in situ via polymerization of the hydrogel with a boronic acid, and gelating the hydrogel between the first and second electrodes.

As herein disclosed, a sample solution containing such low-charge, low molecular-weight molecules can be a bodily fluid, a non-bodily fluid, or a laboratory sample. The bodily fluid can be, for example and without limitation, tears, blood, saliva, mucus, ISF (interstitial fluid), amniotic fluid, lymphatic fluid, pericardial fluid, peritoneal fluid, pleural fluid, sweat, or other bodily fluid of a subject.

The disclosed subject matter further provides systems and methods for detecting small biomolecules using a microfluidic nanosensors including a graphene nanosensor. The disclosed subject matter also provides a microdevice and techniques for monitoring a target analyte. In one aspect, the disclosed subject matter provides a microdevice and techniques for monitoring a target analyte in a sample using an aptamer capable of binding to the target analyte.

In certain embodiments, a microdevice includes a graphene nanosensor, on a substrate platform, wherein the graphene nanosensor can be functionalized with an aptamer that binds the target analyte. Target analyte binding of the aptamer changes the charge density on the graphene nanosensor surface, inducing changes in the carrier concentration of the sensor. In certain embodiments, the aptamers bind reversibly with essentially all analytes. In certain embodiments, the aptamers bind reversibly with the target analyte. In some embodiments, the aptamers can include insulin specific aptamers. For example, the insulin specific aptamers can include guanine-rich IGA3 aptamers.

The nanosensor can have a FET configuration. In accordance with an exemplary embodiment, the nanosensor can include a substrate. The substrate can be, for example, a $SiO_2$-coated silicon wafer. Source and drain electrodes can be patterned on the substrate.

A graphene sheet can be coupled to the source and drain electrodes. The graphene surface can be functionalized with aptamers that binds the target analyte. A polymeric material (e.g., PDMS sheet) can define the well for testing the sample.

The disclosed subject matter also provides a microfluidic aptasensor including an enrichment chamber and a sensing chamber. The enrichment chamber can include one or more microbeads. Aptamers can be immobilized on the surface of the microbeads.

The sensing chamber can include a graphene nanosensor. The nanosensor can have a FET configuration. In accordance with an exemplary embodiment, the nanosensor can include a substrate. The substrate can be, for example, a $SiO_2$-coated silicon wafer. Gate electrodes can be patterned on the substrate. A single-layer graphene sheet can connect the source and drain electrodes. The graphene surface can be functionalized with a control target analyte. A polymeric material (e.g., PDMS sheet) can define microchambers and channels.

The enrichment chamber and the sensing chamber can be coupled via a serpentine channel. In accordance with embodiments of the disclosed subject matter, the aptasensor can further include a temperature control unit, an inlet coupled to the enrichment chamber, a waste outlet coupled to the serpentine channel, and a sample outlet coupled to the sensing chamber.

In accordance with another embodiment, the disclosed subject matter provides methods for detecting small biomolecules using a microfluidic graphene nanosensor. A sample can be introduced into the polymeric well. Target analytes (e.g., IgE) can be selectively captured by aptamers immobilized on the graphene nanosensor. Non-target molecules, including impurities, can then be removed through, e.g., buffer washing. The electrical conductance through the change in conductance caused by the target analyte binding to the aptamer immobilized on the graphene can be measured by measuring the drain current at a fixed drain voltage.

In accordance with yet another embodiment, the disclosed subject matter provides methods for detecting small biomolecules using a microfluidic aptasensor including an enrichment chamber and a sensing chamber. A sample can be introduced into the enrichment chamber. Target analytes (e.g., AVP) can be selectively captured by aptamers immobilized on microbead surfaces. Non-target molecules, including impurities, can then be removed through, e.g., buffer washing. The enriched target molecules can then be released at an elevated temperature and eluted with free aptamer. This mixture can travel to the sensing chamber via a serpentine channel. The eluate can be incubated with graphene pre-functionalized with a control (e.g., reagent) target analyte (e.g., with reagent AVP). The graphene-bound control (e.g., reagent) target analyte can compete with the sample target molecules to bind to and capture some of the free aptamer molecules, which can cause an increase in charge on the graphene. The electrical conductance through the graphene can be measured by measuring the drain current at a fixed drain voltage.

In one aspect, the aptamer can be a single-stranded oligonucleotide or a peptide. In certain embodiments, the aptamer can be a single-stranded oligonucleotide, which can be DNA, RNA, XNA, or a combination thereof. In certain embodiments, the aptamer can be functionalized to the surface of graphene via a linker. The linker can be a pyrene-terminated agent (e.g., 1-pyrenebutanoic acid succinimidyl ester). In certain embodiments, the graphene can be serially functionalized with a polymer (e.g., polyethlene glycol) and aptamers. In accordance with certain embodiments, the polymer can be coupled to the aptamer and the opposite end of the polymer can be coupled to the linker.

In certain embodiments, the nanosensor as disclosed herein can enable reliable monitoring of a target analyte in a sample. In certain embodiments, the sample can be a bodily fluid, a non-bodily fluid liquid, or a laboratory sample. In certain embodiments, the nanosensor can be used to measure the amount or change in the amount of a target analyte in a sample. In certain embodiments, the bodily fluid can be tears, blood, saliva, mucus, interstitial fluid, spinal fluid, intestinal fluid, amniotic fluid, lymphatic fluid, pericardial fluid, peritoneal fluid, pleural fluid, semen, vaginal secretions, sweat, or synovial fluid of a subject. In nonlimiting embodiments, the nanosensor can perform real-time detection of a target analyte concentration.

In accordance with yet another embodiment, the disclosed subject matter provides a microdevice for monitoring a target analyte. The microdevice can include a field effect transistor comprising a substrate, a gate electrode, and a microfluidic channel including graphene. The microfluidic channel can be formed between drain electrodes and source electrodes on the substrate. The microdevice can also include at least one aptamer functionalized on a surface of the graphene. The at least one aptamer can be adapted for binding to the target analyte. Binding of the target analyte to the at least one aptamer can alter the conductance of the graphene.

In certain embodiments, the microfluidic channel can be bound to the substrate for analyte and buffer introduction to initiate association and dissociation of the target analyte to the at least one aptamer.

In certain embodiments, the field effect transistor can include a gate capacitor comprising of an electrical double layer formed at the interface of the graphene and the solution.

In certain embodiments, binding of the target analyte to the at least one aptamer can cause a conformational change of the at least one aptamer, causing the target analyte to be brought into a proximity to the surface of the graphene. The target analyte being brought into proximity to the surface of the graphene can cause electrical properties of graphene to change by at least one of charge transfer and electrostatic interaction. In some embodiments, the conformational change can include parallel G-quadruplex conformation and/or antiparallel G-quadruplex conformation.

In certain embodiments, the microdevice can include at least one of an on-chip temperature sensor and a Peltier module to perform closed-looped temperature control of the microdevice.

In certain embodiments, the microdevice can be configured to provide a label-free direct characterization of biomolecular binding properties with one-step electrical readout.

In certain embodiments, binding of the target analyte to the aptamer can cause a carrier concentration in the graphene to be altered, resulting in a detectable signal. In certain embodiments, the at least one aptamer can be functionalized on the surface of the graphene using a linker. The linker can be configured to be irreversibly attached to the graphene without altering electronic properties of the graphene. In certain embodiments, the at least one aptamer can be directly attached to the linker by forming an amide bond. The linker can be coupled to the graphene via stacking. The at least one aptamer can be attached to the free end of linker by forming an amide bond. In certain embodiments, the linker can include 1-pyrenebutanoic acid succinimidyl ester (PASE). In some embodiments, aptamers can be coupled to PASE through a reaction of an amino group of the aptamer with N-hydroxysuccinimide ester of PASE.

In certain embodiments, the field effect transistor can include a source electrode and a drain electrode. The graphene can make contact with both the source electrode and the drain electrode. In certain embodiments, the graphene can be a single layer sheet.

In certain embodiments, the target analyte can be disassociated from the at least one aptamer by introducing a buffer to the at least one aptamer.

In accordance with yet another embodiment, the disclosed subject matter provides for a method for monitoring a target analyte using an aptamer capable of binding to the target analyte. The method can include placing a nanosensor in contact with target analytes such that the nanosensor includes a first conductance element functionalized with an aptamer configured to detect the target analyte and a second conductance element that is insensitive to the target analyte. The method can include detecting a difference, if any, in the conductance of the first and second conductance elements. The method can include determining, based on the detected difference, a presence of the target analyte. In some embodiments, the method can further include modifying the aptamer to adjust a specificity of the nanosensor to the target analyte.

In certain embodiments, the binding of the aptamer with the target analyte can causes a change in the charge density on the first conductive element surface.

In certain embodiments, the disclosed microdevice and/or nanosensor can detect changes in the target analyte concentration in real-time. In some embodiments, the detection can be continuous over time In certain embodiments, a differential measurement of the conductance of the first conductance element and the second conductive element can provides for determination of the presence of the target analyte. In some embodiments, the target analyte can include an insulin molecule.

In certain embodiments, the first conductive element can include a surface adapted for a change in charge density thereon upon the binding of the aptamer with the target analyte.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTIONS OF THE DRAWINGS

Further features and advantages of the present disclosure will become apparent from the following detailed description taken in conjunction with the accompanying figures showing illustrative embodiments of the present disclosure, in which:

(FIG. 2A) top and (FIG. 2B) cross-sectional views.

Figure 3A:
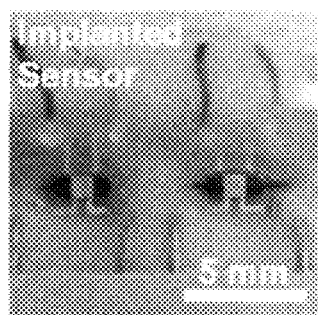
Figure 3B:
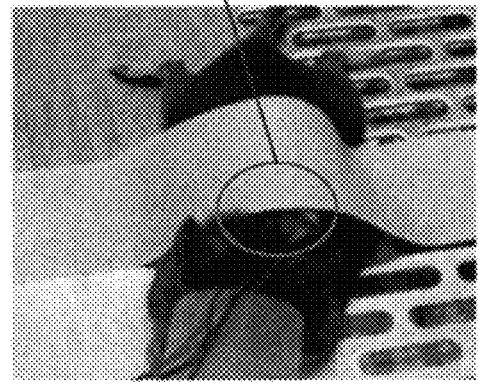
Figure 3C:
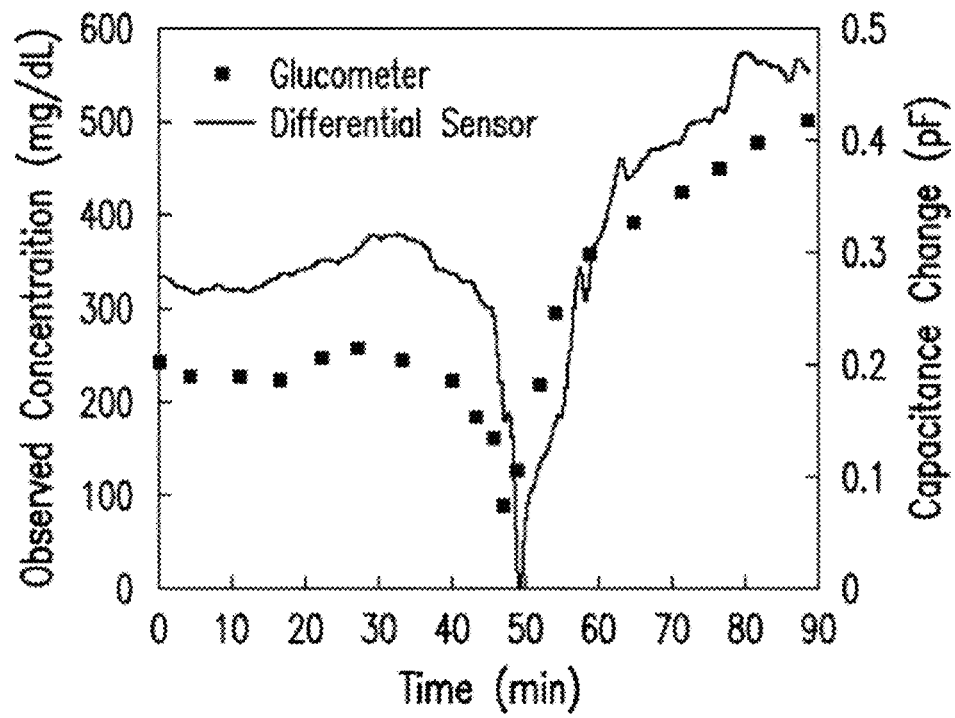

FIGS. 3A-C illustrate a microfabricated differential affinity glucose sensor (FIG. 3A) that can be implanted in a mouse (FIG. 3B), with its capacitance output (reflecting ISF glucose concentration) tracking blood glucose concentration measured with a glucometer (FIG. 3C).

Figure 4A:
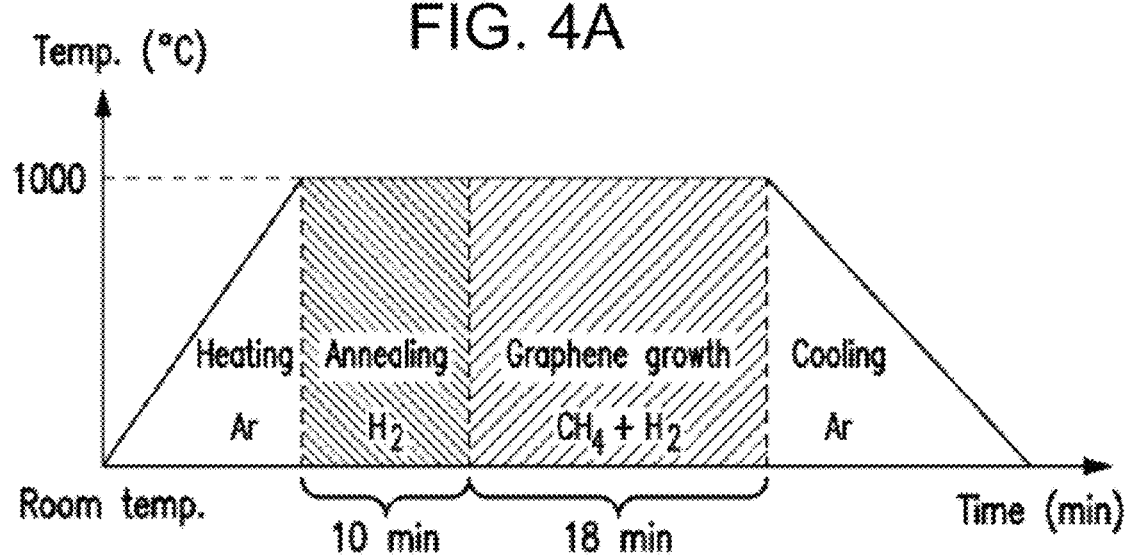
Figure 4B:
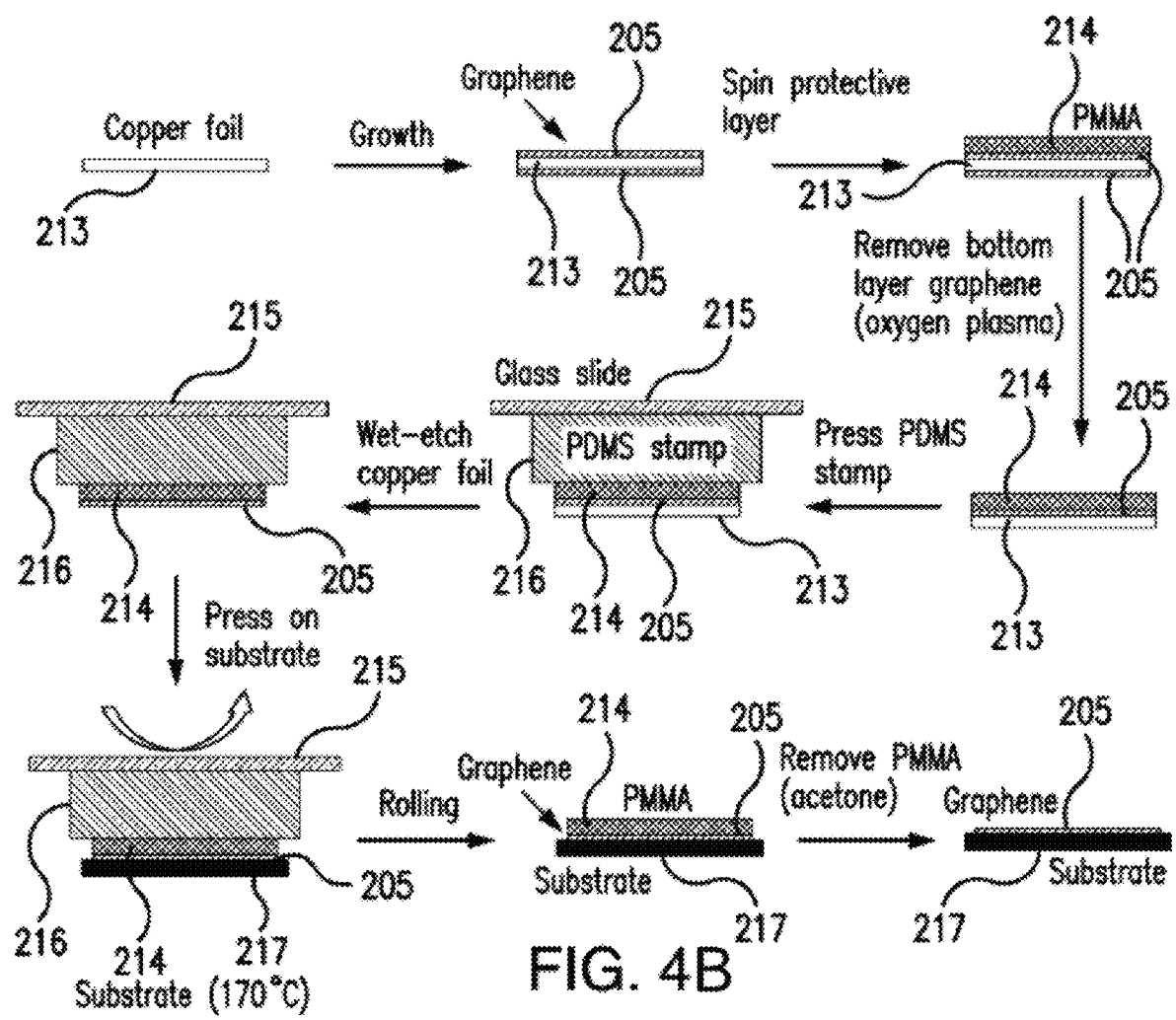

FIGS. 4A-B illustrates a method for CVD graphene (205) synthesis and transfer procedure according to some embodiments of the disclosed subject matter, including (FIG. 4A) CVD graphene synthesis in quartz tubing furnace and (FIG. 4B) CVD graphene (205) transfer onto the substrate (217).

FIGS. 5A-C illustrates a characterization of a graphene sheet according to some embodiments of the disclosed subject matter including (FIG. 5A) AFM micrograph, (FIG. 5B) Height profile, and (FIG. 5C) Raman spectra (532 nm laser excitation).

Figure 6:
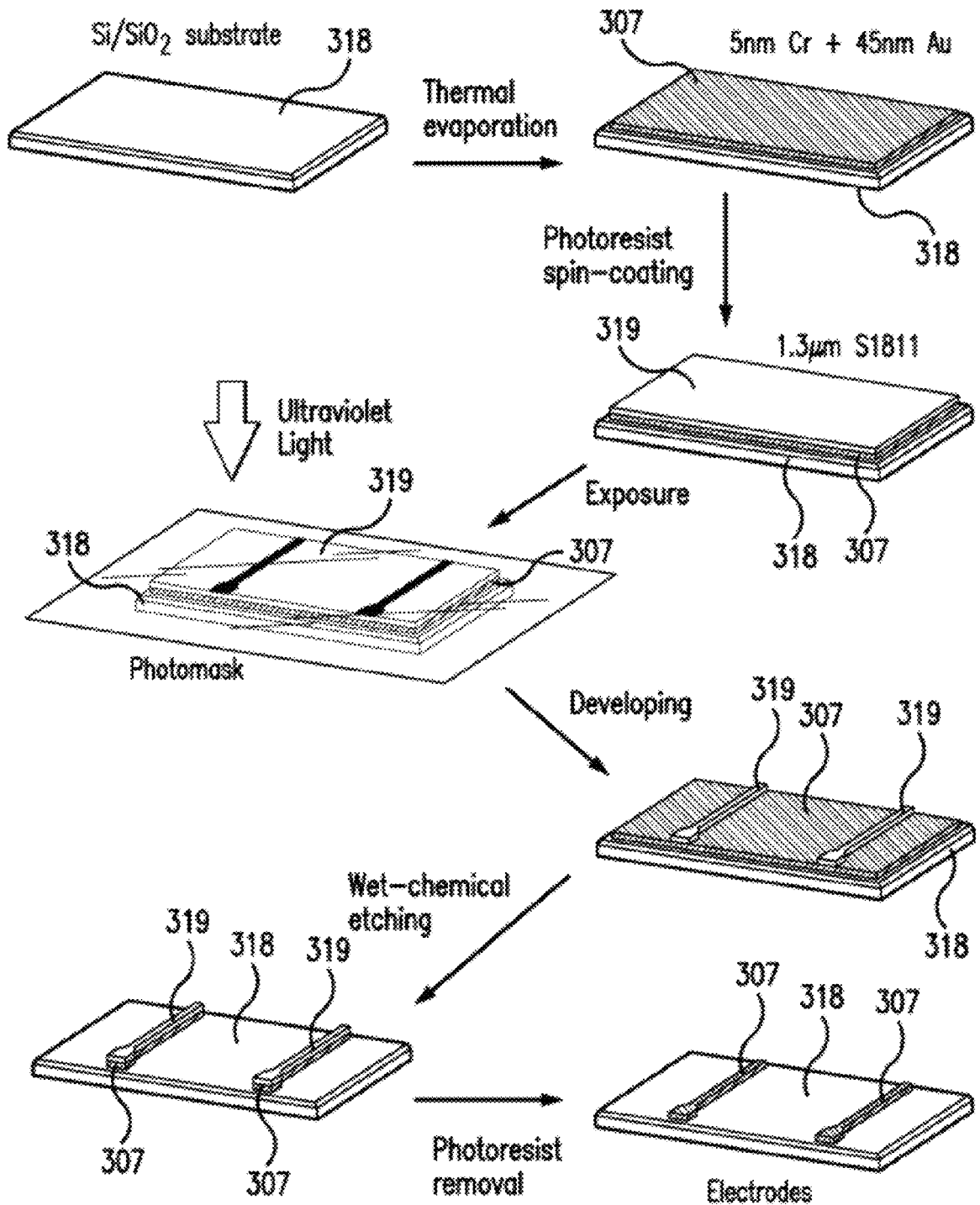

FIG. 6 illustrates an exemplary fabrication method of planar electrodes according to some embodiments of the disclosed subject matter.

Figure 7:
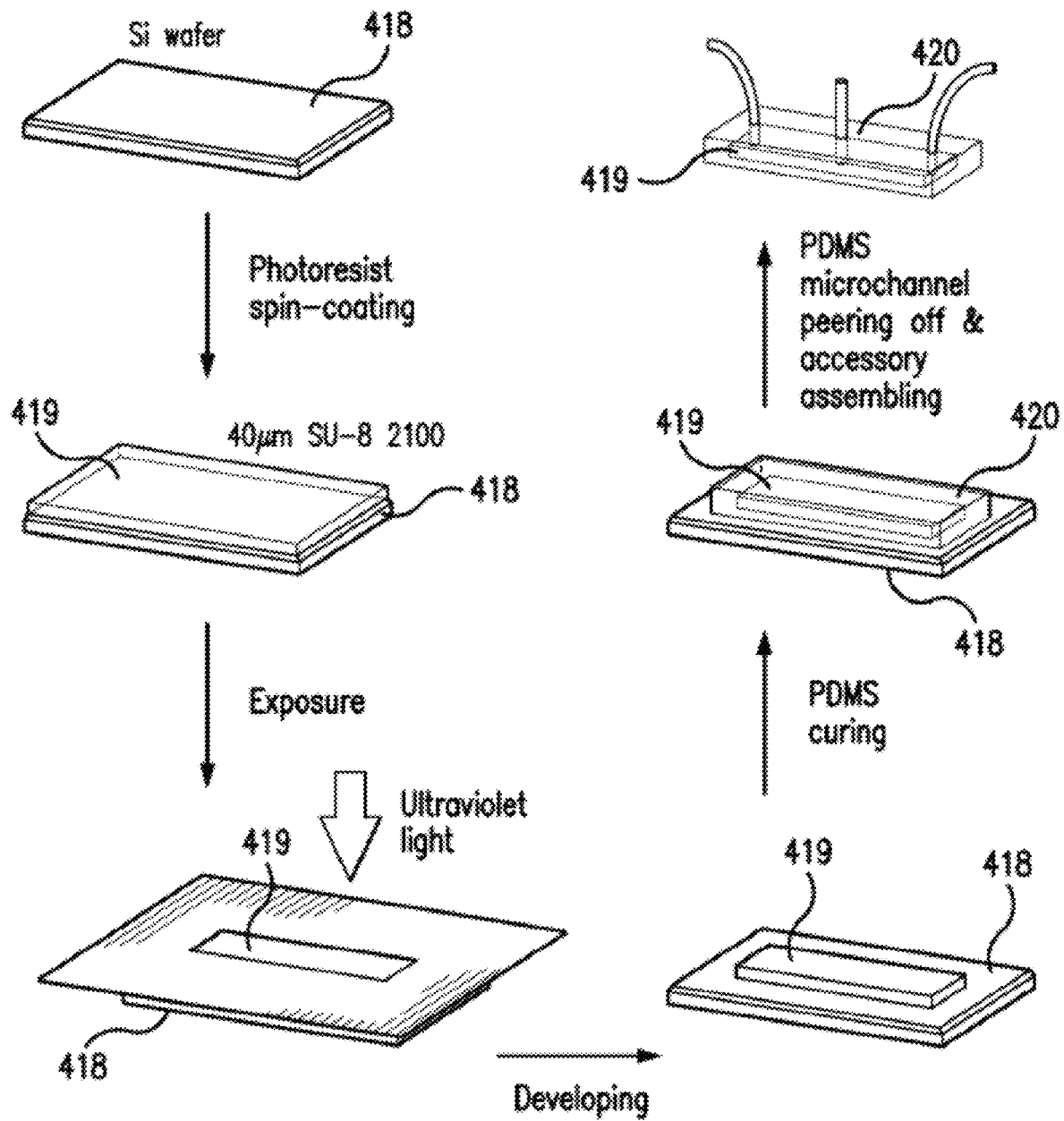

FIG. 7 illustrates an exemplary fabrication method of a PDMS microchannel according to some embodiments of the disclosed subject matter.

FIG. 8 illustrates a schematic of a graphene-based FET nanosensor (502) according to some embodiments of the disclosed subject matter.

FIGS. 9A-D illustrates an exemplary fabrication process of a graphene-based FET nanosensor (502) according to some embodiments of the disclosed subject matter, including (FIG. 9A) Deposition and patterning of 5/45 nm Cr/Au gate electrode (507), (FIG. 9B) deposition of 20 nm HfO2 dielectric layer using ALD (506), (FIG. 9C) fabrication of drain (509) and source (508) electrodes using lift-off, and (FIG. 9D) transfer of graphene (508).

FIGS. 10A-D illustrates micrographs of graphene nanosensors according to some embodiments of the disclosed subject matter: (FIG. 10A) Multiple devices batch-fabricated on the same substrate (left) and close-up view of a single device (right), (FIG. 10B) Detailed view of the source, drain and gate electrodes. Dashed box approximately indicates the region covered by graphene, (FIG. 10 C) Raman spectrum of the graphene, and (FIG. 10D) AFM measurements of the graphene thickness.

Figure 11A:
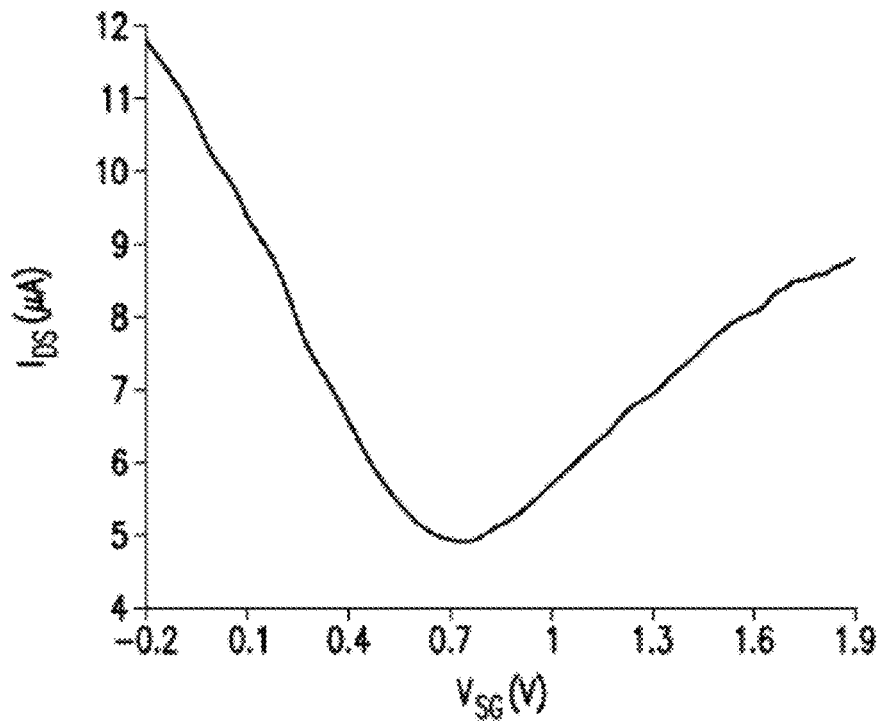
Figure 11B:
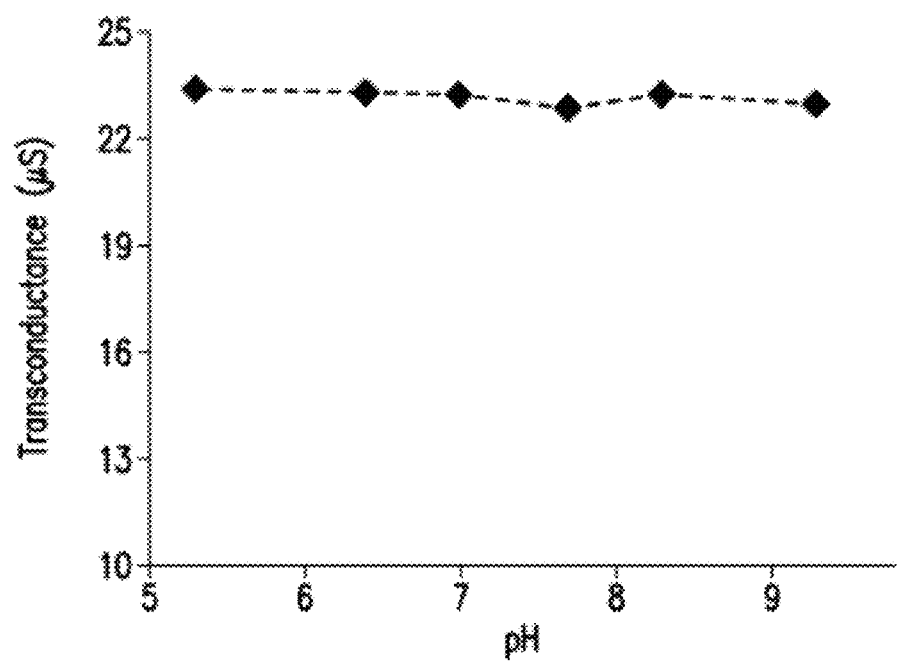

FIGS. 11A-B illustrate a plot showing: (FIG. 11A) Transfer characteristic for graphene in air. The ambipolar curve was observed with $V_{SG,\ DP}$ of 0.7 V, and (FIG. 11B) The transconductance estimated at different pH levels. The value is approximately constant (23 µS).

Figure 12A:
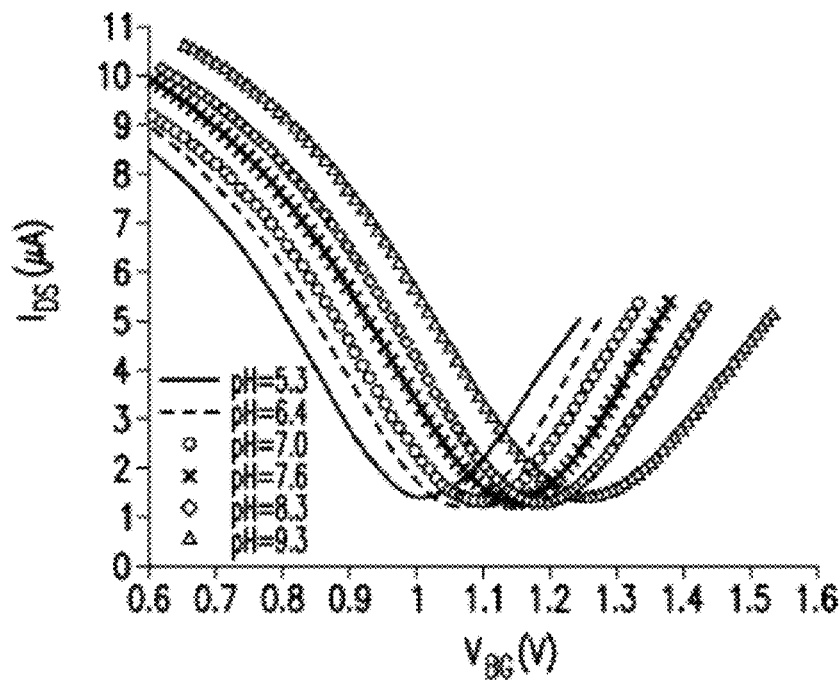
Figure 12B:
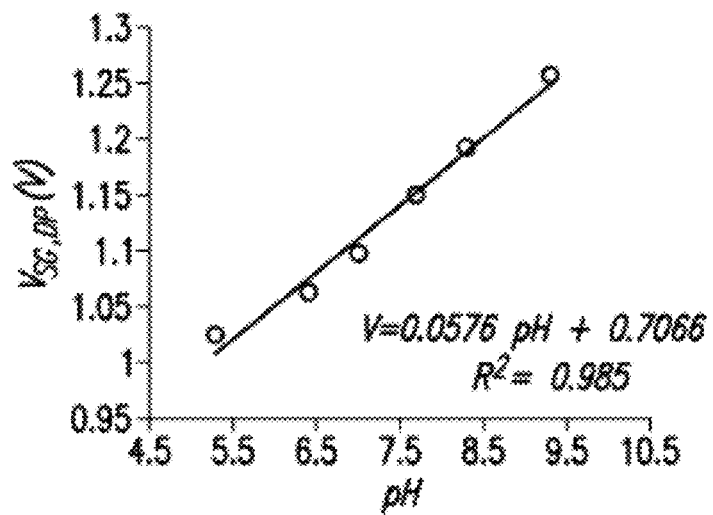

FIGS. 12A-B illustrate a plot showing the dependence of the nanosensor characteristics on pH, including (FIG. 12A) Transfer characteristic curves obtained at varying pH values, where the VSG, DP shifts linearly to higher gate voltages with increasing pH (57.6 mV/pH), and (FIG. 12 B) Dependence of the Dirac point voltage on pH, where the solid line represents a linear fit.

Figure 13A:
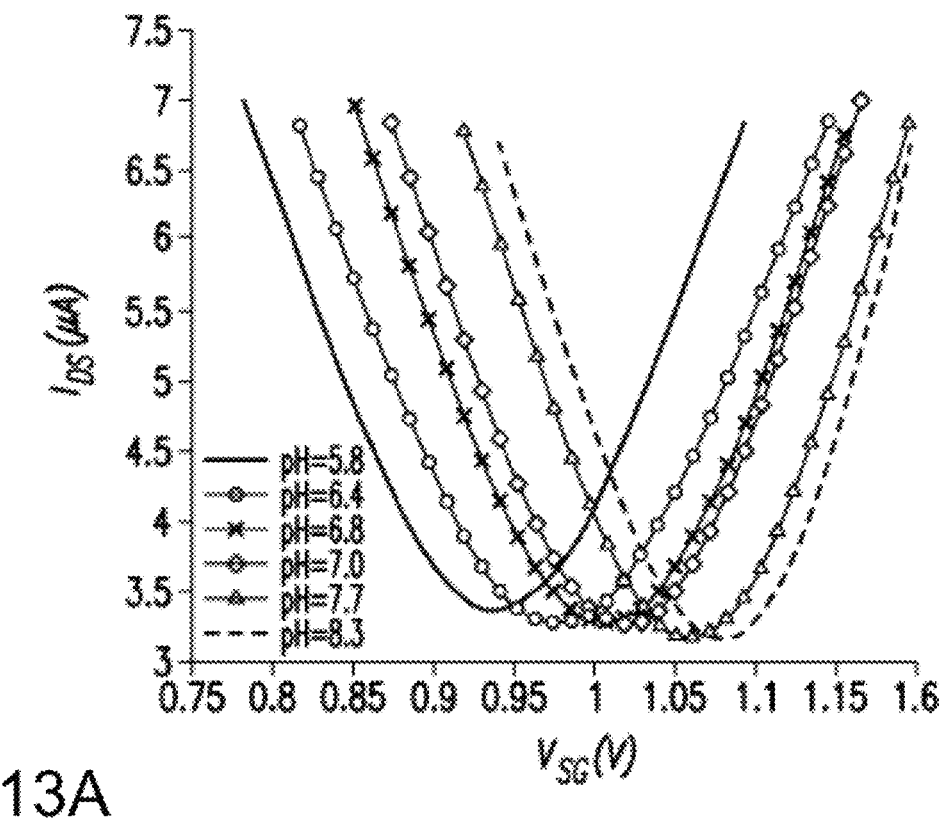
Figure 13B:
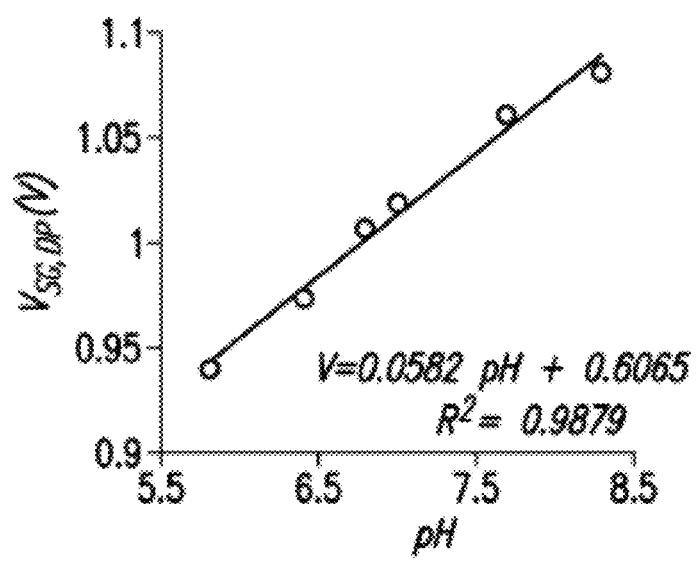

FIGS. 13A-B illustrate a plot showing the results of FIG. 12 on a separate device, including (FIG. 13A) Transfer characteristic curves obtained at varying pH values, and (FIG. 13B) Dependence of the Dirac point voltage on pH, where the $V_{SG,DP}$ shifts linearly to higher gate voltages with increasing pH (58.2 mV/pH), and the solid line represents a linear fit.

Figure 14:
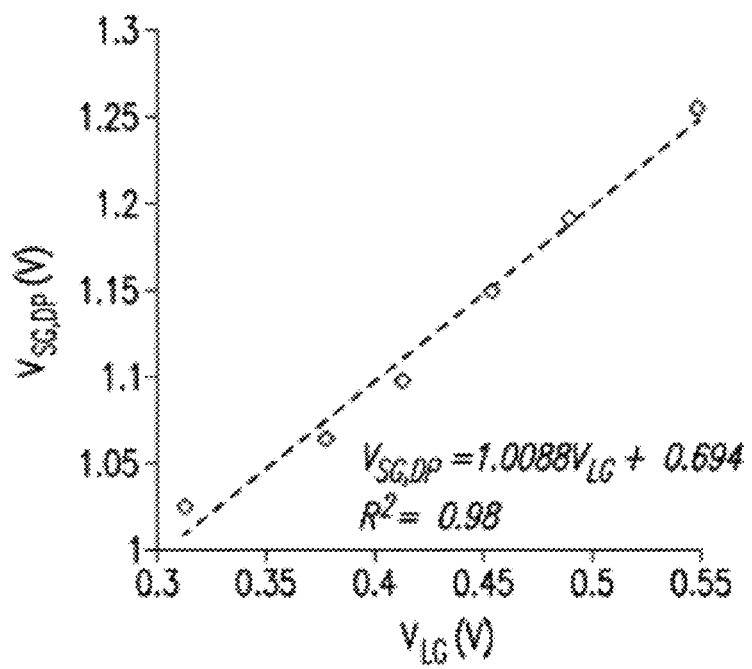

FIG. 14 illustrates a plot showing dependence of $V_{SG,DP}$ on $V_{LG}$ with $E_0$ chosen to be 0. The slope was approximately 1.

Figure 15:
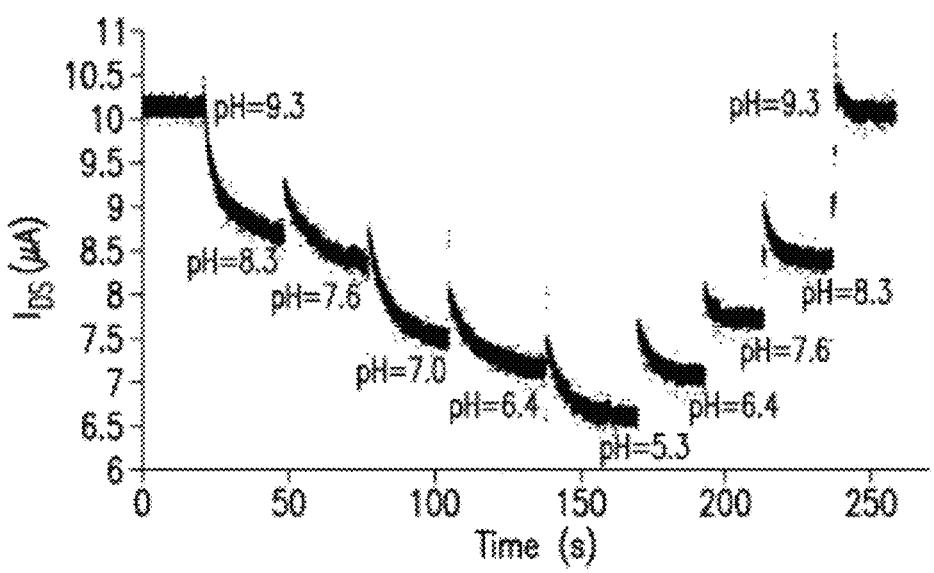

FIG. 15 illustrates a plot showing real time measurements of pH: the source-drain current $I_{DS}$ varied consistently and reversibly with pH at a fixed gate voltage ($V_{BG}$=0.75 V).

FIGS. 16A-C illustrates a plot showing a polymer according to some embodiments of the disclosed subject matter, including (FIG. 16A) Chemical structure of pyrene-PAAPBA, (FIG. 16B) Fluorescence intensity of polymer solution at maximum emission wavelength vs. time of incubation with pyrene substrate, indicating full attachment of pyrene-PAAPBA to graphene in 2 h, and (FIG. 16 C) Fluorescence spectrum of pyrene-PAAPBA attached to graphene.

Figure 17:
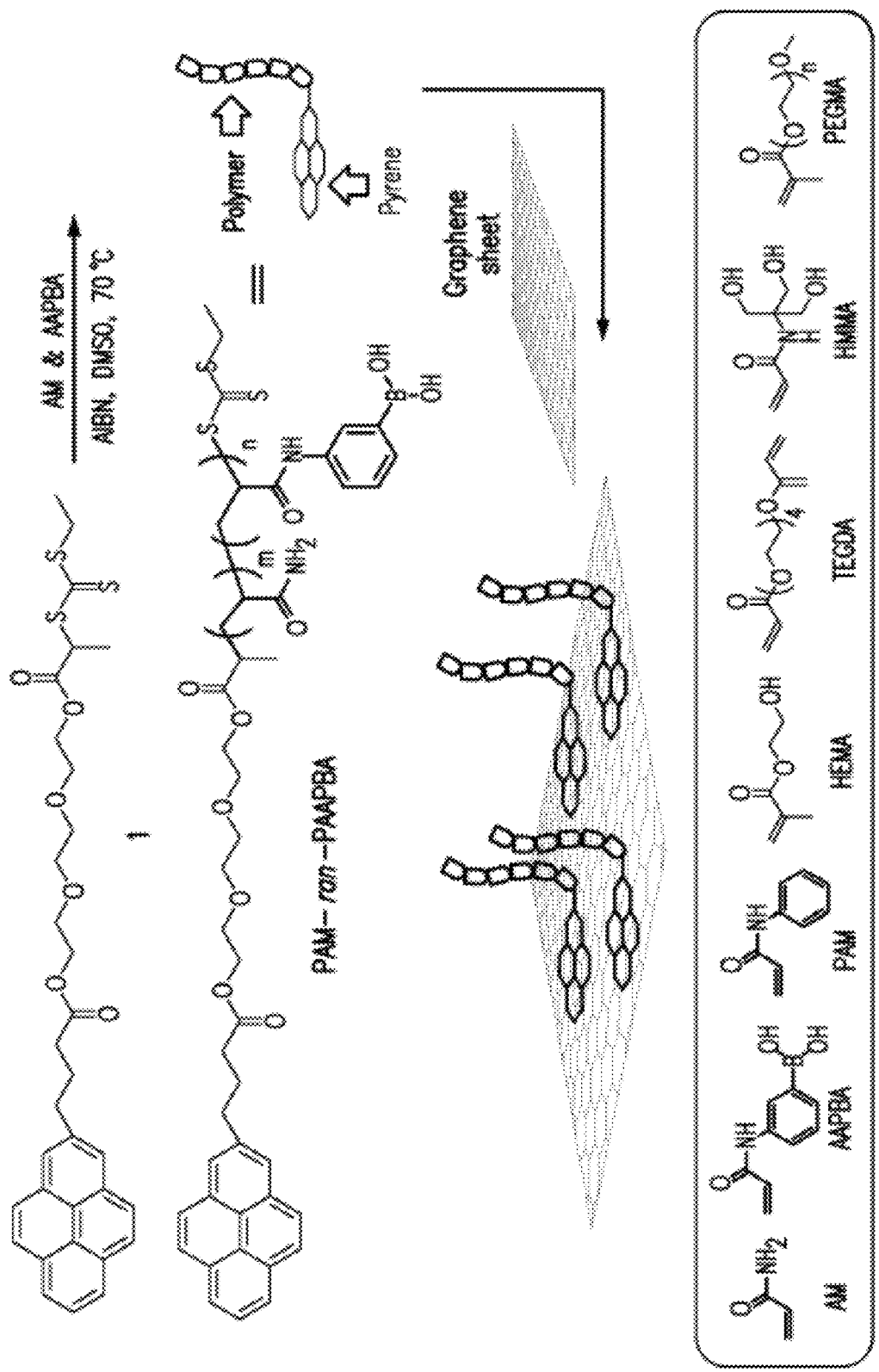

FIG. 17 illustrates a diagram showing the synthesis of pyrene-terminated sensing polymers for graphene attachment (top) and structures of monomers (bottom) according to some embodiments of the disclosed subject matter.

FIG. 18 illustrates a schematic of the affinity glucose sensor (602) configured as a solution top-gated graphene field effect transistor according to some embodiments of the disclosed subject matter.

FIGS. 19A-C illustrates an exemplary fabrication method of a nanosensor according to some embodiments of the disclosed subject matter, including (FIG. 19A) Patterning of drain (609) and source (608) electrodes, (FIG. 19B) Transfer of graphene (605) on to an oxide-coated silicon substrate, and (FIG. 19C) Bonding of the PDMS microchannel to the sensor chip.

FIGS. 20A-B illustrates a nanosensor according to some embodiments of the disclosed subject matter, including (FIG. 20A) Optical micrograph of the graphene covering the source and drain electrodes, (FIG. 20B) Measurement setup.

FIG. 21 illustrates a Raman spectrum of the graphene according to some embodiments of the disclosed subject matter, where the G and 2D bands are indicative of the graphene including a single layer of carbon atoms.

FIGS. 22A-B illustrates AFM images of graphene (FIG. 22A) before and (FIG. 22B) after functionalization with the PAPBA polymer.

FIG. 23 illustrates transfer characteristics measured before (dashed blue line) and after (red line) functionalization of graphene with the PAPBA polymer, where the left shift of the Dirac point indicates that the graphene was n-doped due to the attachment of the polymer molecules.

Figure 24:
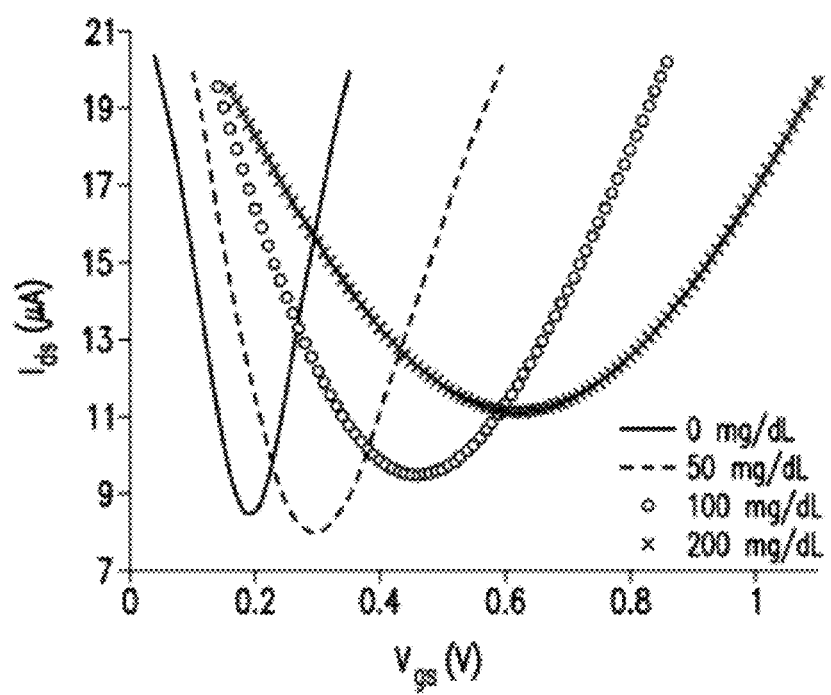

FIG. 24 illustrates transfer characteristics in different glucose solutions at varying glucose concentrations, where in response to increases in the glucose concentration, the Dirac point position Vgs, Dirac shifted to higher gate voltages and the transconductance decreased from 100 to 20 µS.

Figure 25:
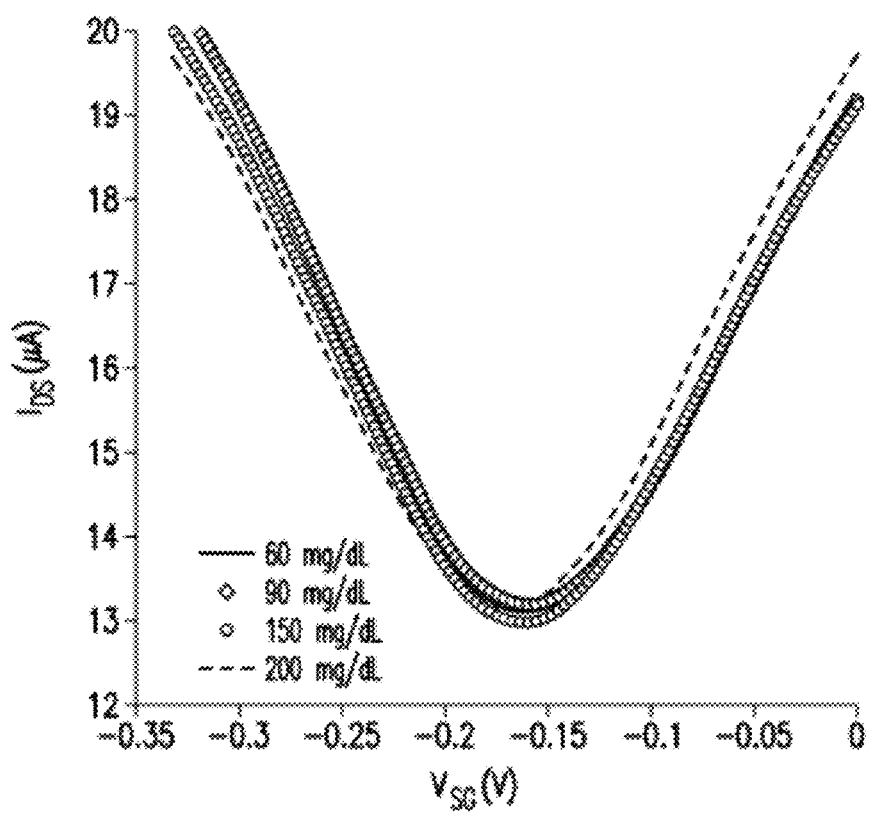

FIG. 25 illustrates control tests using pristine graphene without functionalization of the polymer, where the change in the Dirac point position and transconductance is insignificant compared to FIG. 22, implying that the changes in carrier mobility and density in that figure was caused by the glucose-polymer binding.

Figure 26A:
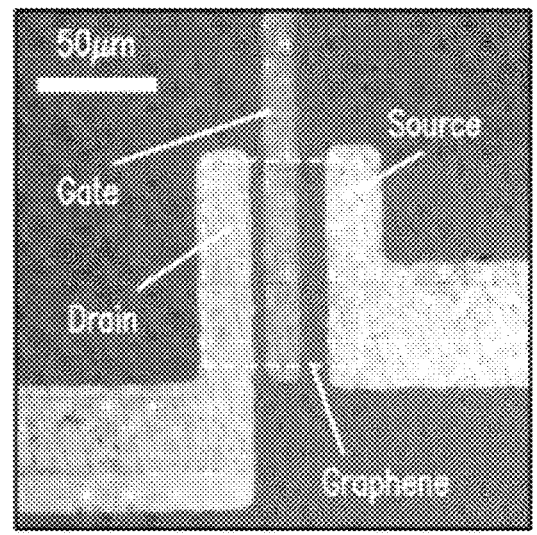
Figure 26B:
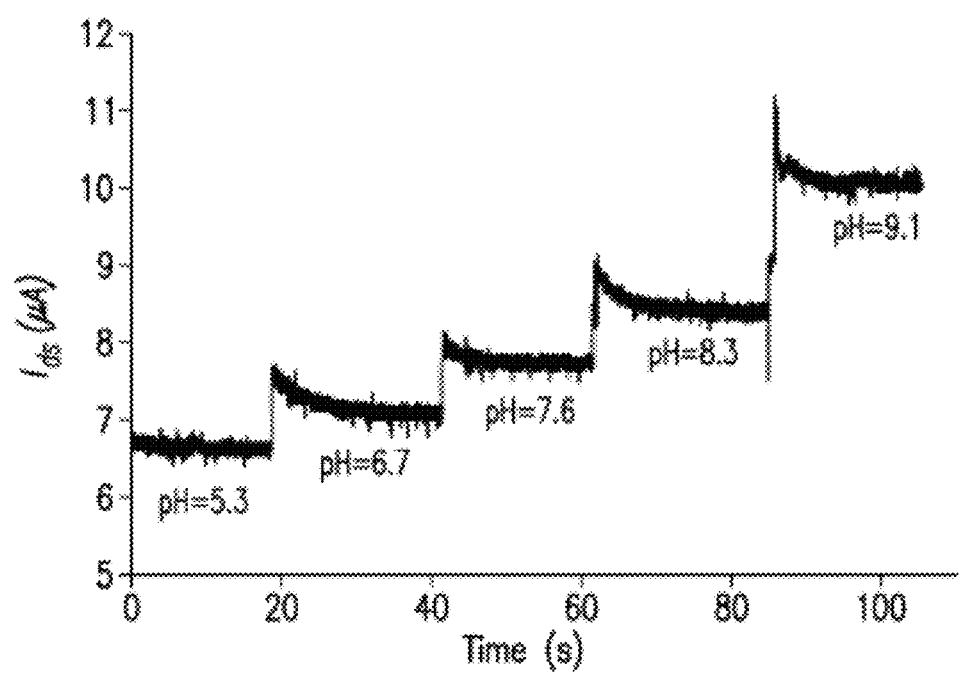

FIGS. 26A-B illustrates a nanosensor according to some embodiments of the disclosed subject matter, including (FIG. 26A) micrograph, and (FIG. 26B) pH-induced changes in the source-drain current Ids (at a fixed gate voltage of 0.75 V) of a solid-gated graphene FET sensor.

Figure 27:
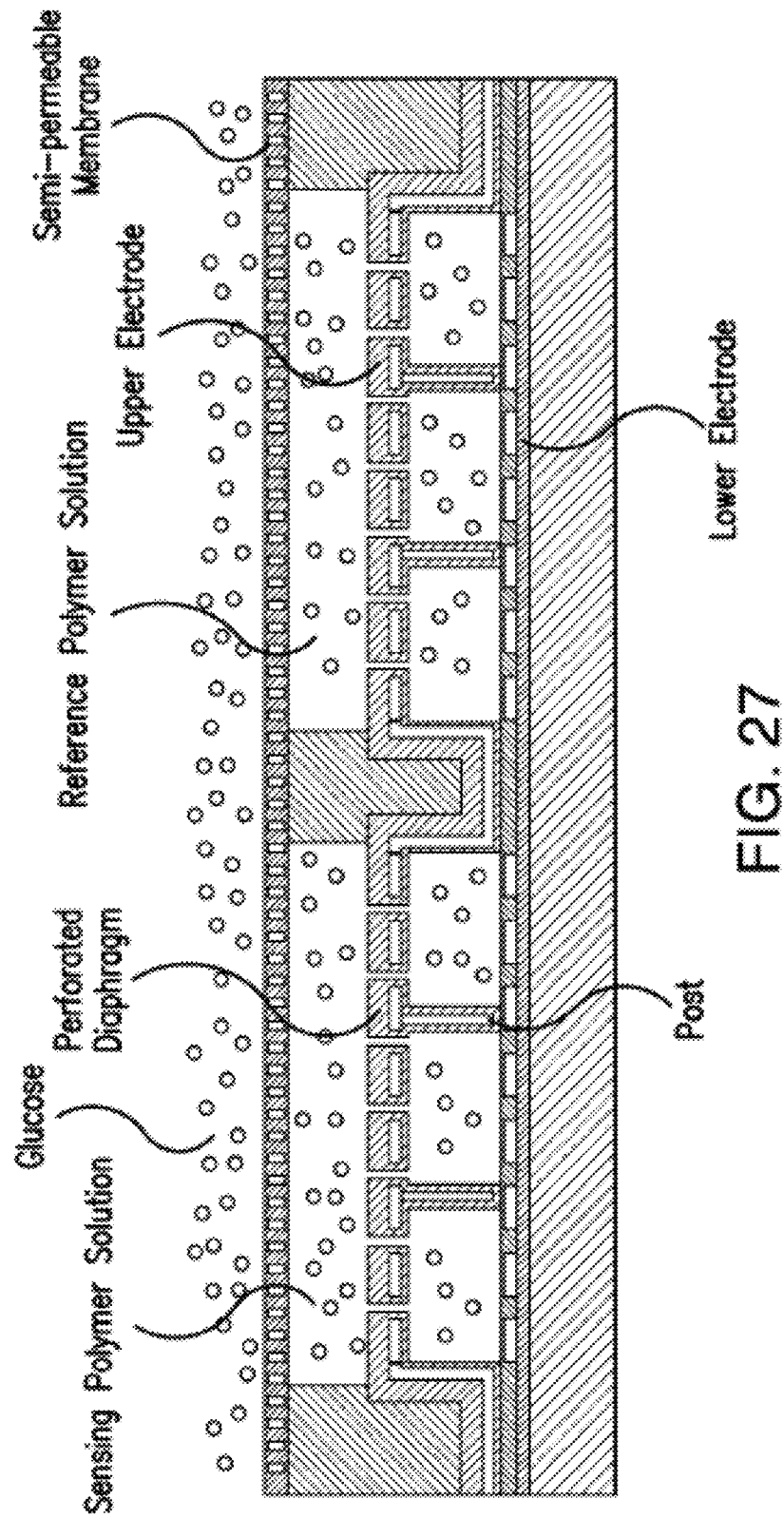

FIG. 27 illustrates a nanosensor design as used in Example 1.

FIGS. 28A-D illustrates a schematic of the nanosensor configured as a solution-gated graphene field effect transistor, including (FIG. 28A) An Ag/AgCl electrode inserted into the solution served as the gate electrode, while the electrical double layer at the solution-graphene interface served as the gate capacitor, (FIG. 28B) Micrograph of a fabricated device. The graphene conducting channel connected the source and drain electrodes, (FIG. 28C) Coupling of boronic acid and graphene via π-π stacking interactions between the pyrene group and graphene, and (FIG. 28D) Formation of a glucose-boronate ester at a physiological pH of 7.4.

Figure 29A:
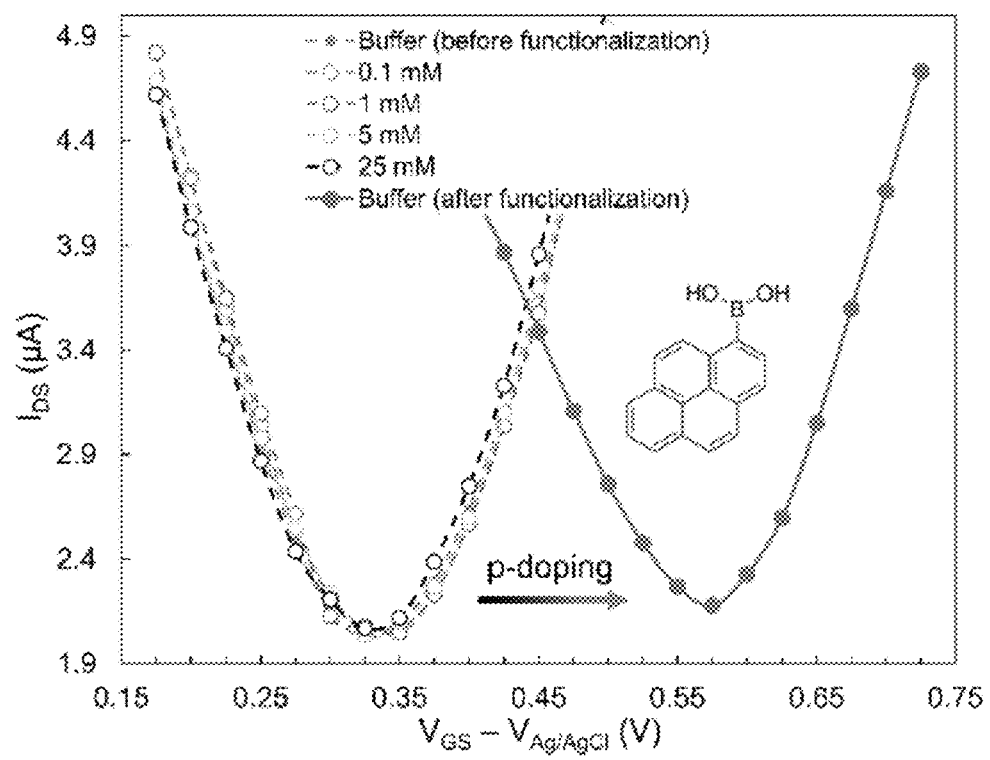
Figure 29B:
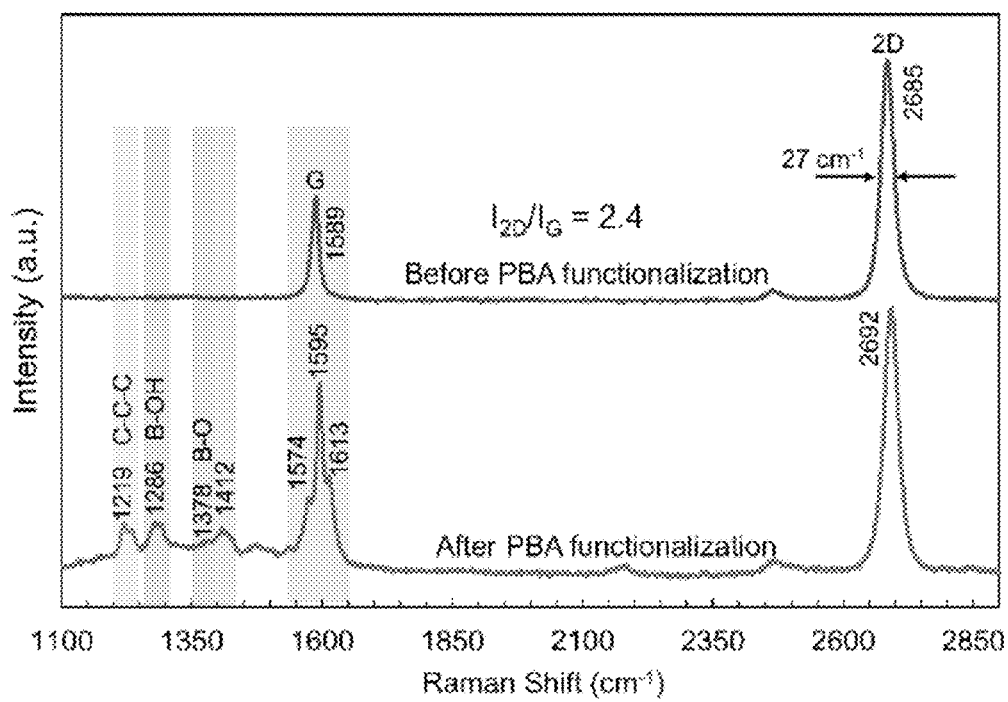

FIGS. 29A-B illustrates transfer characteristics of the pristine graphene and the PBA-functionalized graphene (FIG. 29A). FIG. 29B illustrates Raman spectra of the graphene before and after exposure to PBA solution. Signature peaks of the boronic acid and the graphene-pyrene interaction were observed after immersing in PBA solution.

Figure 30:
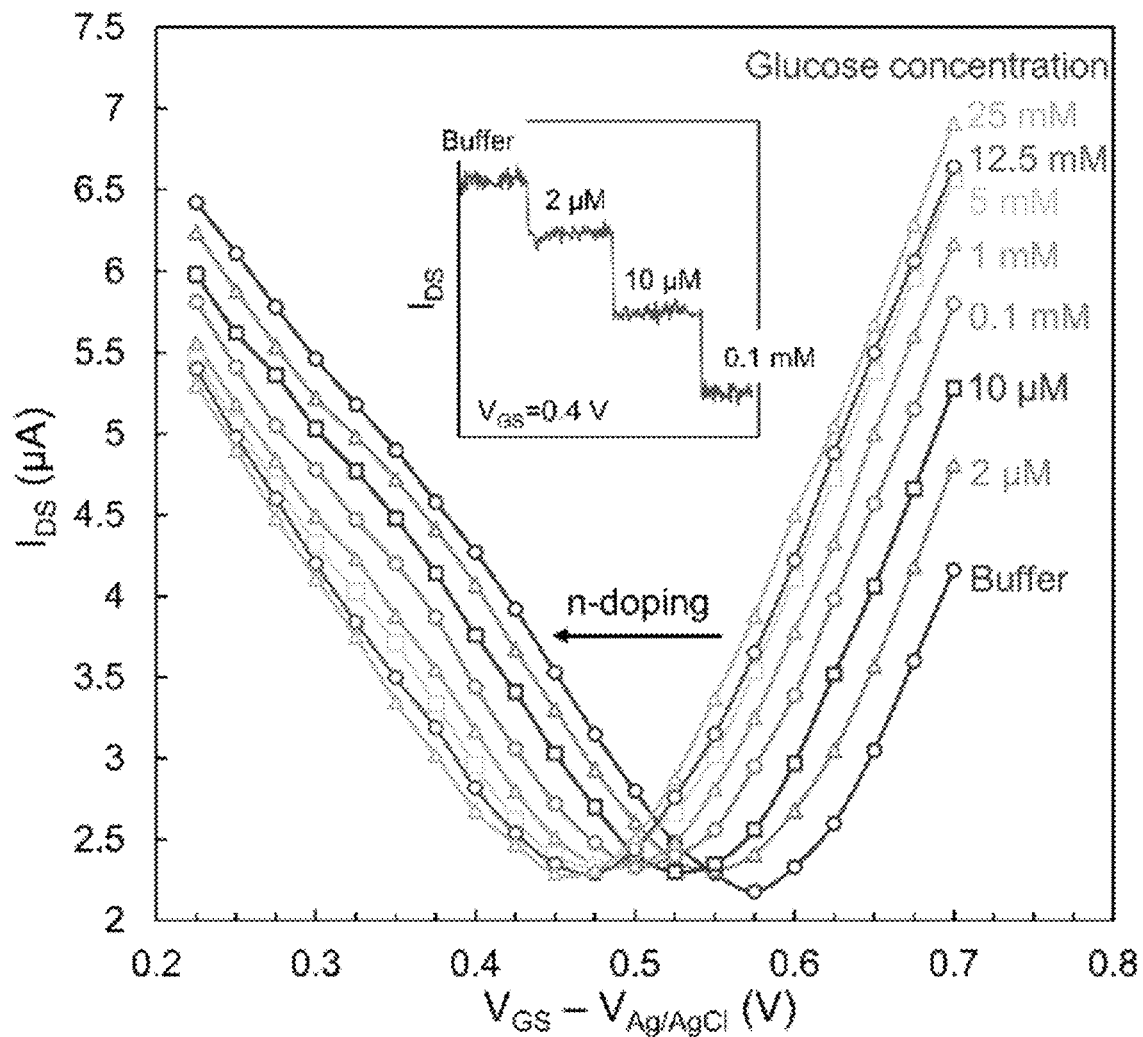

FIG. 30 illustrates a plot depicting transfer characteristics measured when the device was exposed to glucose solutions (concentration ranging from 2 μM to 25 mM).

Figure 31:
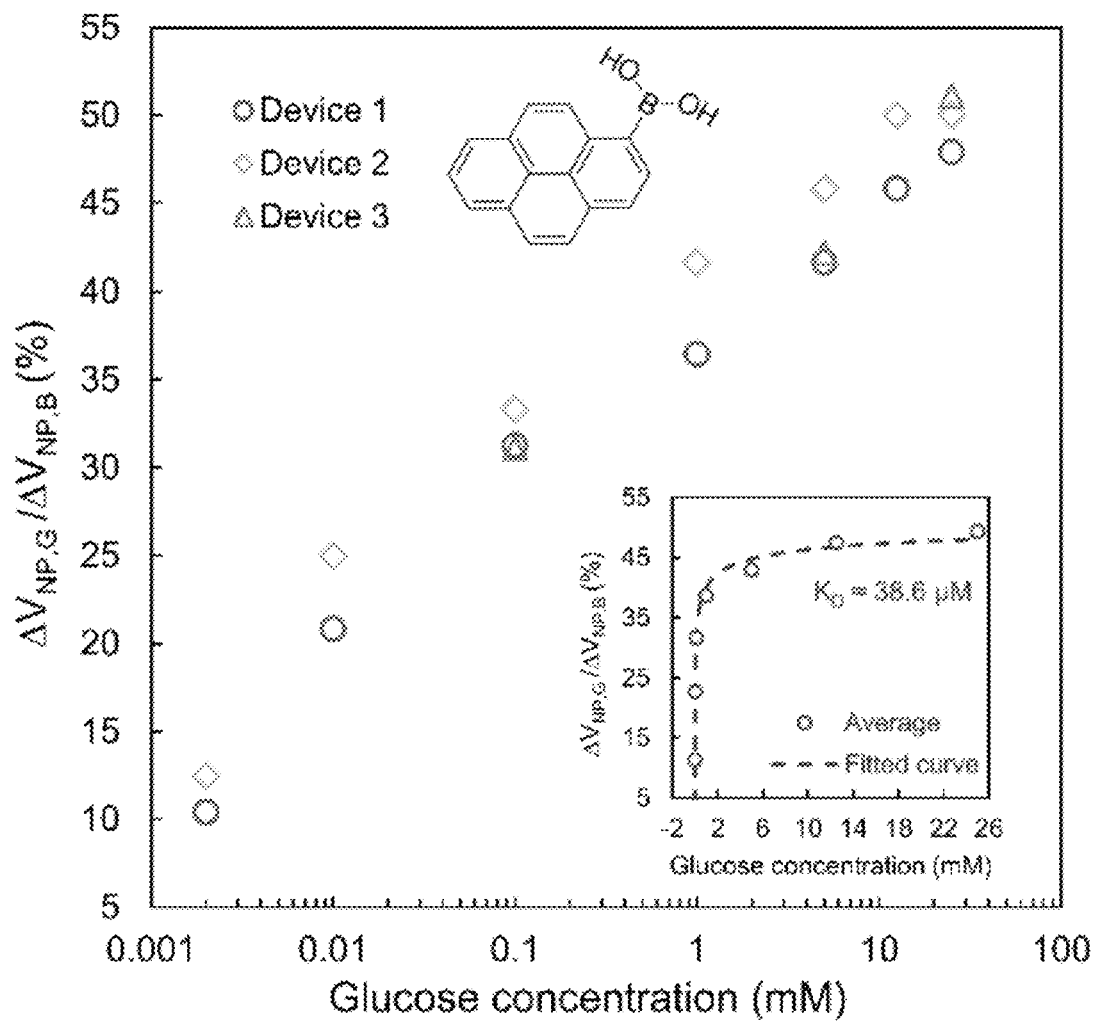

FIG. 31 illustrates a plot depicting the neutral point voltage shift ratio ΔVNP,G/ΔVNP,B as a function of glucose concentration.

Figure 32A:
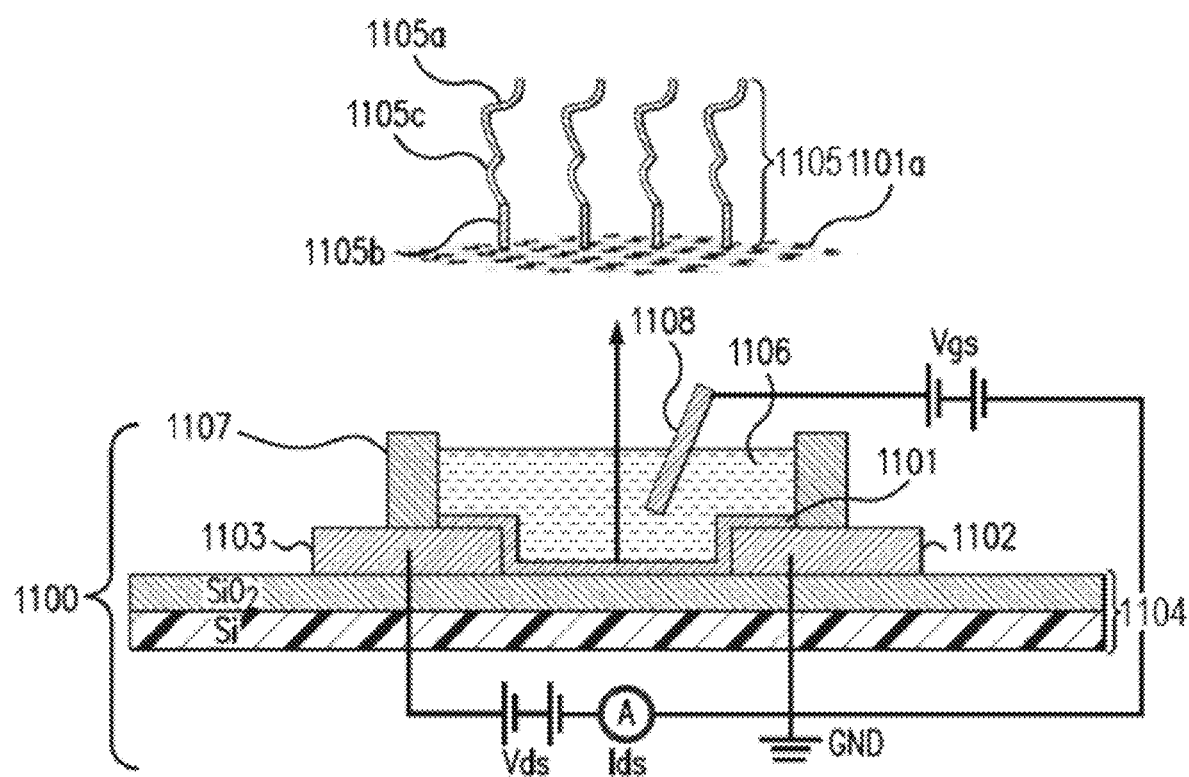

FIGS. 32A-Bii illustrate a schematic of an aptameric graphene nanosensor (100) for analyte detection according to some embodiments of the disclosed subject matter, including (FIG. 32A) principles of aptameric graphene nanosensing according to some embodiments of the disclosed subject matter, (FIG. 32Bi) PEG and aptamer-functionalized graphene; (FIG. 32Bii) Sample incubation; and (FIG. 32Biii) target analyte (e.g., IgE) capture and purification on the graphene surface by the aptamer.

FIG. 33 illustrates an image of a fabricated aptameric graphene nanosensor.

FIG. 34 illustrates a fabrication process of an aptameric graphene nanosensor according to some embodiments of the disclosed subject matter.

FIG. 35 illustrates functionalization of the graphene surface according to some embodiments of the disclosed subject matter.

Figure 36A:
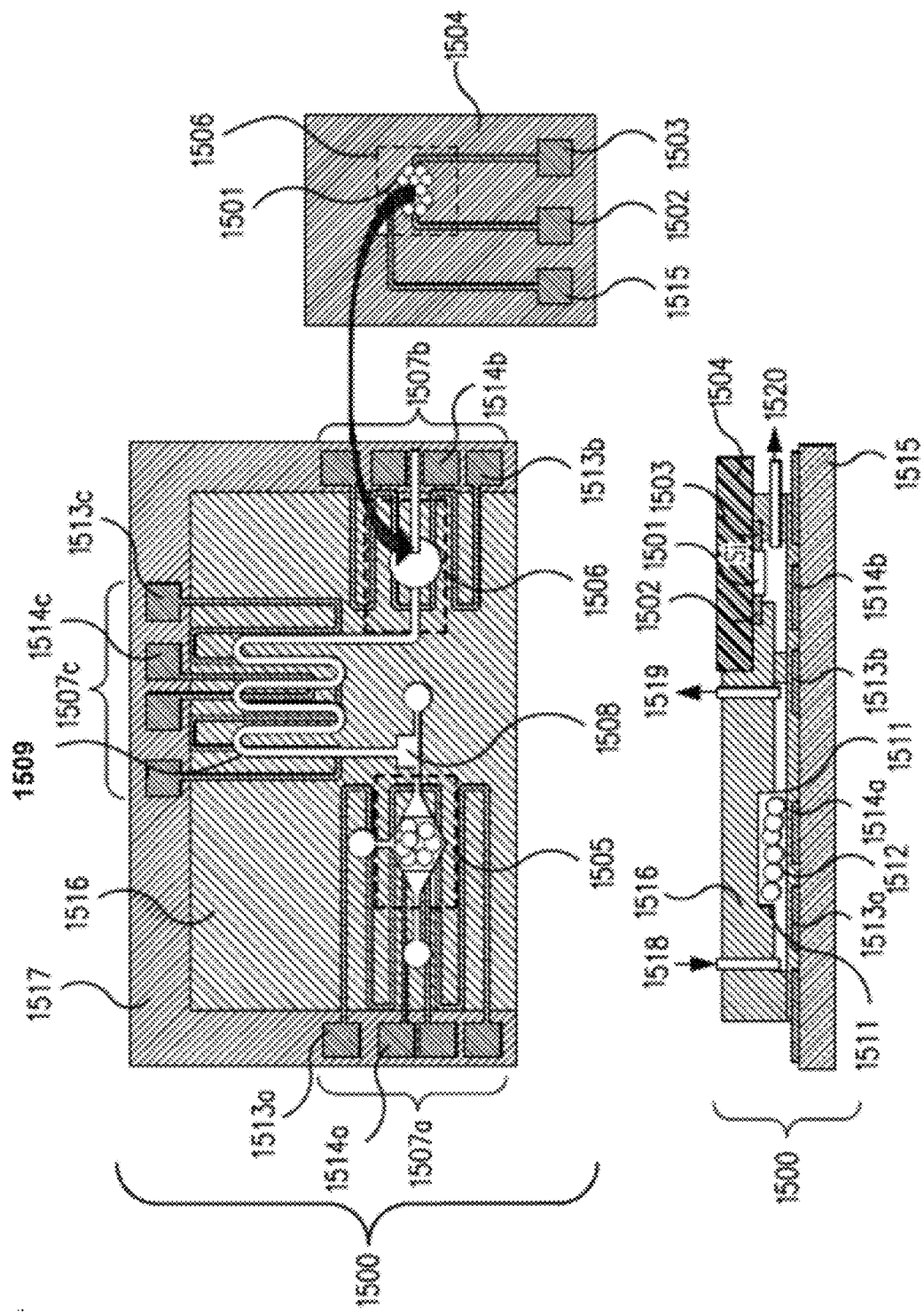
Figure 36B:
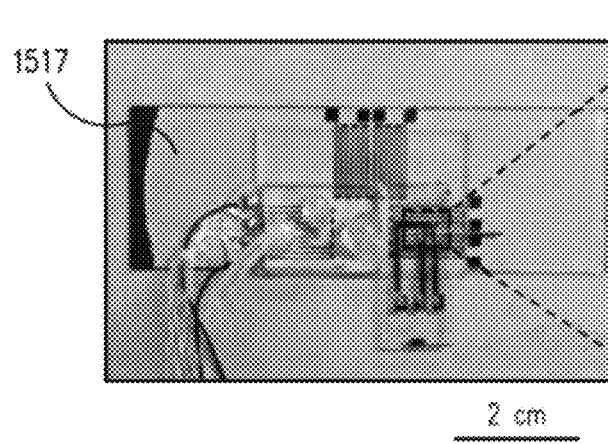
Figure 36C:
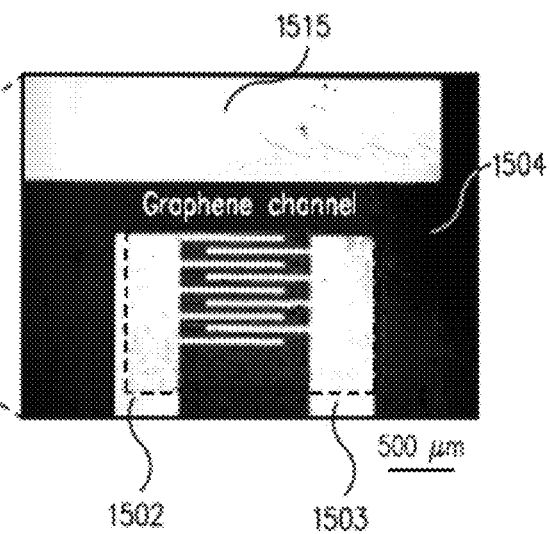

FIGS. 36A-36C illustrate a schematic of a microfluidic graphene nanosensor that integrates aptamer-based selective analyte enrichment and detection (3600 in FIG. 36A) according to some embodiments of the disclosed subject matter and images of a fabricated the graphene nanosensor (FIG. 36B).

FIG. 37 illustrates fabrication method of a microfluidic graphene nanosensor according to some embodiments of the disclosed subject matter.

FIGS. 38A-E illustrates a principle of aptameric graphene nanosensing that integrates aptamer-based selective analyte enrichment according to some embodiments of the disclosed subject matter, including (FIG. 38A) The sample target (e.g., AVP) enriched on microbead surfaces by aptamer binding; (FIG. 38B) buffer washing; (Figured 38C) the temperature raised to 55° C., which disrupted aptamer-sample target (e.g., AVP) complexes and released sample target (e.g., AVP) into a free aptamer solution; (Figured 38D) The mixture of the free aptamer and released sample target (e.g., AVP) was incubated with graphene functionalized with standard target (e.g., AVP), and (FIG. 38E) inducing the binding of the free aptamer to the standard target (e.g., AVP) on graphene via competitive binding, thus changing the graphene conductance.

Figure 39:
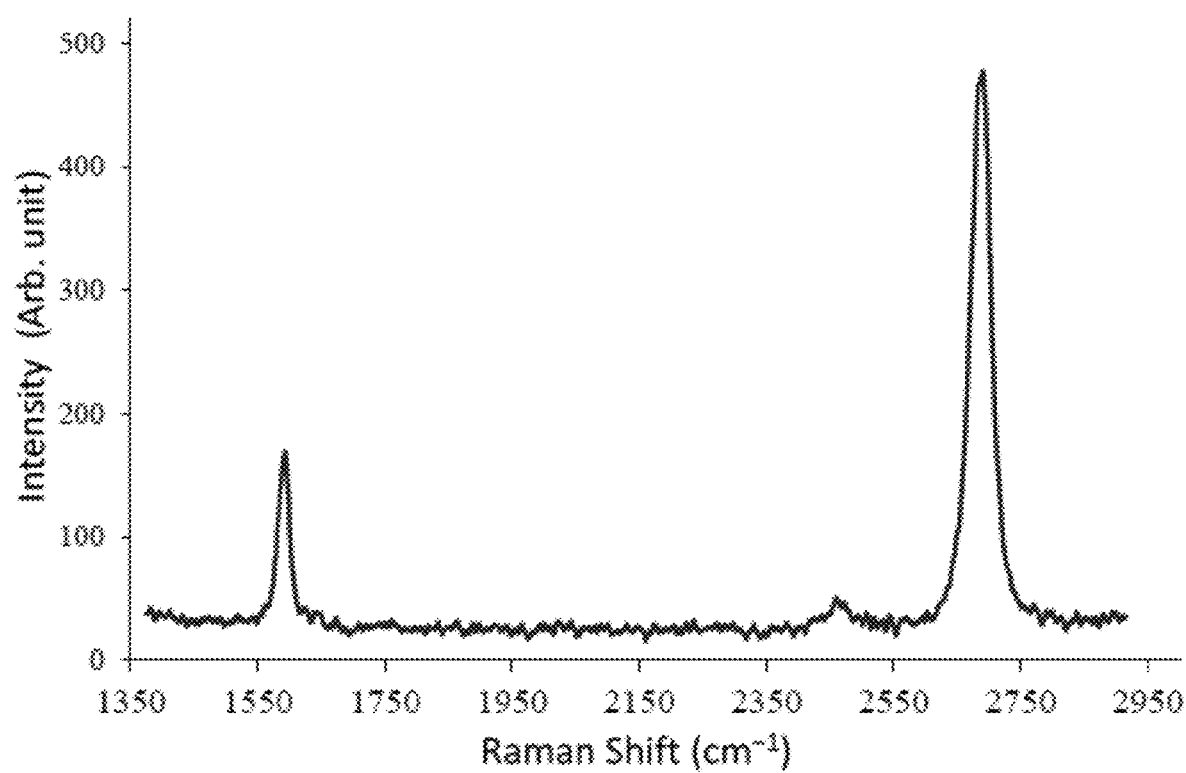

FIG. 39 illustrates a plot showing the Raman spectrum of the graphene used in the aptameric graphene nanosensor.

Figure 40:
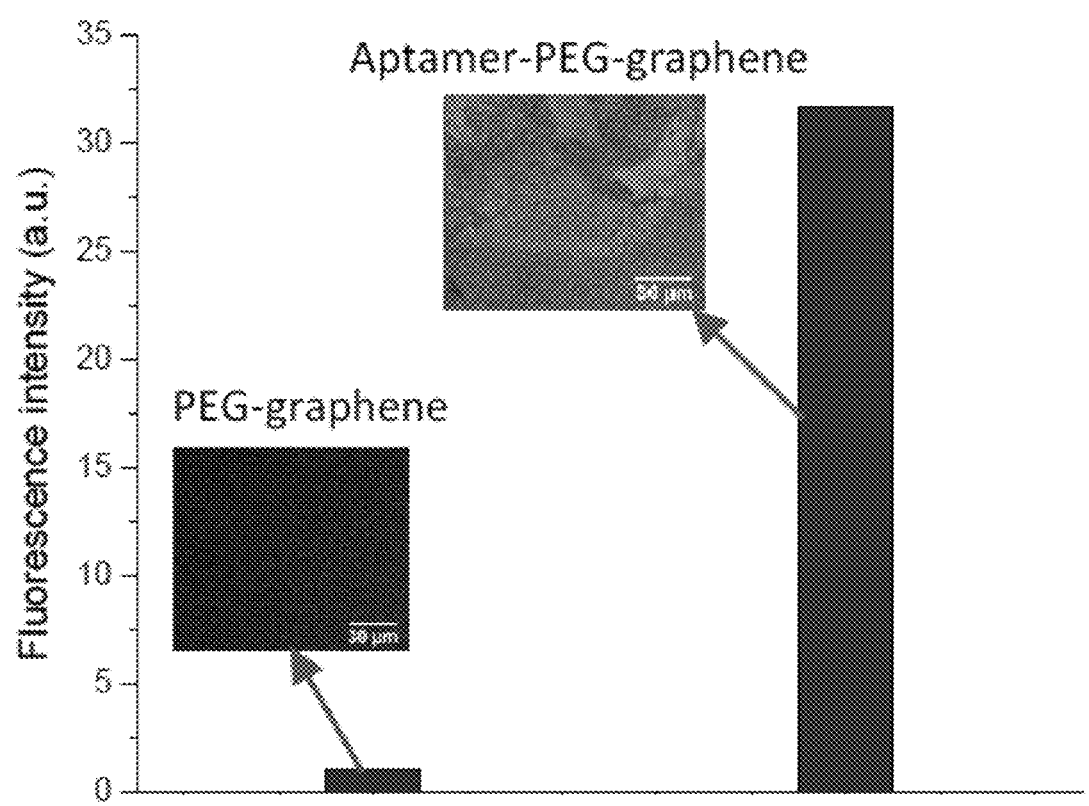

FIG. 40 illustrates a plot showing the fluorescence of single-strand of DNA complementary to an IgE-specific aptamer introduced to graphene with different surface modifications.

Figure 41A:
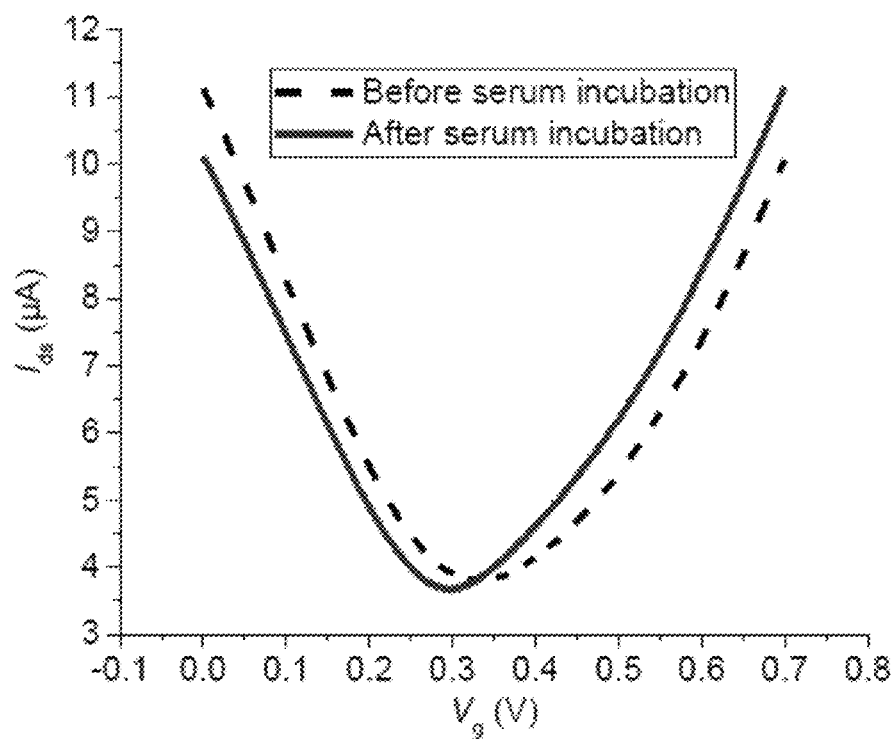
Figure 41B:
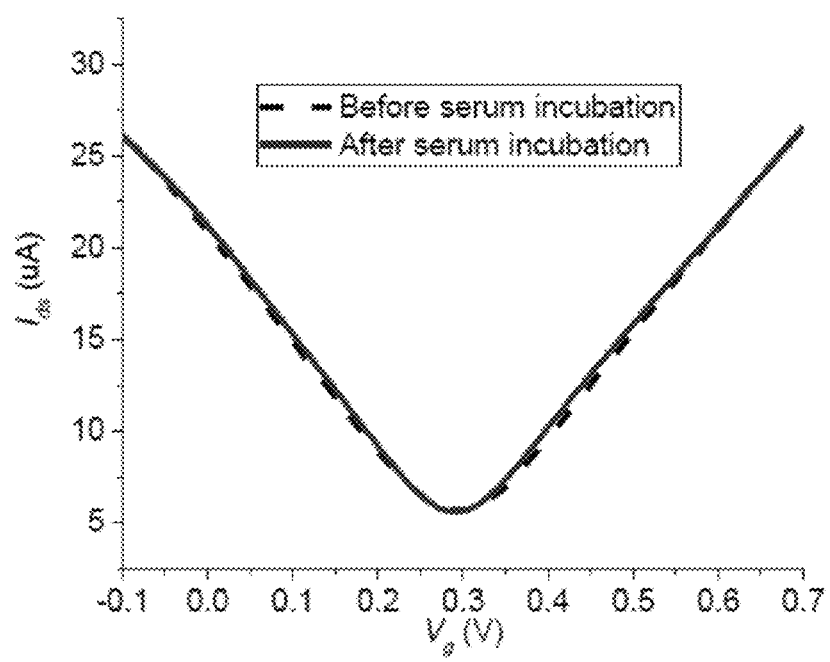

FIGS. 41A-B illustrates a plot showing the transfer characteristics measured before (dashed line) and after (solid line) serum incubation on different surfaces: (FIG. 41A) Serum on bare graphene surface and (FIG. 41B) Serum on PEG-grafted graphene surface.

Figure 42:
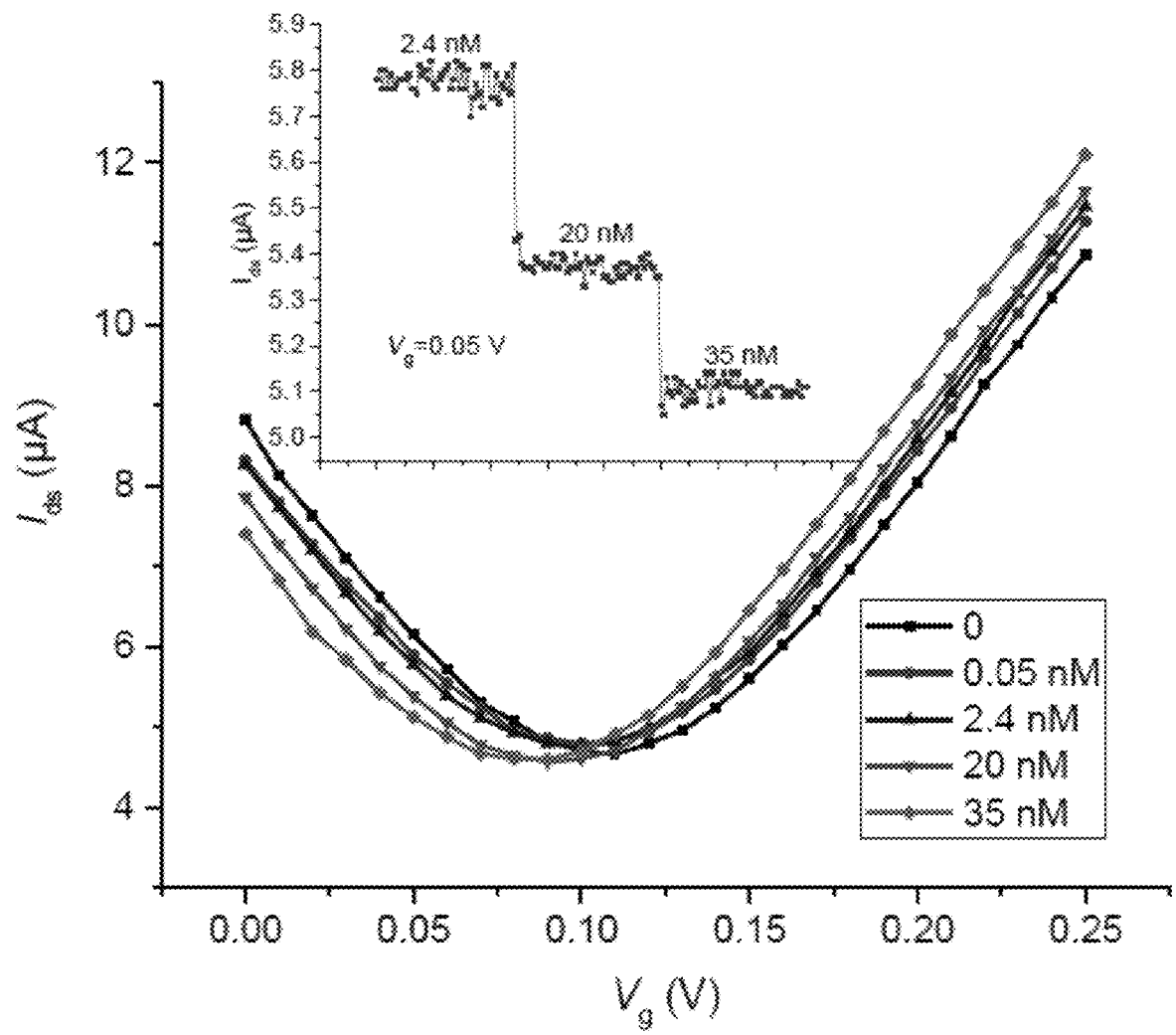

FIG. 42 illustrates a plot showing the transfer characteristics in different serum samples with various IgE concentration, and the reduction in drain-source current with respect to increased IgE concentration at Vg=0.05 V.

Figure 43:
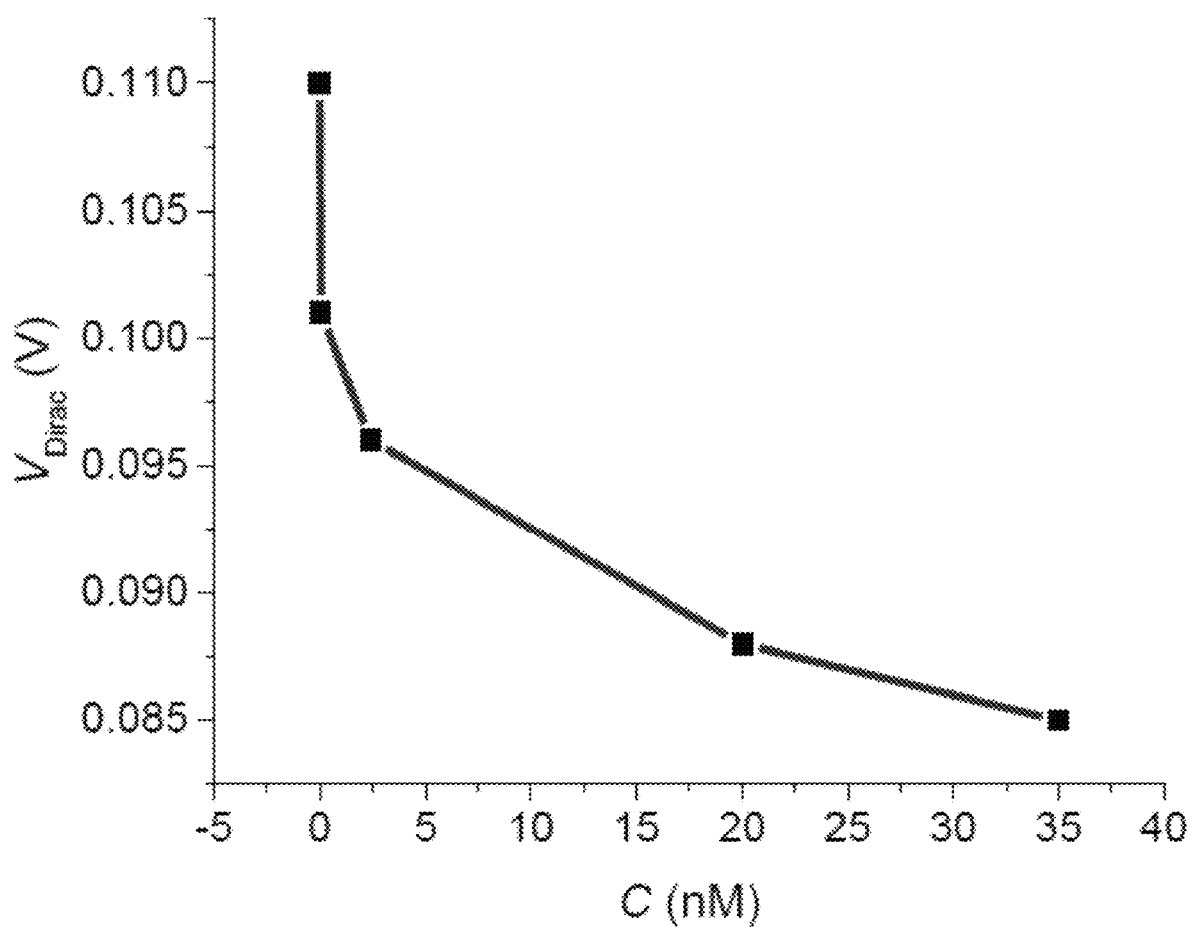

FIG. 43 illustrates a plot showing the dependence of the Dirac point voltage on IgE concentration.

Figure 44:
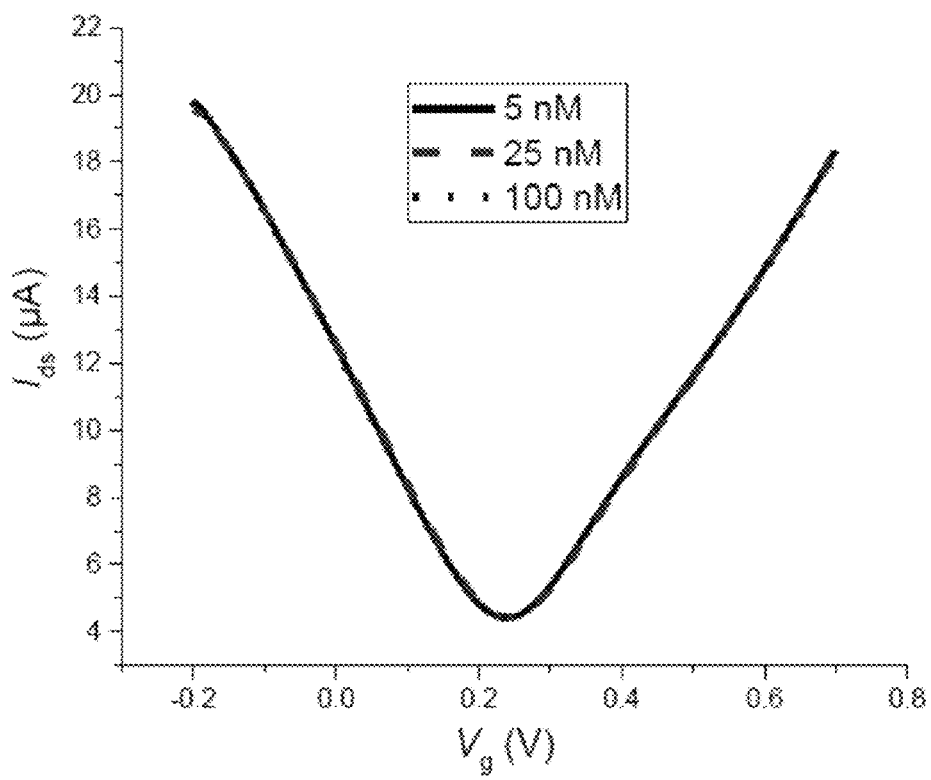

FIG. 44 illustrates a plot showing the control testing on the PEG-aptamer functionalized graphene.

Figure 45A:
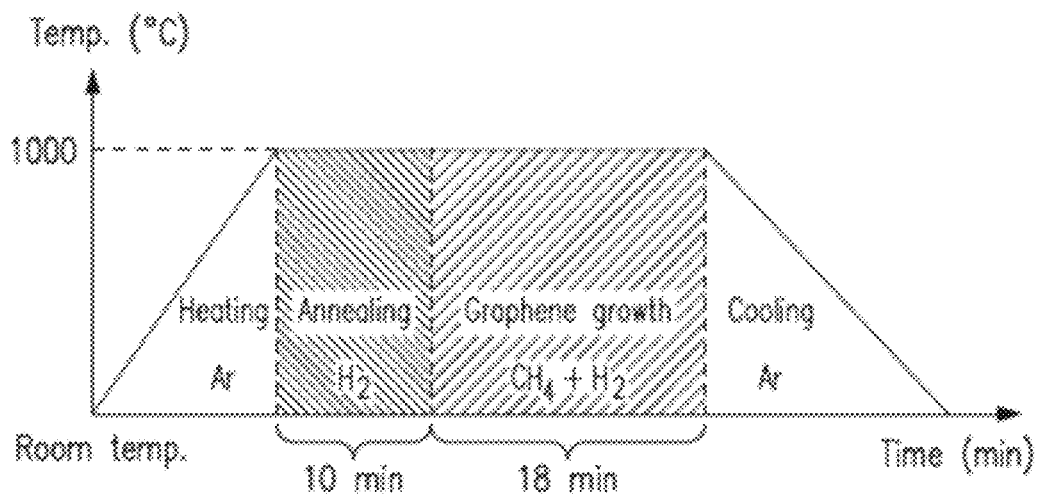
Figure 45B:
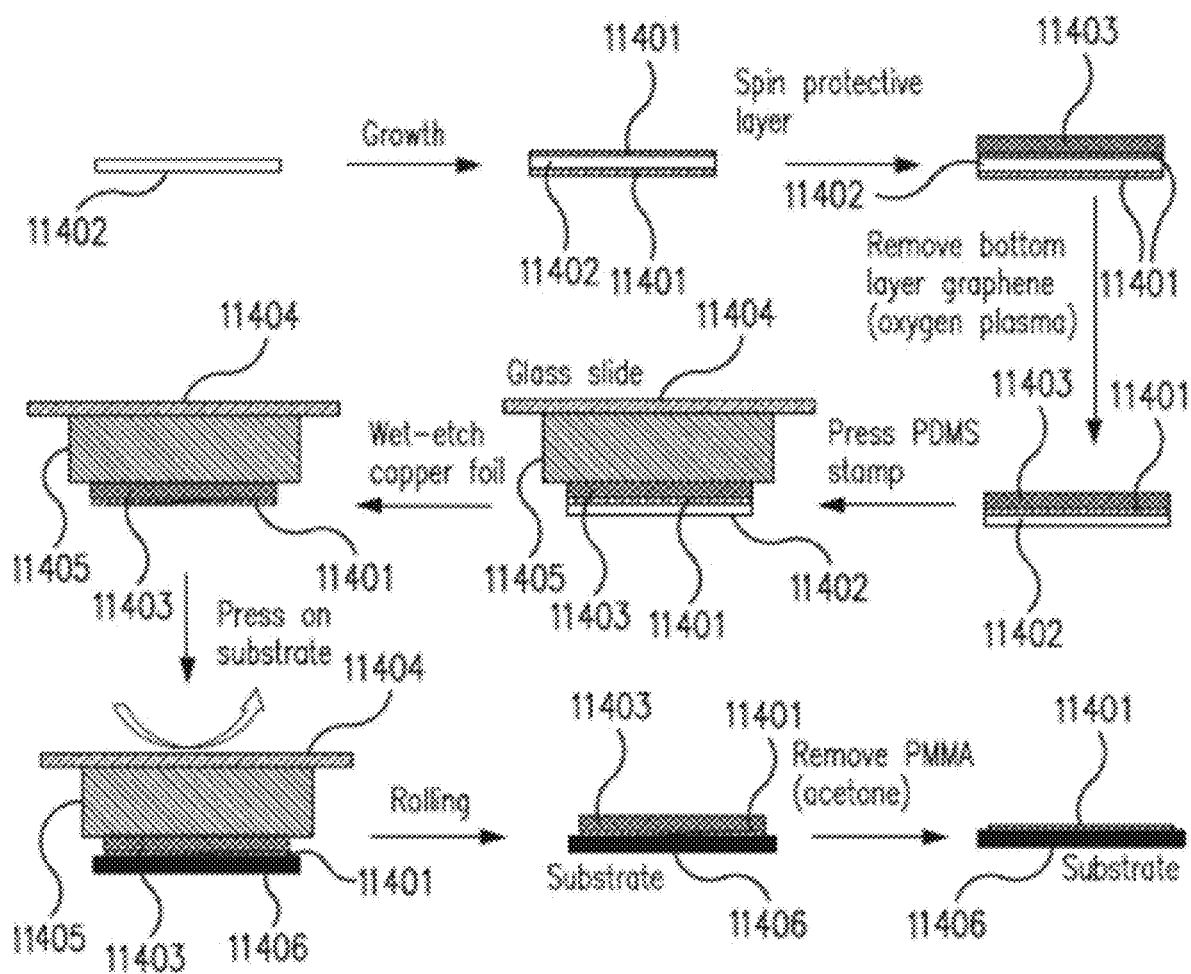

FIGS. 45A-B illustrates a method for CVD graphene synthesis and transfer procedure according to some embodiments of the disclosed subject matter: (FIG. 45A) CVD graphene synthesis in quartz tubing furnace and (FIG. 45B) CVD graphene transfer onto the substrate.

Figure 46A:
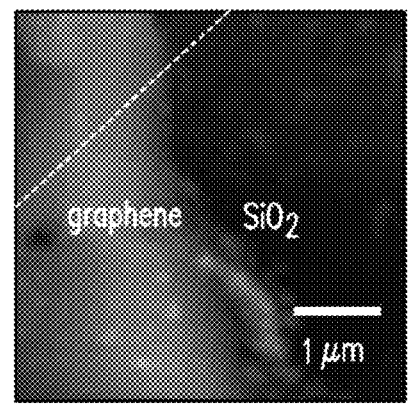
Figure 46B:
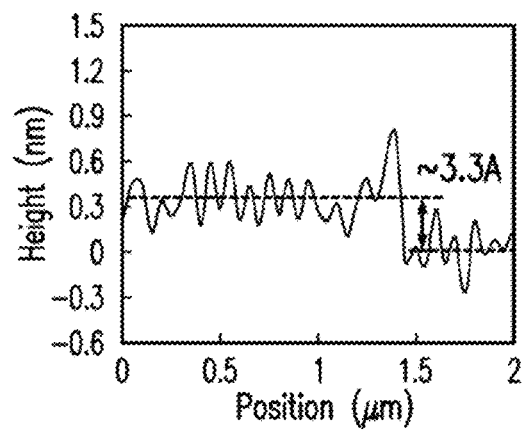
Figure 46C:
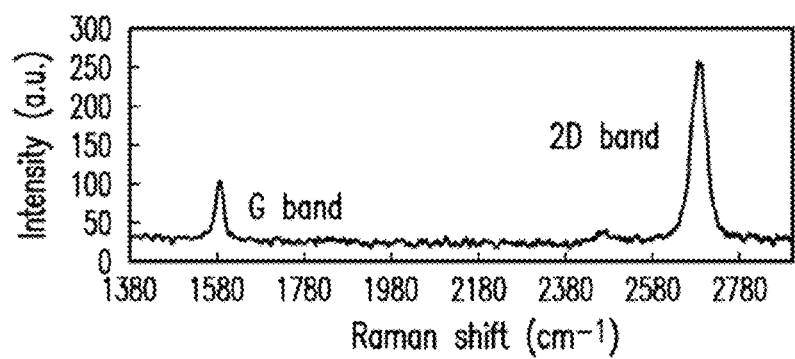

FIG. 46A-C illustrate characterization of a graphene sheet according to some embodiments of the disclosed subject matter: (FIG. 46A) AFM micrograph; (FIG. 46B) Height profile; and (FIG. 46C) Raman spectra (532 nm laser excitation).

Figure 47:
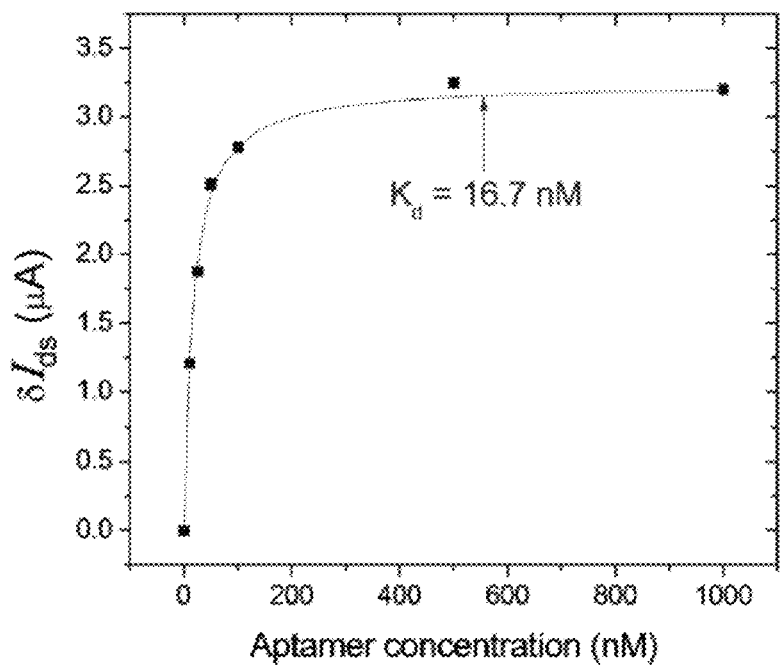

FIG. 47 illustrates a plot showing the characterization of the graphene nanosensor by measuring changes in graphene conductance with varying free aptamer concentrations (0-1000 nM).

Figure 48:
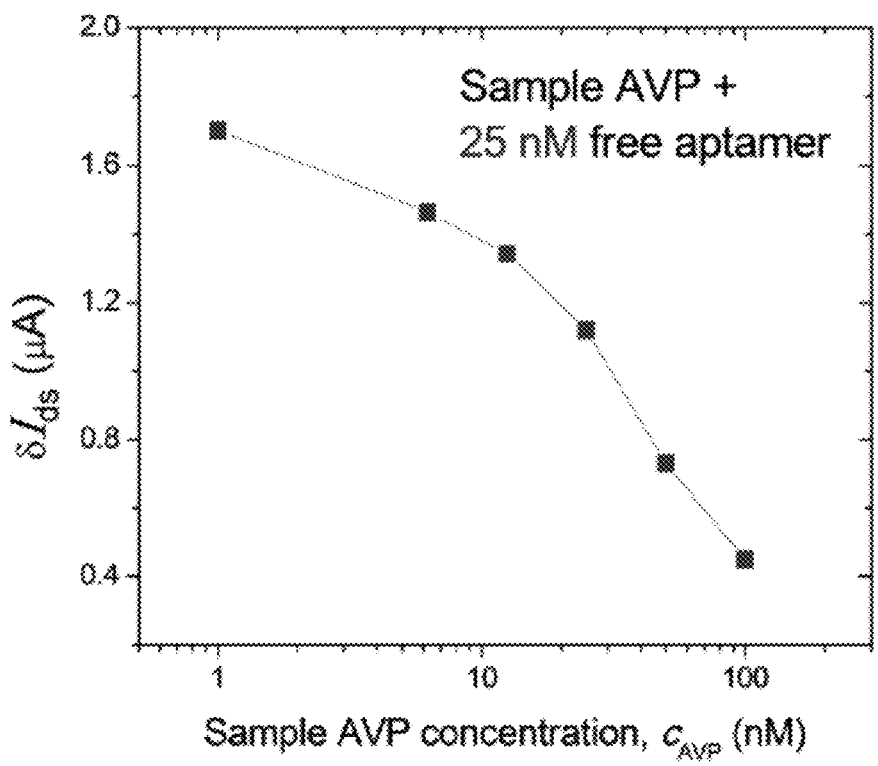

FIG. 48 illustrates a plot showing the measurements with standard mixtures of free aptamer at 25 nM and sample AVP at varying concentrations (1-100 nM).

Figure 49:
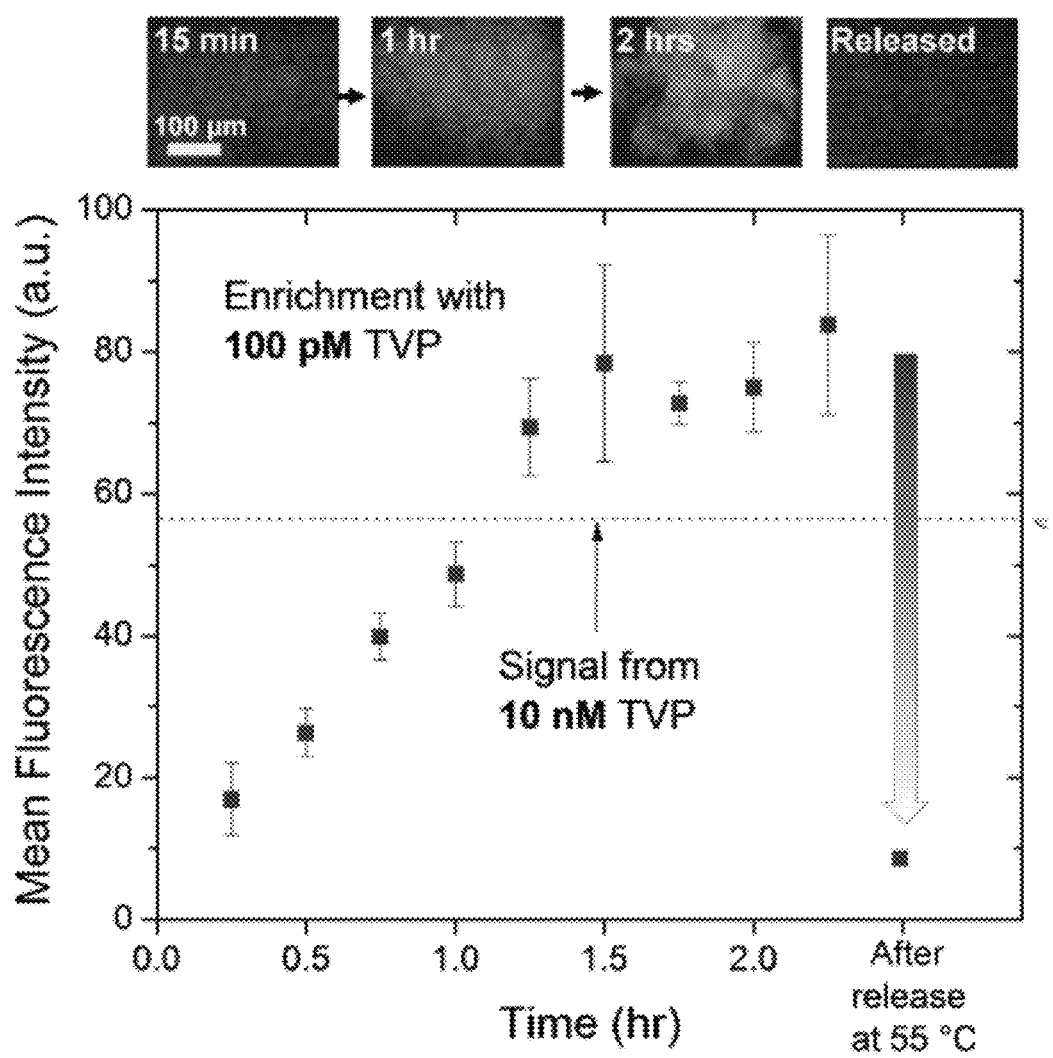

FIG. 49 illustrates fluorescence-based time resolved measurements of aptamer-based specific enrichment during continuous introduction of a 100 pM TAMRA-labeled AVP (TVP) solution at 37° C., followed by infusing a free aptamer solution at 55° C. for thermally-activated release of AVP.

Figure 50:
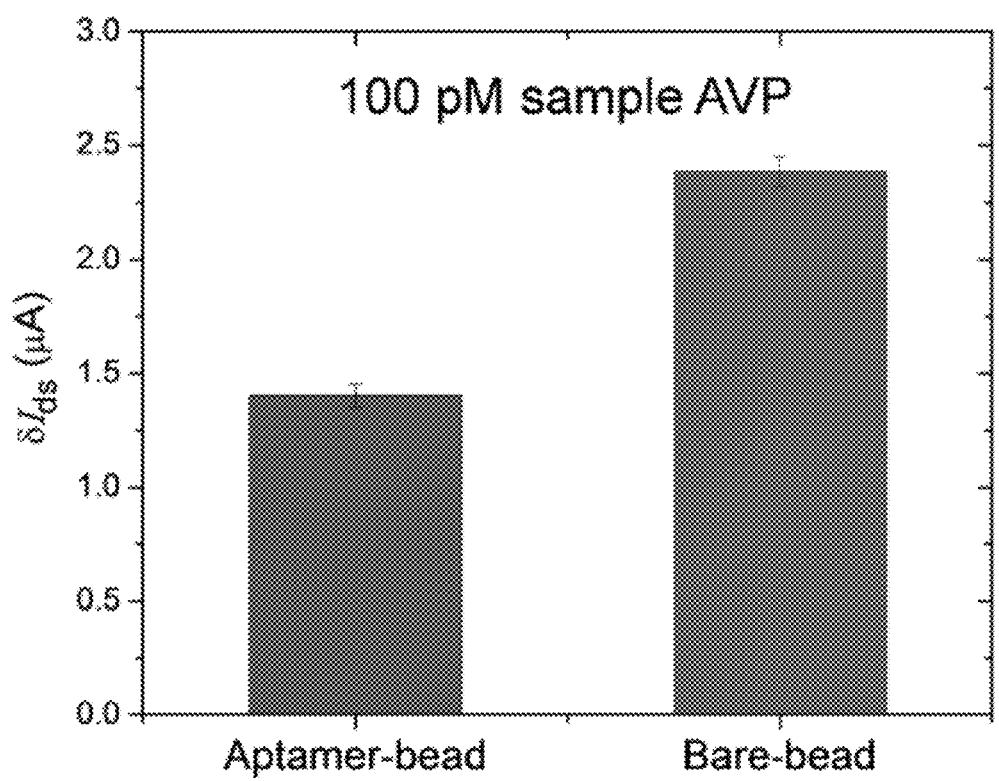

FIG. 50 illustrates a plot showing the bead-control testing. Integrated devices with and without aptamers on microbeads were tested to verify aptamer-based specific enrichment.

Figure 51:
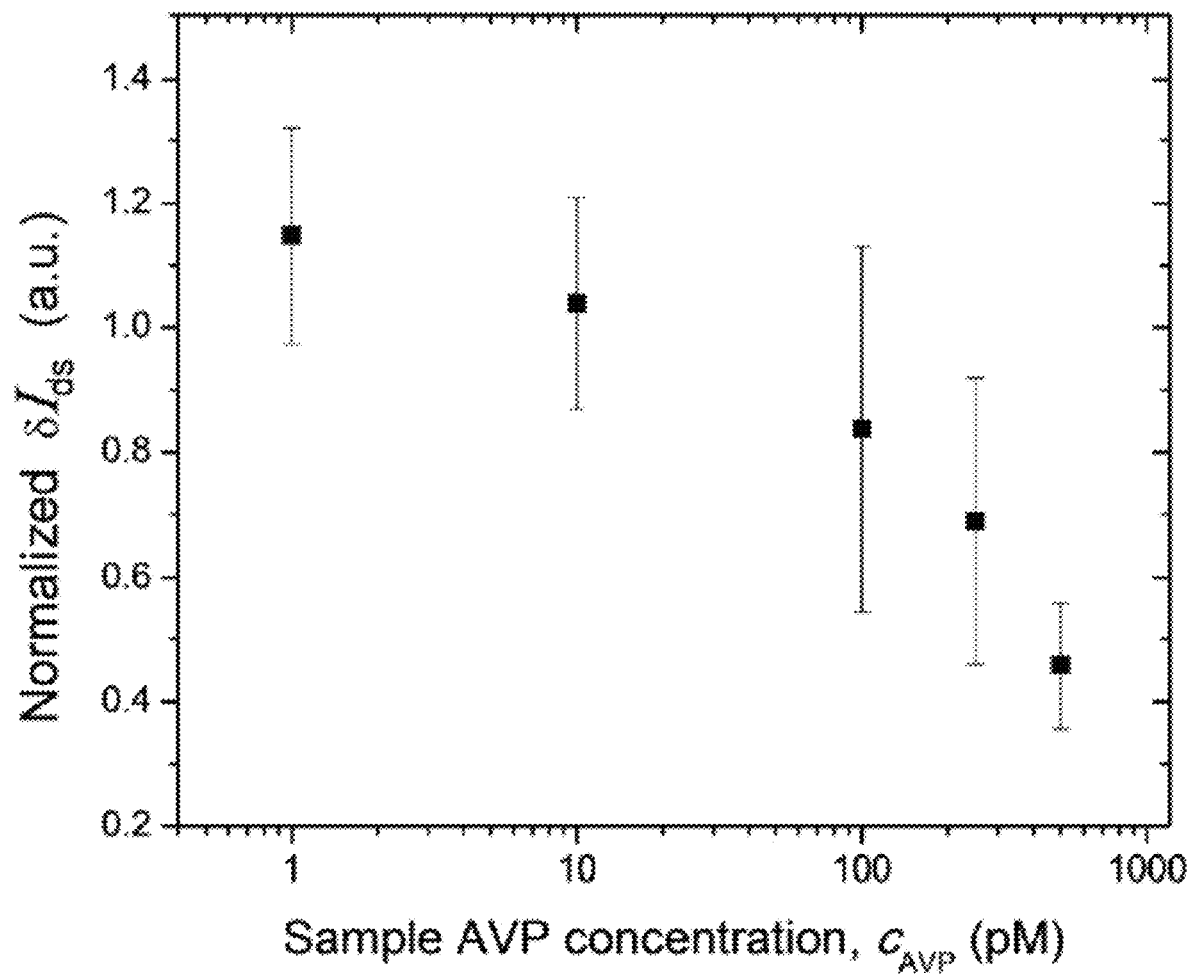

FIG. 51 illustrates a plot showing the normalized signals obtained from testing with varying sample AVP concentrations (1-500 pM). Three independent testings were conducted at each concentration.

Figure 52:
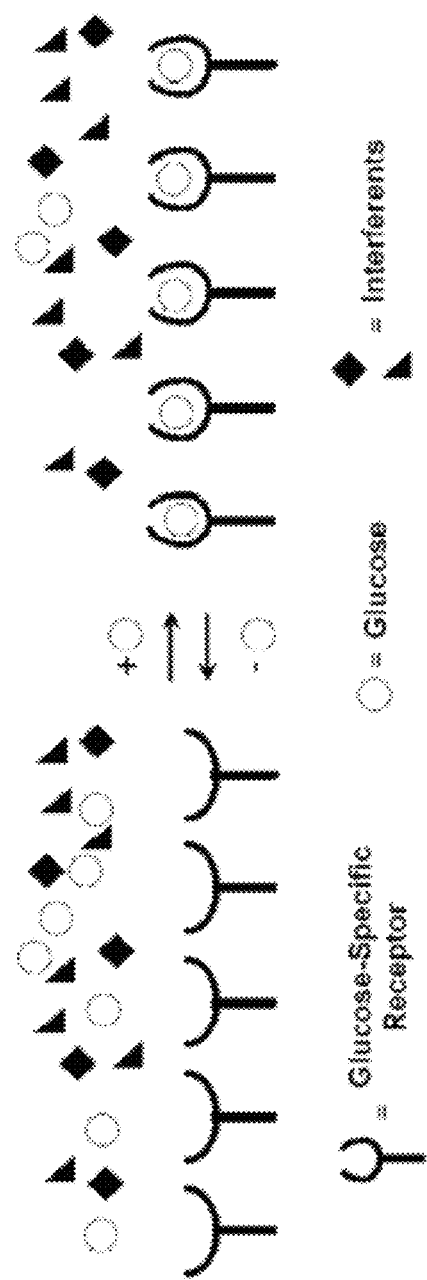

FIG. 52 depicts glucose sensing via affinity binding in accordance with an exemplary embodiment of the disclosed subject matter.

Figure 53A:
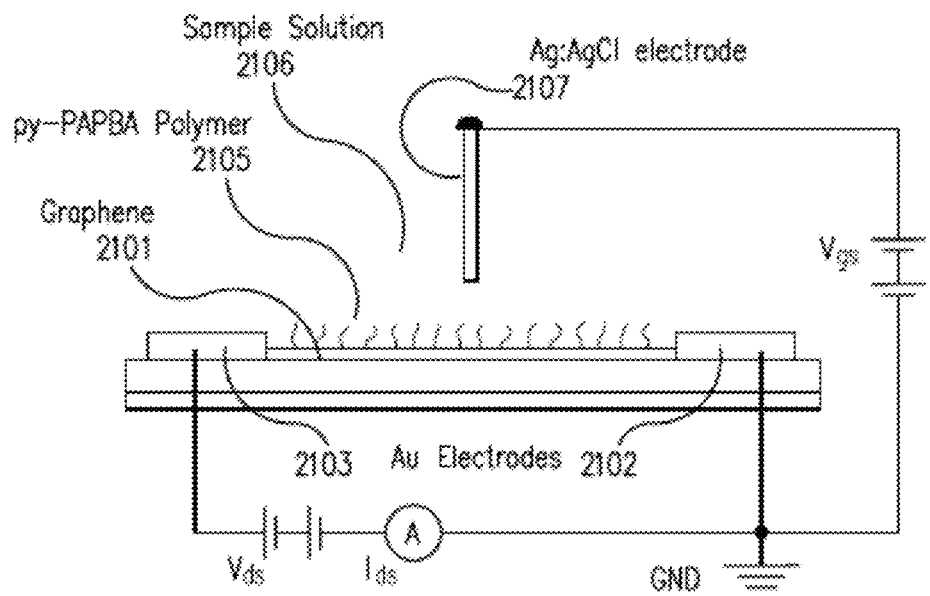

FIG. 53A depicts a schematic representation of a graphene-based affinity nanosensor in accordance with an exemplary embodiment of the disclosed subject matter.

Figure 53B:
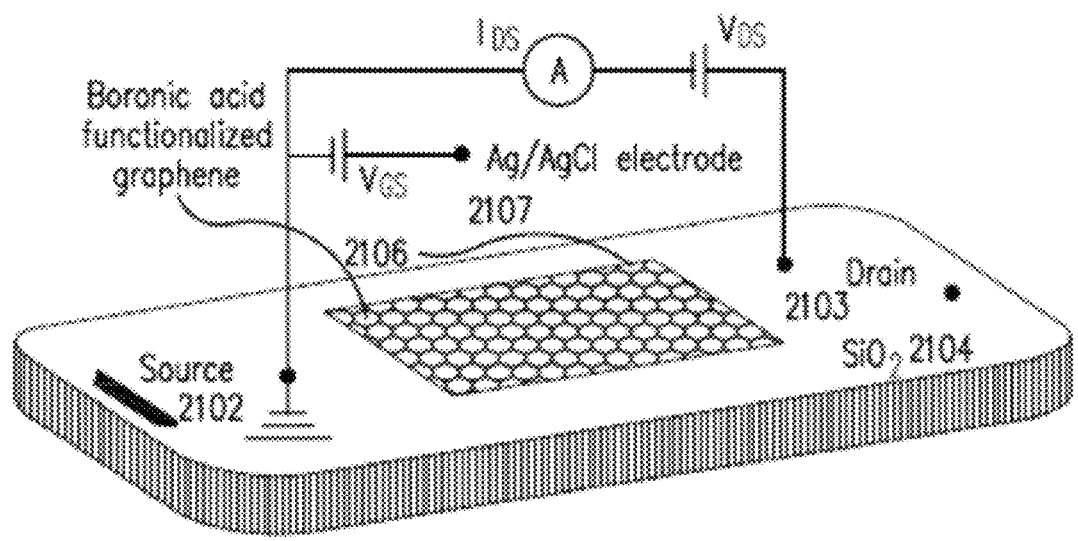

FIG. 53B depicts another schematic representation of a graphene-based affinity nanosensor in accordance with an exemplary embodiment of the disclosed subject matter.

Figure 54:
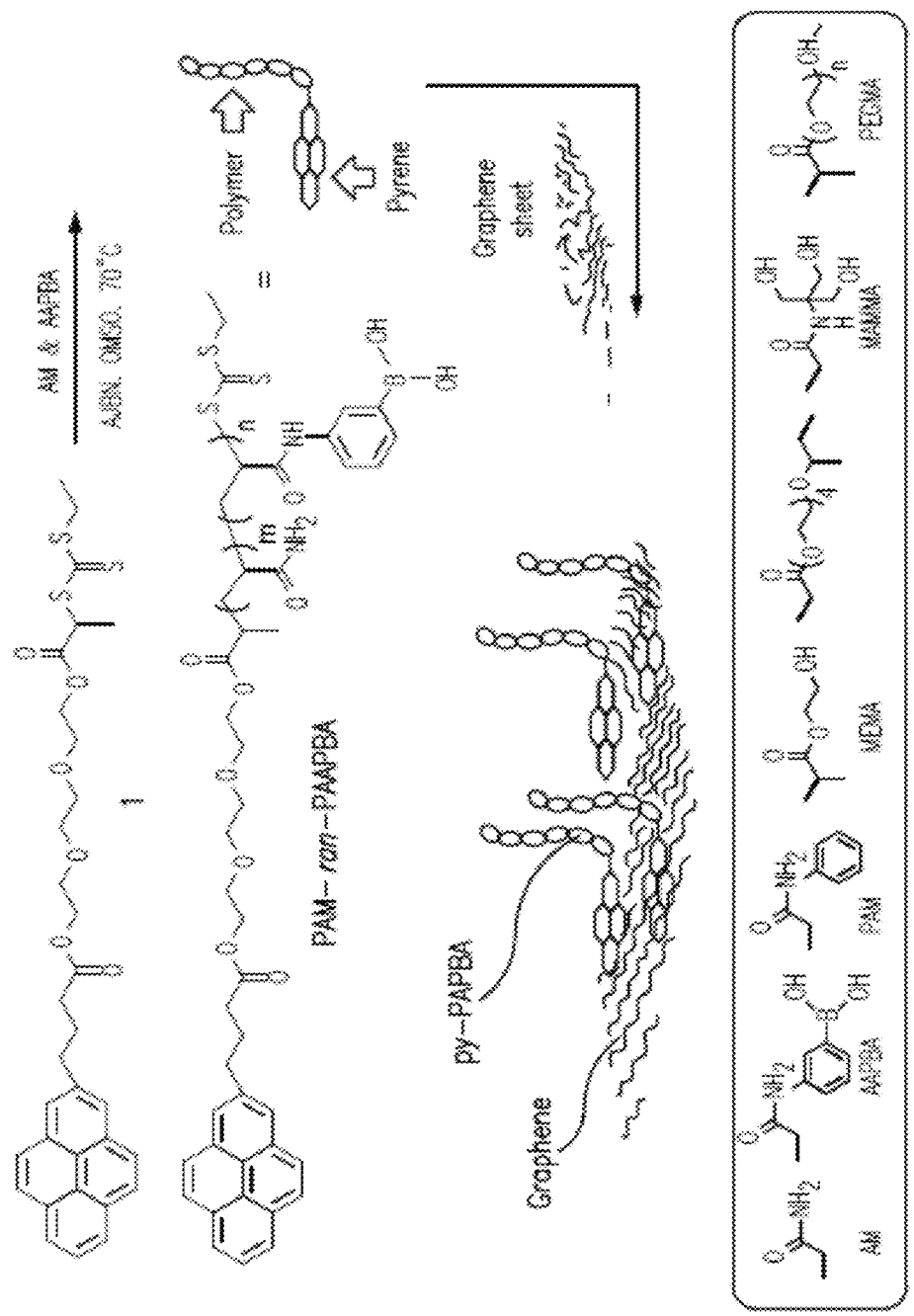

FIG. 54 depicts a synthesis of the pyrene-terminated glucose-sensing polymer PAPBA and its coupling to graphene via π-π stacking interactions in accordance with an exemplary embodiment of the disclosed subject matter.

Figure 55A:
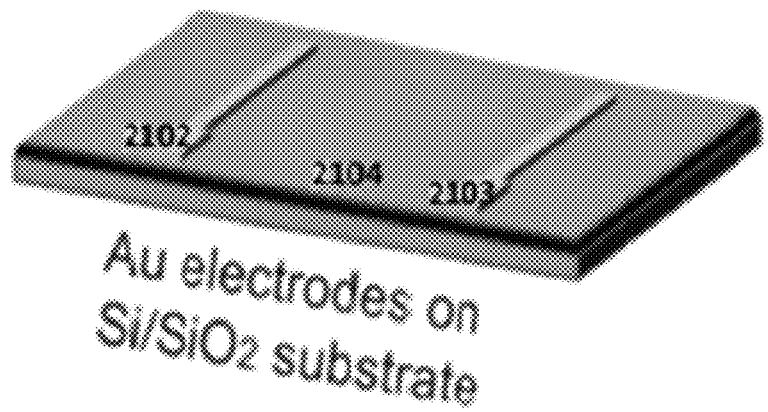
Figure 55B:
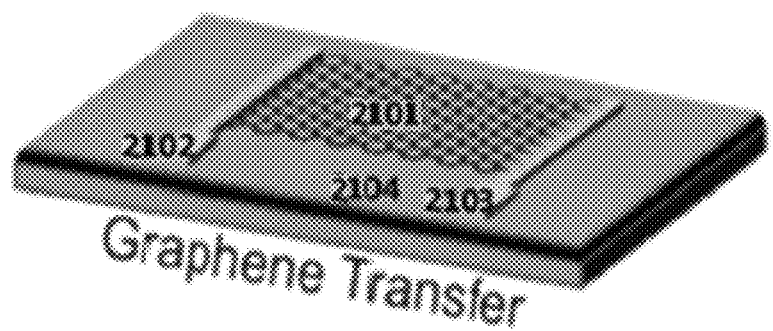
Figure 55C:
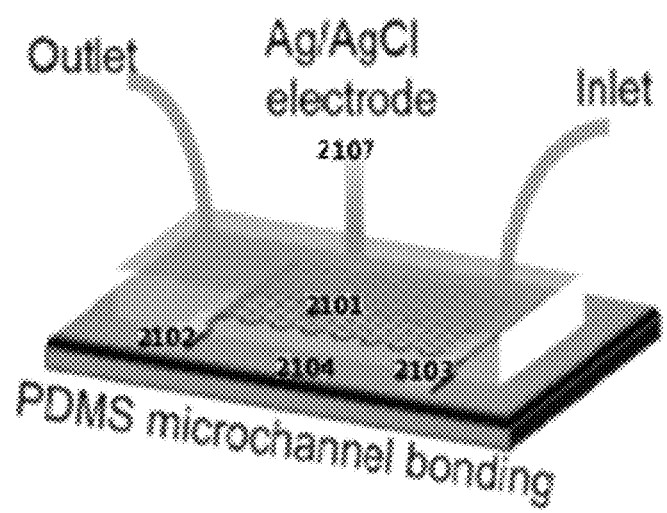

FIGS. 55A-C depict fabrication of the nanosensor in accordance with an exemplary embodiment: (FIG. 55A) depicts patterning of drain and source electrodes, (FIG. 55B) depicts transfer of graphene onto an oxide-coated silicon substrate, and (FIG. 55C) depicts bonding of the PDMS microchannel to the nanosensor chip.

Figure 56:
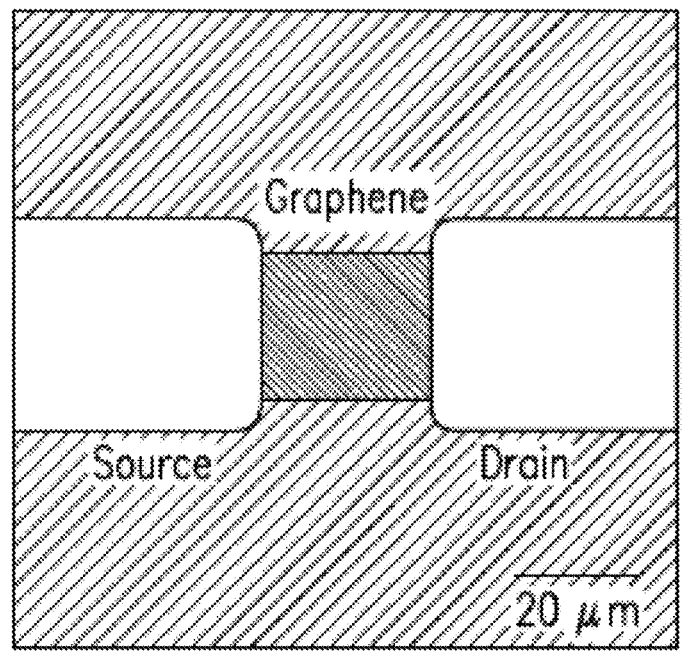

FIG. 56 depicts the graphene conducting channel connecting the source and drain electrodes in accordance with an exemplary embodiment.

Figure 57:
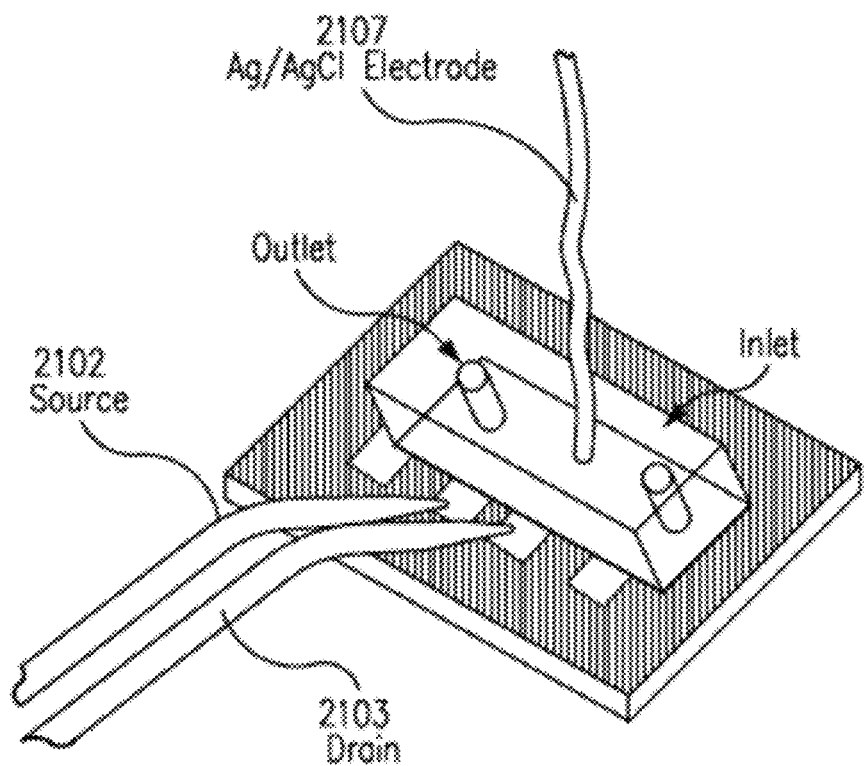

FIG. 57 depicts a measurement setup of the nanosensor in accordance with an exemplary embodiment.

Figure 58:
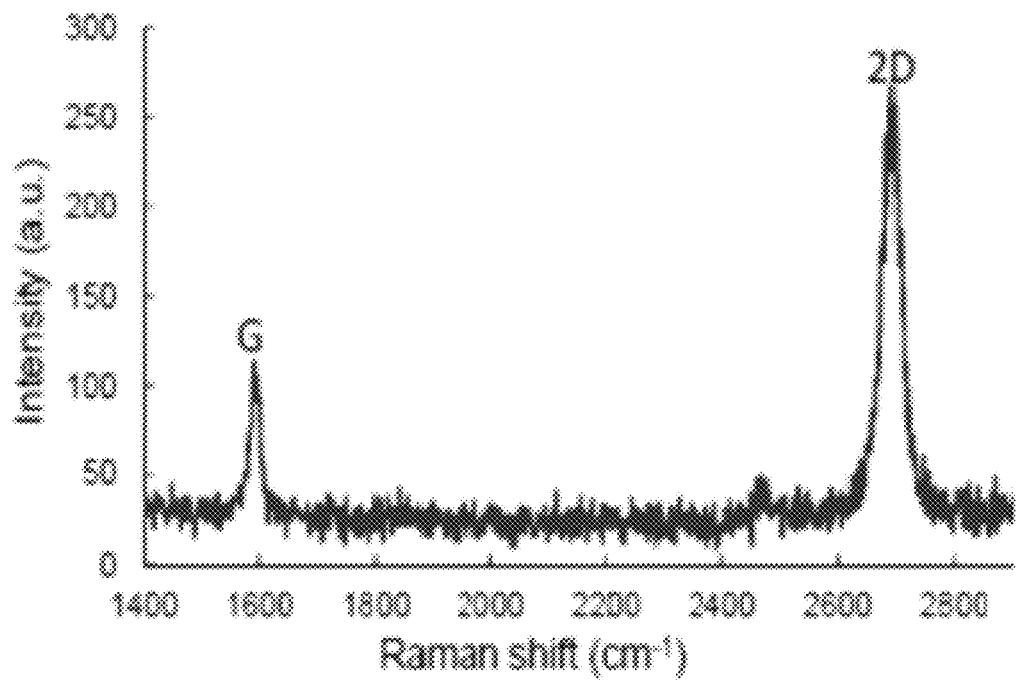

FIG. 58 depicts the Raman spectrum of graphene in accordance with an exemplary embodiment, where the G and 2D bands are indicative of the graphene including a single layer of carbon atoms.

Figure 59A:
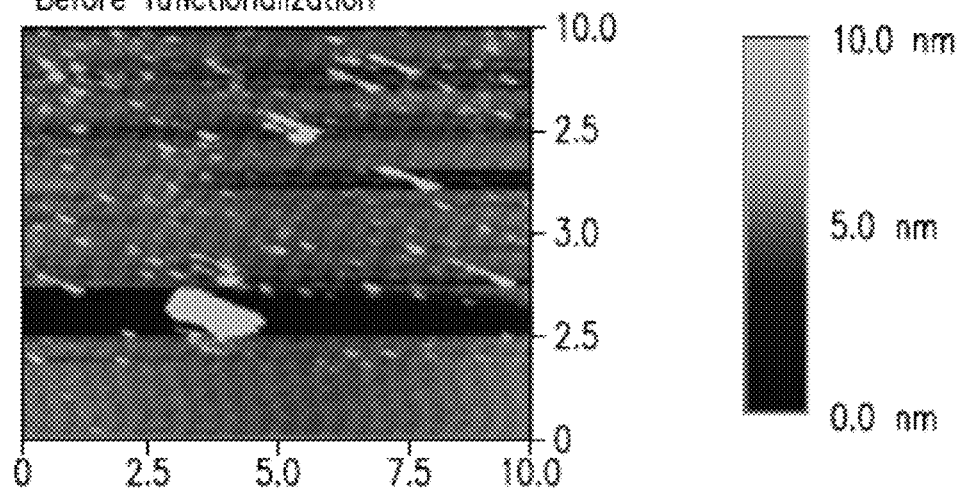
Figure 59B:
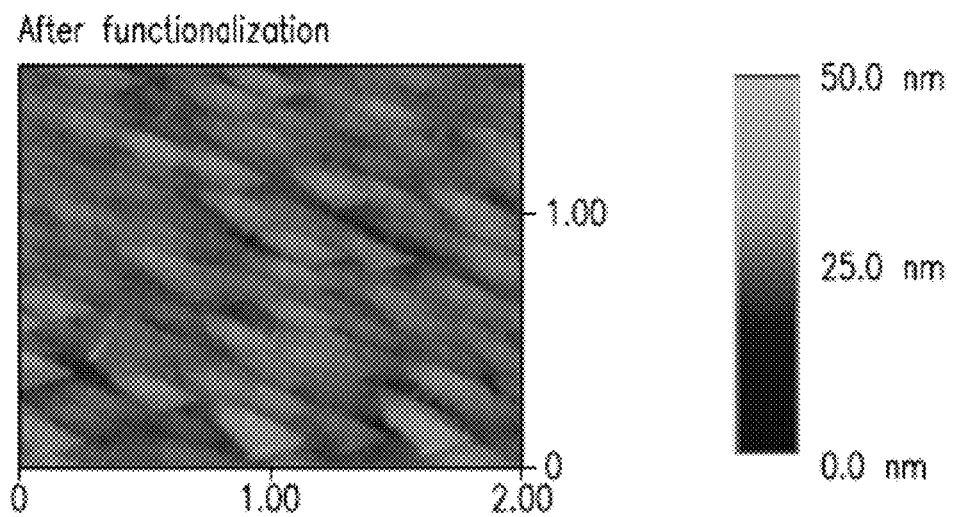

FIGS. 59A-B depict AFM images of graphene before and after functionalization in accordance with an exemplary embodiment, where (FIG. 59A) depicts graphene before functionalization and (FIG. 59B) depicts graphene after functionalization with a PAPBA polymer.

Figure 60:
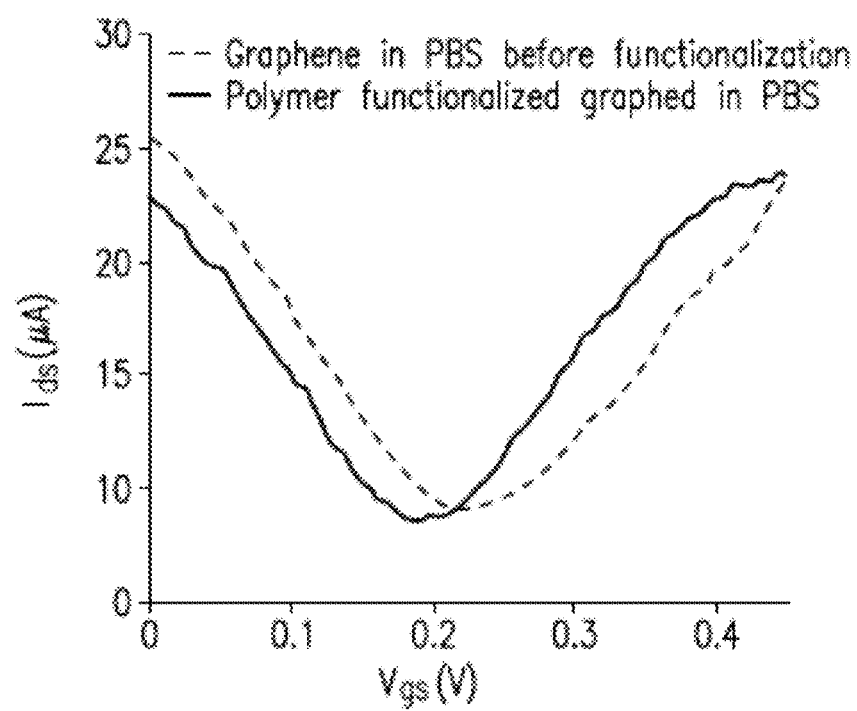

FIG. 60 depicts transfer characteristics measured before (dashed line) and after (solid line) functionalization of graphene with the PAPBA polymer, where the left shift of the Dirac point indicates that the graphene was n-doped due to the attachment of the polymer molecules.

Figure 61:
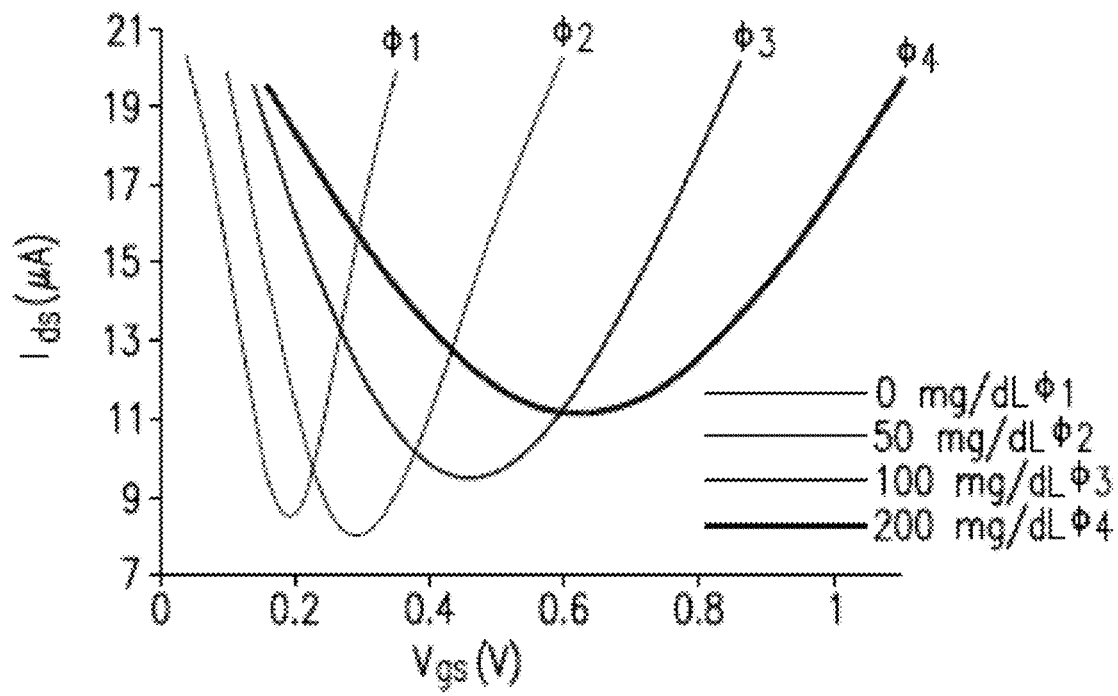

FIG. 61 depicts transfer characteristics in different glucose solutions at varying glucose concentrations in accordance with an exemplary embodiment, where in response to increases in the glucose concentration, the Dirac point position, VGS, Dirac, shifted to higher gate voltages and the transconductance decreased from 100 to 20 μS.

Figure 62:
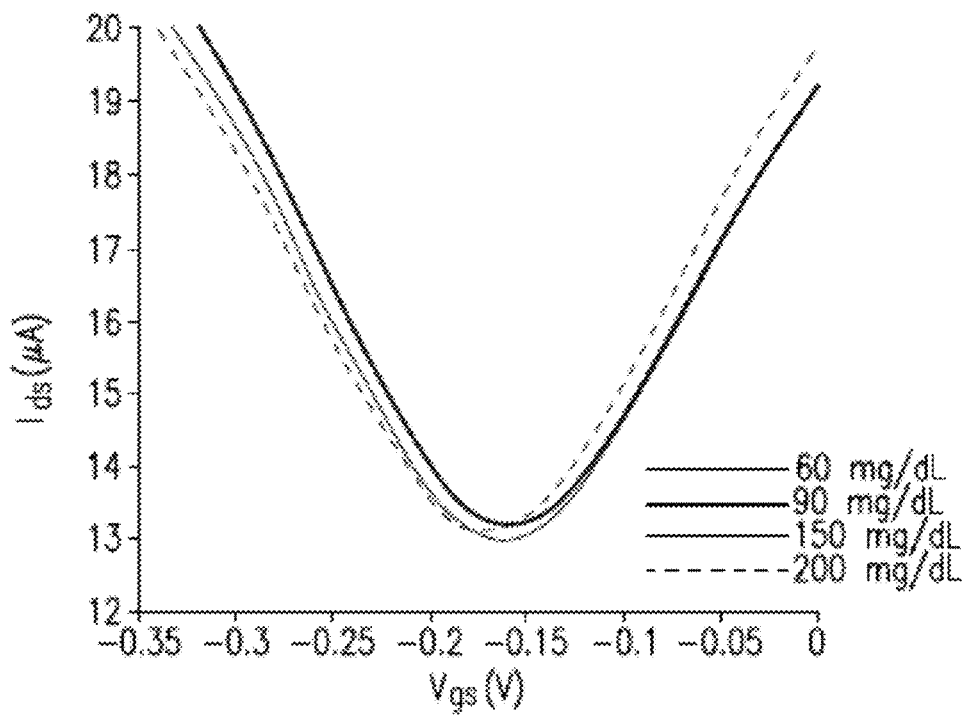

FIG. 62 depicts control tests using pristine graphene without functionalization of the polymer, where the change in the Dirac point position and transconductance is insignificant compared to the embodiment of FIG. 60, and indicates that the changes in carrier mobility and density of FIG. 60 were caused by the glucose-polymer binding.

Figure 63:
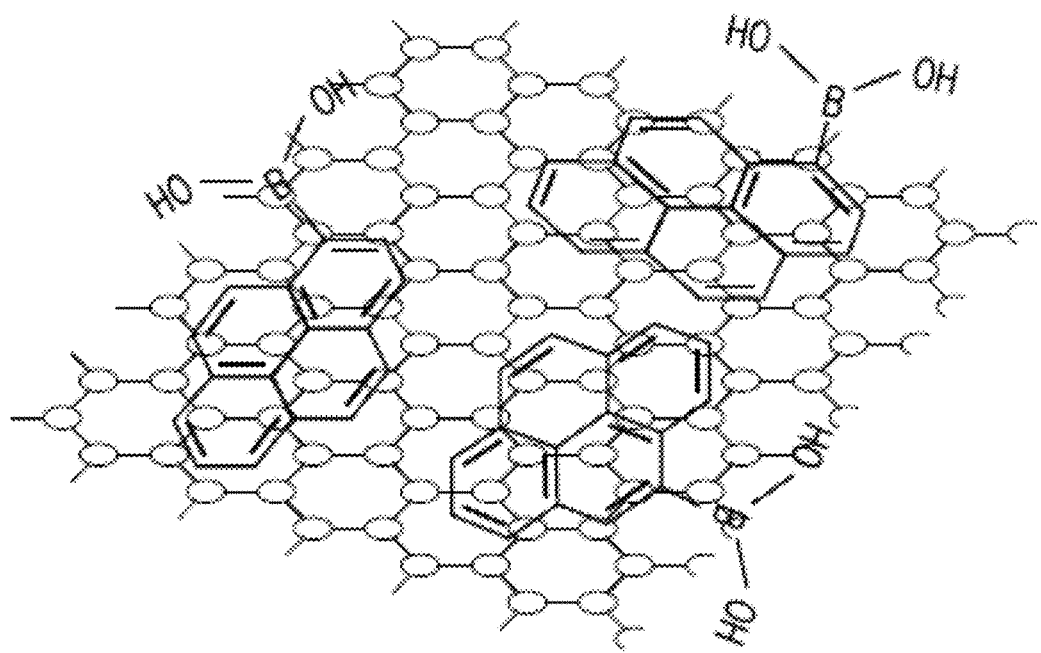

FIG. 63 depicts coupling of boronic acid and graphene via π-π stacking interactions between the pyrene group and graphene in accordance with an exemplary embodiment.

Figure 64:
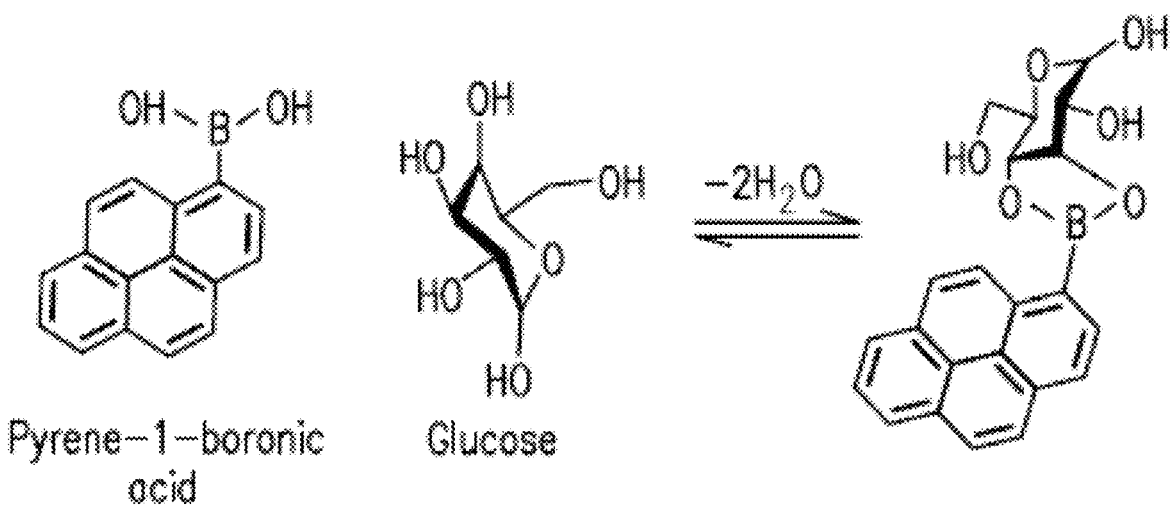

FIG. 64 depicts formation of a glucose-boronate ester at a physiological pH of 7.4 in accordance with an exemplary embodiment.

Figure 65A:
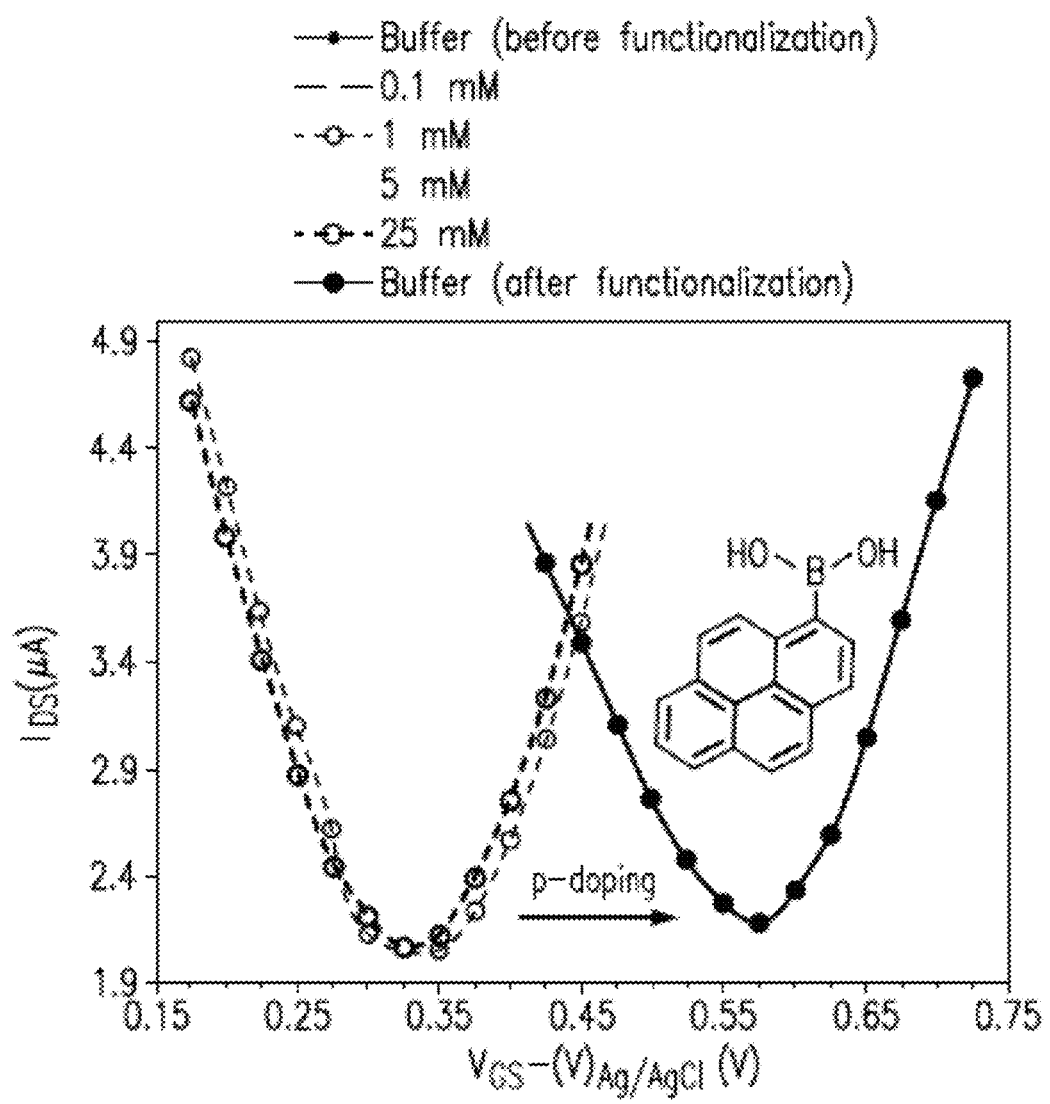
Figure 65B:
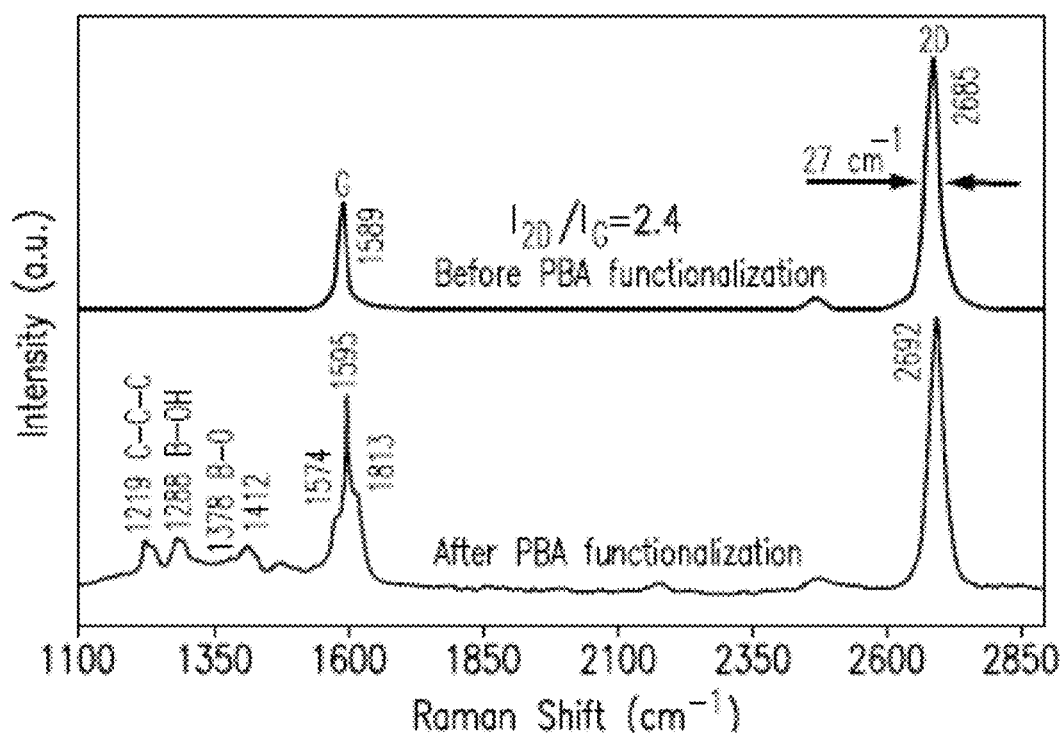

FIGS. 65A-B depict properties of the graphene before and after functionalization in accordance with an exemplary embodiment, where (FIG. 65A) depicts transfer characteristics of pristine graphene and PBA-functionalized graphene, and transfer characteristics of the pristine graphene exposed to glucose solutions (0.1 mM to 25 mM), and transfer characteristics after rinsing with PBA solution show that VNP shifted from 0.33 V to 0.575 V, and (FIG. 65B) depicts the Raman spectra of the graphene before and after exposure to PBA solution, where signature peaks of the boronic acid and the graphene-pyrene interaction were observed after immersing in PBA solution.

Figure 66:
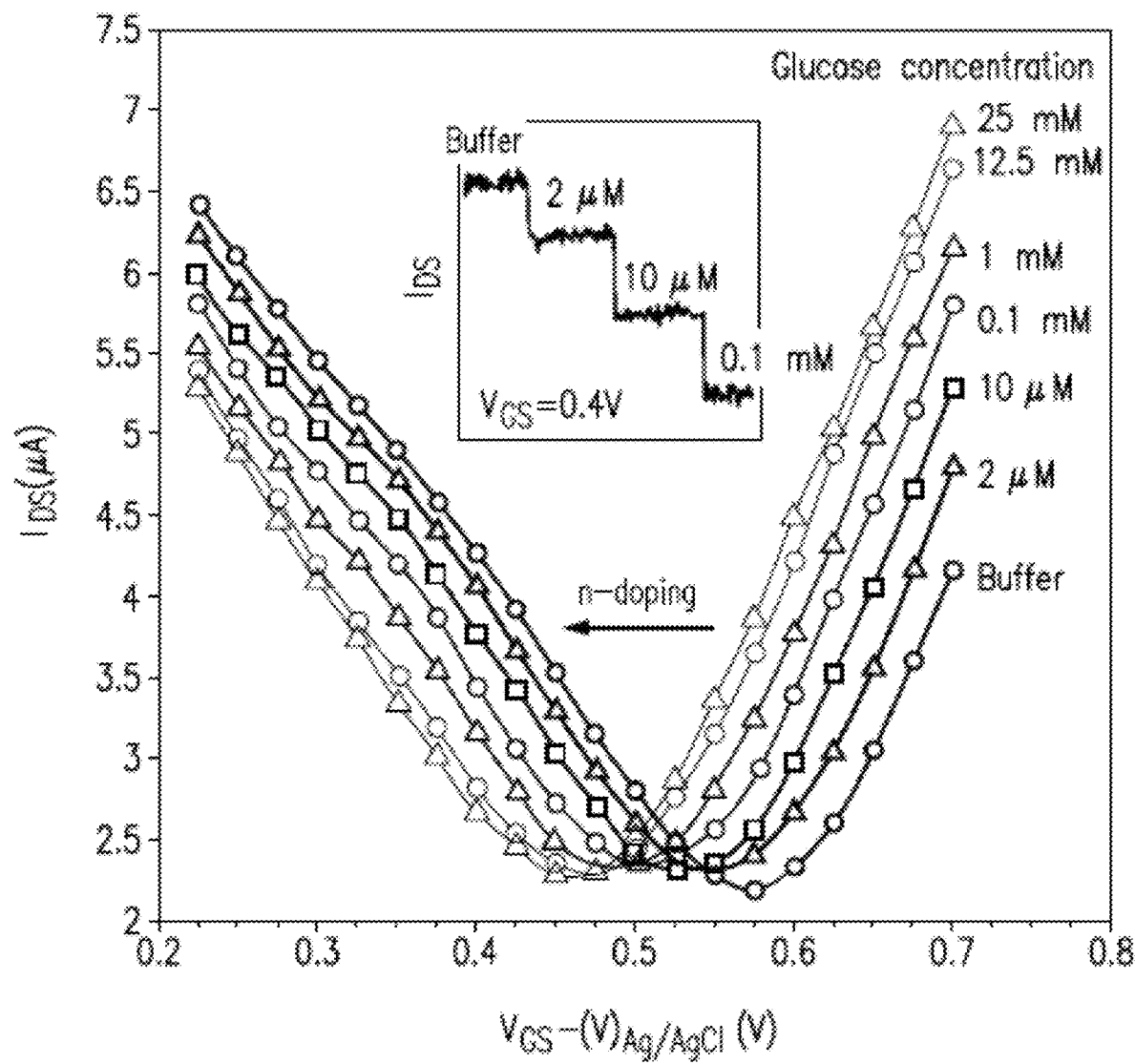

FIG. 66 depicts transfer characteristics measured when the nanosensor was exposed to glucose solutions (concentration ranging from 2 μm to 25 mM) in accordance with an exemplary embodiment, where the curve shifted to the left as a result of the increase in the glucose concentration, i.e., a monotonic decrease of IDS at VGS=0.4 V.

Figure 67:
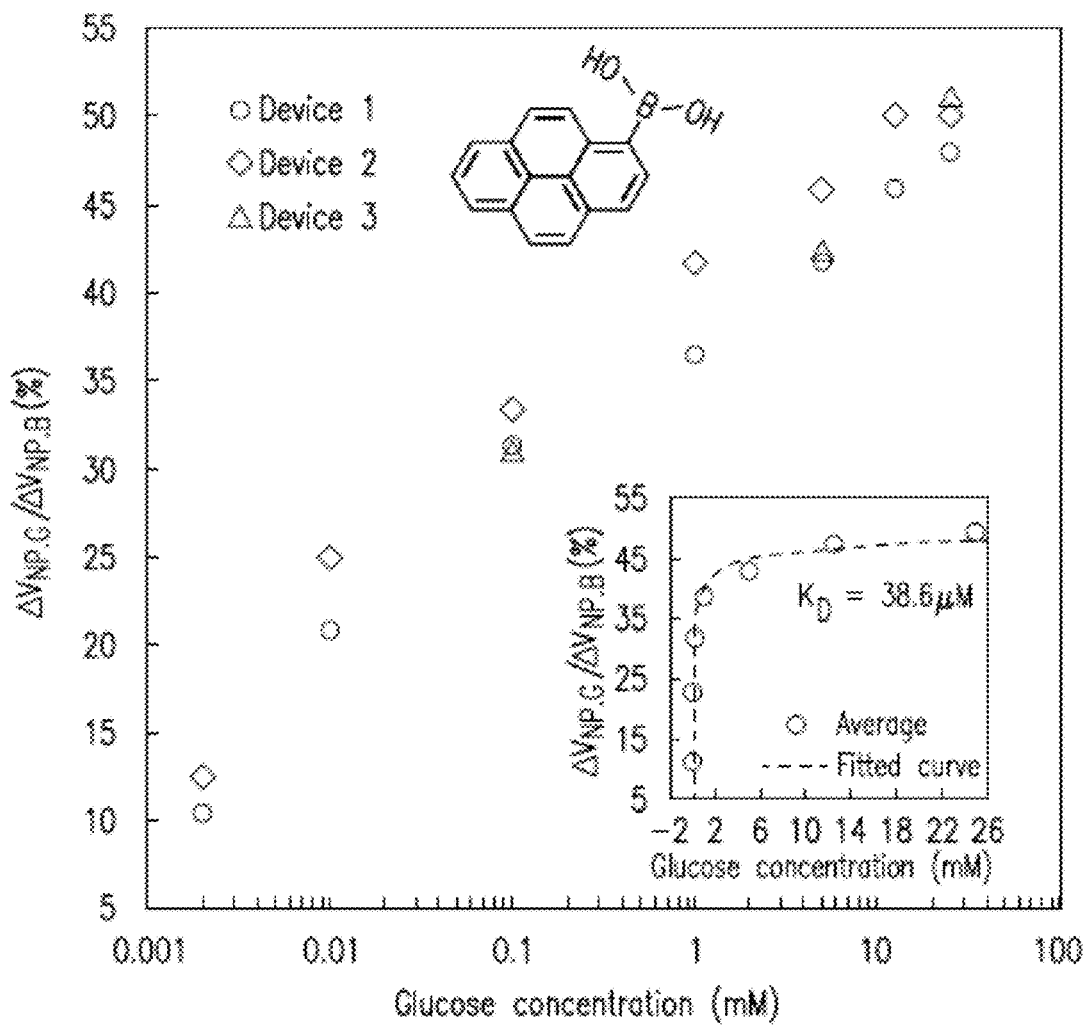

FIG. 67 depicts neutral point shift ratio ΔVNP,G/ΔVNP,B as a function of glucose concentration in accordance with an exemplary embodiment. Glucose concentration is on a logarithmic scale, where the inset depicts a fit to the Hill-Langmuir equation, yielding an equilibrium dissociation constant (KD) of 38.6 μm.

Figure 68A:
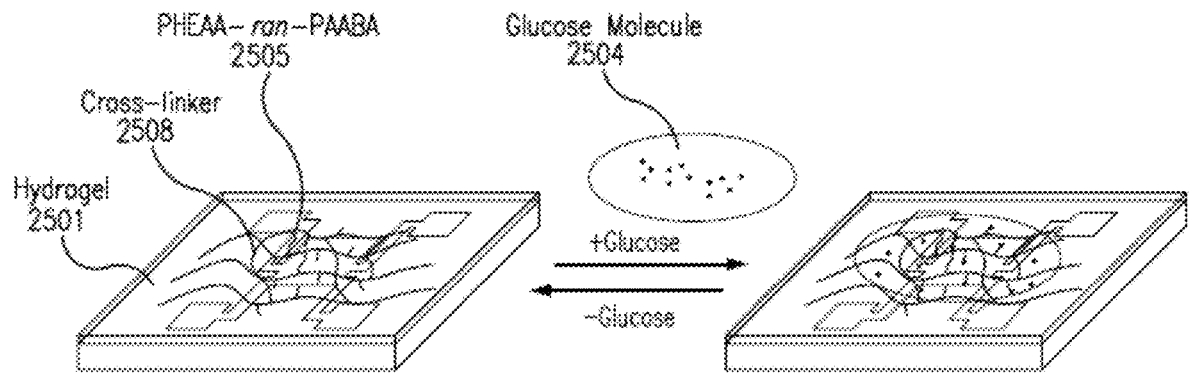
Figure 68B:
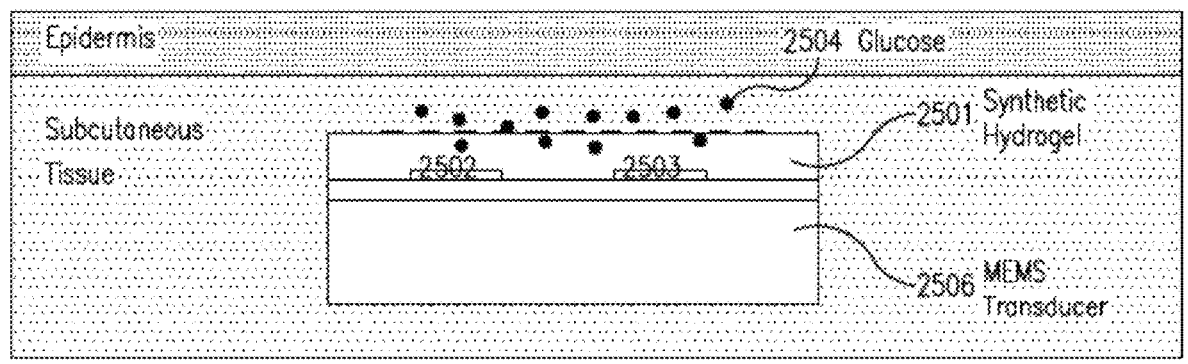

FIGS. 68A-B depict synthetic glucose-affinity hydrogel sensing in accordance with an exemplary embodiment, where (FIG. 68A) depicts the reversible affinity binding of PHEAA-ran-PAAPBA integrated hydrogel to glucose and (FIG. 68B) depicts hydrogel embedded in a capacitive transducer.

Figure 69:
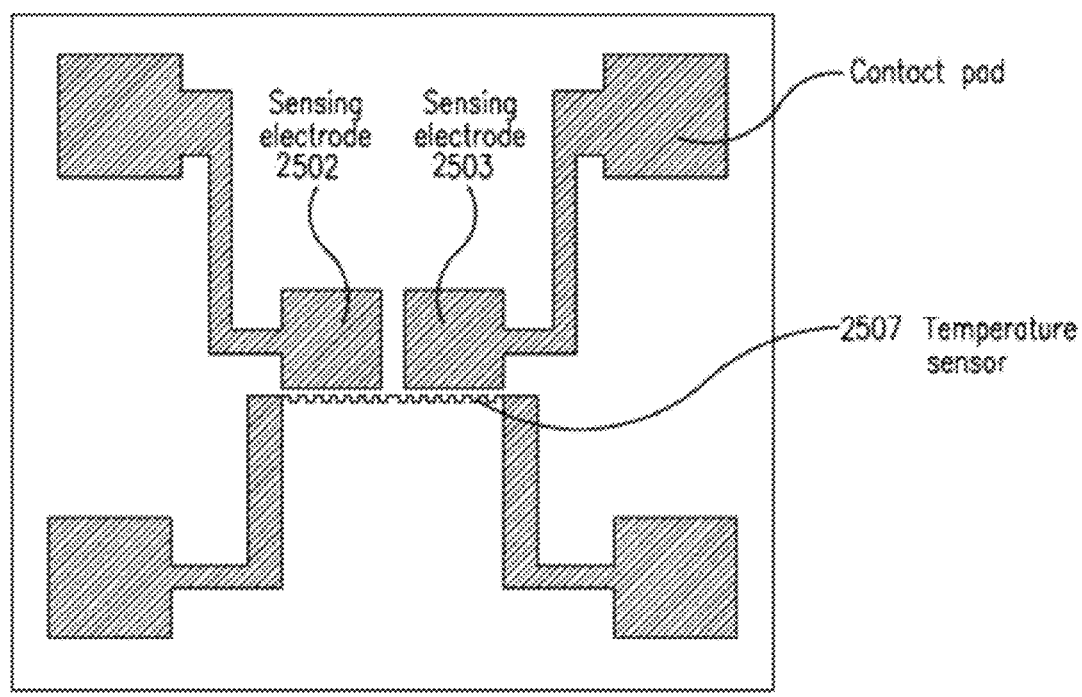

FIG. 69 depicts a schematic of a sensor chip with coplanar electrodes in accordance with an exemplary embodiment.

Figure 70A:
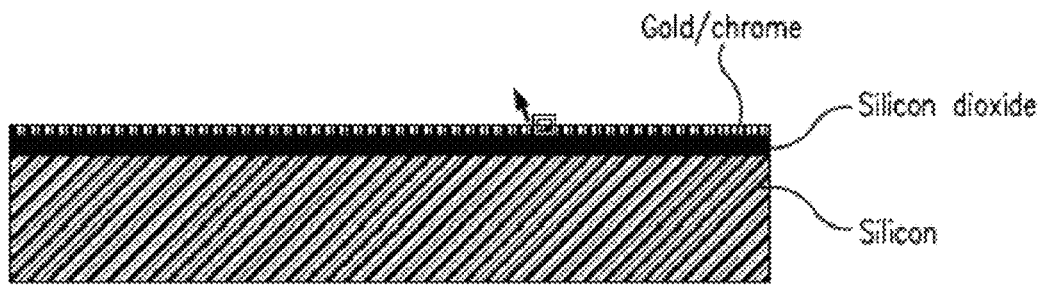
Figure 70B:
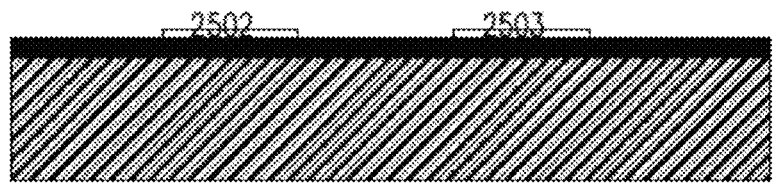
Figure 70C:
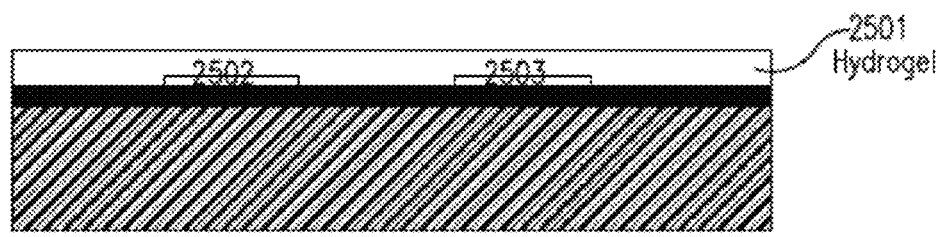
Figure 71A:
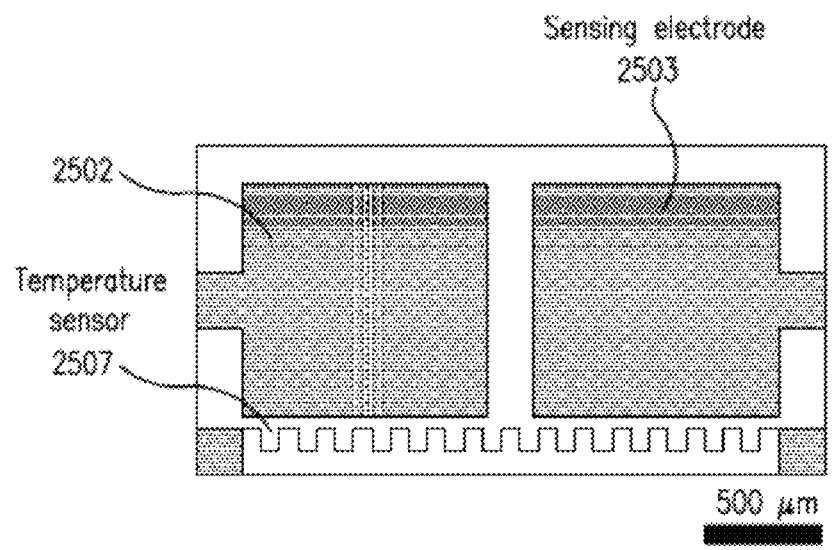
Figure 71B:
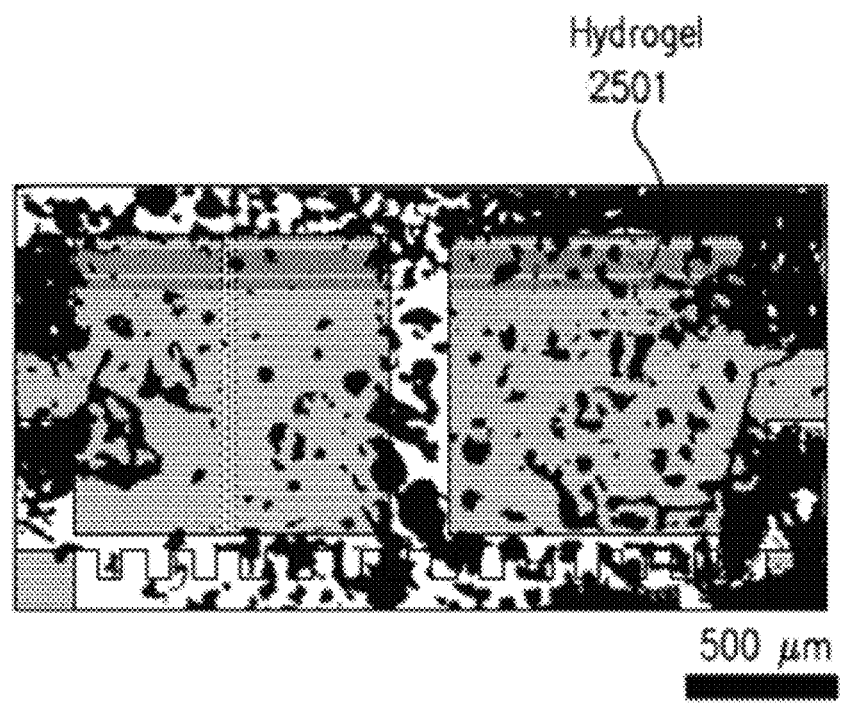
Figure 71C:
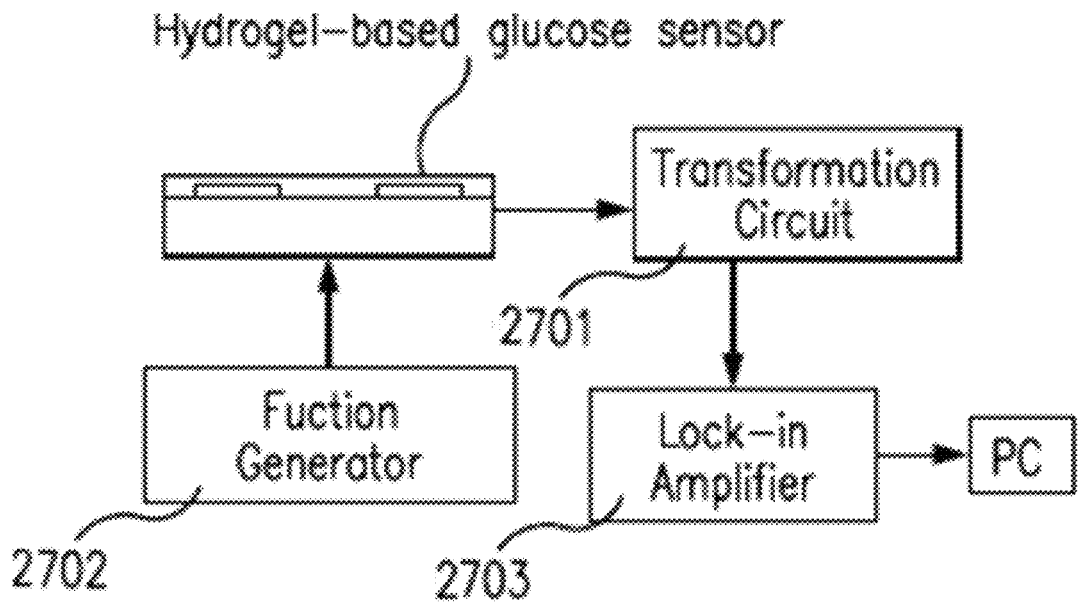
Figure 71D:
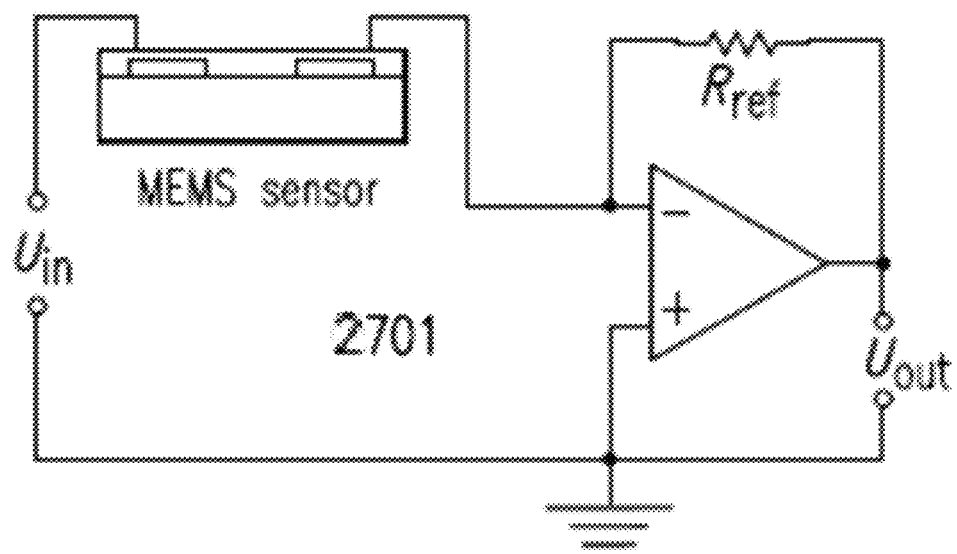
Figure 72A:
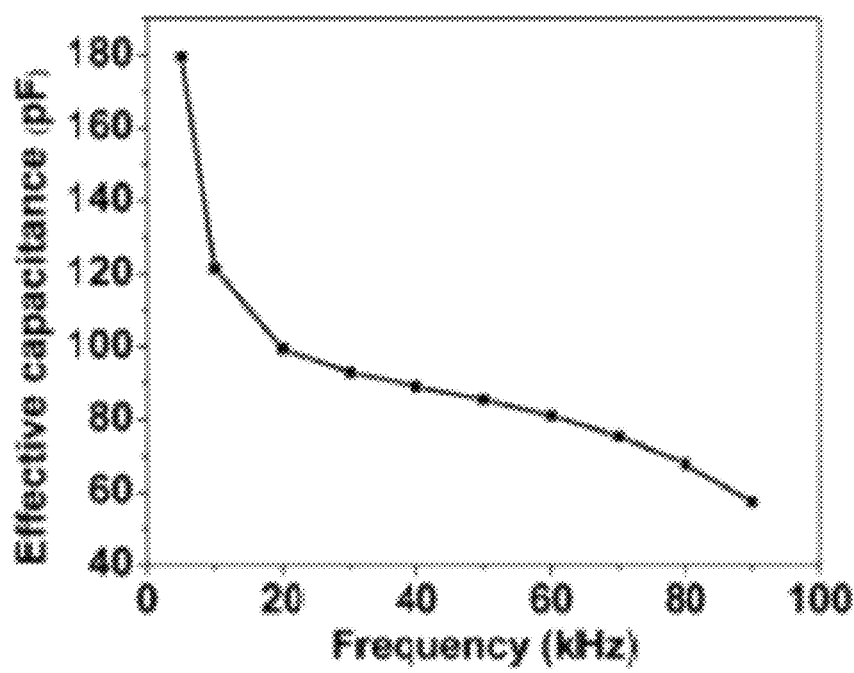
Figure 72B:
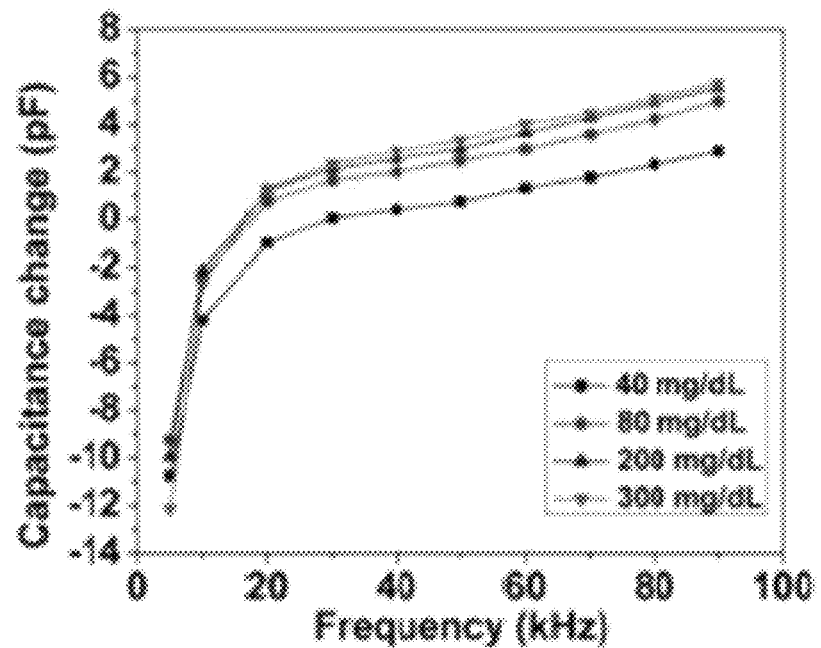
Figure 72C:
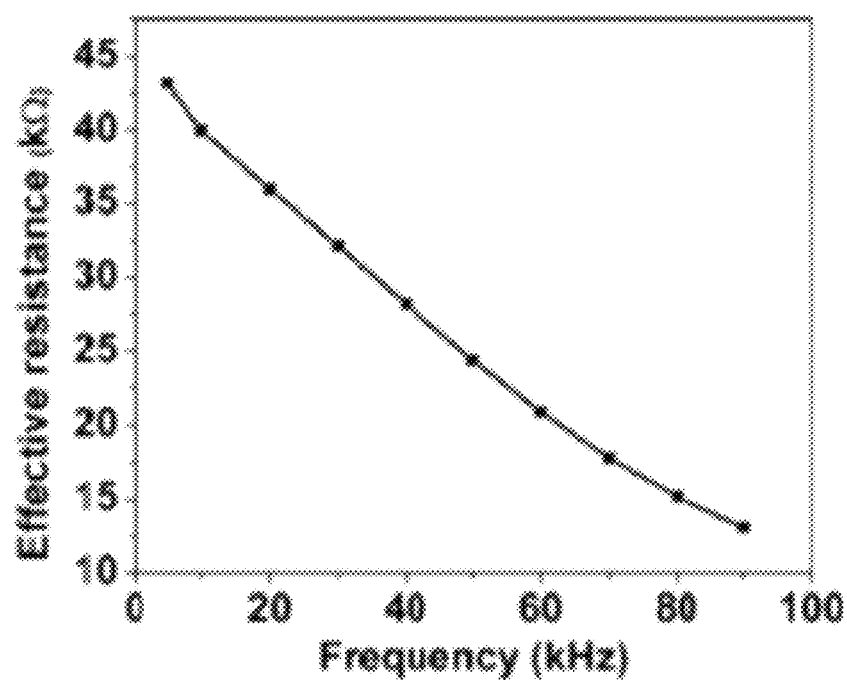
Figure 72D:
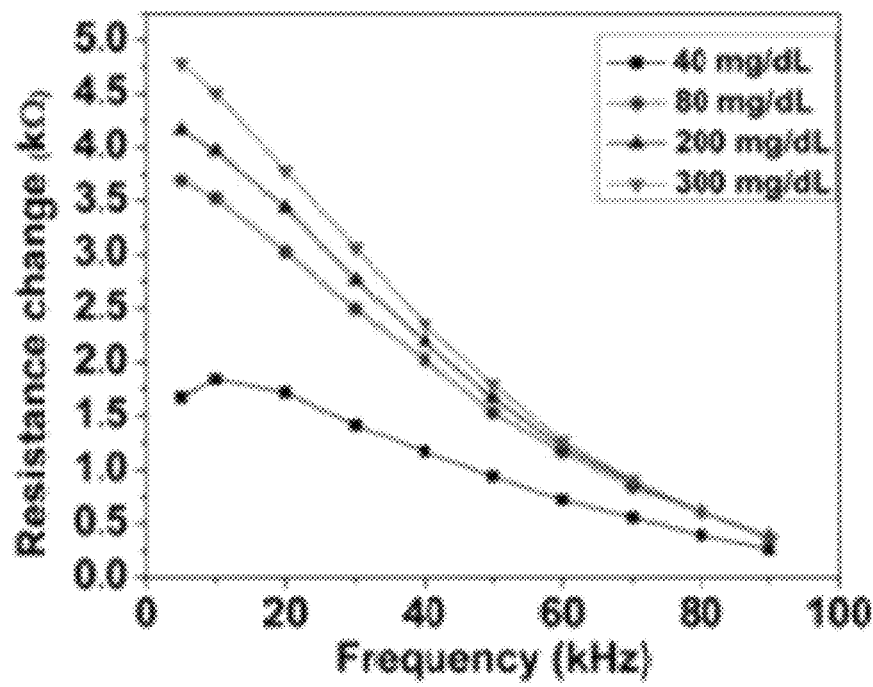

FIG. 70A-C depict fabrication of a sensor chip in accordance with an exemplary embodiment, where ((FIG. 70A) depicts deposition of a gold/chrome layer on a substrate, (FIG. 70B) depicts gold patterning, and (FIG. 70C) depicts hydrogel integration.

FIGS. 71A-D depict an impedance/voltage transformation circuit driven by a sinusoidal input from a function generator connected to a sensor in accordance with an exemplary embodiment, where (FIG. 71A) depicts a sensor chip before hydrogel integration, (FIG. 71B) depicts a sensor after hydrogel integration, (FIG. 71C) depicts a measurement setup in accordance with the above, and (FIG. 71D) depicts an impedance/voltage transformation circuit.

FIGS. 72A-D depict a hydrogel's dielectric relaxation in accordance with an exemplary embodiment, where (FIG. 72A) depicts an effective capacitance as a function of frequency response without glucose, (FIG. 72B) depicts an effective capacitance as a function of frequency response with glucose, (FIG. 72C) depicts an effective resistance as a function of frequency response without glucose, and (FIG. 72D) depicts an effective resistance as a function of frequency response with glucose.

Figure 73:
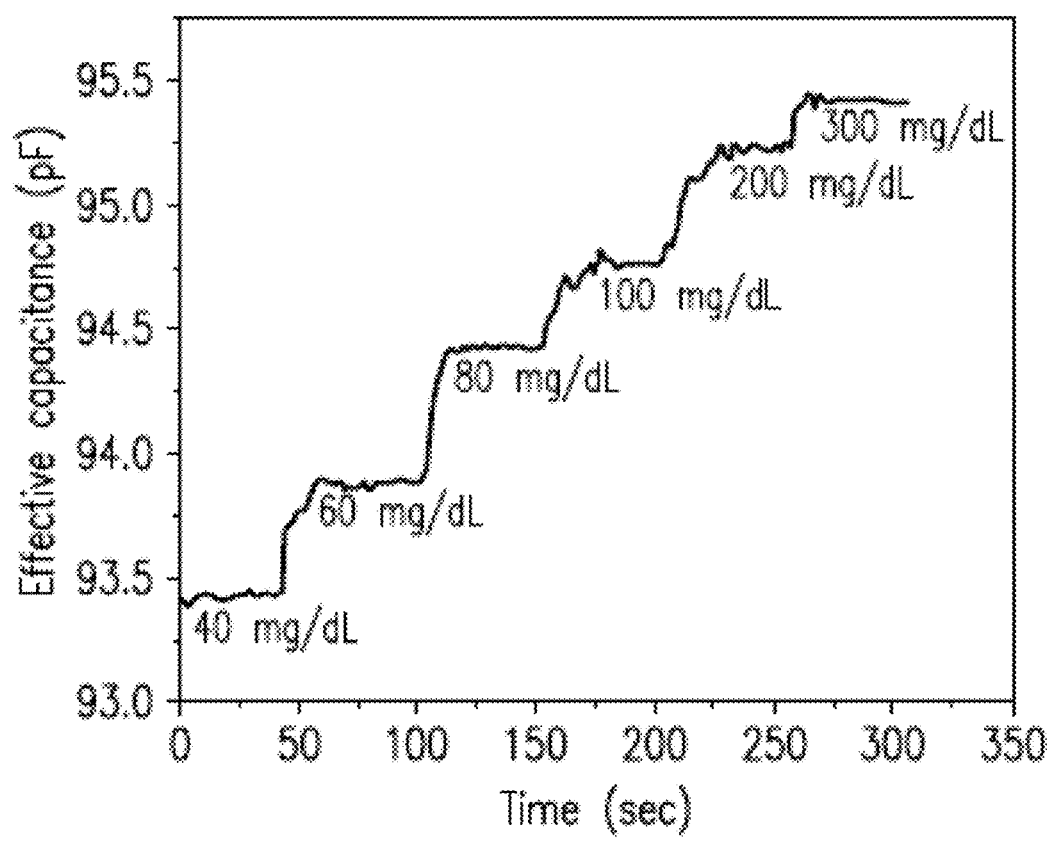

FIG. 73 depicts a time-resolved effective capacitance at 30 kHz in response to changes in glucose concentration in accordance with an exemplary embodiment.

Figure 74A:
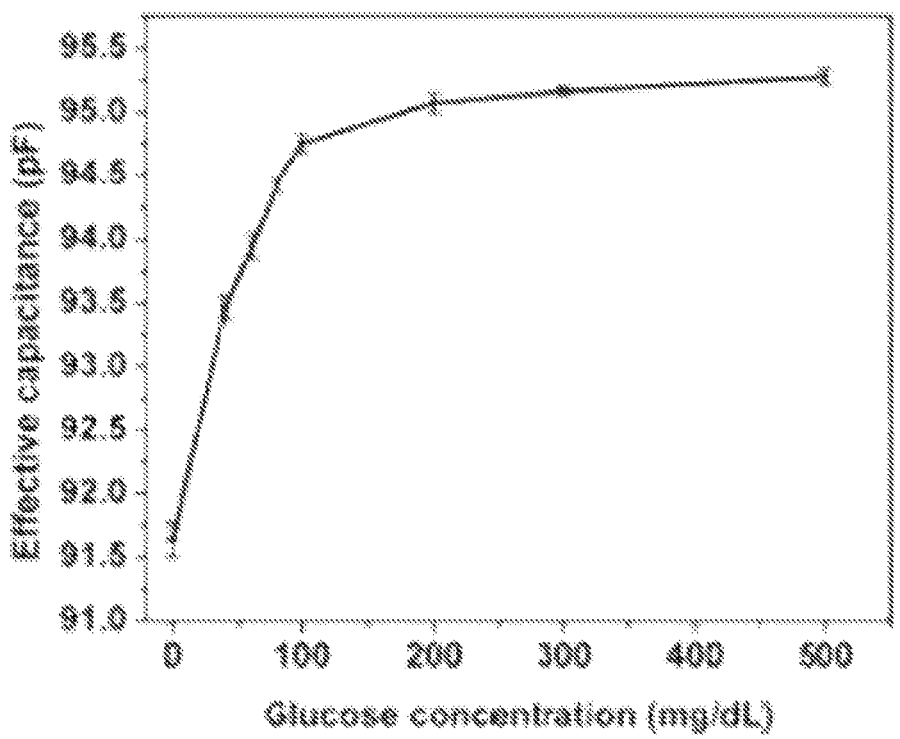
Figure 74B:
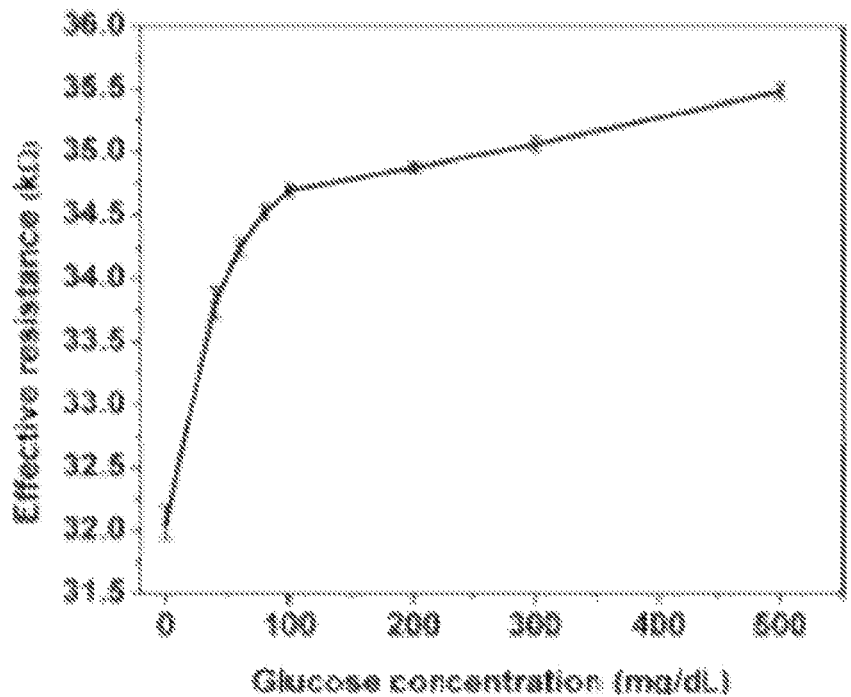

FIG. 74A-B depict a sensor's output as a function of glucose concentration in accordance with an exemplary embodiment, where (FIG. 74A) depicts a sensor's effective capacitance as a function of glucose concentration, and (FIG. 74B) depicts a sensor's effective resistance as a function of glucose concentration.

Figure 75:
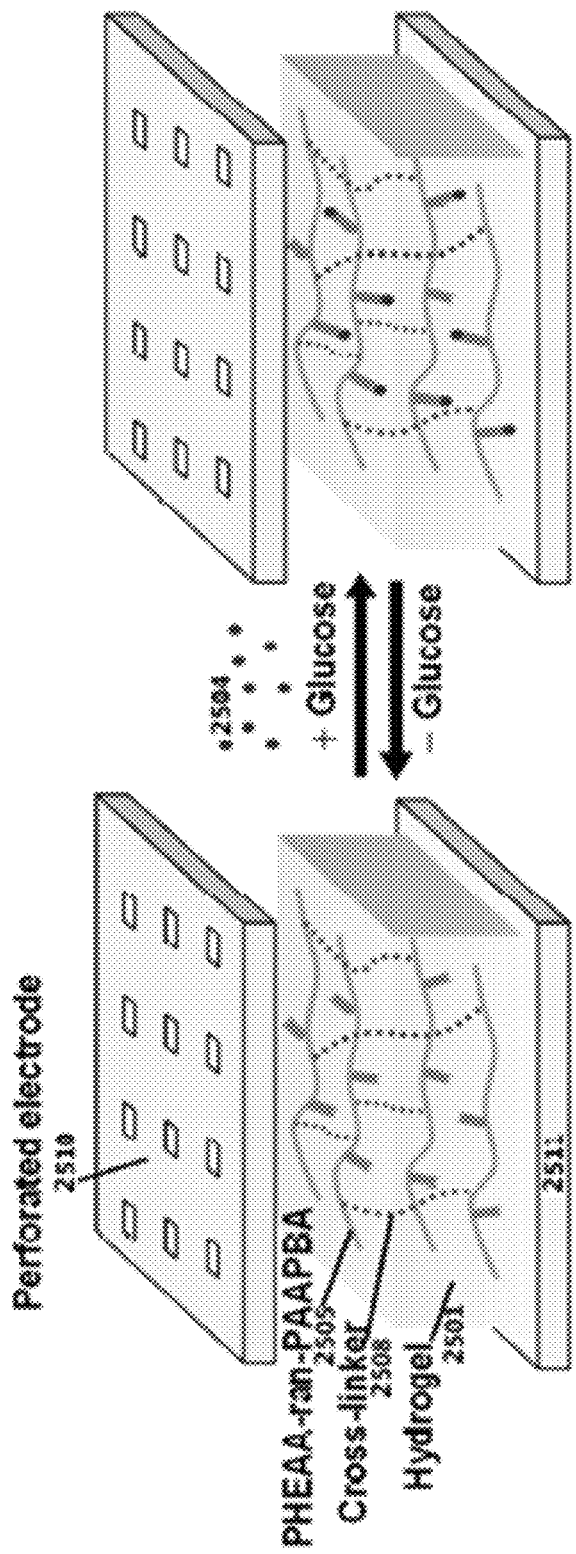

FIG. 75 depicts a hydrogel-based microsensor in accordance with an exemplary embodiment.

Figure 76A:
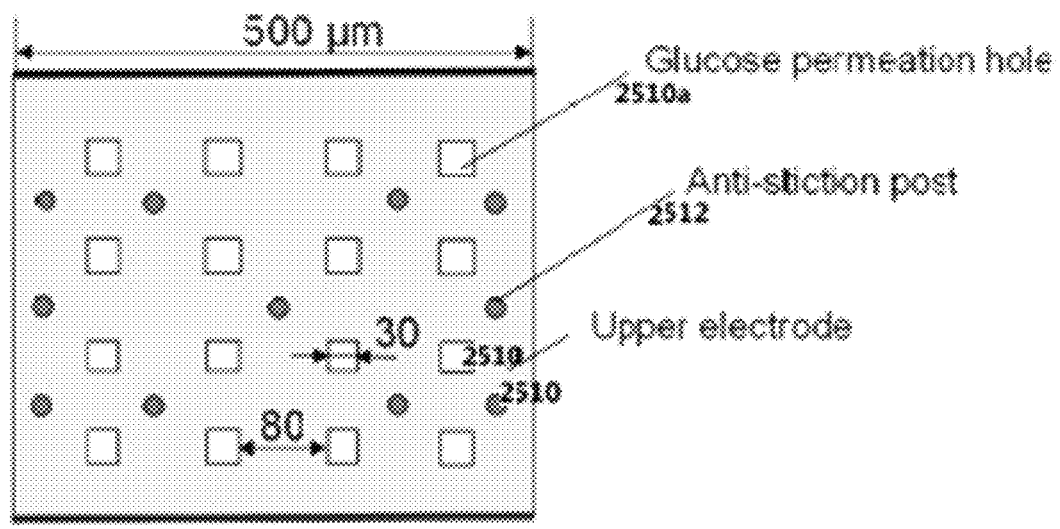
Figure 76B:
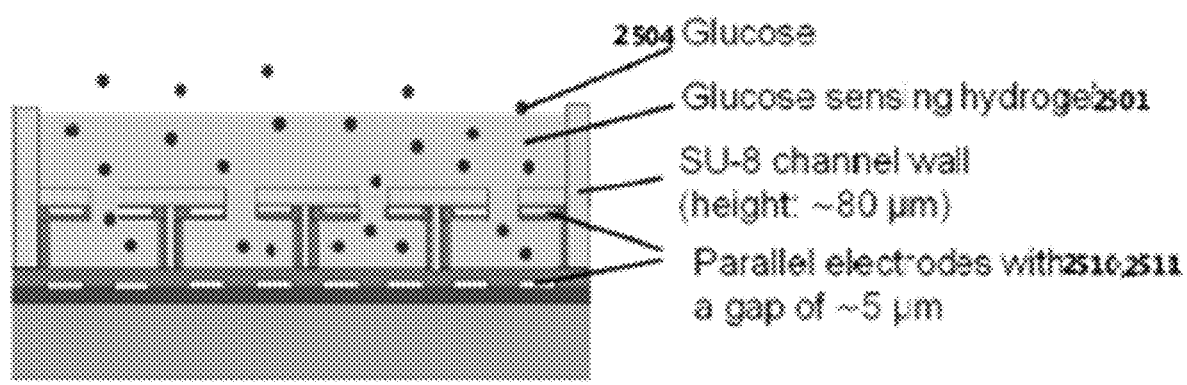
Figure 77A:
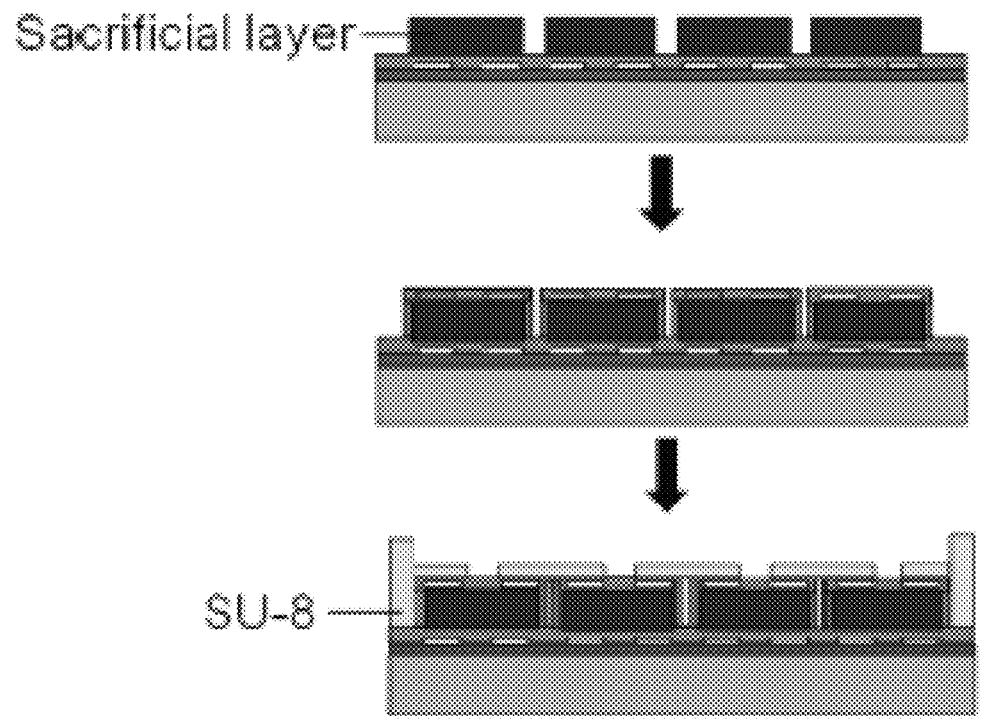
Figure 77B:
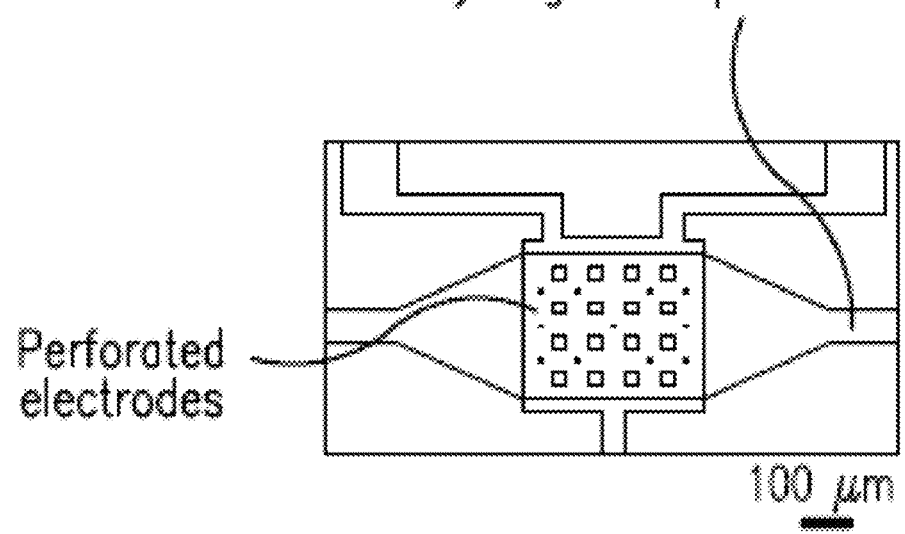
Figure 77C:
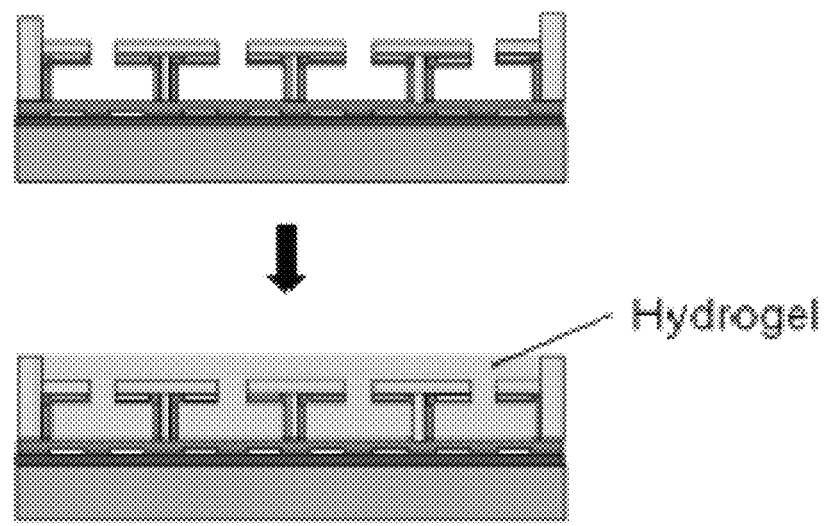
Figure 77D:
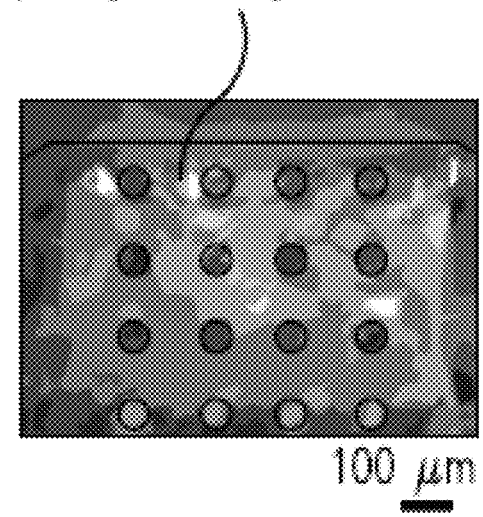
Figure 78A:
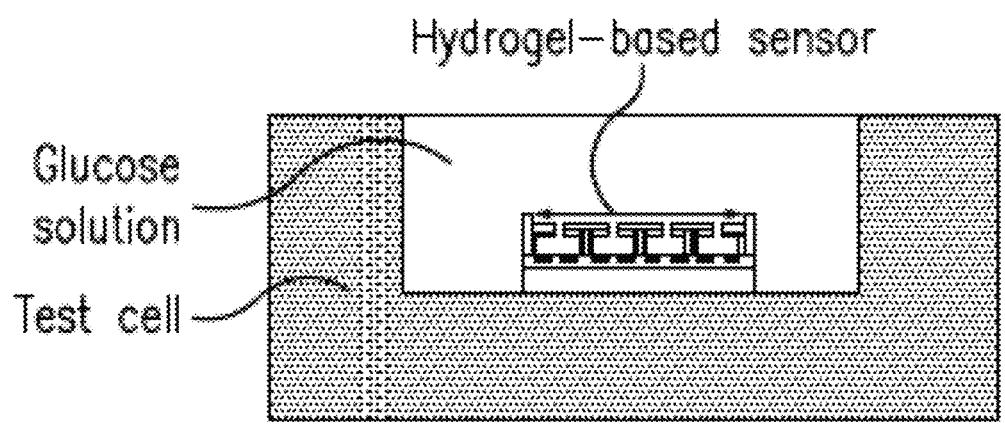
Figure 78B:
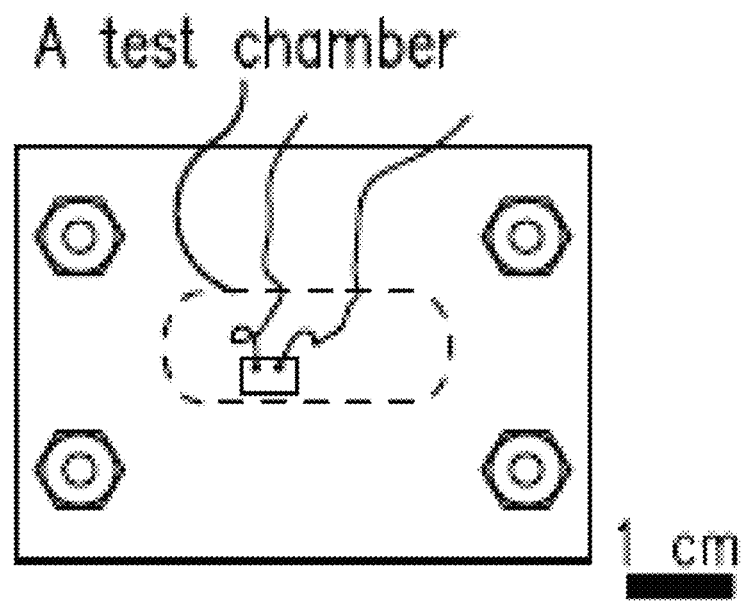
Figure 78C:
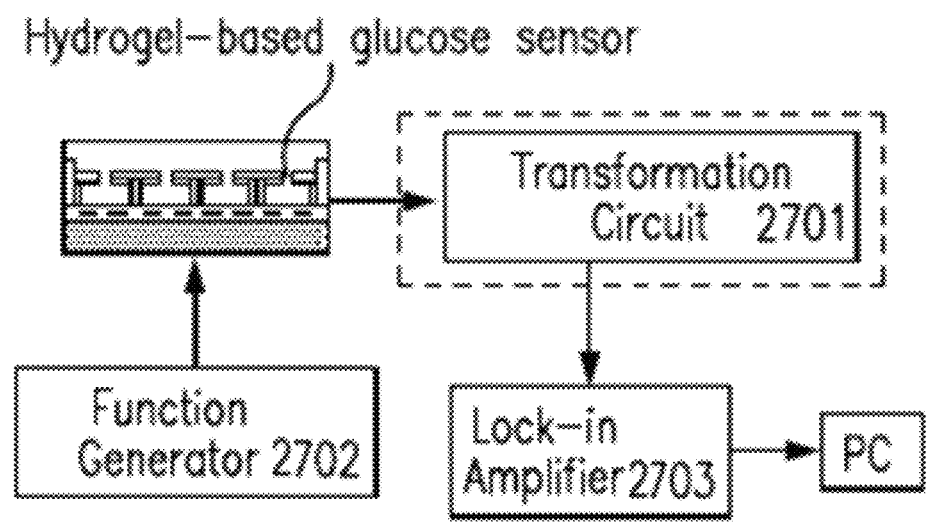
Figure 78D:
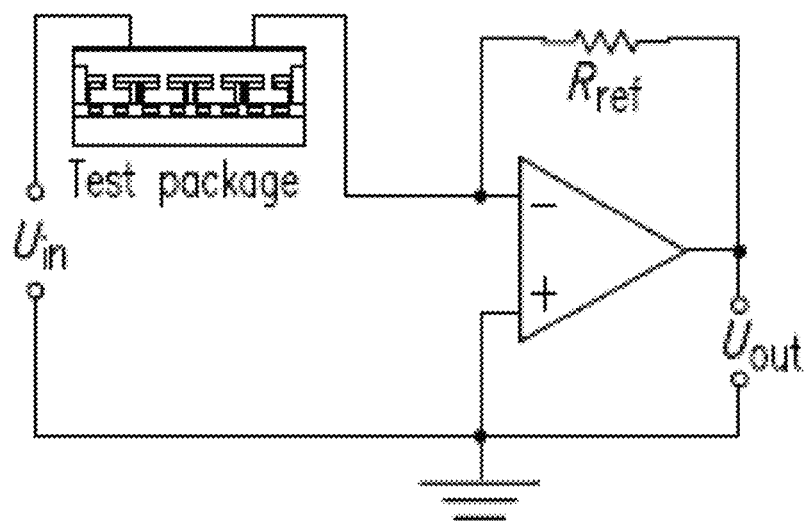

FIGS. 76A-B depicts schematics of an affinity microsensor in accordance with an exemplary embodiment, where (FIG. 76A) depicts a top view of a schematic of an affinity microsensor and (FIG. 76B) depicts a side view of a schematic of an affinity microsensor.

FIGS. 77A-D depict sensor chip fabrication in accordance with an exemplary embodiment, where (FIG. 77A) depicts standard fabrication procedures, (FIG. 77B) depicts an image of a fabricated capacitive transducer, (FIG. 77C) depicts hydrogel integration in a capacitive transducer, and (FIG. 77D) depicts an image of a hydrogel-integrated sensor chip.

FIGS. 78A-D depict a test setup for testing a sensor in accordance with an exemplary embodiment, where (FIG. 78A) depicts a schematic of a testing setup, (FIG. 78B) depicts an image of a testing setup, (FIG. 78C) depicts an example setup, and (FIG. 78D) depicts a capacitance/voltage transformation circuit.

Figure 79A:
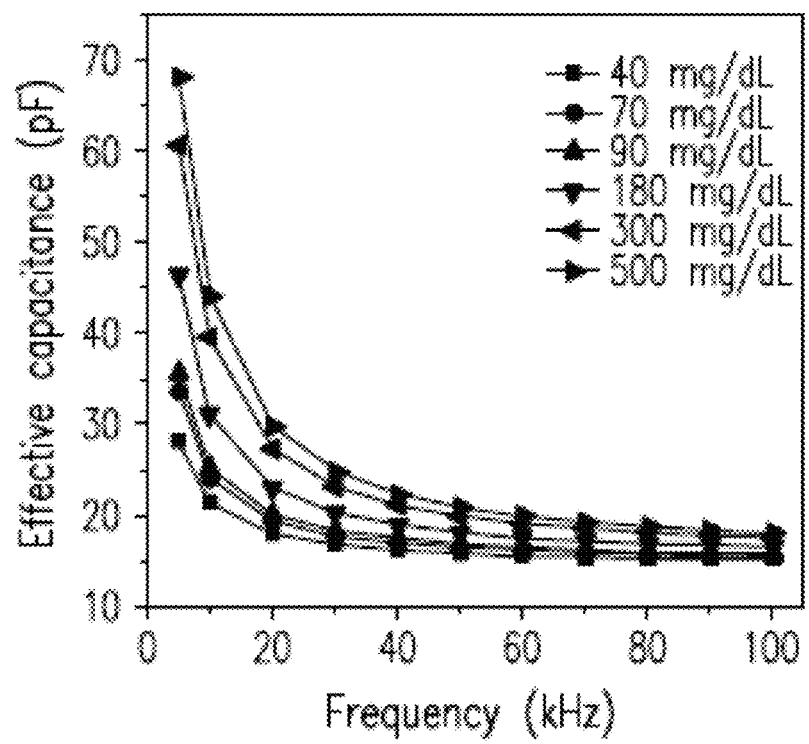
Figure 79B:
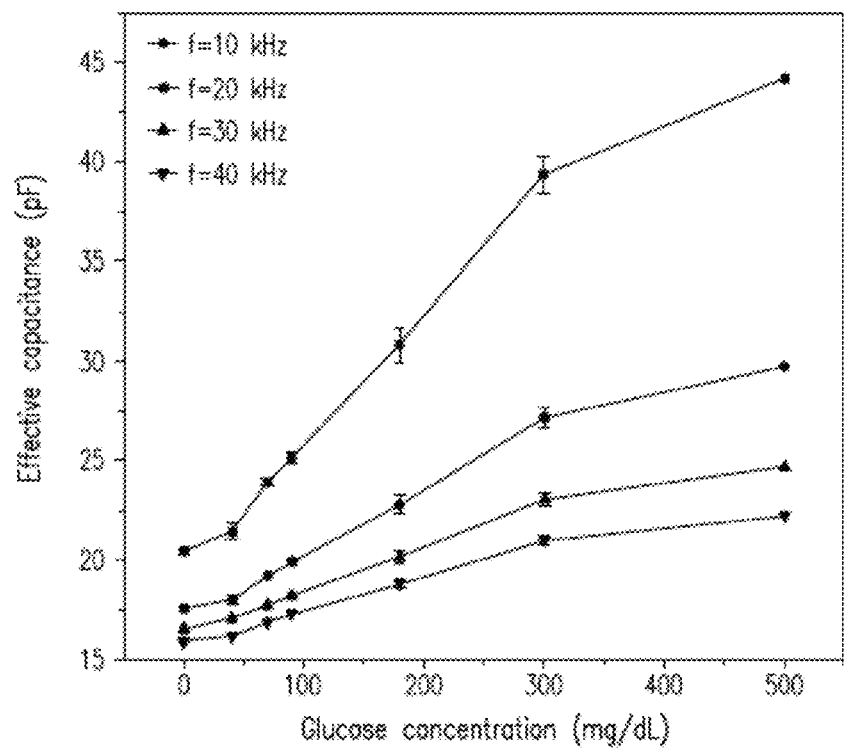

FIGS. 79A-B depict measurements of glucose concentration using a microsensor in accordance with an exemplary embodiment. FIG. 79A depicts dependence of the effective capacitance on measurement frequency. FIG. 79B depicts dependence of the effective capacitance on glucose concentration. Note that exemplary effective capacitance values depicted herein are averages of triplicate measurements, and standard errors are shown as error in FIG. 79B.

Figure 80A:
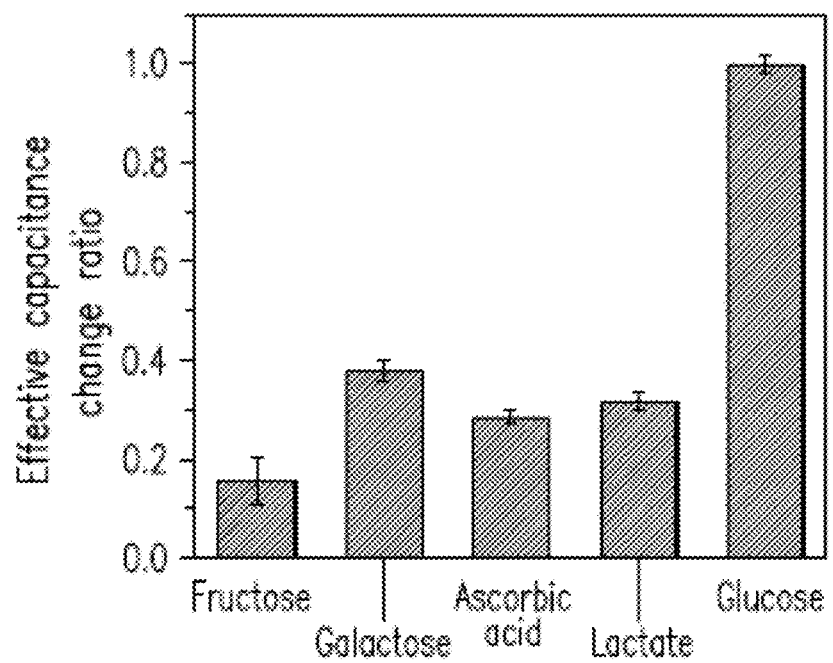
Figure 80B:
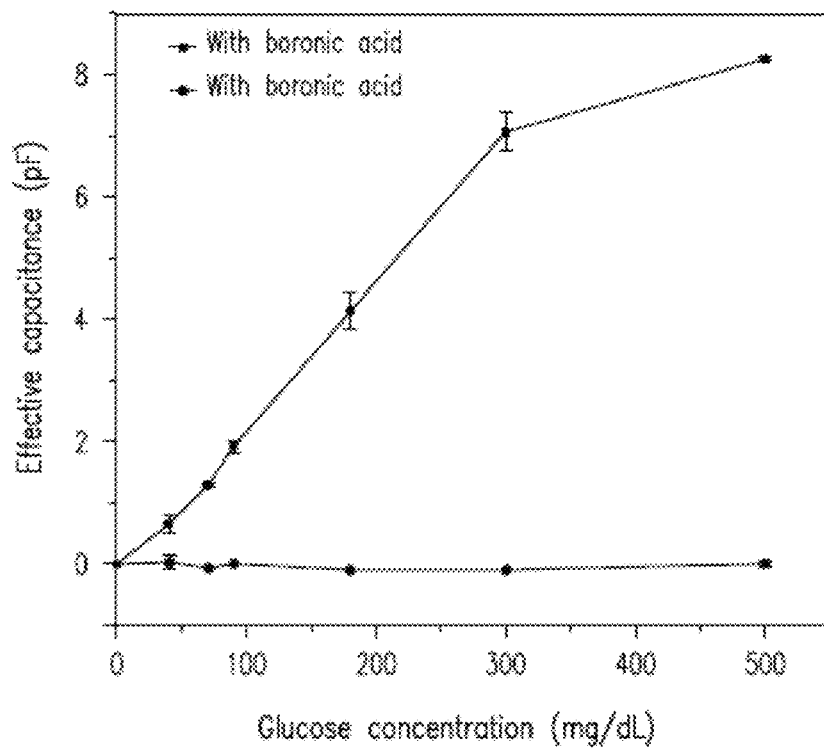

FIGS. 80A-B depict dependence of effective capacitance on glucose concentration in accordance with an exemplary embodiment, where (FIG. 80A) depicts a ratio of interferent-induced effective capacitance change to glucose-induced capacitance change (concentration: 90 mg/dL for glucose and each of the interferents including fructose, galactose, ascorbic acid, and lactate), and (FIG. 80B) depicts sensor response to glucose when boronic acid components are absent in the hydrogel. Note the bias voltage frequency of the embodiments depicted in FIG. 80A-B are 30 kHz.

Figure 81:
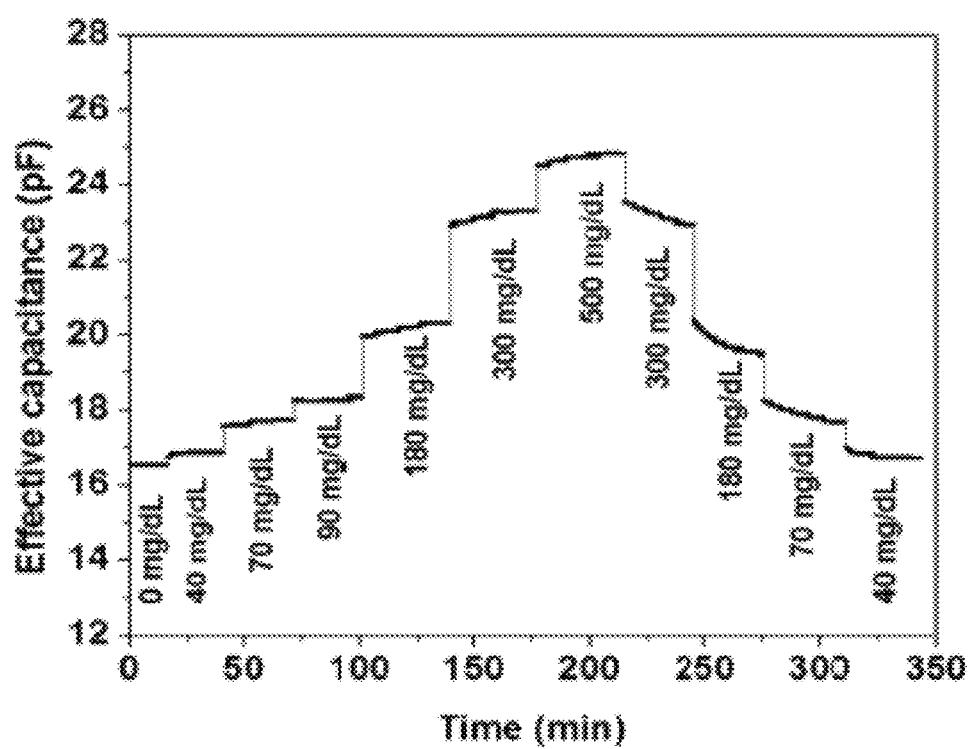

FIG. 81 depicts the time-resolved device response to time-varying glucose concentration with a bias voltage frequency of 30 kHz in accordance with an exemplary embodiment.

Figure 82:
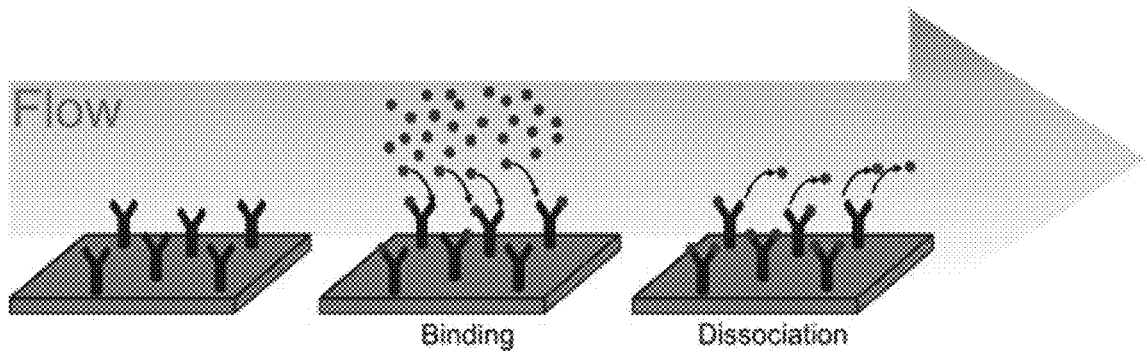

FIG. 82 depicts the process of association and dissociation between aptamers and analytes.

Figure 83:
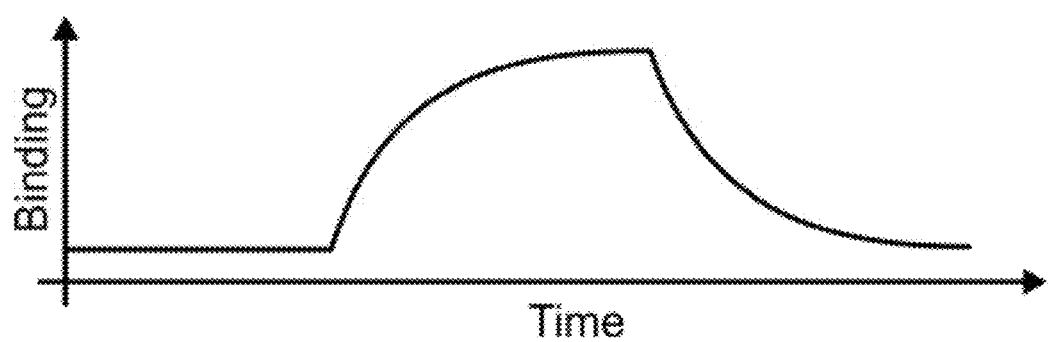

FIG. 83 depicts a graph illustrating the binding kinetics of aptamer-analyte interaction.

Figure 84:
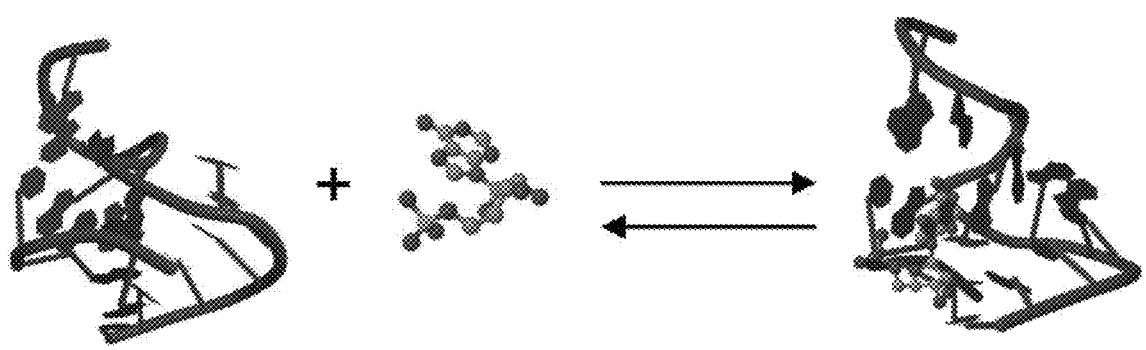

FIG. 84 depicts a diagram illustrating the aptamer-analyte interaction.

FIGS. 85A-E depict diagrams illustrating the process by which a graphene surface can be functionalized with aptamers.

Figure 86:
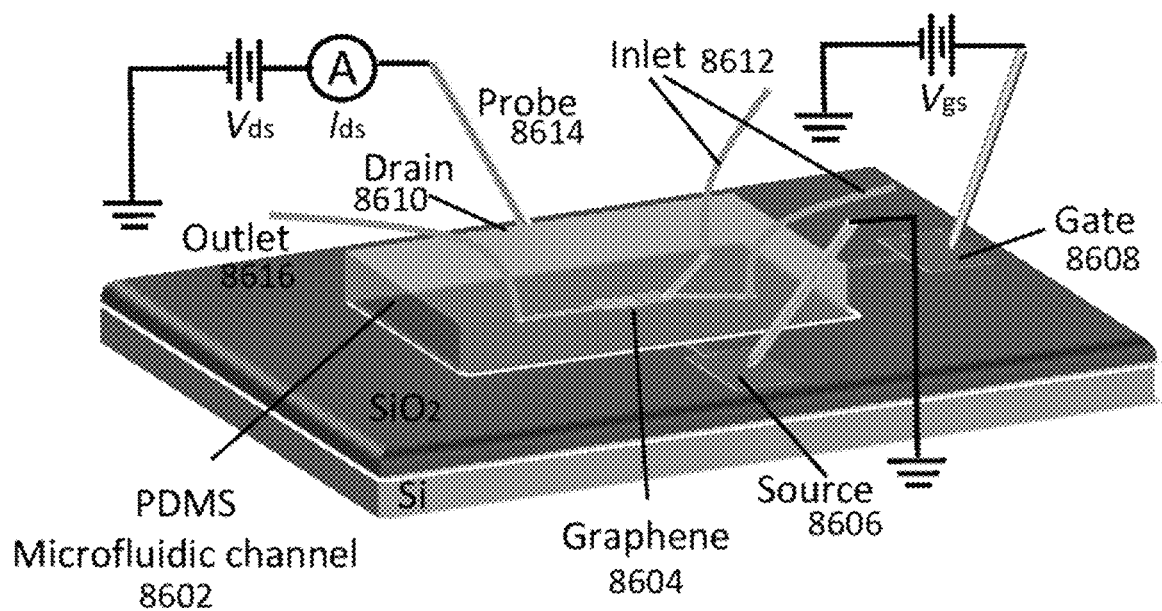

FIG. 86 depicts a diagram illustrating a sensor device used to detect analyte binding to the aptamer functionalized graphene surface.

Figure 87A:
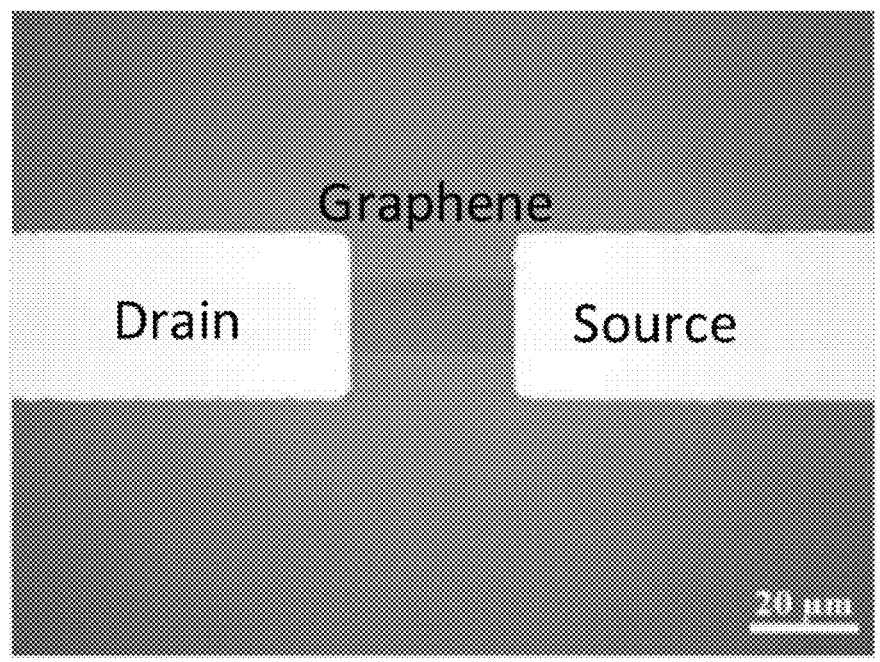
Figure 87B:
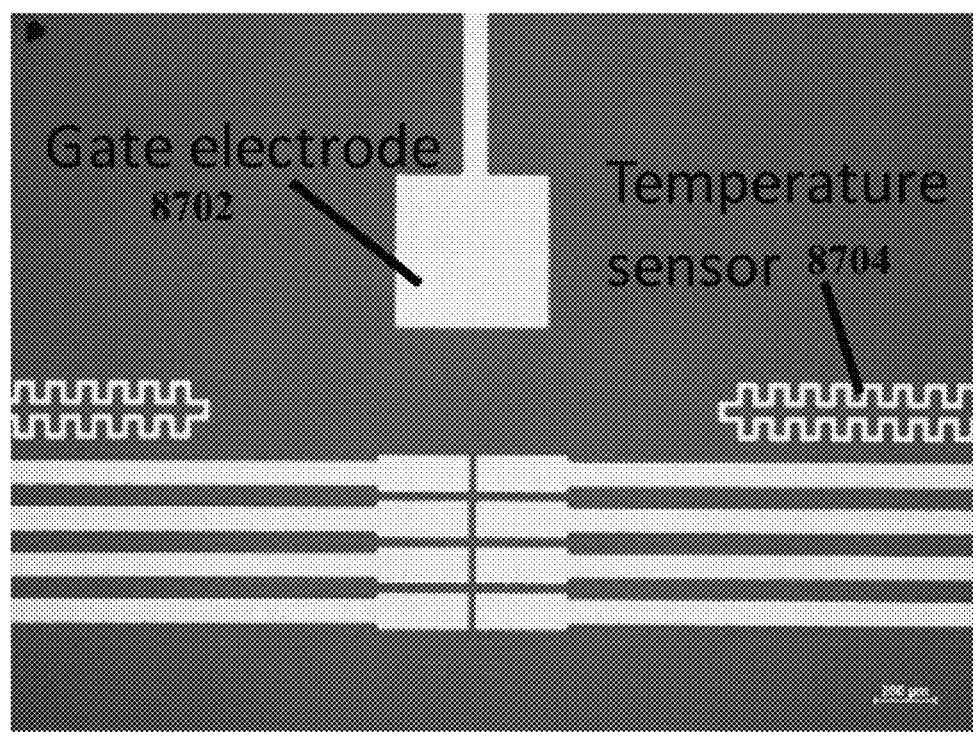
Figure 87C:
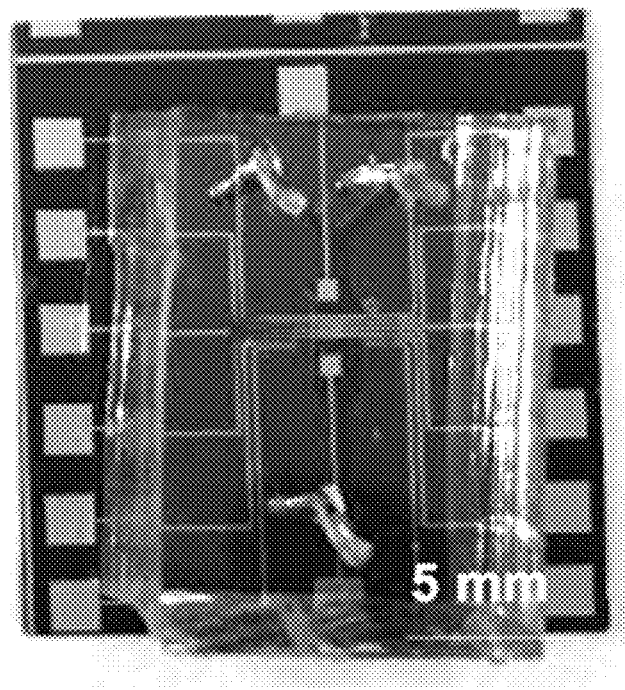

FIGS. 87A-C depict diagrams illustrating different aspects of the fabricated sensor device of FIG. 86.

Figure 88:
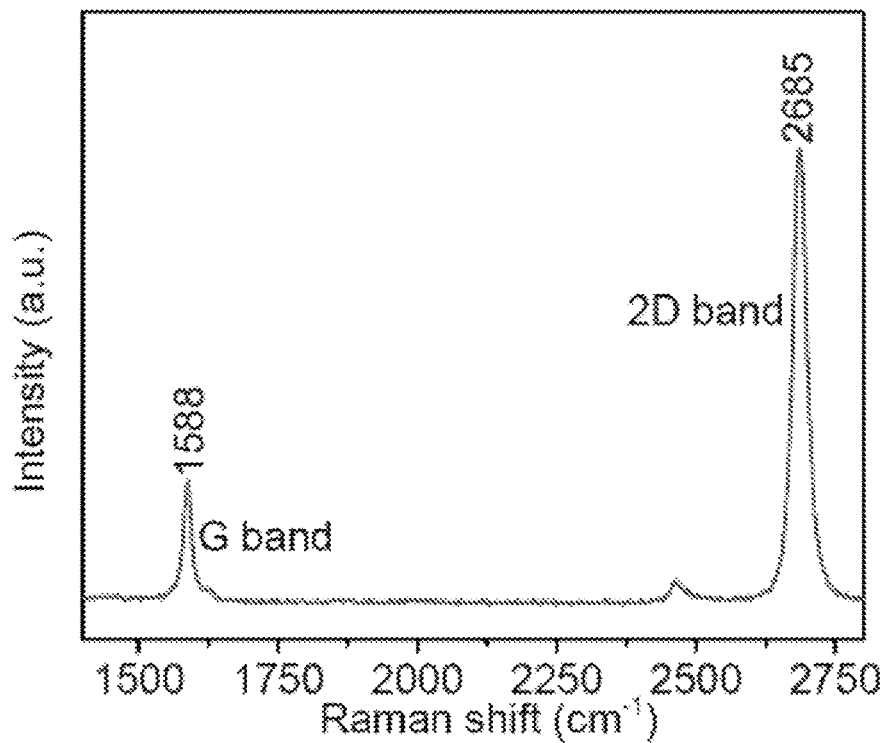

FIG. 88 depicts a graph illustrating Raman spectrum measurements of a single-layer graphene flake used in the sensor device.

Figure 89A:
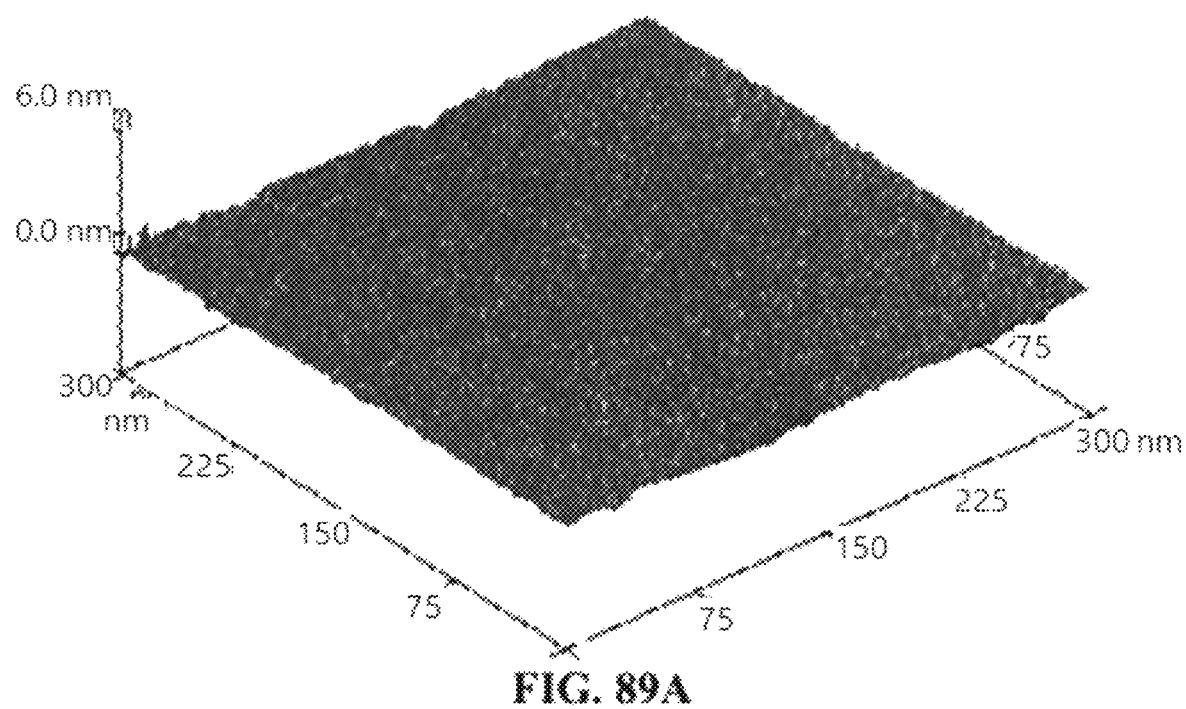
Figure 89B:
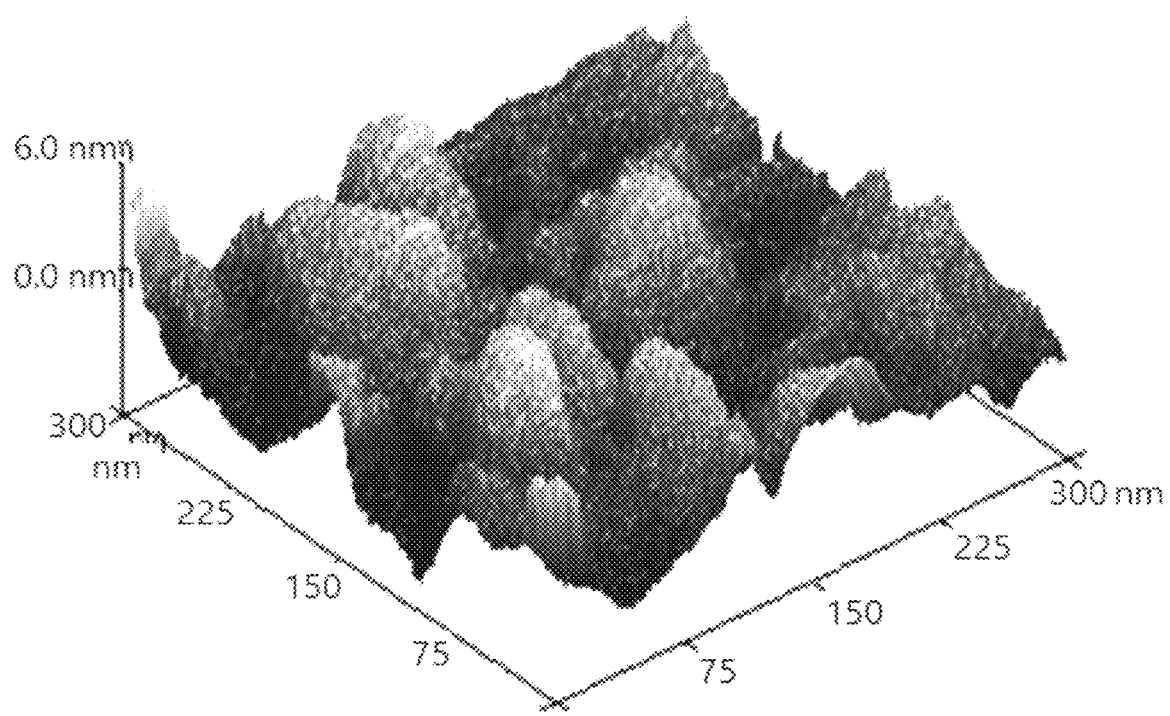

FIGS. 89A-B depict surface morphology images illustrating the surface of the graphene before and after the graphene surface is functionalized with aptamers.

Figure 90:
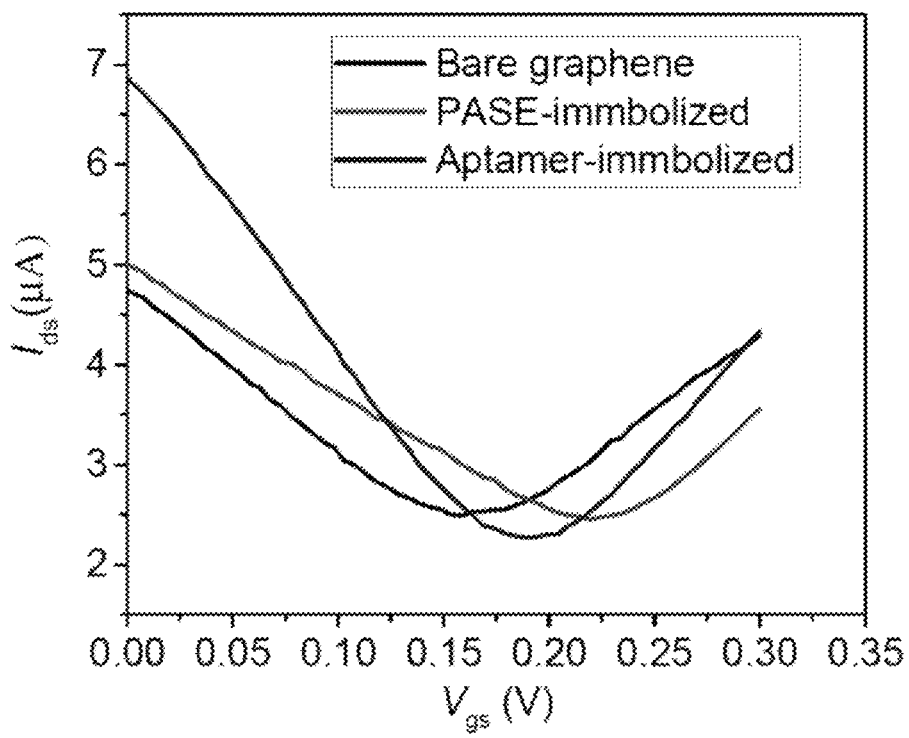

FIG. 90 depicts a graph characterizing the graphene surface functionalization.

Figure 91A:
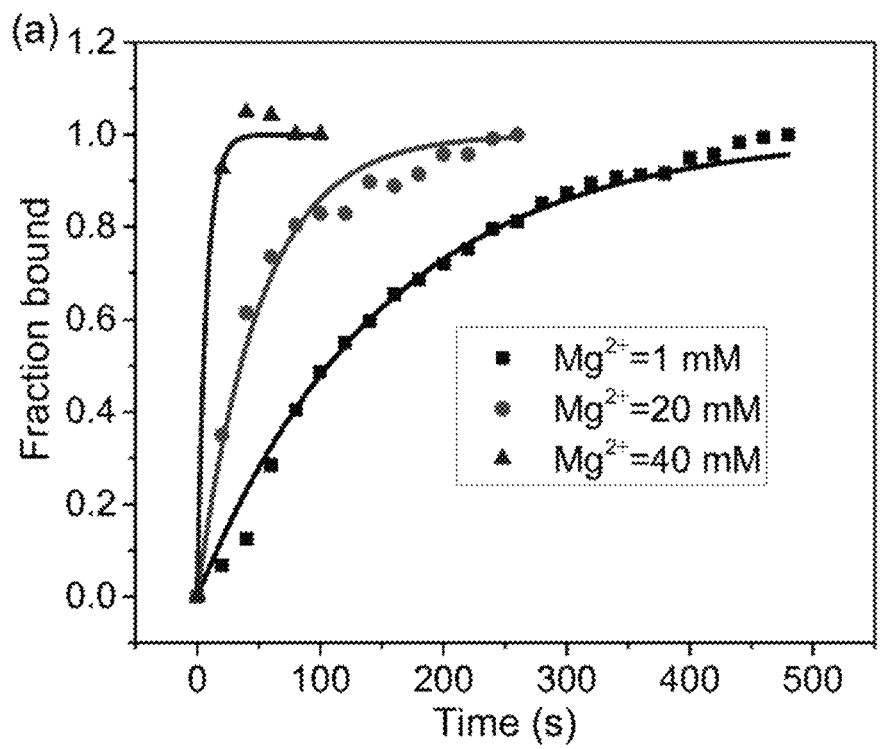
Figure 91B:
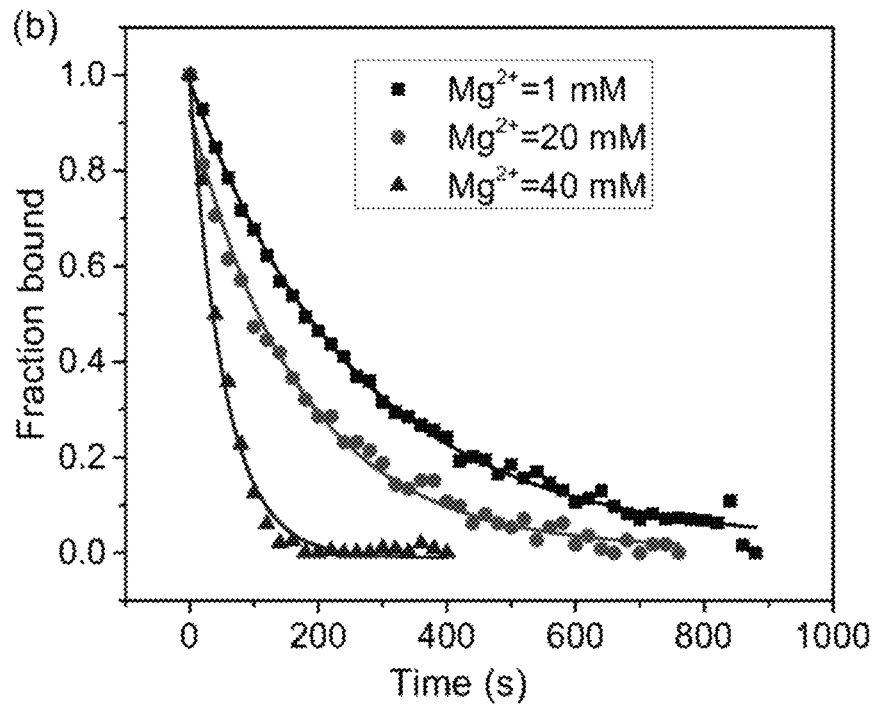

FIGS. 91A-B depict graphs illustrating association and disassociation profiles of the aptamer interaction at different levels of $Mg^{2+}$.

Figure 92A:
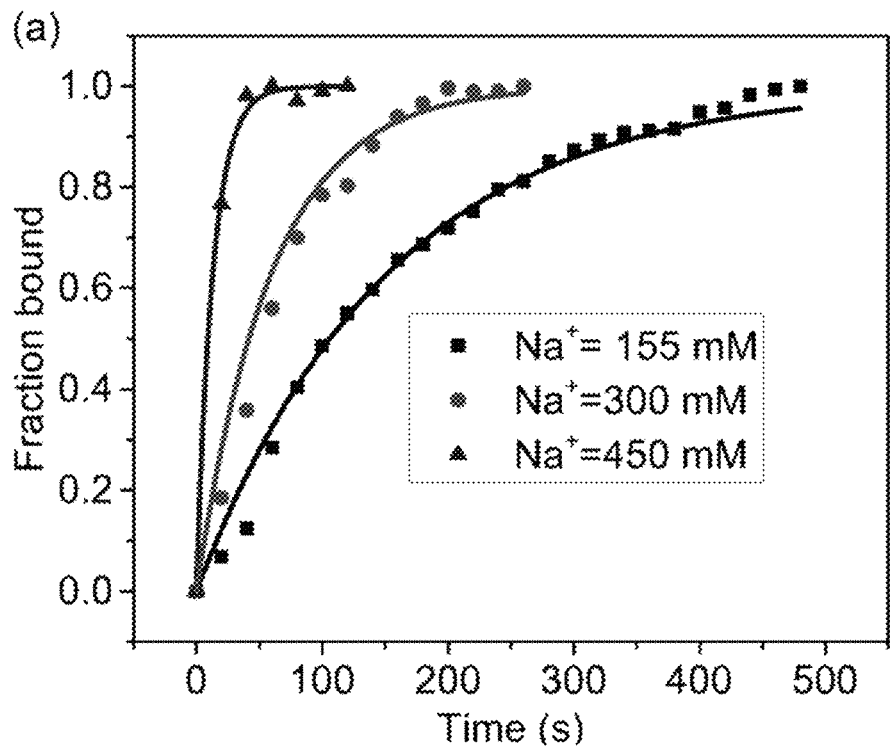
Figure 92B:
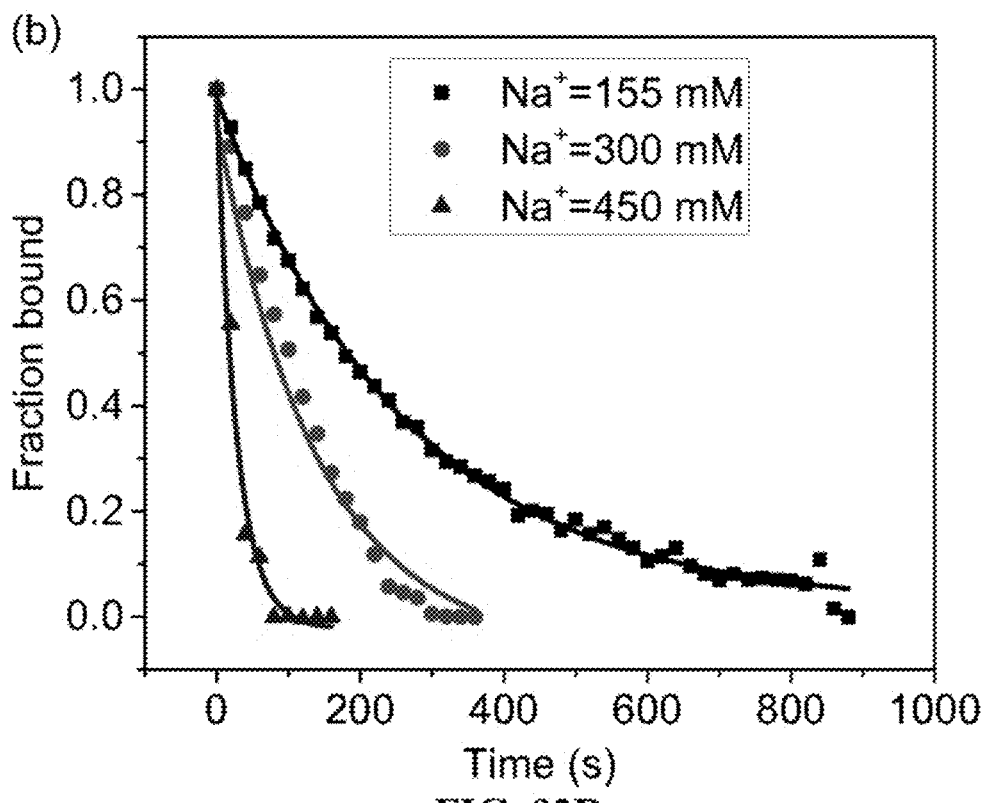

FIGS. 92A-B depict graphs illustrating association and disassociation profiles of the aptamer interaction at different levels of $Na^+$.

Figure 93:
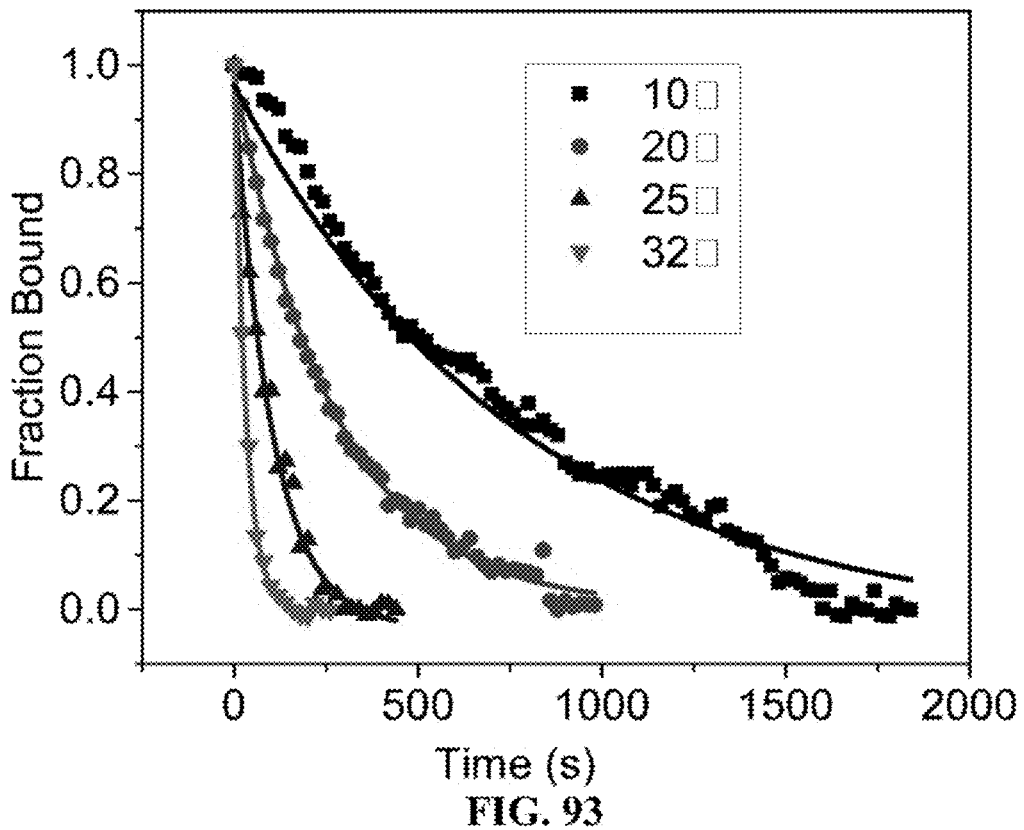

FIG. 93 depicts a graph illustrating the disassociation profiles of the aptamer interaction at varying temperatures.

Figure 94:
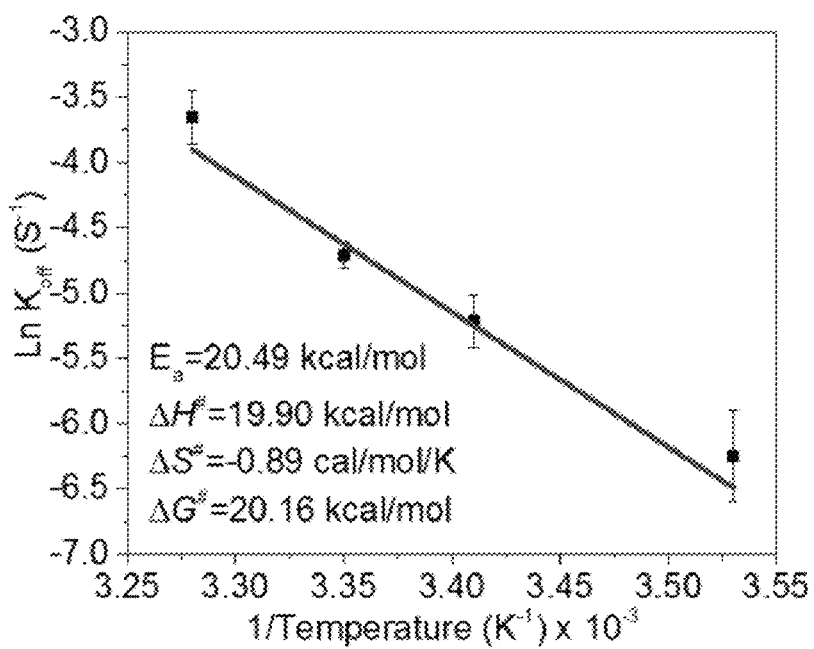

FIG. 94 depicts a graph illustrating an Arrhenius plot for disassociation of aptamers as a function of temperature.

Figure 95:
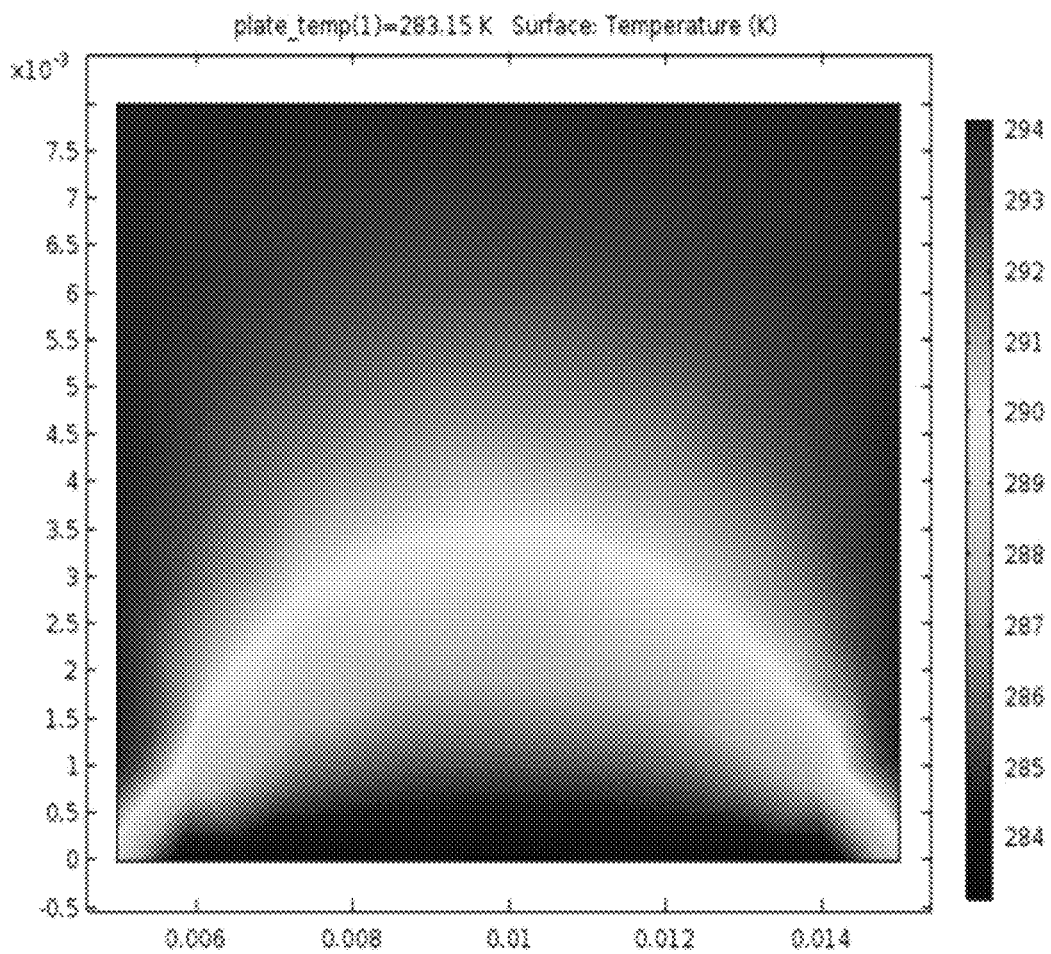

FIG. 95 depicts a temperature map illustrating the temperature distribution in the channel of the sensor device.

Figure 96A:
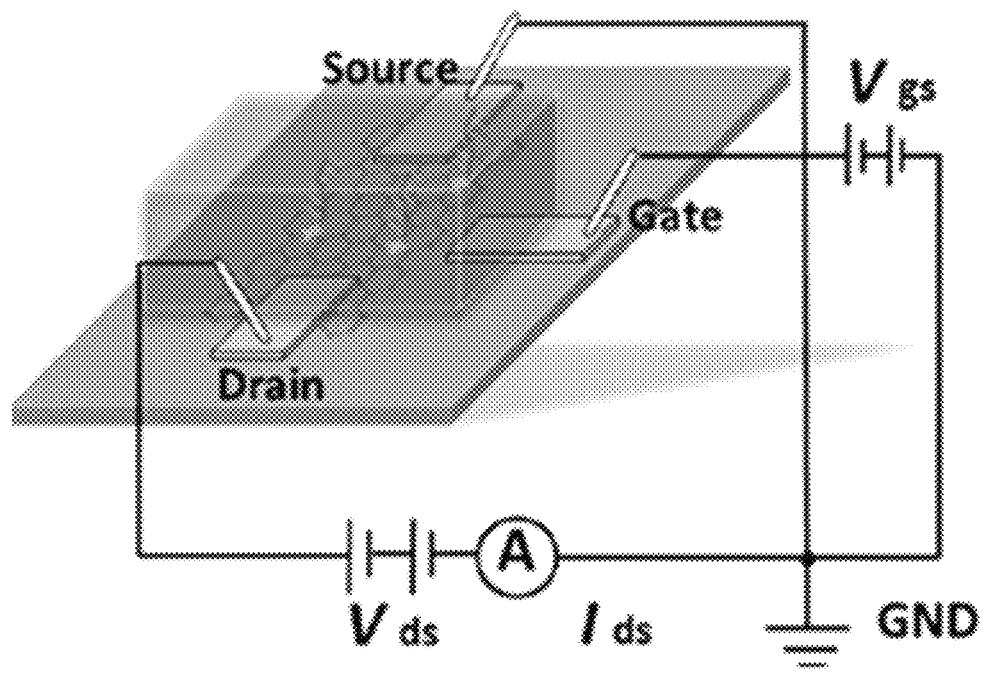
Figure 96D:
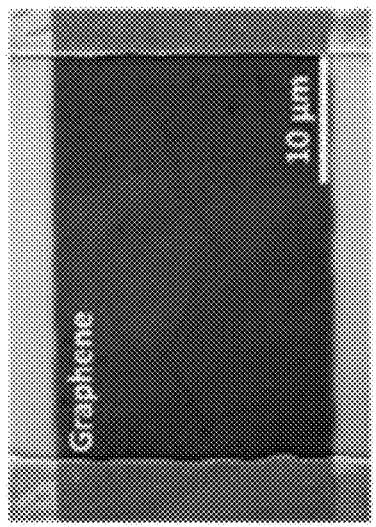
Figure 96C:
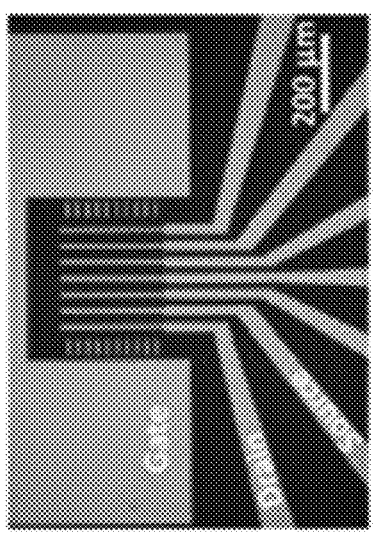
Figure 96B:
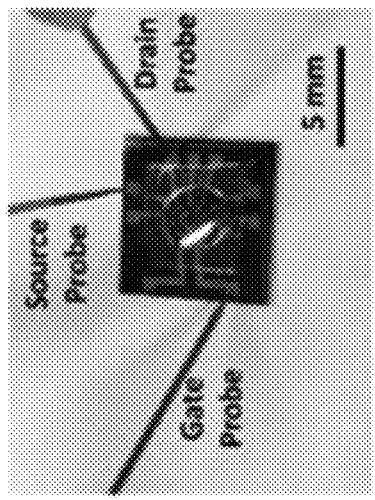

FIG. 96A is a schematic illustration of an exemplary nanosensor system in accordance with the present disclosure. FIG. 96B provides a photograph of exemplary nanosensor packed in a PDMS chamber for liquid handling. FIG. 96C is an optical micrograph of an exemplary fabricated nanosensor. FIG. 96D provides a scanning electron micrograph of an exemplary single-layer graphene-conducting channer in a nanosensor system in accordance with the present disclosure.

Figure 97:
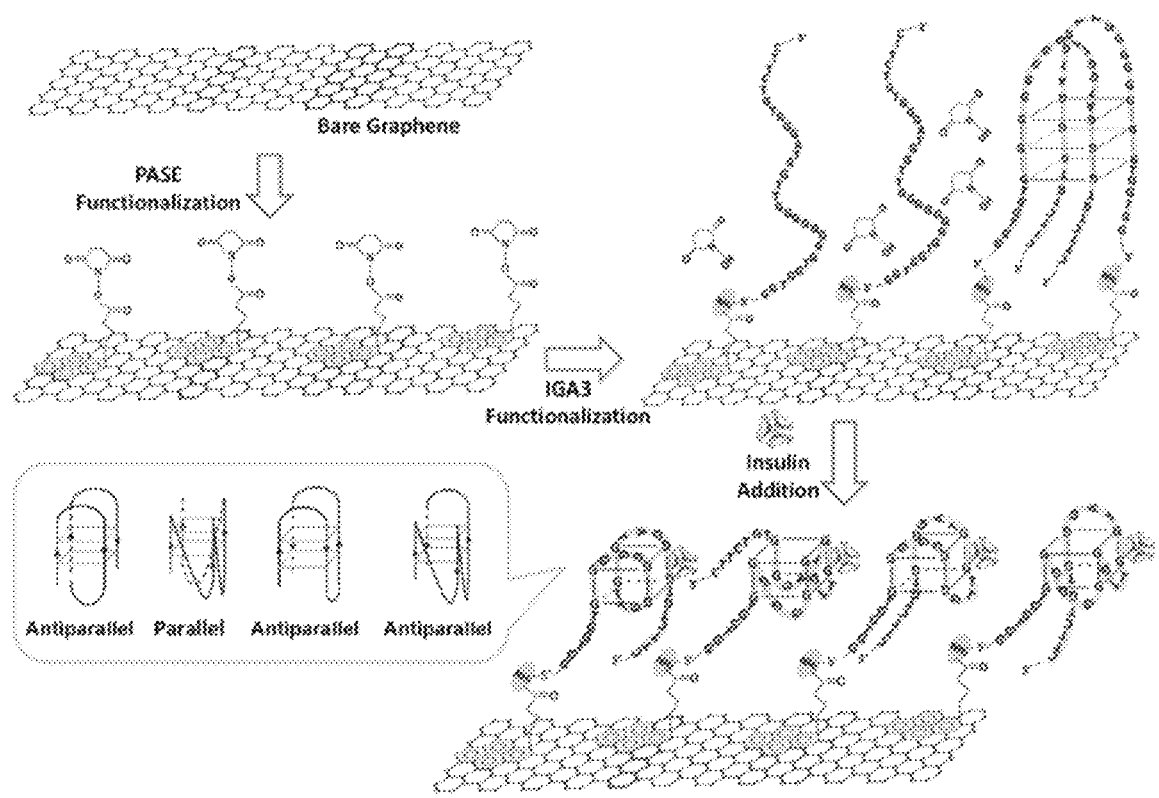

FIG. 97 is a schematic illustration of exemplary insulin detection using the disclosed nanosensor. FIG. 97 discloses "GGTGGTGGGGGGGGTTGGTAGGGTGTCTTC" as SEQ ID NO: 1.

Figure 98A:
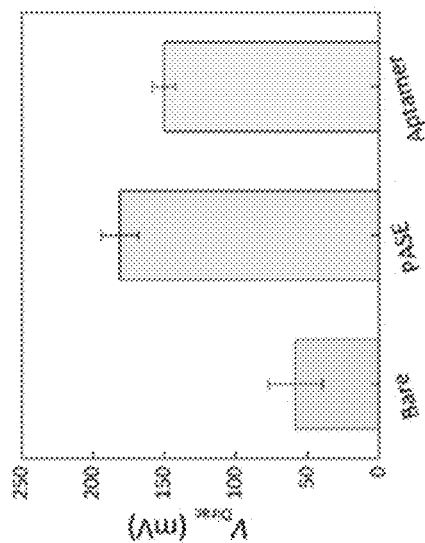
Figure 98B:
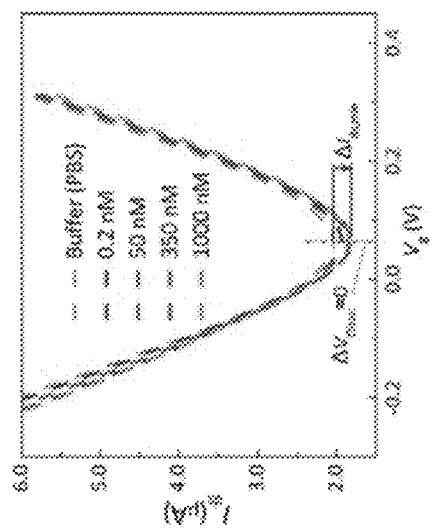

FIG. 98A provides voltage-current plots illustrating exemplary transfer characteristics of bare graphene exposed to insulin solutions (200 pM to 1 µM). FIG. 98B provides a $V_{Dirac}$ (voltage at which the current reaches its minimum) graph illustrating variation in $V_{Dirac}$ of graphene before and after exposure to the 1-pyrenebutanoic acid succinimidyl ester (PASE) solution aptamer functionalization.

Figure 98C:
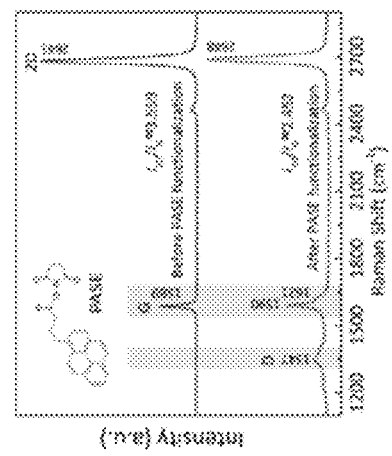
Figure 98D:
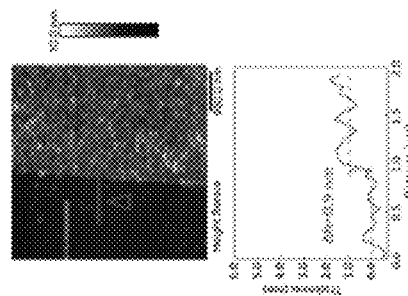
Figure 98E:
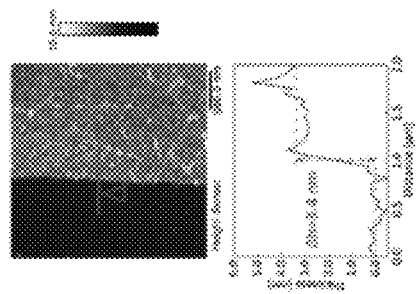

FIG. 98C provides raman spectra of graphene before and after exposure to the PASE solution. FIG. 98D provides an atomic force microscopy (AFM) image of bare graphene and a thickness plot. FIG. 98E provides an AFM image of the aptamer-functionalized graphene and thickness plot.

Figure 99A:
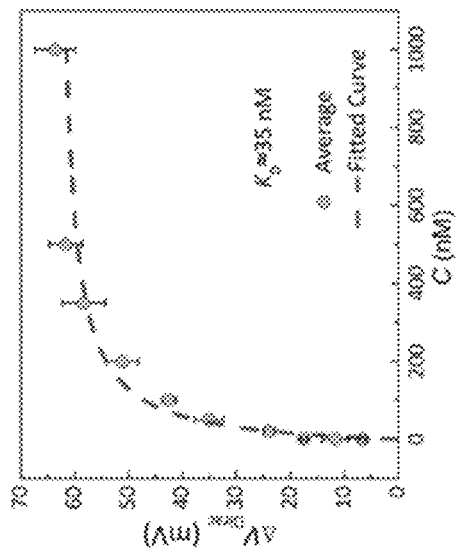
Figure 99B:
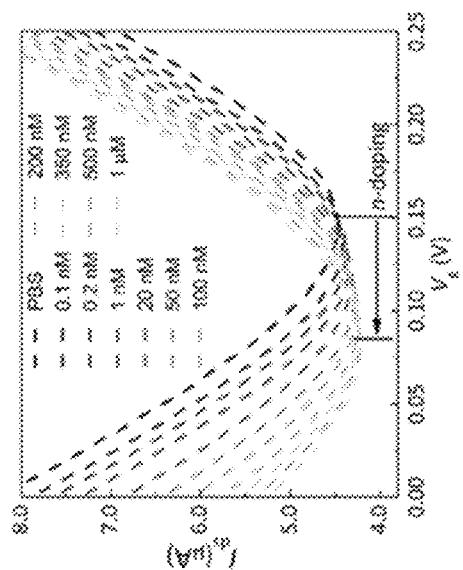

FIG. 99A provides voltage-current plots illustrating transfer characteristic of exemplary the aptamer-functionalized graphene exposed to insulin solutions. FIG. 99B provides a $V_{Dirac}$ graph exemplary the aptamer-functionalized graphene illustrating voltage shift as a function of the insulin concentrations.

Figure 100A:
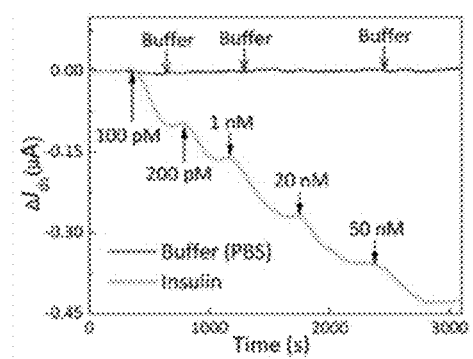
Figure 100B:
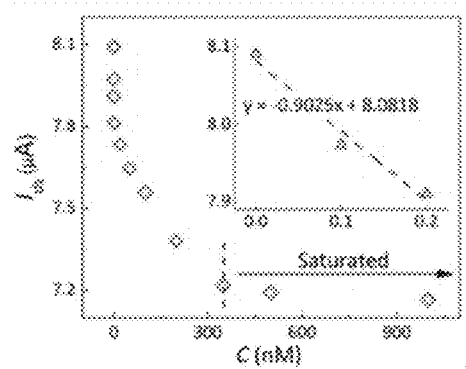

FIG. 100A provides current shift plots illustrating real-time monitoring of changes in the insulin concentration. FIG. 100B provides a drain-source current showing decrease of the drain-source current with increasing insulin concentration.

Figure 100C:
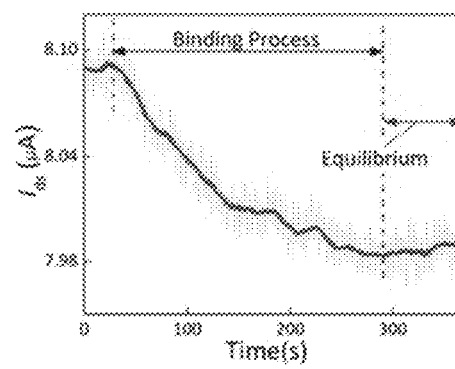

FIG. 100C provides time course of the drain-source current upon introduction of 100 pM insulin solution.

Figure 101B:
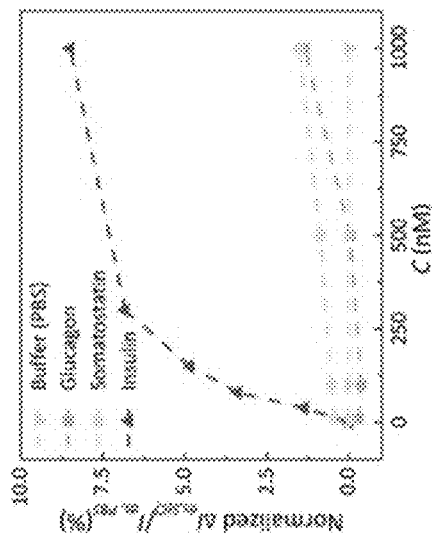
Figure 101A:
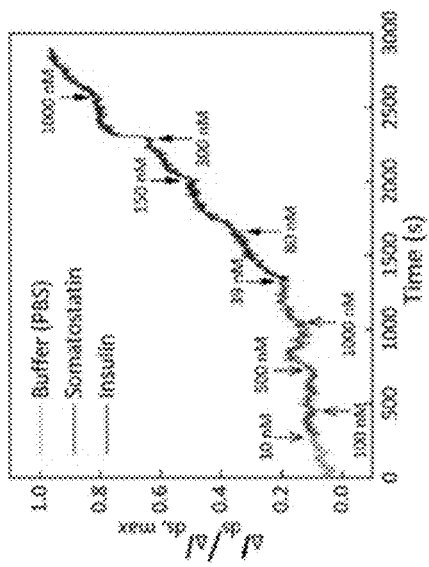

FIG. 101A provides time-resolved responses of exemplary IGA3 aptamer-based graphene sensor to insulin and somatostatin. FIG. 101B provides dose dependent responses of exemplary IGA3 aptamer-based graphene sensor to buffer, insulin, glucagon, and somatostatin illustrating specificity of the nanosensor to insulin.

Figure 102B:
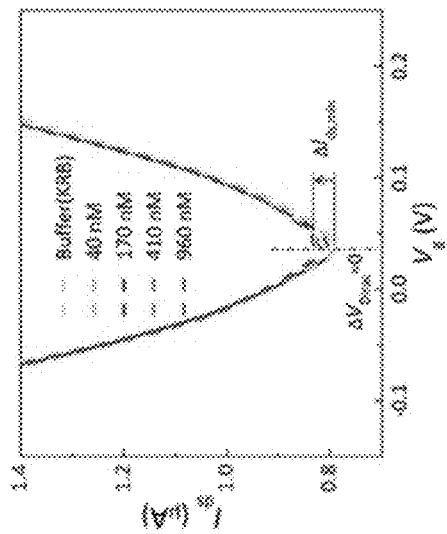
Figure 102A:
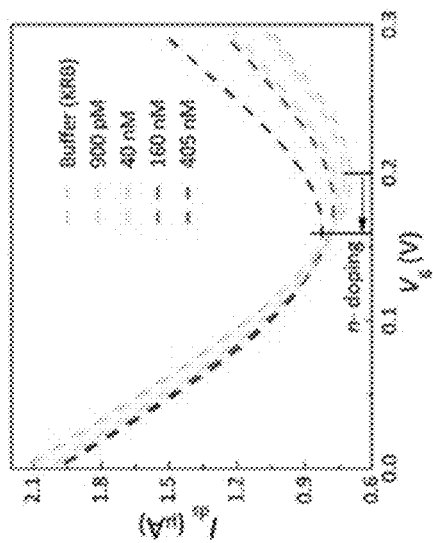

FIG. 102A provides voltage-current plots illustrating transfer characteristics of the untreated graphene exposed to insulin solutions ranging from 40 to 960 nM. FIG. 102B provides voltage-current plots illustrating transfer characteristic measured when the aptamer-immobilized graphene exposed to insulin solutions ranging 900 pM to 405 nM.

Figure 103:
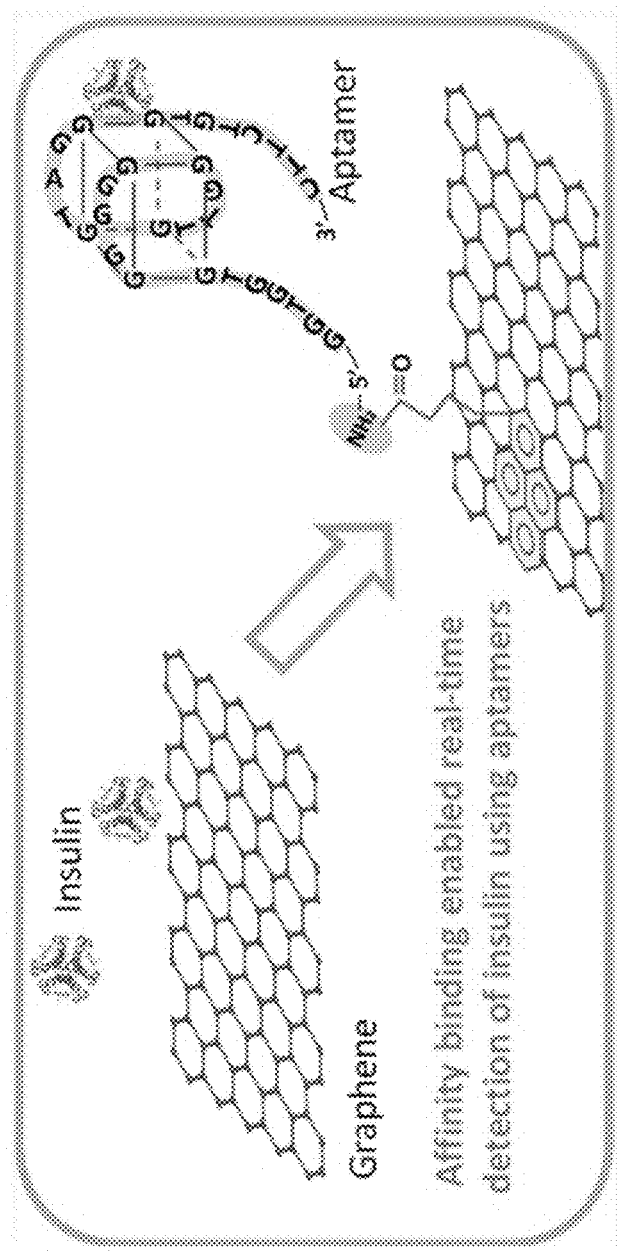

FIG. 103 is a schematic illustration of an exemplary graphene based nanosensor for insulin detection. FIG. 103 discloses SEQ ID NO: 1.

Figure 104:
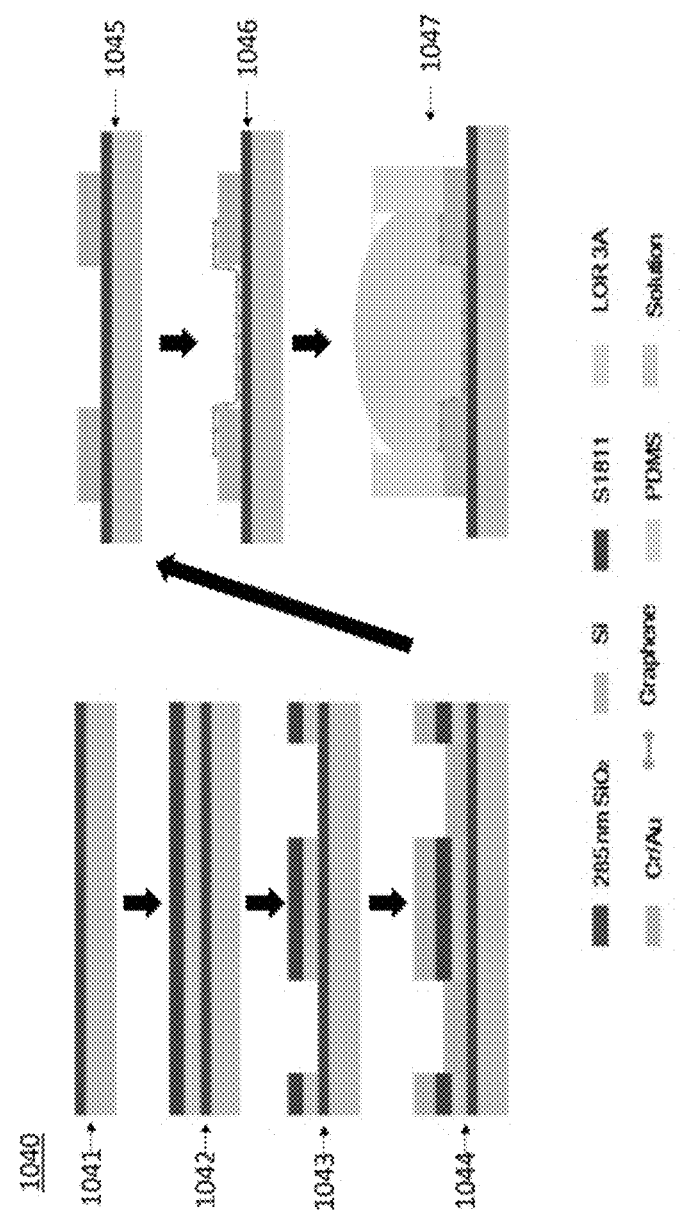

FIG. 104 provides a schematic illustration of an exemplary fabrication process of the disclosed nanosensor.

Figure 105:
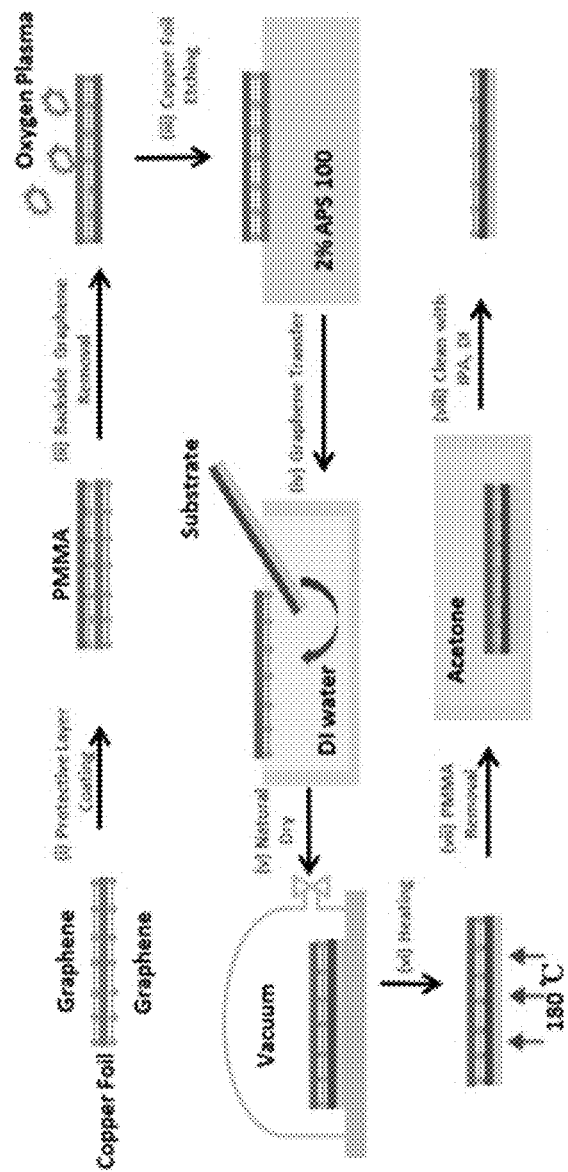

FIG. 105 is a schematic illustration of an exemplary transfer process of monolayer graphene onto arbitrary substrates.

Figure 106A:
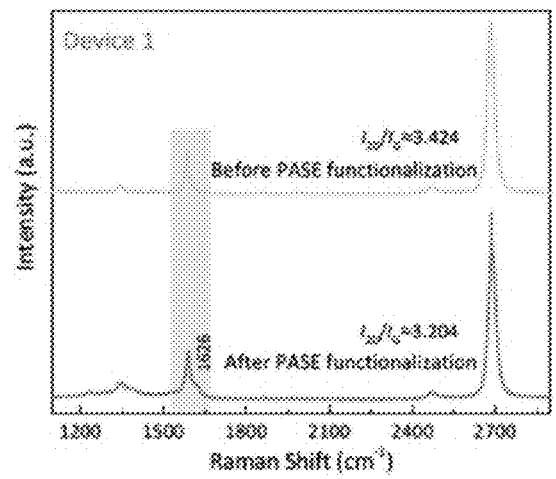
Figure 106B:
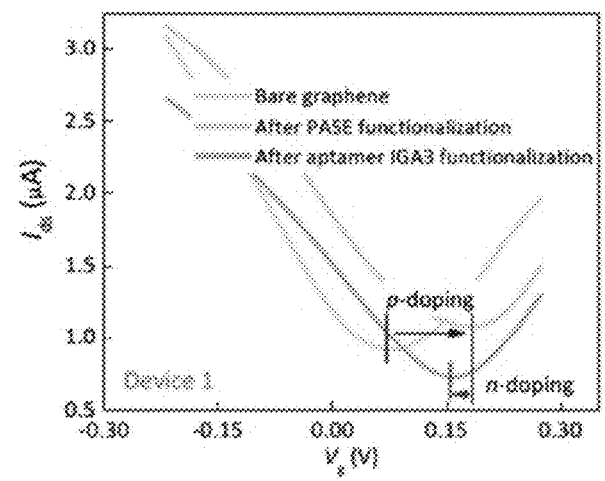
Figure 106C:
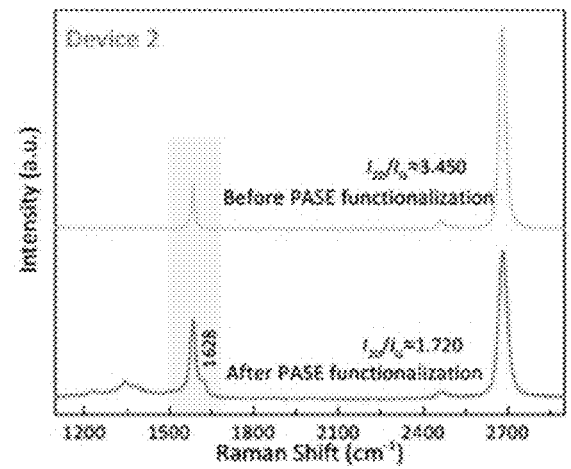
Figure 106D:
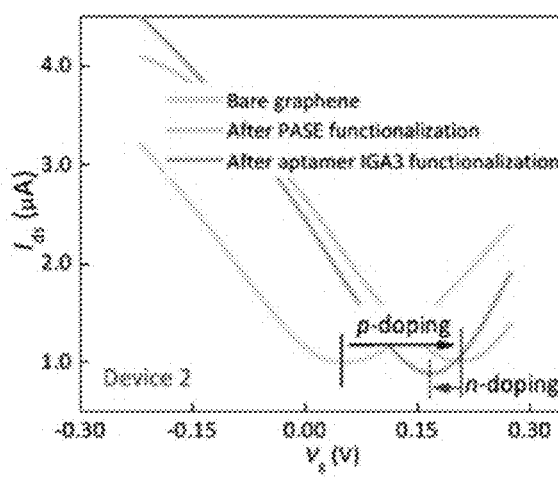
Figure 106E:
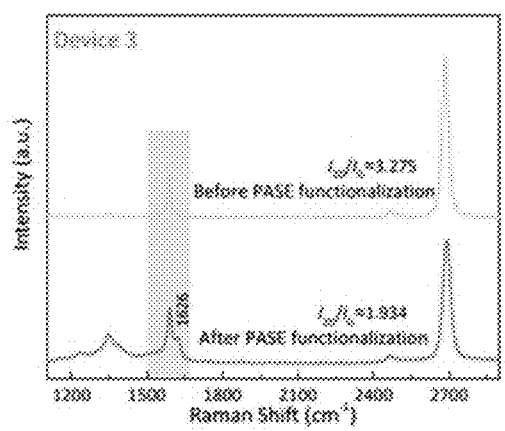
Figure 106F:
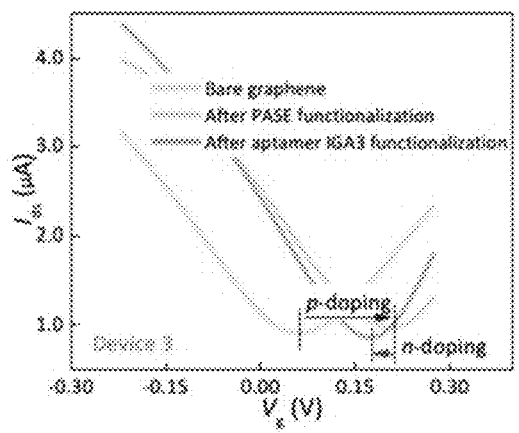
Figure 106G:
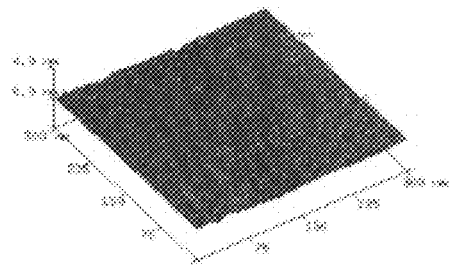
Figure 106H:
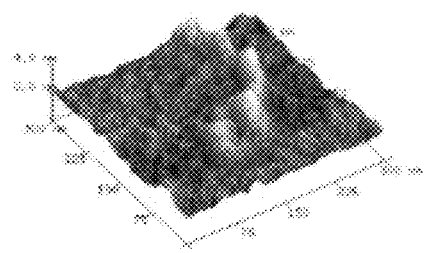

FIG. 106A is a raman spectrum of PASE functionalized graphene-based device 1. FIG. 106B provides voltage-current plots of PASE functionalized graphene-based device 1. FIG. 106C is a raman spectrum of PASE functionalized graphene-based device 2. FIG. 106D provides voltage-current plots of PASE functionalized graphene-based device 2. FIG. 106E is a raman spectrum of PASE functionalized graphene-based device 3. FIG. 106F provides voltage-current plots of PASE functionalized graphene-based device 3. FIG. 106G is an atomic force microscopy (AFM) AFM image of the graphene surface without aptamer functionalization. FIG. 106H is an AFM image of the graphene surface with aptamer functionalization.

Figure 107:
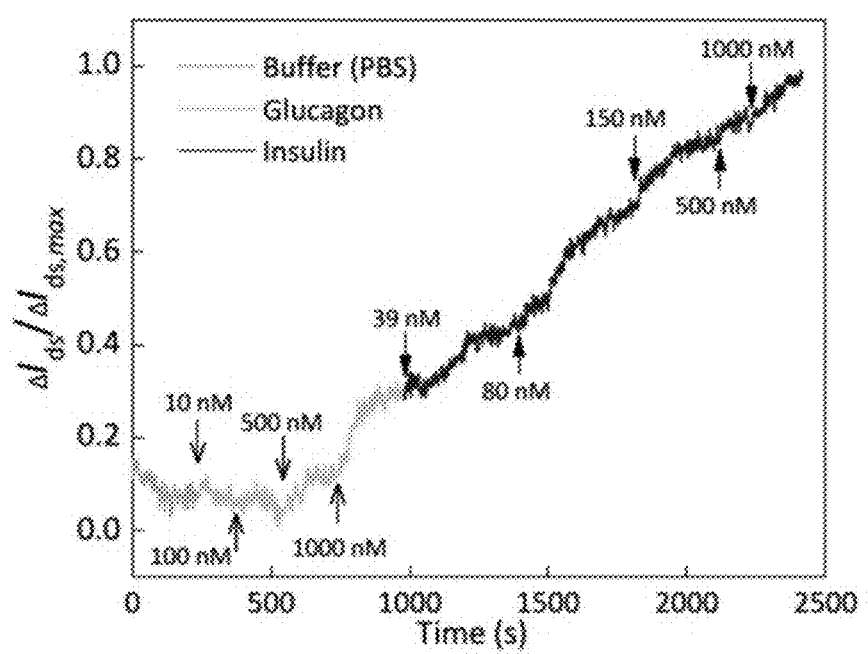

FIG. 107 provides a plot illustrating time-resolved response of the IGA2 aptamer-based graphene nanosensor toward different dose of insulin and glucagon. Throughout the Figures, the same reference numerals and characters, unless otherwise stated, are used to denote like features, elements, components or portions of the illustrated embodiments. Moreover, while the present disclosure will now be described in detail with reference to the Figures, it is done so in connection with the illustrative embodiments.

DETAILED DESCRIPTION

The disclosed subject matter provides for devices and techniques to monitor target analytes. More specifically, the disclosed subject matter provides for field-effect transistor (FET)-based sensors and systems that can be used for continuous analyte monitoring, including but not limited to continuous glucose monitoring (CGM).

As used herein, the term "analyte" is a broad term and is used in its ordinary sense and includes, without limitation, any chemical species the presence or concentration of which is sought in material sample by the sensors and systems disclosed herein. For example, the analyte(s) include, but not are limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, ions, electrolytes, sodium, potassium, chloride, bicarbonate, and hormones. In one embodiment, the analyte can be glucose. In various embodiments, the analytes can be other metabolites, such as lactate, fatty acids, cysteines and homocysteines.

As used herein, the term "functionalized" means to have a capability of being reactive to an analyte. For example, functionalized refers to a substrate that has a substance attached, conjugated, or grafted to it, wherein the substance has a functional group that is capable of reacting with an analyte. For example, the substance can be covalently attached, conjugated, or grafted to the surface of the functionalized substrate.

As used herein, the terms "device," "sensor," and "nanosensor" are interchangeable and used here as a reference to low-charge, low-molecular-weight affinity nanosensor herein disclosed. Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below.

It is to be noted that the term "a" entity or "an" entity refers to one or more of that entity. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e., combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, up to +/−10%, up to +/−5%, or alternatively up to +/−1% of a given value. Alternatively, with respect to biological systems or processes, the term can mean within an order of magnitude, preferably within 5-fold, and more preferably within 2-fold, of a value. As used here, the term "coupled" refers to the connection of a system component to another system component by any suitable means known in the art. The type of coupling used to connect two or more system components can depend on the scale and operability of the system. For example, and not by way of limitation, coupling of two or more components of a system can include connecting the nanosensor to the substrate platform or coupling the enrichment chamber to the sensing chamber via the channel.

As used herein, the term "aptamer" means a stable single-stranded oligonucleotide (e.g., DNA, RNA, Xeno Nucleic Acid (XNA)), or peptide that binds to a specific target analyte. In certain embodiments, the aptamer binds with high affinity and specificity to the target analyte.

In certain embodiments, the disclosed subject matter provides a microdevice as described herein coupled with a wireless interface. The output signal can be a raw data stream that can be used to provide a useful value of the measured target analyte concentration. The wireless interface can include a capacitance digital converter coupled with the microdevice and adapted to produce a digital signal representing a measurement of the target analyte in the bodily fluid of the subject; a microcontroller coupled with the capacitance digital converter; and a transponder coupled with the microcontroller to transmit the digital signal received from the capacitance digital converter to an external reader.

The Nanosensor

The disclosed subject matter provides a nanosensor for monitoring a target analyte. In certain embodiments, the nanosensor utilizes a pair of conductance sensors on a substrate platform, wherein one of the pair of sensors can be functionalized with receptors for binding the target analyte and the other sensor can be functionalized with receptors that can be insensitive to the target analyte. In certain embodiments, the nanosensor utilizes a single conductance sensor on a substrate platform, wherein the sensor can be functionalized with receptors for binding the target analyte. In certain embodiments, the receptors are natural polymers, synthetic polymers, peptides, antibodies, aptamers, or small molecules. In certain embodiments, the nanosensor does not require the sensor to be functionalized with a receptor, wherein the target analyte itself changes the conductance of the sensor.

The nanosensor can be fabricated of biocompatible materials to prevent adverse responses of the surrounding tissue. These include the substrate and passivation materials (e.g., PET and parylene), the sensing and reference receptors (e.g., natural polymers, synthetic polymers, peptides, antibodies, aptamers, or small molecules), and the glucose-permeable hydrogel coating. In addition, the functional, dielectric and metallization materials (e.g., graphene, hexagonal boron nitride (h-BN) and gold) are also biocompatible when their uptake by individual cells can be avoided. Thus, inflammatory, allergic, immunogenic, cytotoxic, and genotoxic responses of tissue to the microdevice can be minimized.

In certain embodiments, the sensor can be made of graphene. Graphene is a flat monolayer of carbon atoms tightly packed into a two-dimensional honeycomb lattice. In certain embodiments, the FET sensing element with graphene as the conducting channel has an electric resistance of about 0.1 k$\Omega$-about 3 k$\Omega$. In certain embodiments, graphene as the conductance channel has an electric resistance of about 0.1 k$\Omega$-about 3 k$\Omega$, about 0.25 k$\Omega$-about 2.75 k$\Omega$, about 0.5 k$\Omega$-about 2.5 k$\Omega$, about 0.75 k$\Omega$-about 2.25 k$\Omega$, about 1 k$\Omega$-about 2 k$\Omega$, about 1.25 k$\Omega$-about 1.75 k$\Omega$, about 1.5 k$\Omega$-about 2 k$\Omega$, or about 2 k$\Omega$-about 3 k$\Omega$. In certain embodiments, graphene as the conductance channel has an electric resistance of at least about 0.1 k$\Omega$, at least about 0.2 k$\Omega$, at least about 0.3 k$\Omega$, at least about 0.4 k$\Omega$, at least about 0.5 k$\Omega$, at least about 0.6 k$\Omega$, at least about 0.7 k$\Omega$, at least about 0.8 k$\Omega$, at least about 0.9 k$\Omega$, at least about 1 k$\Omega$, at least about 1.2 k$\Omega$, at least about 1.4 k$\Omega$, at least about 1.6 k$\Omega$, at least about 1.8 k$\Omega$, at least about 2 k$\Omega$, at least about 2.2 k$\Omega$, at least about 2.4 k$\Omega$, at least about 2.6 k$\Omega$, at least about 2.8 k$\Omega$, at least about 3 k$\Omega$, at least about 4 k$\Omega$, at least about 5 k$\Omega$, at least about 6 k$\Omega$, at least about 7 k$\Omega$, at least about 8 k$\Omega$, at least about 9 k$\Omega$, or at least about 10 k$\Omega$. In certain embodiments, graphene as the conductance channel has an electric resistance of no more than about 0.1 kΩ, no more than about 0.2 kΩ, no more than about 0.3 kΩ, no more than about 0.4 kΩ, no more than about 0.5 kΩ, no more than about 0.6 kΩ, no more than about 0.7 kΩ, no more than about 0.8 kΩ, no more than about 0.9 kΩ, no more than about 1 kΩ, no more than about 1.2 kΩ, no more than about 1.4 kΩ, no more than about 1.6 kΩ, no more than about 1.8 kΩ, no more than about 2 kΩ, no more than about 2.2 kΩ, no more than about 2.4 kΩ, no more than about 2.6 kΩ, no more than about 2.8 kΩ, no more than about 3 kΩ, no more than about 4 kΩ, no more than about 5 kΩ, no more than about 6 kΩ, no more than about 7 kΩ, no more than about 8 kΩ, no more than about 9 kΩ, or no more than about 10 kΩ.

The graphene monoatomic sheet can have the ultimate thinness (0.34 nm) of any known material and possesses unparalleled mechanical strength (Young's modulus: 1 TPa), adheres strongly to underlying substrates, and can be highly flexible, optically transparent, and chemically stable, thereby holding the potential to enable new, transformative methods for detection of biological analytes. The monoatomic structure as well as exceptional electric conductivity (~1738 S/m) and charge carrier mobility ($2 \times 10^5$ cm2/Vs) of graphene can be exploited to enable highly sensitive analyte detection. Holding the potential to enable new, distinctly transformative methods for detection of biological analytes, graphene has been used for electrochemical or affinity detection of analytes such as DNA and proteins, and for electrochemical detection of glucose.

In certain embodiments, the graphene sensor includes a single layer sheet. In certain embodiments, the graphene sensor includes a multilayered sheet. In certain embodiments, the graphene sensor includes at least one layer of graphene. In certain embodiments, the graphene sensor includes at least two layers of graphene, at least three layers of graphene, or at least four layers of graphene. In certain embodiments, the graphene sheet can be formed by mechanical exfoliation, chemical exfoliation, chemical vapor deposition, or silicon carbide. In certain embodiments, the graphene sheet can be formed by chemical vapor deposition (CVD). In certain embodiments, the graphene sheet can be formed by, mechanical exfoliation, which can include the removal of a layer of graphene from a block of graphite using tape or other sticky substance. Exemplary techniques for fabrication of the graphene sheet are illustrated in FIGS. 4A-B and discussed in further detail in Example 2.

The nanosensors as disclosed herein can be highly sensitive, as changes in surface charge due to the presence of the target analyte near the sensor or the target analyte binding effectively penetrates the bulk of the atomically thin graphene, leading to a detectable signal even at low target analyte concentrations.

In using graphene as a functional material on a flexible substrate, the nanosensors disclosed herein can be miniaturized and mechanically flexible for placement on a substrate platform. In certain embodiments, the substrate platform can be rigid. In certain embodiments, the substrate platform can be flexible. The monoatomic thickness can allow the graphene nanosensor to be highly miniaturized. Miniaturization can drastically reduce distances over which diffusive analyte (e.g., glucose) transport occurs, leading to a rapid response to target analyte changes in a bodily fluid. In certain embodiments, the change in target analyte levels can be detected within about 7 to about 60 seconds. In certain embodiments, the change in target analyte levels are detected within about 10 to about 50 seconds, about 12 to about 45 seconds, about 15 to about 40 seconds, about 17 to about 35 seconds, or about 20 to about 30 seconds. In certain embodiments, the change in target analyte levels can be detected within about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, about 20 seconds, about 21 seconds, about 22 seconds, about 23 seconds, about 24 seconds, about 25 seconds, about 26 seconds, about 27 seconds, about 28 seconds, about 29 seconds, about 30 seconds, about 31 seconds, about 32 seconds, about 33 seconds, about 34 seconds, about 35 seconds, about 36 seconds, about 37 seconds, about 38 seconds, about 39 seconds, about 40 seconds, about 41 seconds, about 42 seconds, about 43 seconds, about 44 seconds, about 45 seconds, about 46 seconds, about 47 seconds, about 48 seconds, about 49 seconds, about 50 seconds, about 51 seconds, about 52 seconds, about 53 seconds, about 54 seconds, about 55 seconds, about 56 seconds, about 57 seconds, about 58 seconds, about 59 seconds, or about 60 seconds, or about 1 minute, 2 minutes, 3 minutes, 4 minutes, or 5 minutes. In certain embodiments, the device response time can be within about 1 to about 10 minutes, about 2 to about 9 minutes, about 3 to about 8 minutes, about 4 to about 7 minutes, or about 5 to about 6 minutes. In certain embodiments, the response times of the device can be at least 1 minute, at least about 2 minutes, at least about 3 minutes, at least about 4 minutes, at least about 5 minutes, at least about 6 minutes, at least about 7 minutes, at least about 8 minutes, at least about 9 minutes, or at least about 10 minutes. In certain embodiments, the response time can be between about 1.5 to about 2.5 minutes, which is at least 2-3 times as rapid as existing CGM devices. The decreased response time and aptamer-target analyte binding time can allow real-time detection of changes in the target analyte concentrations. The decreased response time and aptamer-target analyte binding time can further allow for the detection of the disclosed system to be continuous over time.

The microdevices as disclosed herein can also be mechanically flexible because of the use of flexible materials, including graphene on a flexible substrate. Thus, the device can readily conform to the local tissue geometry and minimize irritation and injury to a tissue or organ (e.g., an eye) during the sensor placement, operation and replacement.

In certain embodiments, the miniature size of the device can also prevent the obstruction of vision when integrated on a contact lens. The intimate contact can also facilitate exchange of glucose between the device and tears, leading to improved sensitivity and reliability. Therefore, because of the miniaturization and flexibility, the device can be highly compatible with contact lens-based noninvasive CGM.

To reduce protein adsorption and biofouling, in certain embodiments the entire nanosensor can be coated in a biocompatible hydrogel. In certain embodiments, the nanosensor can be coated with a thin hydrogel layer. In certain embodiments, the hydrogel can be permeable to the target analyte. In certain embodiments, the hydrogel can be permeable to glucose. In certain embodiments, the biocompatible hydrogen can be synthesized in situ. Exemplary techniques for fabrication of the hydrogel are discussed in further detail in Example 10. Hydrogels can be made by any other commonly understood method.

In certain embodiments, the hydrogel can include, but is not limited to, at least one of poly(hydroxyethyl-methacrylate (PHEMA), hydroxyethyl methacrylate (HEMA), tetraethyleneglycol diacrylate (TEGDA), polyethyleneglycol methacylate (PEGMA), or N-[tris(hydroxymethyl)methyl]-acrylamide (HMMA). In certain embodiments, the hydrogel includes hydroxyethyl methacrylate (HEMA), tetraethyleneglycol diacrylate (TEGDA), polyethyleneglycol methacylate (PEGMA) and N-[tris(hydroxymethyl)methyl]-acrylamide (HMMA). In certain embodiments, the hydrogel includes a combination of hydroxyethyl methacrylate (HEMA), tetraethyleneglycol diacrylate (TEGDA), polyethyleneglycol methacylate (PEGMA) and N-[tris(hydroxymethyl)methyl]-acrylamide (HMMA). In certain embodiments, the hydrogel includes hydroxyethyl methacrylate (HEMA), tetraethyleneglycol diacrylate (TEGDA), polyethyleneglycol methacylate (PEGMA) and N-[tris(hydroxymethyl)methyl]-acrylamide (HMMA) at a ratio of 86:3:5.5 mol %.

In certain embodiments, the thickness of the hydrogel layer ranges from about 20-50 μm. In certain embodiments the hydrogel layer can be no thicker than about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, or about 50 μm, In certain embodiments, the thickness of the hydrolayer can be between about 20 μm to about 50 μm.

In certain embodiments, the nanosensor can be constructed on a substrate platform. In certain embodiments, the substrate can be fabricated on the final substrate (e.g., a contact lens). In certain embodiments, the substrate can be fabricated on a thin flexible film and the nanosensor device (including the thin flexible film) is attached to the final substrate platform (e.g., a contact lens). In certain embodiments, the substrate platform and the thin layer film can be made from the same material. In certain embodiments, the substrate platform and thin later film can be made from different material. In certain embodiments, the nanosensor can be formed on a substrate platform that is then formed/molded (e.g., by heating) into a contact lens shape.

In certain embodiments, the nanosensor can be on the inside the contact lens (i.e., towards the eye). In certain embodiments, the nanosensor can be on the outside of the contact lens (i.e., towards the eyelid).

In accordance with certain embodiment, the nanofilms can be transferred in a vacuum to prevent air bubbles from being trapped between the graphene, dielectric layer, and the substrate. In certain embodiments, the nanofilm surfaces can also be treated by heat or low-power oxygen plasma to further improve adhesion.

The design parameters can be varied without departing from the scope of the disclosed subject matter. Such design parameters include, for example, the number and dimensions of atomic layers and substrate platform layers, shape and dimensions of the graphene, molecular weight of the sensing receptor, and the thickness of the hydrogel coating.

Single Channel

A set of sensing receptors functionalized on the conductance sensor can bind to the target analyte. In certain embodiments, the sensing receptor binds specifically to the target analyte. In certain embodiments, the sensing receptor can bind reversibly or irreversibly to the target analyte. In certain embodiments, the sensing receptor can bind reversibly to the target analyte. In certain embodiments, the reference receptor can bind reversibly to essentially all analytes. In certain embodiments, the sensing receptor can bind to more than one target analyte.

In certain embodiments, target analyte binding of the sensing receptor can change the charge density on the sensor surface, inducing changes in the carrier concentration of the sensor.

In certain embodiments, the sensing polymer can bind specifically to the target analyte. Target analyte binding of the sensing polymer can change the charge density on the sensor surface, inducing changes in the carrier concentration of the sensor. In certain embodiments, the polymers can bind reversibly with essentially all analytes. In certain embodiments, the sensing polymer can bind reversibly with the target analyte.

In certain embodiments, the nanosensor can be configured as a solution-gated graphene-based FET (GFET) in that the graphene (e.g., 605) is the conducting channel, which can be formed between two electrodes (source (e.g., 608) and drain (e.g., 609)) on an insulating substrate surface (e.g., 601) (FIG. 18). As shown in FIG. 18, the Ag/AgCl electrode (607) can be inserted into the electrolyte solution (621) in contact with graphene (605) to serve as the gate electrode, while the EDL formed at the solution-graphene interface provides the gate dielectric.

The substrate or platform surface can be one or multi-layered. For example, the substrate or platform surface can include two layers (see FIG. 18, 601) such as, but not limited to a silicon wafer based device. An example of a silicon wafer based device, the lower layer can be silicon as the substrate while the upper later is silicone oxide which can serve as an insulating layer. In certain embodiments, the substrate platform can be a single layer. In certain embodiments the single later substrate platform can be s a polymer substrate.

A monolayer of the synthetic glucose responsive polymer (e.g., 611) can be attached to the graphene surface via π-π stacking interactions (FIG. 17). A sample (e.g., 621) can be in contact with the polymer-functionalized graphene (e.g., 611, 605) in a microchannel, with an electrode wire (e.g., 607) inserted into the solution to serve as a gate electrode. An electrical double layer (EDL) can form at the interface of the graphene and solution, and serves as the gate dielectric layer. During operation, under the control of a voltage applied between the gate and source electrodes (gate voltage Vgs), a bias voltage applied between the drain (e.g., 609) and source (e.g., 608) electrodes (drain-source voltage Vds) can generate a current through the graphene (e.g., 605) (drain-source current $I_{ds}$). In certain embodiments, this can yield the transfer characteristics of the GFET (i.e., the functional dependence of Ids on Vgs) and can allow the determination of the glucose concentration, because the binding of boronic acid moieties of the polymer PAPBA changes the electrical properties of the graphene as follows. In certain embodiments, the wire probe can be replaced with a gate electrode nanolayer (FIGS. 8 and 9A-B). As shown in FIG. 8, graphene (505) serves as the conducting channel, while a 20-nm-thick $HfO_2$ layer (506) between the graphene (505) and the substrate-supported gate electrode (507) serves as the dielectric layer.

In certain embodiments, the nanosensor can be not functionalized with a receptor. The charge of the target analyte can change the charge density on the sensor surface, inducing changes in the carrier concentration of the sensor. In certain embodiments, such a sensor can be used to test a sample or bodily fluid. In certain embodiments, such a sensor can be used to test the pH or electrolyte concentration of a sample or bodily fluid. In certain embodiments, such a sensor can be used to test for the presence or absence of an analyze carrying a charge or capable of eliciting a charge by any means. For example, but not limited to, the analyte can interact with a substance present near the sensor that would allow a charge or change in a charge to occur.

In certain embodiments, the nanosensor can be configured as a solid-gated FET device, in which a graphene sheet, serving as the conducting channel, connected the source and drain electrodes on a dielectric layer, which in turn lies above the gate electrode on the substrate (FIGS. 8 and 9A-B).

In certain embodiments, when the nanosensor is not functionalized with receptors, the presence of ions near the sensor can be detected. The magnitude of the electric potential can depend on the ion concentration (e.g., $H^+$). In certain embodiments, the pH level can be determined by measuring the graphene's electric properties such as its transfer characteristics and conductance, which can be directly related to the carrier concentration. To allow a high level of integration while avoiding the need for high gate voltages, the nanosensor can use about 20 nm thick $HfO_2$, a material with a high dielectric constant ($\kappa \approx 20$, compared to $\kappa \approx 3.9$ for $SiO_2$), as the dielectric layer to provide a high gate capacitance ($\sim 1$ $\mu F/cm^2$). This in general can allow the Dirac point, at which the drain-source current $I_{DS}$ achieves its minimum, to be observed at a lower gate voltage.

In certain embodiments, the electrode wire can be, for example, but not limited to Ag/AgCl, Ag, Pt, or combinations thereof.

In certain embodiments, the dielectric nanolayer can be made from material such as, but not limited to hexagonal boron nitride (h-BN), $HfO_2$, parylene, $SiO_2$, $Si_3N_4$, or combinations thereof.

In certain embodiments, the gate electrode can be made from material such as, but not limited to ITO, Ti/Pd/Pt, gold, copper, chrome, or mixtures thereof.

In certain embodiments, the source and drain electrodes, can be separately made from material such as, but not limited to ITO, Ti/Pd/Pt, chromium, gold, chrome, or combinations thereof.

In certain embodiments, the polymer substrate and or thin layer film can be made from material such as, but not limited to polyethylene terephthalate (PET), polycarbonate polystyrene, polymethyl methacrylate (PMMA), polymacon, silicones, fluoropolymers, silicone acrylate, fluoro-silicone/acrylate, poly hydroxyethyl methacrylate, or combinations thereof.

In certain embodiments, the polymer coating can be made from material such as, but not limited to, parylene, polyimide, organic polymer, hydrophobic polymer, or combinations thereof. In certain embodiments, the nanosensor can be covered with a polymer coating except for the functionalized part of the graphene sheet.

In certain embodiments, the sensing polymer can be, for example, but not limited poly(N-hydroxyethylacrylamide-ran-3-acrylamidophenylboronic acid) (PHEA-ran-PAAPBA) and pyrene-terminated poly(3-acrylamidophenylboronic acid) (py-PAPBA).

In certain embodiments, the copolymer can be liner or branched. Additional receptor polymers are discussed below.

In certain embodiments, the dimensions of the graphene conducting channel in the single channel graphene sensor can be a length of about 10-about 20 μm by a width of about 10-about 20 μm by a thickness of about 1-about 10 nm. In certain embodiments, the graphene channel in the sensor can be about $20\times10$ $\mu m^2$. In certain embodiments, the graphene conducting channel can be functionalized with a polymer.

In certain embodiments, the length of the graphene channel in the sensor can be about 10.2-about 19.8 μm, about 10.4-about 19.6 μm, about 10.6-about 19.4 μm, about 10.8-about 19.2 μm, about 11-about 19 μm, about 11.2-about 18.8 μm, about 11.4-about 18.6 μm, about 11.6-about 18.4 μm, about 11.8-about 18.2 μm, about 12-about 18 μm, about 12.2-about 17.8 μm, about 12.4-about 17.6 μm, about 12.6-about 17.4 μm, about 12.8-about 17.2 μm, about 13-about 17 μm, about 13.2-about 16.8 μm, about 13.4-about 16.6 μm, about 13.6-about 16.4 μm, about 13.8-about 16.2 μm, about 14-about 16 μm, about 14.2-about 15.8 μm, about 14.4-about 15.6 μm, about 14.6-about 15.4 μm, or about 14.8-about 15.2 μm. In certain embodiments, the width of the graphene channel in the sensor can be about 10.2-about 19.8 μm, about 10.4-about 19.6 μm, about 10.6-about 19.4 μm, about 10.8-about 19.2 μm, about 11-about 19 μm, about 11.2-about 18.8 μm, about 11.4-about 18.6 μm, about 11.6-about 18.4 μm, about 11.8-about 18.2 μm, about 12-about 18 μm, about 12.2-about 17.8 μm, about 12.4-about 17.6 μm, about 12.6-about 17.4 μm, about 12.8-about 17.2 μm, about 13-about 17 μm, about 13.2-about 16.8 μm, about 13.4-about 16.6 μm, about 13.6-about 16.4 μm, about 13.8-about 16.2 μm, about 14-about 16 μm, about 14.2-about 15.8 μm, about 14.4-about 15.6 μm, about 14.6-about 15.4 μm, or about 14.8-about 15.2 μm. In certain embodiments, the thickness of the graphene channel in the sensor can be about 1.2-about 9.8 nm, about 1.4-about 9.6 nm, about 1.6-about 9.4 nm, about 1.8-about 9.2 nm, about 2-about 9 nm, about 2.2-about 8.8 nm, about 2.4-about 8.6 nm, about 2.6-about 8.4 nm, about 2.8-about 8.2 nm, about 3-about 8 nm, about 3.2-about 7.8 nm, about 3.4-about 7.6 nm, about 3.6-about 7.4 nm, about 3.8-about 7.2 nm, about 4-about 7 nm, about 4.2-about 6.8 nm, about 4.4-about 6.6 nm, about 4.6-about 6.4 nm, about 4.8-about 6.2 nm, about 5-about 6 nm, about 4.2-about 5.8 nm, about 4.4-about 5.6 nm, about 4.6-about 5.4 nm, or about 4.8-about 5.2 nm.

In certain embodiments, the dimensions of the single channel nanosensor chip can be a length of about 5-about 10 mm by a width of about 5-about 10 mm by a thickness of about 50-about 500 μm. In certain embodiments the graphene sensor can be about $25\times10$ $\mu m^2$. In certain embodiments, the total nanosensor can be about $10\times10$ $mm^2$.

In certain embodiments, the length of the single channel nanosensor chip can be about 5.2-about 9.8 mm, about 5.4-about 9.6 mm, about 5.6-about 9.4 mm, about 5.8-about 9.2 mm, about 6-about 9 mm, about 6.2-about 8.8 mm, about 6.4-about 8.6 mm, about 6.6-about 8.4 mm, about 6.8-about 8.2 mm, about 7-about 8 mm, about 7.2-about 7.8 mm, or about 7.4-about 7.6 mm. In certain embodiments, the width of the single channel nanosensor chip can be about 5.2-about 9.8 mm, about 5.4-about 9.6 mm, about 5.6-about 9.4 mm, about 5.8-about 9.2 mm, about 6-about 9 mm, about 6.2-about 8.8 mm, about 6.4-about 8.6 mm, about 6.6-about 8.4 mm, about 6.8-about 8.2 mm, about 7-about 8 mm, about 7.2-about 7.8 mm, or about 7.4-about 7.6 mm. In certain embodiments, the thickness of the single channel nanosensor chip can be about 75-about 475 μm, about 100-about 450 μm, about 125-about 425 μm, about 150-about 400 μm, about 175-about 375 μm, about 200-about 350 μm, about 225-about 325 μm, or about 250-about 300 μm.

Exemplary techniques for fabrication of the devices illustrated in, for example, FIGS. 4-10, 17-20, and 22 will be discussed in further detail in Examples 2-8.

Multi-Channel

In certain embodiments, one set of receptors (sensing receptors) functionalized on one of the pair of conductance sensors can bind to the target analyte and the other set of receptors (reference receptors) functionalized on a separate conductance sensor can be insensitive to the target analyte. In certain embodiments, the sensing receptor can bind specifically to the target analyte. In certain embodiments, the sensing receptor can bind reversibly or irreversibly to the target analyte. In certain embodiments, the sensing receptor can only bind reversibly to the target analyte. In certain embodiments, the reference receptor can bind reversibly to essentially all analytes. In certain embodiments, the first and second conductive elements can be essentially identical except for the first conductive element being functionalized with the sensing receptor and the second conductance element being functionalized with a reference receptor. In certain embodiments, binding of the target analyte to the sensing receptor can induce changes in the electrical conductance of the graphene of the first conductive element and conductance of the second conductive element only changes due to fluctuations in environmental parameters. In certain embodiments, the sensing receptor can bind to more than one target analyte.

In certain embodiments, at least two channels are present in the nanosensor. In certain embodiments, at least three channels, at least four channels, or at least five channels can be present in the nanosensor. In certain embodiments, four channels can be present. In certain embodiments, at least one of the multichannel sensors can be functionalized with a reference receptor (e.g., polymer). In certain embodiments, at least two of the sensors can be e functionalized with sensing receptors (e.g., polymers). In certain embodiments, at least two of the sensors can be functionalized with two different sensing receptors (e.g., polymers).

In certain embodiments, target analyte binding of the sensing receptor can change the charge density on the sensor surface, inducing changes in the carrier concentration of the sensor. Meanwhile, the reference receptor does not bind to the target analyte and its associated sensor conductance can change only due to fluctuations in environmental parameters. Thus, differential measurement of the target analyte conductance can allow determination of the target analyte concentration in a bodily fluid.

In certain embodiments, one polymer (sensing polymer) can bind specifically to the target analyte, and the other (reference polymer) is insensitive to the target analyte. Target analyte binding of the sensing polymer can change the charge density on the sensor surface, inducing changes in the carrier concentration of the sensor. Meanwhile, the reference polymer does not bind to the target analyte and its associated sensor conductance could change only due to fluctuations in environmental parameters. Thus, differential measurement of the target analyte conductance can allow determination of the target analyte concentration in a bodily fluid. In certain embodiments, the polymers can bind reversibly with most analytes. In certain embodiments, the polymers can bind reversibly with essentially all analytes. In certain embodiments, the sensing polymer can bind reversibly with the target analyte.

Figure 1:
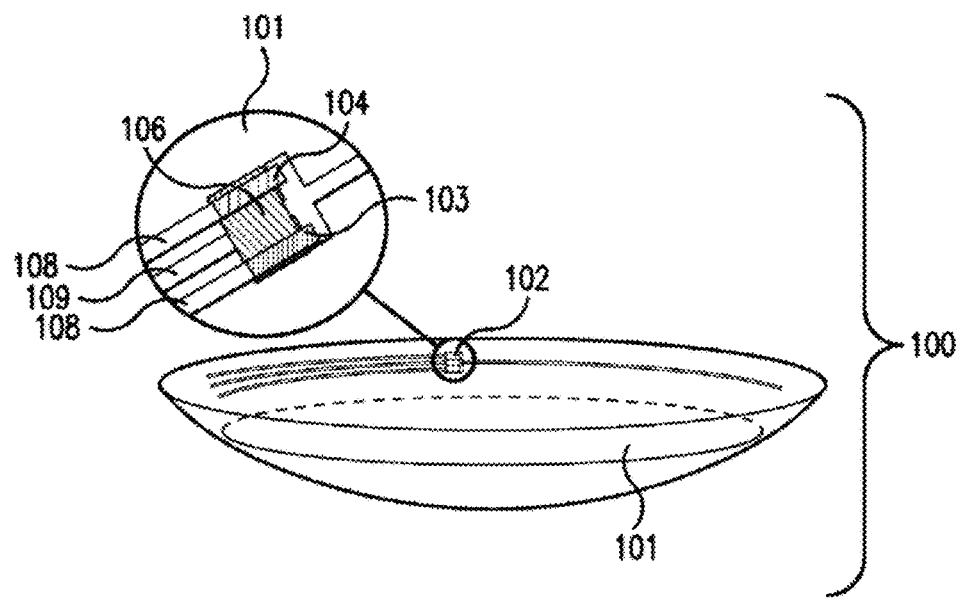
FIG. 1 illustrates a contact lens-based graphene nanosensor (100) for noninvasive CGM in tears according to some embodiments of the disclosed subject matter.
Figure 2A:
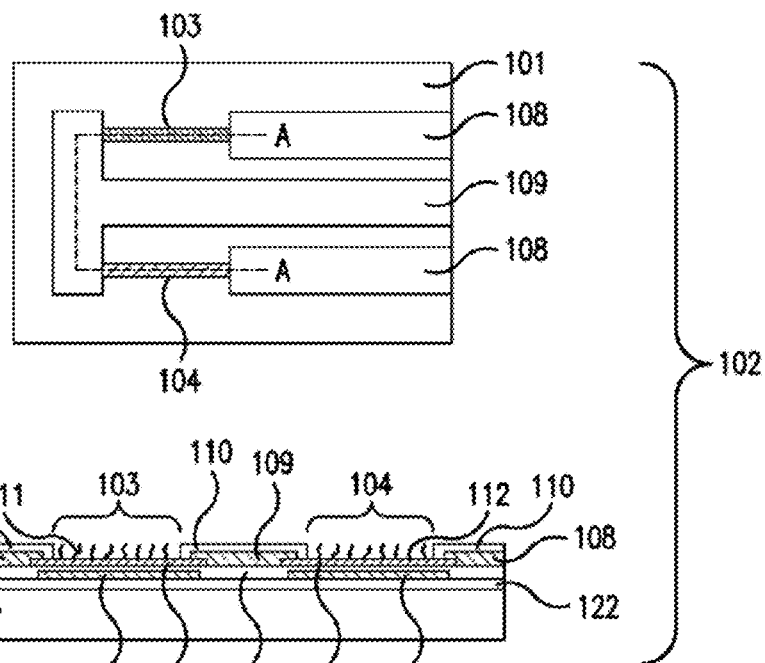
FIG. 2A-2B illustrates the design of a graphene based nanosensor according to some embodiments of the disclosed subject matter.
Figure 2B:
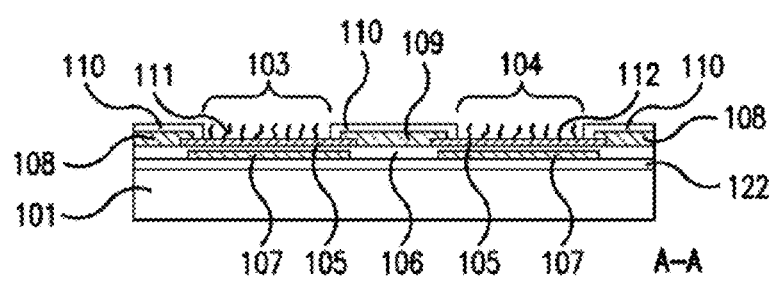

FIGS. 1 and 2A-B illustrate the structure of an example two channel microdevice according to some embodiments of the disclosed subject matter. As shown in these figures, the microdevice e.g., 100 includes a substrate platform 101 (e.g., SiO2, a contact lens or a thin film or layer that can be attached to the inside of the contact lens) and a two channel (103, 104) nanosensor 102 coupled to the substrate platform.

The two channel nanosensor 102 design can include two polymer-functionalized field-effect transistor (FET) modules of identical construction (except for their respective sensing/reference polymers) 103, 104 on the substrate platform 101. In each module a slender graphene strip 105 (the conducting channel) can lie on a dielectric layer 106 (e.g., h-BN or parylene) (which minimizes substrate-induced charge carrier scattering in the conducting channel) passivating a transparent gate electrode 107 (e.g., ITO), and makes contact with source 108 (e.g., ITO) and drain electrodes 109 (e.g., ITO). These nanolayers can lie on a substrate platform 101, and can be covered with a thin polymer layer 110 (e.g., parylene) except the graphene, which is grafted with a monolayer of a glucose-binding polymer (the sensing module) 111 or a glucose-insensitive polymer (the reference module) 112. The entire nanosensor can be coated with a glucose-permeable hydrogel (not shown). In certain embodiments, the nanolayers and polymer layers can be flexible and biocompatible. In certain embodiments, the polymer layer 110 can be a passivating layer. In certain embodiments, an optional passivation layer 122 can be present. In certain embodiments, a passivation layer 122 can be present if the substrate platform 101 is conductive (e.g., $SiO_2$). In certain embodiments, the passivation layer can be not present if the substrate platform 101 is electrically insulated (e.g., PET). This passivation layer can be optionally found in either the single or multi-layer nanosensors.

In certain embodiments, the dimensions of the graphene conducting channel in the dual channel graphene sensor can be a length of about 10-about 20 μm by a width of about 10-about 20 μm by a thickness of about 1-about 10 nm. In certain embodiments, the graphene channel in the sensor can be about 20×10 μm$^2$.

In certain embodiments, the length of the graphene channel in the sensor can be about 10.2-about 19.8 μm, about 10.4-about 19.6 μm, about 10.6-about 19.4 μm, about 10.8-about 19.2 μm, about 11-about 19 μm, about 11.2-about 18.8 μm, about 11.4-about 18.6 μm, about 11.6-about 18.4 μm, about 11.8-about 18.2 μm, about 12-about 18 μm, about 12.2-about 17.8 μm, about 12.4-about 17.6 μm, about 12.6-about 17.4 μm, about 12.8-about 17.2 μm, about 13-about 17 μm, about 13.2-about 16.8 μm, about 13.4-about 16.6 μm, about 13.6-about 16.4 μm, about 13.8-about 16.2 μm, about 14-about 16 μm, about 14.2-about 15.8 μm, about 14.4-about 15.6 μm, about 14.6-about 15.4 or about 14.8-about 15.2 In certain embodiments, the width of the graphene channel in the sensor can be about 10.2-about 19.8 μm, about 10.4-about 19.6 μm, about 10.6-about 19.4 μm, about 10.8-about 19.2 μm, about 11-about 19 μm, about 11.2-about 18.8 μm, about 11.4-about 18.6 μm, about 11.6-about 18.4 μm, about 11.8-about 18.2 μm, about 12-about 18 μm, about 12.2-about 17.8 μm, about 12.4-about 17.6 μm, about 12.6-about 17.4 μm, about 12.8-about 17.2 μm, about 13-about 17 μm, about 13.2-about 16.8 μm, about 13.4-about 16.6 μm, about 13.6-about 16.4 μm, about 13.8-about 16.2 μm, about 14-about 16 μm, about 14.2-about 15.8 μm, about 14.4-about 15.6 μm, about 14.6-about 15.4 or about 14.8-about 15.2 In certain embodiments, the thickness of the graphene channel in the sensor can be about 1.2-about 9.8 nm, about 1.4-about 9.6 nm, about 1.6-about 9.4 nm, about 1.8-about 9.2 nm, about 2-about 9 nm, about 2.2-about 8.8 nm, about 2.4-about 8.6 nm, about 2.6-about 8.4 nm, about 2.8-about 8.2 nm, about 3-about 8 nm, about 3.2 μm, about 7.8 nm, about 3.4-about 7.6 nm, about 3.6-about 7.4 nm, about 3.8-about 7.2 nm, about 4-about 7 nm, about 4.2-about 6.8 nm, about 4.4-about 6.6 nm, about 4.6-about 6.4 nm, about 4.8-about 6.2 nm, about 5-about 6 nm, about 4.2-about 5.8 nm, about 4.4-about 5.6 nm, about 4.6-about 5.4 nm, or about 4.8-about 5.2 nm.

In certain embodiments, the dimensions of the dual channel nanosensor chip can be a length of about 8-about 15 mm by a width of about 8-about 15 mm by a thickness of about 50-about 500 In certain embodiments, the total nanosensor chip can be about 15×15 mm$^2$.

In certain embodiments, the length of the dual channel nanosensor chip can about 8.2-about 14.8 mm, about 8.4-about 14.6 mm, about 8.6-about 14.4, about 8.8-about 14.2 mm, about 9-about 14 mm, about 9.2-about 13.8 mm, about 9.4-about 13.6 mm, about 9.6-about 13.4, about 9.8-about 13.2 mm, about 10-about 13 mm, about 10.2-about 12.8 mm, about 10.4-about 12.6 mm, about 10.6-about 12.4, about 10.8-about 12.2 mm, about 11-about 12 mm, about 11.2-about 11.8 mm, or about 11.4-about 11.6 mm. In certain embodiments, the width of the dual channel nanosensor chip can about 8.2-about 14.8 mm, about 8.4-about 14.6 mm, about 8.6-about 14.4, about 8.8-about 14.2 mm, about 9-about 14 mm, about 9.2-about 13.8 mm, about 9.4-about 13.6 mm, about 9.6-about 13.4, about 9.8-about 13.2 mm, about 10-about 13 mm, about 10.2-about 12.8 mm, about 10.4-about 12.6 mm, about 10.6-about 12.4, about 10.8-about 12.2 mm, about 11-about 12 mm, about 11.2-about 11.8 mm, or about 11.4-about 11.6 mm. In certain embodiments, the thickness of the dual channel nanosensor chip can be about 75-about 475 µm, about 100-about 450 µm, about 125-about 425 µm, about 150-about 400 µm, about 175-about 375 µm, about 200-about 350 µm, about 225-about 325 µm, or about 250-about 300 µm.

The slender graphene strips (e.g., 105) can lie on a dielectric nanolayer (e.g., 106). In certain embodiments, the graphene strips can be two separate strips. The dielectric nanolayer can passivate a gate electrode (e.g., 107) and can make contact with a source (e.g., 108) and drain electrode (e.g., 109). In certain embodiments, these nanolayers can lie on a polymer substrate/substrate platform (e.g., 101) and can be covered with a thin polymer layer (e.g., 110) with the exception of the conducting-channel graphene (e.g., 103, 104), which can be functionalized with a target specific receptor (e.g., glucose-binding polymer (the sensing module)) (e.g., 111) or a target insensitive receptor (e.g., glucose-insensitive polymer (the reference module)) (e.g., 112). In certain embodiments, nanolayers and polymer layers can be all flexible and biocompatible.

In certain embodiments, the dielectric nanolayer can be made from material such as, but not limited to hexagonal boron nitride (h-BN), parylene, SiO$_2$ and Si$_3$N$_4$, or combinations thereof.

In certain embodiments, the gate electrode can be made from material such as, but not limited to ITO, Ti/Pd/Pt, gold, copper, chrome, or mixtures thereof.

In certain embodiments, the source and drain electrodes, can be separately made from material such as, but not limited to ITO, Ti/Pd/Pt, chromium, gold, chrome, or combinations thereof.

In certain embodiments, the substrate platform (e.g., polymer substrate) and/or thin layer film can be made from material such as, but not limited to polyethylene terephthalate (PET), polycarbonate polystyrene, polymethyl methacrylate (PMMA), polymacon, silicones, fluoropolymers, silicone acrylate, fluoro-silicone/acrylate, poly hydroxyethyl methacrylate, or combinations thereof.

In certain embodiments, the polymer coating can be made from material such as, but not limited to, parylene, polyimide, organic polymer, hydrophobic polymer, or combinations thereof. In certain embodiments, the nanosensor is covered with a polymer coating except for the functionalized part of the graphene sheet.

In certain embodiments, the sensing polymer can be, for example, but not limited poly(N-hydroxyethylacrylamide-ran-3-acrylamidophenylboronic acid) (PHEA-ran-PAAPBA) and pyrene-terminated poly(3-acrylamidophenylboronic acid) (py-PAPBA). In certain embodiments, the copolymer can be liner or branched. Additional receptor polymers are discussed below.

During operation, the conducting-channel graphene can be subjected to a gate voltage (e.g., between ±300 mV) with respect to the gate electrode underneath, and the current through the graphene under a bias voltage (10-50 mV) between the source and drain, which can be kept sufficiently small to limit the potential leakage current into the hydrogel coating well below the threshold (~10 µA/mm2) required to prevent undesirable electrochemical effects in tissue. In certain embodiments, the bias voltage is between about 10 to about 50 mV. In certain embodiments, the bias voltage is between about 10 to about 50 mV, about 12 to about 48 mV, about 14 to about 46 mV, about 16 to about 44 mV, about 18 to about 42 mV, about 20 to about 40 mV, about 22 to about 38 mV, about 24 to about 36 mV, about 26 to about 34 mV, or about 28 to about 32 mV.

Exemplary techniques for fabrication of the devices illustrated in, for example, FIGS. 1 and 2A-B will be discussed in further detail in Examples 8, 9, and 11.

Receptors

In various embodiments of the disclosed subject matter, the sensor can be used to determine the level of a target analyte in the body, for example oxygen, lactase, insulin, hormones, cholesterol, medicaments, viruses, or the like. In certain embodiments, the receptors that identify the target analyte can be natural polymers, synthetic polymers, peptides, antibodies, aptamers, or small molecules.

In certain embodiments, the receptor can be a polymer. The sensing polymer can include one in which at least one monomer or moiety interacts with the target analyte. Interaction between the target analyte and the sensing polymer results in a change in conductance of the sensor. In certain embodiments, the reference polymer can include a polymer whose moieties or monomers do not interact with the target analyte. In certain embodiments, the polymer can include at least two monomers, at least three monomers, at least four monomers, at least five monomers, at least six monomers, at least seven monomers, at least eight monomers, at least nine monomer, or at least ten monomers.

In certain embodiments, the target analyte can be glucose. When the target analyte is glucose, through proper adjustment of the composition percentage of the boronic acid moieties on the polymer and polymer concentrations, the polymer can detect and differentiate glucose from other monosaccharides and disaccharides. Applying this polymer to the nanosensor as disclosed herein can enable highly reliable, continuous monitoring of glucose in bodily fluids.

As noted, the binding between the polymer and the analyte of interest can be reversible. For example, the binding and dissociation between the target analyte and the sensing polymer can be an equilibrium phenomenon driven by the concentration of the analyte in the conducting channel. The amount of the analyte bound with the sensing polymer depends on the concentration of the analyte in the conducting channel.

In one embodiment, a suitable polymer having boronic acid moieties can be formed as a copolymer of at least two monomers, where one of the monomers includes at least one boronic acid functional group. A copolymer can be synthesized with these monomers via classic free radical copolymerization processes. In certain embodiments, a suitable polymer can include, but is not limited to, a polymer that contains boronic acid groups, or other receptor groups that recognize the given analytes. In one embodiment, the polymer can be phenyl acrylamide (PAM). In another embodiment, the polymer can be PAM-ran-PAAPBA, which is an amphiphilic copolymer containing two components, hydrophilic polymer segment phenyl acrylamide (PAM) and hydrophobic polymer segment poly(3-acrylamidophenylboronic acid) (PAAPBA). In yet another embodiment, the polymer can be PAM-ran-PPAM, which is an amphiphilic copolymer containing two components, hydrophilic polymer segment phenyl acrylamide (PAM) and hydrophobic polymer segment polymeric allylamine (PPAM).

In certain embodiments, basic monomers, such as, but not limited to, N,N-dimethylacrylamide can be used to increase the ionization of boronate upon binding with diols.

In certain embodiments, the copolymer can be liner or branched. In certain embodiments, the copolymer can include hydrophilic motifs (e.g., polymeric allylamine (PAM), hydroxyethyl methacrylate (HEMA)). In certain embodiments, the copolymers can be in situ gelation prepolymers. In certain embodiments, in situ gelation of polymers is one in which a solution of polymers can form a hydrogel on the sensor chip by methods of heating and UV irradiation.

In certain embodiments the polymer can be conjugated to a substance that can immobilize the polymers on the graphene sensor. In certain embodiments, the substance-terminated polymers can be irreversibly attached to graphene with strength comparable to covalent attachment. In certain embodiments, the substance can be pyrene. A pyrene-terminated polymer can be irreversibly attached to graphene using a sticky point for µ-µ stacking interactions without disrupting the graphene's conjugation or altering its electronic properties, can be synthesized.

The polymer sensors can undergo a viscosity change as well as a permittivity change when interacting with glucose molecules, as discussed in US Patent Application Publication No. 20120043203, assigned to the common assignee, the disclosure of which is incorporated herein by reference in its entirety.

The sensing polymer can include boronic acid groups, which can bind to glucose molecules at a 2:1 ratio to reversibly form cyclic esters of boronic acid, while having almost no response to other potential interferents, such as fructose, galactose, and sucrose. Below is a representative schematic of the reaction:

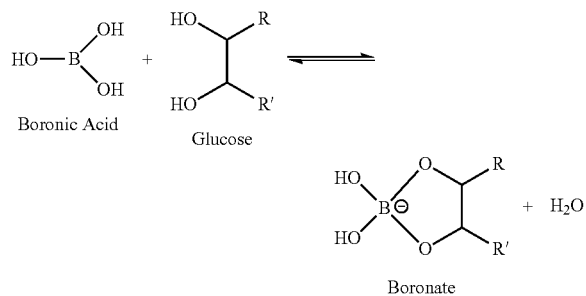

In certain embodiments, the polymer can include as least one boronic acid group, at least two boronic acid group, at least three boronic acid group, at least four boronic acid group, at least five boronic acid group, at least six boronic acid group, at least seven boronic acid group, at least eight boronic acid group, at least nine boronic acid group, at least 10 boronic acid group. The process can cause the overall ionization equilibrium to shift from neutral/insoluble boronic acid moieties to anionic/hydrophilic boronate, thereby changing the surface charge density. This can result in a change in the carrier concentration within the bulk of the atomically thin graphene in the sensing module, and hence a change in the graphene conductance. In certain embodiments, the reference polymer can be glucose-insensitive, the graphene conductance in the reference module would change only due to fluctuations in environmental parameters. Thus, differential measurement of the graphene conductance can allow determination of tear glucose concentration.

To estimate the nanosensor performance, Langmuir's adsorption isotherm can relate the glucose concentration in ISF (c) to the surface density of boronic acid-bound glucose molecules. It can then be shown that the sensitivity of the graphene conductance (G) is approximately:

$$(dG/G)/dc \approx \gamma_{max} K_d / [2N(K_d+c)^2], \qquad (1)$$

where N is the graphene's charge carrier density, $\gamma_{max}$ the surface density of immobilized boronic acid groups, and Kd the equilibrium dissociation constant of the binding system. Thus, for typical material and binding properties (N~$10^{15}$ m$^{-2}$, $\gamma_{max}$ ~$10^5$ µm$^{-2}$ and $K_d$ ~10 mM), over a desired glucose concentration range of 0.5-30 mg/dL (which encompasses the hypoglycemic, normoglycemic and hyperglycemic regimes), the nanosensor sensitivity ~0.5%-0.4%/(mg/dL). For an estimated conductance measurement resolution of 0.1%, glucose concentration can be measured at a resolution of ~0.7-0.02%, which allows accurate affinity detection of glucose in tears.

In certain embodiments, in order to screen out effects not caused by the target analyte, for example, environmental factors such as temperature or other analytes, the reference chamber can include a graphene sensor that is functionalized with another polymer (the reference polymer). The reference polymer cannot bind with the target analyte. Also, the reference polymer cannot bind with or otherwise react with any other substance in the bodily fluid to impact the property of the reference solution in a similar way as the target analyte impacts the corresponding property in the sensing polymer. The reference polymer and sensing polymer can, however, respond similarly to non-target analytes and environmental conditions. The reference polymer can be selected to have similar hydrophilic blocks to those in the sensing polymer, but have no phenylboronic acid moieties. For example, glucose-unresponsive PAA or PHEAA can be used as a reference polymer for glucose detection. The charge and viscosity of PAA (or PHEAA) polymers can be glucose-independent. The analyte-free charge of the sensing polymer can be similar to that of the reference polymer.

In certain embodiments, the polymers can be not immobilized on the graphene sensors. In these embodiments, the proximity of the change in the polymer charge can be sensed by the graphene sensor. In certain embodiments, the polymers can be sequestered near the sensors by the presence of a hydrogel.

In accordance with another embodiment, alternative, covalent attachment methods, e.g., by using residue hydroxyl on graphene to tailor the polymer design can be used. In accordance with a further embodiment, a more basic monomer, such as N,N-dimethylacrylamide, can be used to prepare the polymer, which is known to enable the ionization of boronate upon binding with diols under physiologic conditions.

In certain embodiments, the disclosed receptor can change its structure upon the binding of the target molecules or analytes. The receptor can be coupled to the linker in the first confirmation. The structure of the receptor can be altered into the second confirmation when the target molecules bind to the aptamer. For example, in the absence of insulin, the guanine-rich IGA3 aptamer can be unfolded in the solution or form G-quartet structure as a result of Hoogsteen base pairing. Upon capture of insulin, the existing G-quartet structures can switch to stable, compact parallel or antiparallel G-quadruplex structures. These conformational changes can move the electron-rich aromatic nucleotide strands and insulin to the close proximity of the nanosensor surface, resulting in the direct binding of nucleotide or amino acids in insulin with the nanosensor surface. Such conformation can transfer electrons from either insulin or the deformed IGA3 aptamer into the surface of nanosensor and induce conductance change on the surface of the nanosensor.

Target Analyte

In various embodiments of the disclosed subject matter, the sensor can be used to determine the level of a target analyte in the body, for example oxygen, lactase, insulin, hormones, cholesterol, medicaments, viruses, ions, or the like. The sensor can use any known method to provide an output signal indicative of the concentration of the target analyte. The output signal can be typically a raw data stream that can be used to provide a useful value of the measured target analyte concentration. In certain embodiments, before the device is used to detect or monitor a target analyte, it can be first calibrated using samples containing known amount of the target analyte to obtain correlations between sensor response (e.g., capacitance readout) and the known concentration of the calibration sample. Thereafter, in the monitor of the target analyte, the pre-established correlations can be used to interpret the output signals of the sensor and determine the presence and/or concentration of the target analyte in a test sample.

In certain embodiments, the nanosensor as disclosed herein can enable highly reliable monitoring of a target analyte in a sample. In certain embodiments, the sample can be a bodily fluid, a non-bodily fluid liquid, or a laboratory sample. In certain embodiments, the nanosensor can be used to detect the change in the pH of a sample. In certain embodiments the nanosensor can be used to continuously monitor the change in pH of a sample. In certain embodiments, the nanosensor can be used to measure the amount or change in the amount of a target analyte in a sample. For example, the nanosensor can be part of a stand alone device that monitors the target analyte in a sample added to the device (e.g., a piece of lab equipment or home monitor).

In certain embodiments, the nanosensor as disclosed herein can enable highly reliable, continuous monitoring of glucose in bodily fluids. In certain embodiments, the bodily fluid can be tears, blood, saliva, mucus, interstitial fluid, spinal fluid, intestinal fluid, amniotic fluid, lymphatic fluid, pericardial fluid, peritoneal fluid, pleural fluid, semen, vaginal secretions, sweat, and synovial fluid of the subject.

In certain embodiments, tear fluid can be used to measure target analyte concentrations. Tear fluid can be easily accessible, and the eye is an ideal candidate for the placement of a microdevice (e.g., a contract lens with a nanosensor coupled to it) to monitor analytes. In certain embodiments, tear fluid can be used to test, for example, lactate levels or glucose levels.

In certain embodiments of the disclosed subject matter, the nanosensor can be used to monitor glucose as the target analyte. In these embodiments, the nanosensor can measure a concentration of glucose or a substance indicative of the concentration or presence of the glucose by using a specific receptor (e.g., polymer etc. . . . ) in the nanosensor. In certain embodiments, the present microdevice can include a combination of graphene, a novel biosensing nanomaterial, and a contact lens platform to enable noninvasive CGM in tear fluid.

Glucose concentration in tears has been found to range from 1-6.2 mg/dL in healthy individuals and up to 26 mg/dL in diabetic persons. Significant correlations have been found between tear and blood glucose concentrations, with deviations attributable to artifacts such as inconsistent tear collection methods. Tear fluid can include basal tear, which keeps cornea wet and nourished, and reflex tear, which is induced by irritation of the eye due to foreign particles or irritant substances. No significant differences in glucose concentration have been found in basal and reflex tears.

A contact lens-based graphene affinity nanosensor (FIG. 1) can offer several potential advantages. For example, binding of glucose with an affinity polymer monolayer immobilized on graphene can cause a change in surface charge density, which can penetrate the atomically thin graphene to significantly change the graphene's conductance, leading to a significant detectable signal even at low, hypoglycemic glucose concentrations. Accurate detection of hypoglycemia is of great importance to diabetes care because this condition can cause acute, severe complications to patients, but is challenging in tear where hypoglycemic concentrations are 10s of times lower than those in blood. In certain embodiments, accurate detection of small amounts of glucose can be achieved by the high sensitivity of graphene in combination with differential detection via two small graphene sensing elements placed in close proximity to achieve effective common-mode cancellation of noise and environmental disturbances.

The nanosensor can include the glucose-binding polymer with boronic acid groups (e.g., polymer poly(acrylamide-ran-3-acrylamidophenyl boronic acid) (PAA-ran-3PAAPBA)) that can bind with glucose at 2:1 ratio to form cyclic esters. The resulting changes in physical (e.g., viscometric and dielectric) properties of the polymer can be measured with microfabricated devices, enabling specific measurement of glucose concentrations. The nanosensor can thus be highly sensitive and accurate at clinically important glucose concentrations in tears, in particular in the low, hypoglycemic regime (below 1 mg/dL). In certain embodiments, the glucose concentrations can be measured at a resolution of about 2 μg/dL-about 3 μg/dL. In certain embodiments, the glucose concentrations can be measured with the disclosed microdevice at a resolution of about 1 μg/dL-about 10 μg/dL, 2 μg/dL-about 9 μg/dL, 3 μg/dL-about 8 μg/dL, 4 μg/dL-about 7 μg/dL, or 5 μg/dL-about 6 μg/dL. In certain embodiments, the glucose concentrations can be measured with the disclosed microdevice at a resolution of at least about 1 μg/dL, at least about 2 μg/dL, at least about 3 μg/dL, at least about 4 μg/dL, at least about 5 μg/dL, at least about 6 μg/dL, at least about 7 μg/dL, at least about 8 μg/dL, at least about 9 μg/dL, at least about 10

µg/dL, at least about 12.5 µg/dL, at least about 15 µg/dL, at least about 17.5 µg/dL, or at least about 20 µg/dL.

The nanosensor can also be used for other applications. In addition to diabetes, the proposed CGM microdevice can also be used for glucose monitoring for other diseases (e.g., glycogen storage disease and hyperinsulinaemic hypoglycaemia). In some embodiments, the nanosensor can be used for detecting insulin molecules. For example, the nanosensor can include insulin-specific receptors such as guanine-rich IGA 3 aptamers. For example, the binding of insulin to aptamer IGA3 can alter the carrier concentration in the channel of nanosensor. The altered carrier concentration can further change conductance and current of the channel layer. The conductance and current of the channel layer can be measured to determine the insulin concentration. The disclosed nanosensor can detect insulin concentrations as low as about 1 nM. For example, the graphene nanosensor can monitor insulin levels ranging from about 1 nM to about 500 nM in real time.

The method can be extended to other metabolites, such as lactate, fatty acids, cysteines and homocysteines. For example, in emergency medicine, lactate monitoring can be used to predict possible organ failure of trauma patients, organ transplant patients, and patients with other critical conditions. In non-limiting embodiments, the method can include modifying the aptamer to adjust a specificity of the nanosensor to the target analyte. For example, the aptamers on the surface of the nanosensor can be replaced with other receptors which can be show improved specificity for certain target analytes such as insulin and glucose.

Further, the methods disclosed herein can be used as a reliable method for long-term monitoring of metabolites. Such methods can have great military significance. For example, a miniature device for glucose detection with fully electronic readout would have significant applications in protecting armed forces in the field. It can also provide a platform to enable the delivery of drug treatments and nutritional supplements to protect and enhance performance in military personnel.

Moreover, the disclosed method can be applied to the diagnosis of disease. For example, the development of boronic acid-based glucose sensing systems can be extended to other analytes, such as human viruses and bacteria, as many of those microorganisms carry glycoproteins on the exterior surface that can be targeted by the boronic acid based binding motifs.

Additionally, the disclosed method can be applied to a noninvasive method for monitoring cancer treatment. For example, receptors can be designed to that bind to target microparticles associated with cell apoptosis. The receptors can be specific for apoptosis of the cancer cells. In certain embodiments, the microdevice can be used to track overall cell apoptosis to monitor when levels of cell death before they become too toxic. In certain embodiments, the microdevice is able to detect the level of cancer cells in the bodily fluid.

Furthermore, the methods disclosed herein can be used as a reliable method for determining the drug distribution of a treatment regimen in order to maximize the therapeutic effects of the drug. In such methods, the receptors of the device can be designed to bind to the drug found in the bodily fluid. For example, ocular drug delivery is a major challenge to pharmacologists due to its unique anatomy and physiology (e.g., different layers of cornea, sclera, and retina including blood aqueous and blood-retinal barriers, choroidal and conjunctival blood flow, lymphatic clearance, and tear dilution). The microdevice can be a useful tool to determine what level of the drug reaches the ocular surface.

Metabolic monitoring is of great utility to environmental monitoring. Changes in the concentrations of metabolites are the precursors and products of enzymatic activity, and can be associated with biological function and regulation. Metabolic monitoring hence can be used for environmental monitoring, e.g., risk assessment of chemicals and diagnosis of diseases in wild animals. It can also be used as a tool to better understand the underlying mechanisms of action of toxic compounds in the environment.

Additional aspects and embodiments of the disclosed subject matter are illustrated in the following examples, which are provided for better understanding of the disclosed subject matter and not limitation.

Graphene Aptameric Nanosensor for Detection of Insulin

Techniques for real-time detection of insulin using a nanosensor system are disclosed herein. The disclosed subject matter can allow real-time, label-free, and selective detection of insulin concentration.

As embodied herein, the disclosed subject matter provides a nanosensor system for detecting insulin molecules in a sample. The nanosensor system can be based on a graphene-based field-effect transistor (GFET). The field-effect transistor can include a graphene channel and an aptamer. The aptamer can be coupled to the graphene channel through a linker. The aptamer can be attached to the linker in the first conformation and convert into a second conformation when the aptamer binds to the target molecule. The graphene-based FET can provide improved response speed, specificity, and sensitivity for target detection.

In certain embodiments, the disclosed subject matter provides a graphene channel. Graphene, a monolayer of carbon arranged in a hexagonal lattice, can be located on a substrate between at least two electrodes (e.g., drain electrode and source electrode) with a gate contact. For example, graphene can be transferred onto 285 nm SiO2/Si substrate. Gate, drain, and source electrodes (Cr/Au) can be subsequently fabricated using E-beam evaporation and lift-off techniques. The graphene can be patterned to define the conducting channel using photolithography and oxygen plasma etching. In some embodiments, the graphene channel can serve as a conducting channel between the electrodes. The electrical double later at the interface of graphene and electrolytes can serve as a gate dielectric. The drain and source electrodes can be biased with voltage and generate a current through the graphene channel, as a function of applied gate voltage. Because of insulin's characteristics (e.g., molecular weight of insulin and concentration), insulin is not adsorbed to bare graphene in a few minutes (e.g., <10 min) or the adsorption does not introduce significant variation in the graphene conductivity. Therefore, graphene can be an appropriate channel for insulin detection.

In certain embodiments, the disclosed subject matter provides a linker. The linker can be coupled to the graphene channel. For example, the linker can be noncovalently coupled to the graphene channel via π-π stacking between pyrene group and graphene. The π-π stacking can refer to attractive, noncovalent interactions between aromatic rings. In some embodiments, the linker can include 1-pyrenebutanoic acid succinimidyl ester (PASE). The PASE linker can be immobilized on the surface of the graphene channel. The PASE linker can include the N-hydroxysuccinimide ester group to bind to an aptamer. In non-limiting embodiments, the coupling of PASE to graphene can increase $V_{Dirac}$ (voltage at which the current reaches its minimum), suggesting that PASE can introduce p-type doping in graphene. The thickness of the graphene channel can be increase after functionalization with a linker and can be measured by atomic force microscopy (AFM) to confirm that the linkers are immobilized on the graphene surface.

In certain embodiments, the disclosed subject matter provides an aptamer. The aptamer can be coupled to the graphene channel through the linker. The aptamer can include DNA, RNA, XNA, and peptide aptamer. DNA, RNA, and XNA aptamers can include strands of oligonucleotides, and peptide aptamer can include one or more short variable peptide domains. In some embodiments, an aptamer can be conjugated to the linker by forming amide bone. For example, an amino group of an aptamer can be attached to the N-hydroxysuccinimide ester on PASE. To immobilize an aptamer onto the graphene channel, the graphene channel can be firstly immersed in PASE (e.g., 5 mM) solution at room temperature, sequentially rinsed with dimethylformamide (DMF) and phosphate buffered saline (PBS) buffer to remove free PASE. The graphene channel can be then rinsed with PBS followed by incubation with aptamer solution (e.g., 100 nM) for overnight at room temperature. After rinsing with PBS, ethanolamine (e.g., 100 mM) can be added onto the graphene channel to deactivate and block the excess reactive groups remaining on graphene surface. A polydimethylsiloxane (PDMS)-based open well (~20 µL) used to hold sample solutions can be bonded to the graphene channel.

In certain embodiments, the disclosed aptamer can selectively bind to the target molecule or analyte. For example, any aptamers which selectively binds to insulin molecules can be used for the disclosed nanosensor system. The insulin-specific aptamers can include a particular core sequence which binds to the target molecule or analyte. In some embodiments, the aptamer can include an insulin-specific IGA 3 aptamer. The IGA 3 can be a functionalized guanine-rich aptamer which has a core sequence 5'-NH2-GGT GGT GGG GGG GGT TGG TAG GGT GTC TTC-3' (SEQ ID NO: 1). In some embodiments, the IGA 3 can include a core sequence 5'-ACA GGG GTG TGG GGA CAG GGG TGT GGG G-3'(SEQ ID NO: 2), 5'-GGA GGT GGA TGG GGA GGG GGA GGT GTG TTT-3'3' (SEQ ID NO: 3), or 5'-GGA GGG GGT GGG GAG GGG GCT GGT TGT CC-3' (SEQ ID NO: 4).

In certain embodiments, the disclosed aptamer can change its structure upon the binding of the target molecules or analytes. The aptamer can be coupled to the linker in the first confirmation. Then, the structure of the aptamer can transform into the second confirmation when the target molecules bind to the aptamer. For example, in the absence of insulin, the guanine-rich IGA3 aptamer can be unfolded in the solution while G-quartet structure can be formed as a result of Hoogsteen base pairing. Upon capture of insulin, the existing G-quartet structures can switch to stable, compact parallel or antiparallel G-quadruplex structures. These conformational changes can move the electron-rich aromatic nucleotide strands and insulin to the close proximity of the graphene surface, resulting in the direct binding of nucleotide or aromatic amino acids in insulin with the graphene surface. Such conformation can transfer electrons from either insulin or the deformed IGA3 aptamer into graphene through the π-π stacking interactions between them and generate n-type doping to graphene.

In certain embodiments, the binding of insulin to aptamer IGA3 can alter the carrier concentration in the graphene channel. The altered carrier concentration can further change a conductance of the graphene layer and Ids. In some embodiments, the conductance of the graphene layer and Ids can be measured to determine the insulin concentration. For example, the graphene aptameric nanosensor can be treated with an insulin or/and glucagon solution. During the treatment, both the drain and gate voltage can be supplied by a sourcemeter, and Ids can be simultaneously measured to determine the insulin concentration.

In certain embodiments, the disclosed subject matter can provide methods for preparing the nanosensor. The method can include cleaning the wafer surface with oxygen plasma. As shown in FIG. 104, the wafer (285 nm $SiO_2$/Si) can be employed as the substrate of the device. The wafer can be cleaned successively with acetone, IPA and deionized water, then be dried by $N_2$. The method can further include performing spin coating. For example, the device was fabricated via a bilayer lift-off process. Two layers of resist can be sequentially spin-coated on the wafer using spin coater. The method can include performing photolithography and metal deposition to define the surface of the substrate. The planar source, drain and gate electrodes including a Cr/Au structure (5 nm/45 nm) can be defined on the $SiO_2$ surface using standard photolithography and metal deposition techniques. The method also can include performing photoresist removal. For example, the nanosensor can be kept in a photoresist remover overnight at room temperature for resist removal. The sample can exposure to oxygen plasma to remove the remaining residue on the $SiO_2$ surface. The method can further include patterning a graphene channel. The synthesized graphene can be transferred onto the substrate. To pattern the graphene sheet into a rectangle shape stretching over drain/source electrodes, the photoresist layers can be spin coated on graphene surface in turn for photolithography. After exposure and the resist developing with developer, the graphene sheet in the unprotected area can be etched using oxygen plasma to create the nanosensor with a regular conducting channel. The method can further include immobilizing aptamers onto the graphene channel through a linker. To immobilize the aptamer onto the graphene channel, the sensor can be immersed in PASE solution and sequentially rinsed with dimethylformamide (DMF) to remove any free PASE. Then The device can be rinsed with PBS followed by incubation with aptamer solution. Ethanolamine can be added onto the graphene channel to deactivate and block the excess reactive groups remaining on the graphene surface.

In certain aspect, the disclosed FET can detect a target analyte in a sample. The sample can include ionic solutions, blood, physiological-salt concentration solutions, and high-salt concentration solutions. In some embodiments, the disclosed subject matter provides methods and systems for real time, label-free and specific detection of insulin concentrations as low as about 1 nM. For example, the graphene nanosensor can monitor insulin levels ranging from about 1 nM to about 5000 nM, about 1 nM to 4000 nM, about 1 nM to 3000 nM, about 1 nM to 2000 nM, about 1 nM to 1000 nM, about 1 nM to 500 nM, about 1 nM to 250 nM, about 1 nM to 100 nM, and about 1 nM to 50 nM in real time.

Example 1. In Vivo Testing of a Microdevice

Microdevices with affinity polymers such as poly(acrylamide-ran-3-acrylamidophenyl boronic acid) (PAA-ran-3PAAPBA) were tested in mice. The polymers were constructed with phenylboronic acid groups that bind with glucose at 2:1 ratio to form cyclic esters. The resulting changes in physical (e.g., viscometric and dielectric) properties of the polymer were measured with a microelectromechanical systems (MEMS) device (FIG. 3a), enabling specific measurement of glucose concentrations. Miniaturization led to device response times of (1.5-2.5 min) at least 2-3 times as rapid as existing CGM devices. Using a differential design, the devices were highly stable, with drifts reduced from ~0.3%/hr (non-differential measurement) to less than 50 ppm/hr. Testing the device in mice via subcutaneous implantation (FIG. 3b) yielded output (reflecting interstitial fluid (ISF) glucose concentration) that consistently tracked blood glucose concentration (FIG. 3c) and was clinically accurate or acceptable by Clarke error grid analysis.

The nanosensor used in this test is depicted in FIG. 27.

Example 2. Construction of CVD Graphene

CVD graphene (205) was synthesized by heating annealed Cu foil (213) in a quartz tubing furnace (FIG. 4a). The Cu foil (213) was first sharply heated to 1000° C. in Argon (Ar) environment (200 mTorr), and annealed in hydrogen (H2) environment (10 mTorr). The mixture of methane ($CH_4$) and $H_2$ were then introduced and allowed to react for 18 min ($CH_4$: 170 mTorr, Hz: 10 mTorr), after which the sample was cooled down to room temperature in Ar flow at 200 mTorr and then retrieved from the tube. After graphene growth, 500 nm PMMA (214) was spin coated on top for protection and a PDMS stamp (216) and glass slide (215) was attached by pressing. Cu (213) was removed by wet etching.

Graphene (205) was transferred onto the substrate (217) at 170° C. (FIG. 4b) to realize the graphene conducting channel stretching over drain/source electrodes. After the protective PMMA layer (216) on graphene surface was dissolved by acetone, AFM (XE-100, Park System) and Raman spectroscopy (Renishaw, 532 nm laser) were used to verify the single-layer graphene sheet (FIG. 5A-C).

Example 3. Construction of Sensor Substrate Fabrication

Cr/Au (5 nm/45 nm) layers (307) were deposited on the top of Si/SiO2 substrate (BOC/Auto 306 thermal evaporator, Edwards) (318) (with Photoresist (S1811, Shipley) was then spin-coated on top (319)) and patterned to create the source/drain electrodes using photolithography (MA6 Mask Aligner, Karl-Suss) and wet-chemical etches (FIG. 6). Cu layer was directly deposited on the back side of substrate as the backgate electrode.

Example 4. Construction of Microchannel Fabrication

Microfluidic channel was fabricated using standard soft lithography (FIG. 7). SU-8 photoresist (419) was spin-coated on Si wafer (418) and patterned by photolithography3. Mixture of PDMS precursor and curing agent (420) was poured onto the SU-8 mold (419). The curing reaction was carried at 75° C. for 1 h. Then, cured PDMS microchannel was peeled off from the mold.

Example 5. A Solid Dielectric Gated Graphene Nanosensor in Electrolyte Solutions Illustrated herein is a GFET sensor that can allow accurate detection of a target analyte (e.g., H+).

Graphene can be used to form a conducting channel in field effect transistors (FET), allowing highly sensitive electric detection of analytes. Such graphene FET (GFET) sensors, when operating in liquid media, can be generally constructed in a solution-gated or solid-gated configuration. In a solution-gated GFET sensor, a reference electrode can be inserted into the electrolyte solution that is in contact with graphene to serve as the gate electrode, while the electric double layer (EDL) formed at the solution-graphene interface can play the role of the gate dielectric. Theses solution-gated sensors typically can require an external electrode inserted into the electrolyte solution, which hinders the integration and miniaturization of the device. In addition, the gate capacitance, or the capacitance across the EDL dielectric layer can be susceptible to disturbances in liquid media, which can result in fluctuations in electrical measurements of properties of graphene including the position of the Dirac point. In contrast, in a typical solid-gated GFET, the gate capacitance can be provided by a $SiO_2$ dielectric layer sandwiched between graphene and the underlying silicon substrate, which serves as the gate electrode. By eliminating the need for the external wire insertion into the electrolyte solution, solid-gated sensors can be highly miniaturized and integrated. However, due to the intrinsically low capacitance of the $SiO_2$ layer, usually the solid-gated GFET sensors can require undesirably high gate voltages (4050 V), consequently impeding their application to biosensing in liquid media.

This example presents a GFET nanosensor in liquid media using a thin layer of $HfO_2$ with a high dielectric constant ($\kappa$) as a gate dielectric layer (506). The $HfO_2$ layer can be sandwiched between the conducting-channel graphene (505) and a gate electrode (507) (FIG. 8) and can be embedded within the sensor. This can enable a high level of integration in the construction and passivation of electrically conducting elements in the sensor, as is highly desirable for analyte detection in liquid media. The use of the high-$\kappa$ dielectric material ($HfO_2$) can provide two orders of magnitude higher specific capacitance than conventional $SiO_2$ solid-gated sensors, thereby rendering high transconductance and allowing the device to operate at low gate voltages. In addition, the gate dielectric was isolated from the liquid media, thus eliminating errors caused by disturbances (e.g., bulk motion of sample solution). Furthermore, the sensor was amenable to time- and cost-effective microfabrication using photolithography without the need for manual assembly of discrete components (e.g., electrodes) with graphene, thereby simplifying the fabrication process. pH sensing was demonstrated using this high-$\kappa$ GFET nanosensor. Results show that the device is capable of measuring pH in a range of 5.3 to 9.3 with a sensitivity of ~57.6 mV/pH, and at a gate voltage of less than 1.5 V, which is approximately a factor of 30 lower than that used in $SiO_2$ solid-gated sensors.

Nanosensor Design

The nanosensor was configured as a solid-gated FET device, in which a graphene sheet (505), serving as the conducting channel, connected the source (508) and drain electrodes (509) on a $HfO_2$ dielectric layer (506), which in turn lies above the gate electrode (507) on the substrate (FIG. 8). When a buffer solution was introduced onto the graphene surface, the carrier concentration in the bulk of the graphene can undergo a change due to variations in the electric potential in the buffer next to the graphene. As the magnitude of the electric potential depends on the ion concentration (e.g., $H^+$), the pH level can be determined by measuring the graphene's electric properties such as its transfer characteristics and conductance, which can be directly related to the carrier concentration. To allow a high level of integration while avoiding the need for high gate voltages, the nanosensor used 20 nm thick $HfO_2$, a material with a high dielectric constant ($\kappa \approx 20$, compared to $\kappa \approx 3.9$ for $SiO_2$), as the dielectric layer to provide a high gate capacitance ($\sim 1$ $\mu F/cm^2$). This in general can allow the Dirac point, at which the drain-source current $I_{DS}$ achieves its minimum, to be observed at a lower gate voltage.

Nanosensor Fabrication

The nanosensor (FIGS. 8-11a) was fabricated on a $SiO_2$-coated silicon substrate (518) by first depositing and patterning the gate electrodes (Cr/Au 5/45 nm) (507)(FIG. 9a). Subsequently, a 20 nm $HfO_2$ layer (506) was deposited over the wafer using atomic layer deposition (ALD) (FIG. 9b). A lift-off process was used to create the drain (509) and source (508) electrodes, onto which a single-layer graphene sheet (505) synthesized by chemical vapor deposition (CVD) was transferred (FIG. 10b). A microchamber (2.5 µL), fabricated in a polydimethylsiloxane (PDMS) sheet via soft lithography, was placed on the resulting nanosensor chip to confine sample liquid on the device.

In particular, the nanosensor was fabricated on a $SiO_2$-coated silicon substrate (518, 519). After cleaning by piranha, 5/45 nm Cr/Au was deposited using thermal evaporation (BOC 306 Thermal Evaporator, Edward) (FIG. 9a). Photoresist (S1811, Shipley) was then spin-coated on top of Au at 5000 rpm for 1 min, and baked at 115° C. for 1 min. Photolithography (MA6, Suss MicroTec) was then used to pattern the shape of the gate electrode on the wafer. The wafer was then developed in developer (AZ MIF 300, AZ Electronic Materials) and local wet etched in gold and chrome etchant subsequently (FIG. 9a). The wafer was cleaned with piranha solution followed by oxygen plasma. Next, a 20 nm $HfO_2$ layer (506) was deposited on top of the gate electrode (507) using atomic layer deposition (ALD, Savannah 200, Cambridge Nano Tech) at $3.6 \times 10^{-1}$ Torr and the temperature as high as 200° C. (FIG. 9b) (FIG. 9b). Another layer of photoresist (S1811, Shipley) was spin-coated and patterned to define the shape of source and drain electrodes, followed by deposition of 5/45 nm Cr/Au. Lastly, the wafer was immersed in photoresist stripper (AZ MIF 400 Stripper) and acetone sequentially to dissolve the photoresist and shape the drain and source electrodes (FIG. 9c). After the completion of the fabrication process, a single-layer graphene sheet (505) synthesized by chemical vapor deposition (CVD) was subsequently transferred onto the sensor to cover the source (508), drain (509) and gate electrodes (507) (FIG. 9d). A Raman spectrum was taken to confirm the monolayer graphene sheet throughout the conducting channel. A polydimethylsiloxane (PDMS)-based microchamber was used to confine the liquid sample on top of the graphene.

Results

Raman spectroscopy and atomic force microscopy (AFM) was first used to confirm that the graphene used to fabricate the device consisted of a single atomic layer. The Raman spectrum revealed G mode and 2D mode, which are characteristic of single-layer graphene (FIG. 10c). AFM data were used to determine the thickness of the graphene to be 0.3-0.4 nm (FIG. 10d), which reflected the van der Waals diameter of carbon and was, hence, also indicative of single-layer graphene.

The transfer characteristics of bare graphene in air was determined. $I_{DS}$ was measured while the solid-gate voltage $V_{SG}$, which makes a major contribution to the overall gate voltage, was varied sinusoidally from −0.2 to 1.9 V. An ambipolar curve was observed; the Dirac point solid-gate voltage, or the gate voltage value at which the $I_{DS}$ achieves the minimum (FIG. 11a), was hence determined to be $V_{SG,DP}$=0.7 V. This confirmed that the conductivity of the graphene was being altered by the field effect.

The nanosensor was tested for pH sensing in liquid media. Samples at various pH values (5.3 to 9.3) were prepared by mixing NaOH or HCl with phosphate buffered saline (PBS) buffer (Life Technologies, ionic strength ~150 mM). A sample solution was incubated with our nanosensor, during which $I_{DS}$ values were measured while the gate voltage $V_{BG}$ was swept from 0.6 V to 1.6 V. $V_{SG,DP}$<1.5 V at all pH levels (FIG. 12A-B). These significantly reduced gate voltage values, compared to 40-50 V for $SiO_2$ based solid-gated sensor, can be attributed to the high gate capacitance and hence the high transconductance provided by the high-κ $HfO_2$ dielectric layer. $V_{SG,DP}$ was found to linearly increase with the pH value at a sensitivity of ~57.6 mV/pH (FIG. 12a), which would otherwise not be attainable by a conventional dielectric ($SiO_2$)-based device operating at similarly low gate voltages.

It was also determined that these measurements were reproducible, with a different device of the same design yielding a closely agreeing sensitivity of 58.2 mV/pH (FIG. 13A-B). When pH increased, the electrostatic potential above graphene increased due to the decrease of $H^+$; therefore, the curve shifted to the right to compensate for the increase in the electrostatic potential. The leakage current between drain/source and gate electrodes was found to be much smaller than $I_{DS}$ and therefore negligible.

There can be two possible physical processes that have been used to explain how adsorption of ions on graphene causes variations in the conductivity. The first process can involve the charging of the EDL capacitor by adsorbed ions, thereby causing variations in the potential in the solution in contact with the graphene, and therefore changing the Fermi level and carrier density of graphene, e.g., the electric field tuning. In the second process, which is known as the surface charge transfer doping, adsorbed ions serve as dopants, from which electrons can be exchanged into the bulk of the graphene. The solid-gated sensor, which avoids the influence of the externally applied top gate voltage on the EDL, can be used to investigate the effect of either the EDL capacitor charging or the surface charge transfer doping. From the transfer characteristics obtained at different pH levels (FIG. 12a), the transconductance was found to be within 0.3 µS of a constant value of 23.2 µS (FIG. 11b), implying that the carrier mobility was also approximately a constant regardless of the pH variations. Therefore, the surface transfer doping cannot be a dominant effect, which would otherwise have altered the carrier mobility significantly.

To investigate the effect of the charging of the EDL capacitor the nanosensor was modeled as a dual-gate field effect transistor including the solid gate (with $HfO_2$ as the dielectric) below the graphene and a solution gate formed by the EDL above the graphene at its interface with the solution. The voltage on the top solution gate, $V_{LG}$, which was equal to the potential drop across the EDL capacitor, depended on the ion concentration in the electrolyte solution. This solution gate voltage, which leads to the charging of the EDL capacitor, can be estimated by the Nernst equation[18], $V_{LG}=E_0 -2.3 \log(H^+)RT/nF$, where $E_0$ is a constant reference potential, R the universal gas constant, T the temperature of 298.15 K, n the ionic charge (1 for $H^+$), F the Faraday constant. With $pH=-\log(H^+)$, the following was obtained:

$$V_{LG}=E_0+(59.2\ mV)pH \quad (2)$$

Thus, the highly linear dependence of the experimentally determined $V_{SG,DP}$ on pH (FIG. 12b) raised the conclusion that the right shift of $V_{SG,DP}$ with pH was due to the increase in $V_{LG}$. In addition, it was seen that $V_{SG,DP}$ depended on $V_{LG}$ in a roughly linear manner in the pH range tested (FIG. 14). As the slope of this dependence (estimated to be ~1) was equal to the ratio of the solution-gate capacitance ($C_{LG}$) to the solid-gate capacitance ($C_{SG}$), $C_{LG}/C_{SG}\approx1$. That is, the solid-gate capacitance was comparable to the liquid-gate capacitance (typically on the order of 1 $\mu F/cm^2$) in the nanosensor, representing a significance improvement over $SiO_2$ solid-gated GFET devices. This allowed the nanosensor to operate at the low gate voltages as demonstrated. In addition, it should be noted that at a given pH level, a significant increase in the ionic strength of alkali cations (e.g. $Na^+$, $K^+$) can decrease the measurement sensitivity. This is because the electrostatic gating effects produced by the alkali cations compete with the gating effects from the $H^+$. Therefore, to measure the concentration of $H^+$, the concentration of the nonspecific ions can be maintained at a constant level to obtain a constant sensitivity. Indeed, the concentrations of the alkali cations were approximately constant in the tests, as the NaOH was added to the buffer at a very dilute concentration (~0.1 mM) and hence had negligibly effects on the on the ionic strength of the buffer (150 mM). Therefore, the sensitivity in pH measurements was approximately constant and not affected by the addition of NaOH for control of pH values.

To demonstrate the ability of the nanosensor to perform real-time pH measurements, $I_{DS}$ was measured at a fixed gate voltage ($V_{BG}=0.75$ V), while successively introducing samples with different pH values (FIG. 15). As pH decreased from 9.3 to 5.3 (i.e., the solution becomes more acidic), the $V_{TG}$ also decreased (Eq. (2)), and the EDL capacitor accordingly underwent partial discharging. This caused a decrease in the carrier concentration of the graphene, and $I_{DS}$ hence correspondingly decreased. These phenomena were reversed as pH continued to change, but now in a reversed direction by increasing from 5.3 to 9.3. This reflected that the EDL capacitor underwent charging, thereby causing the carrier concentration in the graphene, and hence $I_{DS}$, to increase. Throughout the entire set of measurements, the values of $I_{DS}$ were found to be consistent at a given pH value, regardless of whether this value was reached by pH increasing from a lower value or decreasing from a higher value, with small deviations attributable to the hysteresis in the electronic transport in the graphene. Thus, it was concluded that pH measurements by the nanosensor were reversible, which is important for practical applications.

This example describes a high-κ solid-gated GFET nanosensor in liquid media. The embedded solid gate eliminates the need for an external gate electrode and is hence amenable to the complete integration of the nanosensor as is highly desirable for analyte detection in liquid media. The use of a high-κ dielectric allows the device to operate at low gate voltages and avoids errors caused by gate capacitance variations. Example data from the nanosensor showed measurements of pH in a range of 5.3 to 9.3 with a sensitivity of ~57.6 mV/pH. The pH-dependent electrical responses of the nanosensor responsible for the measurements were found to be caused by the charging of the electric double layer capacitor, rather than surface transfer doping. These results suggest that the GFET nanosensor can be potentially used to enable highly integrated sensing of chemical and biological analytes.

Example 6. Polymer Synthesis and Graphene Immobilization

A series of pyrene-terminated polymers were synthesized, e.g., poly(N-3-acrylamidophenylboronic acid) (pyrene-PAAPBA), using a radical addition-fragmentation chain transfer (RAFT) polymerization (FIGS. 16a and 17), using an established protocol for synthesis of sugar-responsive copolymers of PAAPBA and N,N-dimethylacrylamide with pyrene-derived RAFT agent. N-3-acrylamidophenylboronic acid (AAPBA) monomer (e.g., 8-10%) was mixed with acrylamide (AM) and RAFT polymerization was initiated with AIBN. The reference polymer can use AM as monomer or replace AAPBA in PAM-ran-PAAPBA with phenyl acrylamide (PAM). The chemical structure confirmed by $^1$H NMR. Three sizes of pyrene-PAAPBA were prepared with a molar mass dispersity less than 1.2 as determined by gel permeation chromatography.

Pyrene-terminated polymers were irreversibly attached to graphene with strength comparable to covalent attachment, using a sticky point for π-π stacking interactions without disrupting the graphene's conjugation or altering its electronic properties (FIG. 16b,c) The polymers (PAM-ran-PAAPBA, PAM or PAM-ran-PPAM) were attached to graphene surfaces via incubation with graphene for 30 minutes followed with extensive washing.

Example 7. A Graphene-Based Affinity Glucose Nanosensor

This example presents a synthetic polymer-functionalized graphene nanosensor for affinity-based, label-free detection of low-molecular-weight, low-charged glucose molecules. In this sensor, graphene was functionalized with a synthetic polymer monolayer derivatized with a boronic acid group (FIG. 18) whose reversible complexation with glucose generates a detectable signal. The binding of the polymer monolayer with glucose on the graphene surface induced changes in the carrier density and mobility in the bulk of graphene, thereby potentially offering a high detection sensitivity. The small size of the graphene as the transduction element can allow miniaturization of the sensor dimensions. Moreover, the polymer functionalization of the graphene can eliminate needs for physical barriers such as semipermeable membranes commonly used in existing glucose sensors, thereby simplifying the device design and enabling rapidly responsive measurements for reliable glucose monitoring.

Nanosensor Design

The nanosensor was configured as a solution-gated graphene-based FET (GFET) in that the graphene (605) was the conducting channel, formed between two gold electrodes (source (608) and drain (609)) on an insulating substrate surface (601) (FIG. 18). A monolayer of the synthetic glucose responsive polymer, pyrene-terminated poly(3-acrylamidophenylboronic acid) (py-PAPBA) (611), was attached to the graphene surface via π-π stacking interactions (FIG. 17). A glucose solution (621) in phosphate buffered saline (PBS) was held directly above the polymer-functionalized graphene in a polydimethylsiloxane (PDMS) microchannel, with an Ag/AgCl wire (607) inserted into the solution to serve as a gate electrode. An electrical double layer (EDL) formed at the interface of the graphene (605) and solution (621), and serves as the gate dielectric layer. During operation, under the control of a voltage applied between the gate and source electrodes (gate voltage Vgs), a bias voltage applied between the drain and source electrodes (drain-source voltage Vds) generated a current through the graphene (drain-source current Ids) that was measured. This can yield the transfer characteristics of the GFET (i.e., the functional dependence of Ids on Vgs) and can allow the determination of the glucose concentration, because the binding of boronic acid moieties of the polymer PAPBA changes the electrical properties of the graphene as follows.

First, the polymer-glucose binding can change the position of the Dirac point (Vgs,Dirac), i.e., the value of the gate voltage at which the charge carriers neutralize and the drain-source current Ids can achieve its minimum. Cyclic esters of boronic acid can form as a result of the binding of boronic acid groups to glucose molecules, and this can cause the overall ionization equilibrium to shift from neutral/insoluble boronic acid moieties to anionic/hydrophilic boronate. Thus, the carrier density can vary because of the electron exchanges between the graphene and the solution when the charge density in the solution changes. This can alter the Fermi level of the graphene, thereby shifting the Dirac point position.

The polymer-glucose binding can also change the transconductance, gm, i.e., the drain-source current change rate with respect to the gate voltage (∂Ids/∂Vgs) in the linear region of the GEFT transfer characteristics. The charged polymer molecules lying on the graphene surface can be considered charged impurities, and induce electron scattering that degrades the carrier mobility, µ, of the graphene. This accordingly can decrease the transconductance according to:

$$\mu = L(WC_g V_{ds})^{-1} g_m \quad (3)$$

where W and L are respectively the width and length of the graphene conducting channel, and Cg is the gate capacitance per unit area.

Nanosensor Fabrication

The device was fabricated using micro and nanofabrication techniques (FIG. 19A-C) on an oxidized silicon wafer (601). After cleaning by piranha, a layer of 5/45 nm Cr/Au was deposited (609, 608) using thermal evaporation. A layer of photoresist was then spin-coated on top of Au layer and baked at 115° C. for 1 min. Photolithography was used to pattern the gate electrode, and the wafer was then developed and etched in gold and chrome etchant sequentially. Graphene (605) synthesized via chemical vapor deposition (CVD) on a copper sheet was transferred onto the substrate following an established protocol to cover the source (608) and drain (609) electrodes (FIG. 20a).

To perform PAAPBA polymer functionalization, the graphene and the underlying substrate were immersed in a solution of the pyrene-terminated polymer (py-PAAPBA/methanol 3% w/v) for 4 hours at room temperature, and then washed thoroughly using methanol. During testing of the nanosensor, glucose solution was placed directly above the graphene and held in a PDMS open microchannel (~2.5 µL in volume), which was fabricated using soft lithography and reversibly bonded to the device. An Ag/AgCl reference electrode was inserted into the solution above the graphene to serve as the gate electrode for application of a gate voltage (FIG. 20b).

Results

It was verified that single-layer graphene was used in the nanosensor via Raman spectroscopy (FIG. 21). The G band at ~1580 cm$^{-1}$ in the Raman spectrum, characteristic of the planar geometry of sp$^2$ bonded carbon, indicated that the material was graphene. Moreover, the sharp and symmetric 2D band at ~2685 cm$^{-1}$ indicated that the graphene consisted of a single layer of carbon atoms. Next, the polymer functionalization of the graphene was verified. Atomic force microscope (AFM) was performed, and the resulted images (FIG. 22A-B) showed that there was a significant increase (~10 nm) in the apparent height of the graphene sheet after the functionalization, suggesting the successful grafting of the polymer molecules.

The polymer functionalization of the graphene was also verified by measurement of the GFET transfer characteristics. The shape of the $I_{ds}$-$V_{gs}$ curve was similar before and after the functionalization protocol, while the Dirac point position $V_{gs,Dirac}$ was found to have shifted from 0.22 V to 0.18 V (FIG. 23). The lack of change in shape of the $I_{ds}$-$V_{gs}$ curve suggested that changes in the carrier mobility in the graphene were insignificant. This was consistent with the polymer, and in particular the boronic acid moieties, being electrically neutral and would cause little electron scattering to change the graphene's carrier mobility. On the other hand, the shift in $V_{gs,Dirac}$ was believed to be caused by n-doping (i.e., electron doping) of the graphene, and was consistent with the surface-attached polymer inducing electron transfer from the solution to the graphene. Therefore, concluded graphene had been successfully functionalized with the PAAPBA polymer.

The nanosensor was tested to obtain the graphene's transfer characteristics at varying glucose concentrations. It was observed that the transfer characteristics changed consistently as the binding of glucose to the boronic acid shifted the electrically neutral boronic acid groups to anionic boronate esters (FIG. 24). In response to increases in the glucose concentration, the Dirac point position $V_{gs,Dirac}$ shifted to higher gate voltages with a sensitivity of ~2.5 mV/(mg/dL), while the $I_{ds}$-$V_{gs}$ curve broadened in shape. The shift in $V_{gs,Dirac}$ indicated that the graphene was p-doped, or hole-doped, which could be caused by changes in the amount of electric charge on the EDL gate capacitor due to the formation of anionic boronate esters. On the other hand, the broadening of the transfer characteristic curve reflected a decrease in the transconductance from 100 to 20 µS. According to the equation above, this corresponded to a decrease in the carrier mobility and was a consequence of the polymer-glucose binding, as the negatively charged boronate esters, in the role of charged impurities, caused electron scattering.

To investigate the influence of the potential contributors other than polymer-glucose binding, control measurements were performed on pristine graphene that was not functionalized with the PAPBA polymer. Neither the Dirac point position nor the transconductance changed significantly as the glucose concentration was varied from 60 to 200 mg/dL (FIG. 25), indicating that when not functionalized the PAAPBA polymer, there was negligible response of the graphene to glucose concentration changes. Thus, the response of the polymer-functionalized nanosensor to the changes in glucose concentration resulted from the glucose-polymer binding.

The device was tested for the detection of glucose in a concentration range of 0 to 200 mg/dL with a sensitivity of ~2.5 mV/(mg/dL). These results demonstrate the potential of the device for blood glucose monitoring and control in diabetes care.

Example 8. A Graphene-Based Affinity Glucose Nanosensor

In order to construct a nanosensor that can be integrated and miniaturized enough to be coupled to a contact lens, graphene, $HfO_2$ and gold were successively laid on an $SiO_2$-coated silicon substrate. The gold layer, lying below graphene, served as the gate, and the 20-nm $HfO_2$ layer as the dielectric to form a solid-gated FET (FIG. 26a), similar to the configuration to be used in Example 7. Using such a nanosensor demonstrated real-time monitoring of pH changes (FIG. 26b).

Example 9. A Graphene-Based Affinity Glucose Nanosensor

This nanosensor is built to use a mechanically flexible, CVD-prepared hexagonal boron nitride (h-BN) nanolayer to replace $HfO_2$ (which can be brittle and not flexible) as the dielectric.

The graphene of this nanosensor can be functionalize with an optimized synthetic polymer and coupled to a contact lens-based flexible substrate.

Example 10. Preparation of a Hydrogel

A poly(hydroxyethyl-methacrylate) (PHEMA) based hydrogel, which has excellent biocompatibility and glucose permeability, can be synthesized in situ. A mixture of hydroxyethyl methacrylate (HEMA), tetraethyleneglycol diacrylate (TEGDA), polyethyleneglycol methacylate (PEGMA) and N-[tris(hydroxymethyl)methyl]-acrylamide (HMMA) in a ratio 86:3:5:5 mol % can be prepared, and applied to the device surfaces to form a hydrogel under UV irradiation in $N_2$, which is then conditioned via sequential immersion in mixtures of ethanol and deionized water. The hydrogel synthesis can be optimized to enable high glucose permeability while preventing permeation of larger molecules (e.g., proteins) from tissue.

Example 11. Preparation of a Two Channel Sensor

Nanosensor Design

The graphene nanosensor design can include two field-effect transistor (FET) modules of identical construction on a contact lens-based flexible substrate (FIGS. 1 and 2A-B). In each module a slender graphene strip (the conducting channel) can lie on a sheet of h-BN (106) passivating a Ti/Pd/Pt gate electrode (107) (with h-BN minimizing substrate-induced charge carrier scattering in the conducting channel)), and can make contact with Ti/Pd/Pt source (108) and drain electrodes (109). These nanolayers can lie on a polymer substrate (e.g., PET) (101), and can be covered with a thin polymer (e.g., parylene) layer (110) with the exception of the conducting-channel (103, 104) graphene, which can be functionalized with a glucose-binding polymer (the sensing module) (111) or a glucose-insensitive polymer (the reference module) (112). The entire nanosensor can be coated with a glucose-permeable hydrogel. The nanolayers and polymer layers can be all flexible and biocompatible. During operation, the conducting-channel graphene can be subjected to a gate voltage (e.g., between ±300 mV) with respect to the gate electrode underneath, and the current through the graphene under a bias voltage (~100 mV) between the source and drain, which can be kept sufficiently small to limit the potential leakage current into the hydrogel coating well below the threshold (~10 μA/mm2) required to prevent undesirable electrochemical effects in tissue.

The nanosensor can be designed as summarized in the FIG. 2A-B. FIG. 2A-B illustrates the nanosensor can include glucose sensing (103) and reference modules (104), each including an FET sensing element with graphene (105) as the conducting channel and h-BN as the dielectric (106). ITO serves as the gate (below graphene) (107) as well as source (108) and drain (109) (on either side of graphene). The graphene (105) can be grafted with a specific glucose-binding (111) or reference polymer (112) monolayer. Glucose concentration in tears can be determined by differential measurement of the graphene conductance. The device can be based on a flexible substrate (101) and coated in a biocompatible hydrogel (not shown). To estimate the associated performance, Langmuir's adsorption isotherm can relate the glucose concentration in tears (c) to the surface density of boronic acid-bound glucose molecules. It can then be shown that the sensitivity of the graphene conductance (G) can be approximately:

$$(dG/G)/dc \approx \gamma_{max} K_d / [2N(K_d+c)^2], \qquad (4)$$

where N is the graphene's charge carrier density, $\gamma_{max}$ the surface density of immobilized boronic acid groups, and Kd the equilibrium dissociation constant of the binding system. Thus, for typical material and binding properties (N ~$10^{15}$ $m^{-2}$, $\gamma_{max}$ ~$10^5$ $\mu m^{-2}$ and $K_d$ ~10 mM)[86,87], it can be estimated that over a desired glucose concentration range of 0.5-30 mg/dL (which encompasses the hypoglycemic, normoglycemic and hyperglycemic regimes), the nanosensor sensitivity ~0.5%-0.4%/(mg/dL). For an estimated graphene conductance measurement resolution of 0.1%, hence it is anticipated that glucose concentration can be measured at a resolution of ~0.7-0.02%, which allows accurate affinity detection of glucose in tears.

The device's time response can be determined by the diffusive transport of glucose between the tissue and the implanted device, over a distance primarily given by the hydrogel coating (thickness ~20-50 μm and glucose diffusivity ~$6 \times 10^{-11}$ $m/s^2$). This can allow the device time constant to be estimated in the range of 7-42 seconds, affording a rapid response to tear glucose concentration changes.

Nanosensor Fabrication

To fabricate the device, a Ti/Pd/Pt layer can be deposited onto a substrate and then covered with CVD-deposited h-BN, forming the gate electrode (107), followed by deposition and patterning of another Ti/Pd/Pt metallization as the drain (109) and source electrodes (108). A single-layer CVD graphene sheet (505) can be transferred using a protective poly(methyl methacrylate) (PMMA) layer onto the substrate and patterned to form the conducting channel. With graphene still protected by PMMA and photoresist, a thin layer (1-2 μm) of Parylene can be deposited and patterned using oxygen plasma. After dissolving the PMMA and photoresist in organic solvent, the conducting-channel graphene can be exposed and then grafted with the sensing or reference polymer, and the entire device is coated with a hydrogel. A nanosensor prototype can be fabricated on a rigid silicon substrate, and then on a flexible PET substrate. For the flexible nanosensor the device can be fabricated on a flat sheet of PET, which can then be thermally molded into a contact lens shape. PET and Parylene can be chosen for their biocompatibility as well as their excellent mechanical and chemical stability.

The nanosensor can be fabricated in a two part process with increasing complexity, first on a rigid $SiO_2$-coated silicon substrate, and then on a flexible polymer substrate. In the case of a rigid substrate, ITO can be deposited onto a substrate and then covered with CVD-deposited h-BN, forming a transparent gate electrode. This can be followed by deposition and patterning of another ITO layer as the drain and source electrodes. A single-layer CVD graphene sheet (105) can be then transferred using a protective poly(methyl methacrylate) (PMMA) layer onto the substrate and patterned to form the conducting channel. With graphene still protected by PMMA and photoresist, a thin layer (<1 μm) of Parylene can be deposited and patterned using oxygen plasma. After dissolving the PMMA and photoresist in organic solvent, the graphene can be exposed and then grafted with the sensing or reference polymer, and the entire device is coated with a hydrogel.

Building on experience from rigid substrates, the nanosensor can be then be fabricated on a flexible substrate. To identify suitable materials to serve as the substrate for our nanosensor, materials that have been used in existing contact lens sensors can be measured, and also investigate materials commonly used in commercially available contact lenses. Contact lens-based sensors in the literature have used polymers such as polyethylene terephthalate (PET), which can be unfortunately opaque and not appropriate for practical use, and silicone. Commercially available contact lenses include "soft lenses" and "rigid lenses". Soft lenses can be made of hydrogels or silicone-hydrogel copolymers that have high water content but a low mechanical stiffness. In comparison, rigid lenses, with low water content, have significant stiffness to retain their shape. PMMA can be used as the substrate for fabrication of our nanosensor. Other materials include soft lens materials such as silicone (e.g., NuSil Technology MED-6015), and rigid lens materials such as silicone acrylates (e.g., Dow Corning® FA 4001 CM Silicone Acrylate) and fluorosilicone acrylates (e.g., XCEL Contacts Fluoroperm® 92).

PMMA can be the material of which the first contact lenses were made, and can be still in use in commercially available contact lenses today. It has excellent optical qualities, durability and biocompatibility, and micro- and nanofabrication techniques using PMMA are well established and have been used in our preliminary studies as a sacrificial substrate for transfer of graphene. The fabrication process described above for rigid substrates can be generally compatible with PMMA used as substrate. Using the process, the nanosensor is fabricated on a flat sheet (~50 μm thick) of PMMA placed on a carrier silicon wafer. Upon the completion of the fabrication process, the flat PMMA sheet along with the fabricated device can then be thermally molded into the shape of a contact lens. The device could also be fabricated on suitable handling substrate (e.g., PET), and then transferred onto PMMA that has been pre-molded into a contact lens shape.

Graphene can be grafted with sensing and reference receptors (e.g., polymers), and the nanosensor can be coated with a biocompatible hydrogel.

Example 12. Understanding the Physics of Nanosensor Operation

To understand the sensing mechanisms and inform the optimal design of the graphene nanosensor, the conductance change of graphene due to polymer-glucose binding-induced changes in surface charge and compare the results with experimental data can be investigated using a simplified model in which a rectangular graphene sheet (with length l and width w) sandwiched between an insulating substrate and a solution of an electrolyte, and is biased longitudinally with a voltage without being subject to a gate voltage. The graphene surface can be charged (density: σ) due to the presence of charged (polymer and bound glucose) molecules.

The distribution can be determined of the electric potential ϕ in the electrolyte solution near the graphene surface and then consider the charge balance at the graphene surface. While two- and three-dimensional effects (as well as those of a nonzero gate voltage) can be considered, here for simplicity it is assumed that the potential is only a function of the coordinate normal to the graphene surface (x), and that the electrolyte includes anions and cations of equal charge number z. More general cases can be considered in a conceptually similar manner. The potential distribution can be governed by the Poisson-Boltzmann equation of the form $$\frac{d^2\phi}{dx^2} = \frac{\beta}{\lambda} \sinh\left(\frac{\phi}{\beta}\right) \quad (5)$$

where $\lambda=(\varepsilon kT/2z^2e^2c_0)^{1/2}$ can be the Debye length and $\beta=kT/ze$ Here $c_0$ is the concentration (number of molecules per unit volume) of the electrolyte in the bulk solution, ε the solution's dielectric constant, T the temperature, k the Boltzmann constant and e the electron charge. Since $d\phi/dx \to 0$ in the bulk of the solution ($x \to \infty$), the equation can be solved to obtain $\phi=-2\beta \ln[(1+\Gamma_0 e^{-x/\lambda})/(1-\Gamma_0 e^{-x/\lambda})]$ where $\Gamma_0=-\tan h(\phi_s/4\beta)$ and $\phi_s=\phi(0)$ is the (yet-to-be-determined) potential at the graphene surface.

The charge per area induced in the graphene by the surface potential can be approximately given by $\sigma_{gr}=C_q(\phi_s-\phi_0)$ where $\phi_0$ is the surface potential at the Dirac point, and $C_q$ is the quantum capacitance of graphene per unit area[92]:

$$C_q=(N/\pi)^{1/2}e^2/v_f\hbar \quad (6)$$

with $v_f$ the Fermi velocity and $\hbar$ the Planck constant. Here N is the number of charge carriers per unit area, which depends on $\sigma_{gr}$ (and hence $C_q$):

$$N=(N_0^2+[C_q(\phi_s-\phi_0)/e]^2)^{1/2} \quad (7)$$

where $N_0$ is the sheet charge carrier concentration due to disorder and thermal excitation[93].

On the graphene surface and within the graphene, conservation of charge (Gauss's law) requires that $-\varepsilon\phi'(0)+C_q\phi_s=\sigma$, i.e., $$C_q(\phi_s-\phi_0)=\sigma-2(\beta\varepsilon/\lambda)\sin h(\phi_s/2\beta) \quad (8)$$

The graphene's conductance, or equivalently resistance, can then be computed from the resulting charge carrier concentration by $$R=l/(\mu ewN) \quad (9)$$

where μ is the carrier mobility in graphene. Thus, the graphene resistance R can be measured to obtain the charge carrier concentration N. Then Eqs. 6, 7, and 8 can be solved to obtain the surface potential $\phi_s$, quantum capacitance $C_q$, and in particular the surface charge density σ, which is directly related to surface density of the captured glucose molecules, γ. Meanwhile, the volumetric glucose concentration (c) is related to γ by the Langmuir adsorption isotherm:

$$\gamma = \xi[c/2(K_d+c)] \qquad (10)$$

where (as defined above) ξ is the surface density of immobilized polymer molecules and $K_d$ the equilibrium dissociation constant of the binding system. Thus, using Eq. 10, measurement of the graphene resistance eventually allows determination of the glucose concentration c.

Example 13. In Vitro and In Vivo Characterization of the Graphene Nanosensor The polymeric materials (including PMMA, Parylene, and the synthetic functional polymer monolayers and hydrogel coating) of the nanosensor are biocompatible, as are the transducing (graphene), dielectric (h-BN) and metallization (ITO) materials when their uptake by individual cells is avoided. The in vitro characterization does thus not involve compatibility testing, and focuses on the device's response to glucose concentration changes in the absence and presence of biofouling to assess its potential for accurate glucose monitoring. Verification that the device is biocompatible in in vivo studies is conducted, where in particular issues relevant to the contact lens platform, such as oxygen and ion permeability, wettability, water content, and cytoxicity, as well as protein adsorption and biofilm formation are determined.

The nanosensor's characteristics in glucose detection can be determined by exposing the nanosensor of varying design parameters (e.g., the number of atomic layers, shape and dimensions of the graphene, molecular weight of the sensing polymer, and the thickness of the hydrogel coating) to glucose or unspecific mono- and disaccharides dissolved in buffer. Measurement of the graphene conductance in these tests can allow assessment of the specificity of the device in glucose detection. The sensitivity and dynamic range of the nanosensor can be investigated by measuring the graphene conductance at physiologically relevant concentrations (0.5-30 mg/dL), with an emphasis on hypoglycemic concentrations (below 1 mg/dL). The sensitivity can then be used along with an assessment of the intrinsic noise levels in the graphene sensor and in readout instrumentation to determine the nanosensor resolution in the glucose concentration range of interest. In addition, time-resolved data from the measurements can be used to determine the device's time response.

The characterization can be also performed under varying operating parameters including temperature, pH, ionic strength and oxygen concentrations, which can significantly influence affinity binding and graphene's electronic properties. This can also be used to evaluate the ability of the device's differential design to reject the effects of variations of these parameters during sensor operation for reliable CGM.

The nanosensor's response to glucose in the presence of simulated_biofouling can be investigated by repeating the tests above but with the device exposed to artificial tear fluid including sodium chloride, potassium chloride, sodium bicarbonate, urea, ammonia chloride, lactic acid, pyruvic acid, citric acid, Vitamin C, albumins, γ-globulins, and lysozyme. The goal is to evaluate the effects of the accumulation of biological materials, via protein adsorption and biofilm formation, on the nanosensor performance. Adsorption of proteins to the lenses can lead to the buildup of unwanted bacteria and other materials, causing contamination and degradation of the sensor sensitivity. Protein adsorption can be monitored using fluorescence spectroscopy and labeled model proteins incubated on lens surfaces. Biofilms can be collections of microorganisms encased in a matrix that is often comprised of both bacterial and host materials. The ability of microorganisms to attach to abiotic surfaces and to grow in highly stable communities greatly confounds devices that have direct contact with tissue. On the contact lens sensor, the microorganism community can form a barrier between tear and sensor, preventing detection of glucose. The attachment of biofilms to lens surfaces can be monitored using scanning electron microscopy methods while measuring the sensor response under simulated biofouling by incubating the device in bacterial cell suspension.

Affinity sensing, based on non-reactive equilibrium binding of analyte with an affinity receptor, neither consumes the target analyte nor produces any byproduct, therefore can potentially be implanted for stable and accurate glucose monitoring. Affinity glucose sensing can be implemented using optical, mechanical, and electrical methods on conventional or microscale platforms. While demonstrating the potential of affinity glucose sensing, these methods can require complex sensor structures (e.g., moving mechanical components or physical barriers), and cannot have sufficient sensitivity in human bodily fluids such as tears or saliva, in which glucose concentrations are one or two orders of magnitude lower than that in. Conventional techniques for affinity glucose sensing using functional nanomaterials to date has been rather scarce. Boron-doped graphene quantum dots have been used for affinity glucose sensing, although its requirement of an additional optical measurement system is not amenable to miniaturization. Boronic acid functionalized carbon nanotubes (CNTs) have also been used for glucose detection in deionized water. Nevertheless, these sensors relied on the contact among the randomly distributed, entangled nanotubes and is not necessarily well suited to practical applications because of a lack of consistency and stability. Furthermore, the underlying sensing mechanisms have not been clarified due to the difficulties in precise determination of the weak doping induced by the affinity binding in the semiconducting CNTs.

The disclosed subject matter provides an atomically thin, graphene-based sensor for affinity-based detection of glucose, an uncharged, low-molecular-weight molecule. The disclosed nanosensor can include a graphene FET in which graphene can be functionalized with boronic acid for glucose recognition. In contrast to a multi-step chemical modification procedure that is required for certain enzyme based graphene glucose sensors, the functionalization in the disclosed sensor can be enabled by a simple single procedure method via the interaction of graphene with pyrene-terminated boronic acid. The disclosed method can allow boronic acid to be closely attached to the graphene surface, thereby the binding of boronic acid with glucose can significantly change the electrical properties of graphene and can enable sensitive detection of the glucose molecules. Moreover, the bipolar transfer characteristics of graphene, due to its vanishing bandgap and high mobility, can exhibit significant and definitive shifts upon glucose-boronic acid binding. This shift can reflect affinity binding-induced charge transfer to graphene, or changes in the electrostatic potential in the immediate proximity of graphene, thereby allowing for insights into the underlying physicochemical mechanisms for affinity glucose recognition on the nanomaterial. The coupling of graphene with boronic acid via stable chemical bonding can eliminate the need for mechanical movable structures or physical barriers used in existing affinity glucose sensors. Accordingly, the disclosed subject matter can simplify the device design and potentially enable a consistent, rapidly responsive measurement for noninvasive glucose monitoring. For example, wearable glucose monitoring devices can be realized by integrating these sensors with contact lens to detect the glucose concentration in tears.

FIG. 28A illustrates a schematic of the disclosed nanosensor configured as a solution-gated graphene field effect transistor. An Ag/AgCl electrode inserted into the solution can serve as the gate electrode, while the electrical double layer at the solution-graphene interface served as the gate capacitor. FIG. 28B illustrates a micrograph of a fabricated device. The graphene conducting channel can connect the source and drain electrodes. FIG. 28C illustrates the coupling of boronic acid and graphene via π-π stacking interactions between the pyrene group and graphene. FIG. 28D illustrates the formation of a glucose-boronate ester at a physiological pH of 7.4.

The affinity glucose nanosensor was configured as a solution-gated graphene FET (FIG. 28a). The graphene, serving as the conducting channel (FIG. 28b), was functionalized with pyrene-1-boronic acid (PBA) via π-π stacking interactions (FIG. 28c). The device was fabricated using micro and nanofabrication techniques (see details in Supporting Information). A polydimethylsiloxane (PDMS)-based open well (~20 µL) was bonded to the substrate; and glucose solution was placed into the well. An Ag/AgCl reference electrode, mounted on a three-axis positioner, was inserted into the solution to serve as the gate electrode. An electrical double layer (EDL) formed at the interface of the graphene and solution served as the gate capacitor. Binding of glucose and the boronic acid formed a glucose-boronate ester complex (FIG. 28d), inducing changes in the electric conductance of the graphene, which was measured to determine the glucose concentration.

In a solution-gated FET, the capacitance of the double layer can be influenced by the solution composition. Prior to any chemical functionalization of the graphene, the fluctuations of the EDL capacitance that can possibly be attributed to changes in the glucose concentration were examined. Glucose was dissolved in phosphate buffered solution (pH 7.4) to obtain desired concentrations (2 µM to 25 mM). The same solutions were used in all of the subsequent tests. Without any chemical functionalization of graphene, the transfer characteristics (source-drain current IDS as a function of gate voltage VGS) measured at the different glucose concentrations were almost indistinguishable (FIG. 29a). This suggested that glucose, at the selected concentration range, did not either interact with graphene or vary the capacitance of the double layer.

This device was then immersed in PBA solution for 4 hours at room temperature, followed by sequentially rinsing in acetonitrile, isopropanol and deionized water to remove free PBA. In prior to the chemical functionalization, in the Raman spectrum (FIG. 29b) of the graphene at the channel region, the ratio of the intensity of the 2D band to the G band (I2D/IG) was 2.5, and the full width at half maximum (FWHM) of the 2D band was ~27 from Lorentz fitting, both of which were further evidence of monolayer graphene in addition to the color contrast observed under microscope (FIG. 28b). The Raman spectrum of the PBA solution-rinsed graphene exhibited signature peaks of BOH bending (1286 cm-1), B-O stretching (1378 cm-1), and G-band splitting (1574, 1595, 1613 cm$^{-1}$) due to the graphene-pyrene π-π stacking interaction. Also, the 2D band shifted to a higher wavenumber (from 2685 to 2692 cm$^{-1}$), which was considered as a result of chemical doping. The measured transfer characteristics (FIG. 29a) also verified the chemically induced p-type doping, represented by the increase of the neutral point voltage VNP (the gate voltage at which IDS attains its minimum) from 0.33 V to 0.575 V. These observed characteristics of the boronic acid as well as the graphene-pyrene interaction confirmed that the PBA molecules were successfully immobilized on the graphene.

After functionalization, it was confirmed that replenishment of sample solution to the nanosensor did not interrupt the pyrene-graphene coupling. Then the sensor was tested by exposure to glucose solution at different concentrations. The transfer characteristics curve was found to shift to the left significantly. For example, the shift was ~0.115 V as the glucose concentration increased from 0 to 25 mM (FIG. 30). This suggests that the binding of glucose and boronic acid generated n-type doping to graphene. As the estimated transconductance (e.g., the slope of linear sections of the transfer characteristics curve) did not change significantly, the carrier mobility of the graphene were believed to be approximately constant (see details in Supporting Information). Rather, changes in the carrier concentration of graphene was considered the main contributor to the observed shift of VNP. Measurements using butyric-acid functionalized graphene were also performed to serve as control (see details in Supporting Information). Variations in the source-drain current IDS were examined with the glucose concentration at a fixed gate voltage VGS. It was observed that IDS decreased monotonically with glucose concentration when VGS was lower than the neutral point voltage VNP, and this trend was reversed when VGS >VNP (FIG. 30), which was due to the shift of the transfer characteristics. Using this observed dependence of IDS on the glucose concentration, we estimate that, with a noise level of ~17 nA for IDS, the resolution of the nanosensor for glucose measurements was approximately 0.46 µM, appropriate for monitoring of glucose in human bodily fluids such as saliva and tears. The change of VNP before and after PBA functionalization was measured, denoted as ΔVNP,B, and the further changes of VNP after the graphene was exposed to glucose, denoted ΔVNP,G. Here, ΔVNP,B equals VNP,B−VNP,P, and ΔVNP, G=VNP,B −VNP,G, where VNP,P and the VNP,B are the neutral point voltages measured in fresh buffer for pristine graphene and PBA-functionalized graphene, respectively. VNP,G is the neutral point voltage for PBA-functionalized graphene measured in glucose solution. Both ΔVNP,B and ΔVNP,G were observed to vary from device to device, possibly because of artifacts such as organic residue left on graphene from the fabrication process. These artifacts could have caused a device-to-device disparity in chemical functionalization of graphene, and hence in the doping level at a given glucose concentration. At a given concentration, the ratio ΔVNP,G/ΔVNP,B did not vary significantly from device to device, with a variation of less than 6% for the three nanosensor devices tested (FIG. 31). To explain this observation, ΔVNP,B can be noted as the shift of VNP caused by functionalization of boronic acid and ΔVNP,G can be by glucose-boronic acid binding, therefore ΔVNP,G/ΔVNP,B can be regarded as a measure of the fraction of boronic acid that is occupied by glucose. Since under conditions of constant temperature and pH as were approximately the case in our test, the fraction of boronic acid that binds to glucose can be solely dependent on the glucose concentration. This suggests that ΔVNP,G/ΔVNP,B can be a function of glucose only and independent of the device or the order in which the sample solution was added. The measured dependence of this ratio on glucose concentration followed the Hill-Langmuir equation for equilibrium ligand-receptor binding. A least squares fit can yield an equilibrium dissociation constant (KD) of 38.6 µM (FIG. 31).

While the exact mechanisms for the graphene affinity sensing remain open, some theoretical considerations can offer insight into the observed doping effects induced by chemical functionalization and glucose-boronic acid binding. First, to explain the observed p-type doping due to the attachment of PBA (FIG. 29a), it can be noted that while pyrene group is electron-rich and not expected to induce p-doping, boronic acid is electron deficient and its electron-withdrawing nature could induce p-doping in the graphene. For example, immobilization of electron-rich groups on graphene (such as butyric acid, a carboxylic acid) resulted in n-type doping in the graphene. Additionally or alternatively, the observed n-type doping due to the boronic acid-glucose binding can result from an increase in the local electrostatic potential in the proximity of graphene, as suggested by results from a potentiometric study of glucose detection by boronic acid which resembles the disclosed graphene nanosensor in electrode configuration. This electrostatic potential increase can be attributed to the formation of boronate, which would increase the electron donating ability of boronic acid while weakening its electron-withdrawing ability.

These conjectured sensing mechanisms suggest that immobilization of boronic acid on graphene or even other semiconducting materials, using other attachment groups can also allow for glucose recognition. Indeed, measurements of glucose using graphene that was modified with 9-anthracene-boronic acid were found to be qualitatively consistent with results obtained with PBA as presented above. The corroboration of these mechanisms, however, require a systematic study in future work. Although adequate for practical glucose detection in physiological fluids where glucose is present at dominant concentrations, boronic acid-based receptors can be chemically modified to impart glucose-specificity to the nanosensor over other monosaccharides.

In certain embodiments, the disclosed graphene nanosensor can perform affinity-based detection of low-charge, low-molecular-weight molecules, using glucose as a representative analyte. The nanosensor can use a graphene field-effector transistor in which graphene can be functionalized with boronic acid for glucose recognition. The boronic acid can be attached to graphene via the interaction between graphene and pyrene groups, allowing sensitive detection of electrically neutral glucose molecules. Testing results demonstrated that the nanosensor was capable of measuring glucose in a practically relevant range of 2 µM to 25 mM, with a resolution of 0.46 µM. The observed shifts of the transfer characteristics strongly suggested that recognition of glucose was due to the formation of glucose-boronate ester, which could reduce the boronic acid-induced p-type doping in the graphene. The disclosed nanosensor can be highly miniaturized without the use of mechanical moving parts or physical barriers, and hence be of practical utility in glucose monitoring.

The disclosed subject matter further provides for devices and techniques to monitor target analytes. More specifically, the disclosed subject matter provides for field-effect transistor ("FET")-based sensors and systems that can be used with aptamers that bind to targets with high specificity and affinity.

The disclosed subject matter provides a graphene nanosensor for monitoring a target analyte. In certain embodiments, the graphene nanosensor utilizes a single conductance sensor on a substrate platform, wherein the graphene sensor can be functionalized with aptamers for binding the target analyte. In certain embodiments, the graphene nanosensor utilizes microbeads functionalized with aptamers which can allow for selective enrichment and isocratic elution of the target analyte. In certain embodiments, the concentration of the enriched target analyte can be measured on a graphene surface functionalized with a target analyte of interest.

In certain embodiments, the sensor can be made of graphene. Graphene is a flat monolayer of carbon atoms tightly packed into a two-dimensional honeycomb lattice. In certain embodiments, the FET sensing element with graphene as the conducting channel has an electric resistance of about 0.1 k$\Omega$-about 3 k$\Omega$. In certain embodiments, graphene as the conductance channel has an electric resistance of about 0.1 k$\Omega$-about 3 k$\Omega$, about 0.25 k$\Omega$-about 2.75 k$\Omega$, about 0.5 k$\Omega$-about 2.5 k$\Omega$, about 0.75 k$\Omega$-about 2.25 k$\Omega$, about 1 k$\Omega$-about 2 k$\Omega$, about 1.25 k$\Omega$-about 1.75 k$\Omega$, about 1.5 k$\Omega$-about 2 k$\Omega$, or about 2 k$\Omega$-about 3 k$\Omega$. In certain embodiments, graphene as the conductance channel has an electric resistance of at least about 0.1 k$\Omega$, at least about 0.2 k$\Omega$, at least about 0.3 k$\Omega$, at least about 0.4 k$\Omega$, at least about 0.5 k$\Omega$, at least about 0.6 k$\Omega$, at least about 0.7 k$\Omega$, at least about 0.8 k$\Omega$, at least about 0.9 k$\Omega$, at least about 1 k$\Omega$, at least about 1.2 k$\Omega$, at least about 1.4 k$\Omega$, at least about 1.6 k$\Omega$, at least about 1.8 k$\Omega$, at least about 2 k$\Omega$, at least about 2.2 k$\Omega$, at least about 2.4 k$\Omega$, at least about 2.6 k$\Omega$, at least about 2.8 k$\Omega$, at least about 3 k$\Omega$, at least about 4 k$\Omega$, at least about 5 k$\Omega$, at least about 6 k$\Omega$, at least about 7 k$\Omega$, at least about 8 k$\Omega$, at least about 9 k$\Omega$, or at least about 10 k$\Omega$. In certain embodiments, graphene as the conductance channel has an electric resistance of no more than about 0.1 k$\Omega$, no more than about 0.2 k$\Omega$, no more than about 0.3 k$\Omega$, no more than about 0.4 k$\Omega$, no more than about 0.5 k$\Omega$, no more than about 0.6 k$\Omega$, no more than about 0.7 k$\Omega$, no more than about 0.8 k$\Omega$, no more than about 0.9 k$\Omega$, no more than about 1 k$\Omega$, no more than about 1.2 k$\Omega$, no more than about 1.4 k$\Omega$, no more than about 1.6 k$\Omega$, no more than about 1.8 k$\Omega$, no more than about 2 k$\Omega$, no more than about 2.2 k$\Omega$, no more than about 2.4 k$\Omega$, no more than about 2.6 k$\Omega$, no more than about 2.8 k$\Omega$, no more than about 3 k$\Omega$, no more than about 4 k$\Omega$, no more than about 5 k$\Omega$, no more than about 6 k$\Omega$, no more than about 7 k$\Omega$, no more than about 8 k$\Omega$, no more than about 9 k$\Omega$, or no more than about 10 k$\Omega$. In certain embodiments, graphene as the conductance channel has an electric resistance of no more than about 3 k$\Omega$.

The graphene monoatomic sheet can be thin (0.34 nm), possess strong mechanical strength (Young's modulus: 1 TPa), adhere to underlying substrates, and be flexible, optically transparent, and chemically stable. Such properties can enable new, transformative methods for detection of biological analytes. The monoatomic structure as well as electric conductivity (~1738 S/m) and charge carrier mobility ($2 \times 10^5$ cm$^2$/Vs) of graphene can be exploited to enable sensitive analyte detection.

In certain embodiments, the graphene sensor can include a single layer sheet. In certain embodiments, the graphene sensor includes a multilayered sheet. In certain embodiments, the graphene sensor can include at least one layer of graphene. In certain embodiments, the graphene sensor can include at least two layers of graphene, at least three layers of graphene, or at least four layers of graphene. In certain embodiments, the graphene sheet can be formed by mechanical exfoliation, chemical exfoliation, chemical vapor deposition, or silicon carbide. In certain embodiments, the graphene sheet can be formed by chemical vapor deposition ("CVD"). In certain embodiments, the graphene sheet can be formed by mechanical exfoliation, which can include the removal of a layer of graphene from a block of graphite using tape or other sticky substance. Exemplary techniques for fabrication of the graphene sheet is illustrated in FIG. 45A-B and discussed in further detail in Example 15.

In certain embodiments, the nanosensor can be constructed on a substrate platform. In using graphene as a functional material on a substrate, the nanosensors disclosed herein can be miniaturized and mechanically flexible for placement on a substrate platform. In certain embodiments, the substrate platform can be rigid. As used herein, "rigid" means self-supporting over its length when held at an edge. In certain embodiments, the substrate platform can be flexible. As used herein, "flexible" refers to a material that is not rigid and that conforms to the surface of whatever object the material contacts.

A graphene nanosensor as disclosed herein can be used in several ways. For example, binding of the target analyte with the aptamer immobilized on graphene can cause a change in surface charge density, which can penetrate the atomically thin graphene to significantly change the graphene's conductance, leading to a detectable signal even at low analyte concentrations.

In certain embodiments, the nanosensor as disclosed herein can enable reliable monitoring of a target analyte in a sample. In certain embodiments, the sample can be a bodily fluid, a non-bodily fluid liquid, or a laboratory sample. In certain embodiments, the nanosensor can be used to measure the amount or change in the amount of a target analyte in a sample. For example, the nanosensor can be part of a standalone device that monitors the target analyte in a sample added to the device (e.g., a piece of lab equipment or home monitor). In certain embodiments, the bodily fluid can be tears, blood, serum, saliva, mucus, interstitial fluid, spinal fluid, intestinal fluid, amniotic fluid, lymphatic fluid, pericardial fluid, peritoneal fluid, pleural fluid, semen, vaginal secretions, sweat, or synovial fluid of the subject.

The disclosed method can be applied to the diagnosis testing. For example, the development of nanosensing systems can be used to detect analytes, such as the presence of organics, peptides, proteins, cells, tissues, or the like in a sample. For example, but not by way of limitation, the target analyte can be immunoglobulin molecules (e.g., IgA, IgD, IgE, IgG, IgM), hormones (e.g., AVP, ADH, glucagon, amylin, GIP, GLP, epinephrine, cortisol, and growth hormone, estrogens (e.g., estradiol, strone, estriol), calcitriol, progesterone, HPL, LH, FSH, PRL, oxytocin, androgens, DHEA, DHT, orexin, EPI, MT, $T_3$, $T_4$, prostalandins, leukotrienes, prostacylin, thromboxane, Insulin, leptin, inhibin, PTH, somatostatin, thrombopoietin, TSH, TRH, VIP, sectetin, relaxin, renin, GnRH, GHRH, HAMP, or the like), complement factors (e.g., Complement factor C3, complement factor C4A (Anaphylatoxin) complement factor C9, complement factor D (CFAD), or the like), enzymes (e.g., lysozyme, carboxypeptidase N, pancreatic trypsin inhibitor, enzyme inhibitors: cystatin C, plasminogen, a-2-antiplasmin, inter-a-trypsin inhibitor complex component II (ITI2), a-1-antitrypsin, hexokinase type II, ribonuclease, or the like), transport proteins (e.g., transthyretin, serotransferrin, retinol binding protein (RBP), transforming growth factor-binding protein (TGF-BP), insulinlike growth factor-binding protein (IBP3), or the like), or plasma proteins (e.g., albumin, fibrinogen A (RGD Peptides), fibrinogen B, a-1-microglobulin, b-2-microglobulin, zinc-a-2-glycoprotein (ZAG), a-2-HS-glycoprotein (fetuin), serum amyloid A protein (SAA), haptoglobin, profilin, vitronectin, desmocollin, thymosin b4, apolipoprotein uteroglobin, ubiquitin, gelsolin, somatomedin B, hemopexin, or the like), oligo nucleotides, glucose.

The disclosed method can be applied to the diagnosis of disease, for example, to detect analytes, such as human viruses and bacteria, as many of those microorganisms carry glycoproteins on the exterior surface that can be targeted by the aptamers. Additionally, the disclosed techniques can be applied to a noninvasive method for monitoring cancer treatment. For example, aptamers can be designed to bind to target analytes associated with the cancer cell itself. In certain embodiments, the aptamers can be specific for apoptosis of the cancer cells. In certain embodiments, the microdevice can be used to track overall cell apoptosis to monitor when levels of cell death before they become too toxic. In certain embodiments, the microdevice is able to detect the level of cancer cells in the bodily fluid.

Furthermore, the methods disclosed herein can be used for determining the drug distribution of a treatment regimen in order to maximize the therapeutic effects of the drug. In such methods, the aptamers of the device can be designed to bind to the drug found in the bodily fluid. The design parameters can be varied without departing from the scope of the disclosed subject matter. Such design parameters include, for example, the number and dimensions of atomic layers and substrate platform layers, shape and dimensions of the graphene, and molecular weight of the aptamers, linkers, and polymers.

Aptameric Graphene Nanosensor

In certain embodiments, a graphene nanosensor can utilize a single conductance sensor on a substrate platform, wherein the graphene sensor can be functionalized with aptamers for binding the target analyte. The graphene nanosensor can be functionalized with the aptamer via a linker. In certain embodiments, the nanosensor can include a nanolayer of polymer. In certain embodiments, the polymer can be conjugated to a linker attached to the graphene and also conjugated to an aptamer.

In certain embodiments, the aptamer can bind specifically to the target analyte. The aptamer can bind reversibly or irreversibly to the target analyte. The aptamer can bind to more than one target analyte. The graphene can be functionalized with at least one type of aptamer. The graphene can be functionalized with two or more types of aptamers specific for either the same or different analyte. In certain embodiments, target analyte binding with the aptamer changes the charge density on the nanosensor surface, inducing changes in the carrier concentration of the nanosensor.

With reference to FIG. 32A-Biii, the nanosensor can be configured as a solution-gated graphene-based FET ("GFET") in that the graphene layer (1101) is the conducting channel, which can be formed between two electrodes (source (1102) and drain (1103)) on an substrate platform (1104). The substrate platform can be one or multi-layered. For example, the substrate platform can include two layers (see 1104) such as, but not limited to a silicon wafer based device. An example of a silicon wafer based device, the lower layer can be silicon as the substrate while the upper layer can be silicone oxide which can serve as an insulating layer. In certain embodiments, the substrate platform can be a single layer. In certain embodiments the single later substrate platform can be a polymer substrate.

In certain embodiments, the graphene layer can be formed between the source and drain electrodes. In certain embodiments, the graphene layer lies over at least a portion of the source and drain electrodes.

In certain embodiments, the graphene surface (1101a) can be functionalized with aptamers (1105a) via π-π stacking interactions between the linker (1105b) attached to the aptamer (1105a) and the graphene surface (1101a) (FIG. 32A-Biii). The graphene (1101) can be modified with a polymer layer (105c) that can be serially functionalized between the linker (1105b) and aptamer (1105a) layers. In certain embodiments, the polymer layer can be a nanolayer. The linkers, polymers, and aptamers are further discussed below.

In certain embodiments, the analyte sample solution (1106) can be added above the aptamer or polymer/aptamer modified graphene in a polymeric well (1107). In certain embodiments, a wire electrode can be inserted to the solution as a gate electrode (1108). In this configuration, an electrical double layer ("EDL") can be formed at the interface of the graphene and solution serving as the gate dielectric layer.

During operation and with reference to FIG. 32b, the modified graphene nanosensor (FIG. 32b(i)) can be incubated with the sample (1106) containing the target analyte (1109) (FIG. 32b(ii)). After removal of the sample followed with buffer washes (FIG. 32b(iii)), the target analyte can be purified from the sample by the aptamer (1105a) that binds the target analyte. In certain embodiments, the aptamer can be functionalized along with a polymer (1105c), which can reduce the nonspecific adsorption of background molecules (1110) to the graphene surface (1101a).

The transfer characteristics of graphene can be measured in buffer by sweeping the gate voltage. A bias drain-source voltage ($V_{ds}$) can be applied between the drain (1103) and source (1102) electrodes which can generate a drain-source current ($I_{ds}$) through the graphene channel, and the $I_{ds}$ can be controlled by the applied gate voltage ($V_g$). This can yield the transfer characteristics of the GFET (i.e., the functional dependence of $I_{ds}$ on $V_g$). When the target analyte (1109) in a sample (1106) can be captured by the aptamer (1105a), the charged target analyte can alter the carrier concentration of the graphene (1101), and thus induce a shift of the Dirac point ($V_{Dirac}$), the voltage at which the $I_{ds}$ reaches its minimum.

In certain embodiments, the electrode wire/gate electrode can be, for example, but not limited to ITO, Ti/Pd/Pt, Ag/AgCl, Ag, Pt, Cu, Cr, or combinations thereof.

In certain embodiments, the source and drain electrodes, can be separately made from material such as, but not limited to ITO, Ti/Pd/Pt, Ag/AgCl, Ag, Pt, Cu, Cr, or combinations thereof.

In certain embodiments, the polymeric well can be made of a silicone substance, such as a polymeric organosilicon compound. In certain embodiments, the polymeric organosilicon compound can be polydimethylsiloxane ("PDMS").

In certain embodiments, the substrate support can be made from material such as, but not limited to polyethylene terephthalate ("PET"), polycarbonate polystyrene, polymethyl methacrylate ("PMMA"), polymacon, silicones, $SiO_2$, $SiO_2$-coated silicon wafer, fluoropolymers, silicone acrylate, fluoro-silicone/acrylate, poly hydroxyethyl methacrylate, $HfO_2$, parylene, $Si_3N_4$, or combinations thereof.

In certain embodiments, the dimensions of the graphene conducting channel can be a length of about 10 μm to about 20 μm by a width of about 10 μm to about 20 μm by a thickness of the graphene layer. In certain embodiments, the graphene conducting channel can have a length of about 5 μm to about 15 μm, about 7.5 μm to about 22.5 μm, about 10 μm to about 20 μm, or about 12.5 μm to about 17.5 μm. In certain embodiments, the graphene conducting channel can have a width of about 5 μm to about 15 μm, about 7.5 μm to about 22.5 μm, about 10 μm to about 20 μm, or about 12.5 μm to about 17.5 μm. In certain embodiments, the graphene channel in the sensor can be about 20×10 μm$^2$ with a thickness of about 0.34 nm.

Exemplary techniques for fabrication of the devices is illustrated in, for example, FIGS. 16A-C and 17 and certain embodiments will be discussed in further detail in Examples 14 and 15.

With reference to FIG. 34, in certain embodiments, the device can be fabricated using micro and nanofabrication techniques on a substrate platform (1300), such as an oxidized silicon wafer. After cleaning the substrate platform, a layer of the material for the source and drain electrodes can be deposited on the substrate (1301). The electrodes can be deposited by any technique known to one skilled in the art. For example, the material can be placed using thermal evaporation. Next, a layer of photoresist can be added (e.g. spin-coated) on top of the electrode material (1302) and then baked (1303). For example, the material can be baked at 115° C. for 1 min. The source and drain electrodes can be patterned (1304). The electrodes can be patterned by any technique known to one skilled in the art, such as but not limited to photolithography. The wafer can be developed (1305) and then etched in gold (1306) and chrome etchant (1307) sequentially. Graphene can be synthesized via methods known to those of skill in the art. For example, the graphene layer can be synthesized using chemical vapor deposition ("CVD") substrate (see Example 15 for an example protocol) and transferred on top of the source and drain electrodes (see FIGS. 32a, 32b, and 34) (1308). A polymeric well (e.g., 1407) can be placed above the graphene sensing region (4309) that could be filled with a sample. A wire can be inserted into the solution to apply the gate voltage (e.g., 4108).

With reference to FIG. 35, in certain embodiments, to achieve functionalization of the graphene surface (1400), the GFET can be immersed with a solution of the linker (1401). For example, the GFET can be immersed with a solution of the linker for at least 1, at least 2, at least 3, at least 4, or at least 5 hours at room temperature. After rinsing thoroughly with ethanol and then with phosphate buffered saline ("PBS") buffer (1402), the GFET can optionally be immersed in a solution of polymer (1403). For example, the GFET can be immersed with a solution of polymer for at least 2 hours, at least 4 hours, at least 6 hours, at least 8 hours, at least 10 hours, at least 12 hours, at least 14 hours, at least 16 hours, at least 18 hours, or at least 20 hours at room temperature. In certain embodiments, the GEFT can then be immersed with a mixture of 1-ethyl-3-(3-dimethylaminepropyl) carbodiimide hydrochloride (EDC.HCl) and N-hydroxysulfosuccinimide ("NETS") (e.g., at a pH=6 in PBS solution) to activate the free end of the polymer (1404). In other embodiments, the polymer activated using solutions such as, but not limited to, DIC/DIPC, DCC, HATU, HBTU, HCTU, BOP, PyOxim, or T3P. For example, the GFET can be immersed with a solution of EDC.HCl and NETS for at least 1, at least 2, at least 3, at least 4, or at least 5 hours at room temperature. Finally, the GFET can be immersed in a solution of aptamer (1405). For example, the GFET can be immersed with a solution of aptamer for at least 2 hours, at least 4 hours, at least 6 hours, at least 8 hours, at least 10 hours, at least 12 hours, at least 14 hours, at least 16 hours, at least 18 hours, or at least 20 hours at room temperature.

In certain embodiments, the aptamer can be attached directly to the linker. For example, the aptamer can be an amino group-terminated aptamer which can be directly attached to the linker by forming an amid bond with the carboxylic group on the linker.

Graphene Nanosensor with Integrated Selective Enrichment

In certain embodiments, the graphene nanosensor can utilize microbeads functionalized with aptamers. In certain embodiments, aptamers which can allow for selective enrichment and isocratic elution of the target analyte. In certain embodiments, the aptamer can bind specifically to the target analyte. In certain embodiments, the aptamer can bind reversibly to the target analyte. In certain embodiments, the concentration of the enriched target analyte can be measured on a graphene surface functionalized with a target analyte of interest.

In certain embodiments, the microbeads can be functionalized with at least one type of aptamer. In certain embodiments, the graphene nanosensors can use at least one set of microbeads functionalized with one type of aptamer. In certain embodiments, the graphene nanosensors can use at least two sets of microbeads, where each set of microbeads can be functionalized with a different set of aptamers specific for either the same or different analyte.

In certain embodiments, the nanosensor can be configured as a FET in that the graphene (1501) can be the conducting channel, which is formed between two electrodes (source (1502) and drain (1503)) on a graphene nanosensor substrate platform (1504) (FIG. 46A-C). A sweeping voltage of about 0-1 V can be applied to the gate electrode (1515) forming a gate voltage ($V_{gs}$) through a sample solution. In certain embodiments, the electrical conductance through graphene (1501), which depends on the charge on the graphene surface, can be measured from the drain current ($I_{ds}$) at a fixed drain voltage ($V_{ds}$). In certain embodiments, the graphene surface can be functionalized with target analyte. In certain embodiments, the graphene layer can be formed between the source and drain electrodes. In certain embodiments, the graphene layer can lie over at least a portion of the source and drain electrodes.

In certain embodiments, the integrated microdevice can include at least one enrichment microchamber (1505), at least one graphene-based sensing microchamber (1506) combined with at least one graphene nanosensor (1501), at least three temperature control units (1507), and at least one flow gate (1508) connected to at least one serpentine channel (1509) for sample (1510) transfer to the sensing microchamber (1506). As used herein, a serpentine channel can include a channel with several segments that alternate in direction. In certain embodiments, the channels can have at least 4, at least 6, at least 8, or at least 10 alternating sections. In certain embodiments, the channel can be a straight channel. In certain embodiments, a weir structure (1511) in the at least one enrichment microchamber (1505) can retain microbeads (1512) within the enrichment microchamber (1505) during the selective enrichment process. A magnet can hold the microbeads in the enrichment microchamber (1505).

In certain embodiments, the microdevice can include at least three temperature control units (1507) which can include a resistive heater (1513) and a temperature sensor (1514) separately control temperatures inside the at least one enrichment (1505 (heater 1513a; sensor 1514a)) and sensing (1506 (heater 1513b; sensor 1514b)) microchambers and the at least one serpentine channel (1509 (heater 1513c; sensor 1514c)) for forming or disrupting aptamer-target analyte complexes. The microchambers (1505 and 1506) and the channels (e.g., 1509) can be formed by a polymeric material (516). In certain embodiments, the polymeric material can also include at least one buffer/sample inlet (1518), at least one waste outlet (1519), and at least one sample outlet (1520). In certain embodiments, the microdevice can be formed on a support platform (1517). In certain embodiments, an inlet (1518) can be coupled to the enrichment chamber, a waste outlet (1519) can be coupled to the serpentine channel, and a sample outlet (1520) can be coupled to the sensing chamber.

In certain embodiments, the microdevice can have at least 1, at least 2, at least 3, at least 4, at least 5, at least 6, at least 7, at least 8, at least 9, or at least 10 enrichment chambers. In certain embodiments, each enrichment chamber can have its own separate temperature control unit.

In certain embodiments, the microdevice can have at least 1, at least 2, at least 3, at least 4, at least 5, at least 6, at least 7, at least 8, at least 9, or at least 10 sensing chambers.

In certain embodiments, there can be a sensing chamber for each enrichment chamber. In certain embodiments, there can be two sensing chambers for each enrichment chamber. In certain embodiments, each sensing chamber can have its own separate temperature control unit. In certain embodiments, valves (e.g., pneumatic) can control the movement of the sample and/or buffer to the different chambers.

In certain embodiments, the dimensions of the enrichment chamber can be a length of about 1 mm to about 5 mm by a width of about 1 mm to about 5 mm by a height of about 100 μm to about 1 mm. In certain embodiments, the enrichment chamber can be a length of about 2 mm by a width of about 2 mm by a height of about 200 μm. In certain embodiments, the length can be from about 1.25 mm to about 4.75 mm, about 1.5 mm to about 4.5 mm, about 1.75 mm to about 4.25 mm, about 2 mm to about 4 mm, or about 2.25 to about 3.75 mm. In certain embodiments, the width can be from about 1.25 mm to about 4.75 mm, about 1.5 mm to about 4.5 mm, about 1.75 mm to about 4.25 mm, about 2 mm to about 4 mm, or about 2.25 to about 3.75 mm. In certain embodiments, the height can be from about 200 μm to about 900 μm, about 300 μm to about 800 μm, about 400 μm to about 700 μm, or about 500 μm to about 600 μm.

In certain embodiments, the enrichment chamber can have a volume of about 0.1 μl to about 25 μl. In certain embodiments, the enrichment chamber can have a volume of about 0.5 μl to about 20 μl, about 1 μl to about 15 or about 5 μl to about 10 μl. In certain embodiments, the enrichment chamber can have a volume of about 0.1 μl to about 1 μl, about 0.2 μl to about 0.9 μl, about 0.3 μl to about 0.8 μl, about 0.4 μl to about 0.7 or about 0.5 μl to about 0.6 μl.

In certain embodiments, the dimensions of the sensing chamber can be a length of about 2 mm to about 5 mm by a width of about 2 mm to about 5 mm by a height of about 1 mm to about 3 mm. In certain embodiments, the dimensions of the sensing chamber can be a length of about 2.25 mm to about 4.75 mm, about 2.5 mm to about 4.5 mm, about 2.75 to about 4.25 mm, about 3 mm to about 4 mm, or about 3.25 mm to about 3.75 mm. In certain embodiments, the dimensions of the sensing chamber can be a width of about 2.25 mm to about 4.75 mm, about 2.5 mm to about 4.5 mm, about 2.75 to about 4.25 mm, about 3 mm to about 4 mm, or about 3.25 mm to about 3.75 mm. In certain embodiments, the dimensions of the sensing chamber can be a height of about 1.25 mm to about 2.75 mm, about 1.5 mm to about 2.5 mm, or about 1.75 mm to about 2.25 mm. In certain embodiments, the sensing chamber can be a length of about 2 mm by a width of about 2 mm by a height of about 1 mm.

In certain embodiments, the sensing chamber can have a volume of about 4 µl to about 7 µl. In certain embodiments, the sensing chamber can have a volume of about 4.25 µl to about 6.75 µl, about 4.5 µl to about 6.5 µl, about 4.75 µl to about 6.25 µl, about 5 µl to about 6 or about 5.25 µl to about 5.75 µl.

In certain embodiments, the dimensions of the serpentine channel can be a width of about 500 µm to about 1 mm by a height of about 20 µm to about 50 µm. In certain embodiments, the serpentine channel can be a width of about 500 µm by a height of about 20 µm. In certain embodiments, the serpentine channel can have a length of about 4 cm to about 10 cm. In certain embodiments, the dimensions of the serpentine channel can be a width of about 550 µm to about 950 µm, about 600 µm to about 900 µm, about 650 µm to about 850 µm, or about 700 µm to about 800 µm. In certain embodiments, the dimensions of the serpentine channel can be a height of about 22.5 µm to about 47.5 µm, about 25 µm to about 45 µm, about 27.5 µm to about 42.5 µm, about 30 µm to about 40 µm, or about 32.5 µm to about 37.5 µm. In certain embodiments, the serpentine channel can have a length of about 4.5 cm to about 9.5 cm, about 5 cm to about 9 cm, about 5.5 cm to about 8.5 cm, about 6 cm to about 8 cm, or about 6.5 cm to about 7.5 cm.

In certain embodiments, the weir structure can be from about ⅕ to about 1/20 the height of the enrichment chamber. In certain embodiments, the weir structure can be from about ⅙ to about 1/19, from about 1/7 to about 1/18, from about ⅛ to about 1/17, from about 1/9 to about 1/16, from about 1/10 to about 1/15, or from about 1/11 to about 1/14 the height of the enrichment chamber. In certain embodiments, the dimensions of the weir structure can be slightly smaller than the microbeads. In certain embodiments, the weir structure can be from about ½ to about ¼ the size of the microbeads. In certain embodiments, the weir structure can be from about 10 µm to about 70 µm, about 20 µm to about 60 µm, or about 30 µm to about 50 µm. In certain embodiments, the weir structure can be about 20 µm.

In certain embodiments, the microbeads can have a diameter of about 40 µm to about 90 µm, about 50 µm to about 80 µm, or about 60 µm to about 70 µm.

In certain embodiments, the gate electrode can be made from material such as, but not limited to ITO, Ti/Pd/Pt, Ag/AgCl, Ag, Pt, Cu, Cr, or combinations thereof.

In certain embodiments, the source and drain electrodes, are separately made from material such as, but not limited to ITO, Ti/Pd/Pt, Ag/AgCl, Ag, Pt, Cu, Cr, or combinations thereof.

In certain embodiments, the substrate and/or support platform can be made from material such as, but not limited to polyethylene terephthalate ("PET"), polycarbonate polystyrene, polymethyl methacrylate ("PMMA"), silicones, silicon wafers, $SiO_2$, $SiO_2$-coated silicon wafer, fluoropolymers, silicone acrylate, fluoro-silicone/acrylate, poly hydroxyethyl methacrylate, $HfO_2$, parylene, $Si_3N_4$, or combinations thereof.

In certain embodiments, the polymeric material can be made of a silicone substance. In certain embodiments, the silicone substance can be a polymeric organosilicon compound. In certain embodiments, the polymeric material can be polydimethylsiloxane ("PDMS").

In certain embodiments, the temperature control unit can be a Cr/Au or Cr/Pt resistive microheater and temperature sensor.

Exemplary techniques for fabrication of the devices are illustrated in, for example, FIG. 37 and certain embodiments will be discussed in further detail in Examples 15 and 16.

With reference to FIG. 37, in certain embodiments, the device can be fabricated using micro and nanofabrication techniques on a substrate platform (1600), such as an oxidized silicon wafer. After cleaning the substrate platform, a layer of the material for the source and drain electrodes can be deposited on the substrate platform (1601). The electrodes can be deposited by any technique known to one skilled in the art. For example, the material can be placed using thermal evaporation. graphene can be transferred to connect the source and drain electrodes (1602). In certain embodiments, one layer of graphene is transferred to connect the source and drain electrodes. Graphene can be synthesized via methods known to those of skill in the art. For example, the graphene layer can be synthesized using chemical vapor deposition ("CVD") substrate (see Example 15 for an example protocol). The graphene surface can be functionalized with control (e.g., reagent) target analyte (1603). The graphene can be functionalized by any technique known to one skilled in the art. For example, the graphene can be immersed with a solution of the linker. for at least 1, at least 2, at least 3, at least 4, or at least 5 hours at room temperature. After rinsing the graphene can be immersed with a solution of target analyte for least 1, at least 2, at least 3, at least 4, or at least 5, at least 6 hours, at least 7, at least 8 hours, at least 9, at least 10 hours, at least 12 hours, at least 14 hours, at least 16 hours, at least 18 hours, or at least 20 hours at room temperature.

The microchambers and channels can be fabricated in polymeric material (1604). The microchambers and channels can be patterned by any technique known to one skilled in the art, such as but not limited to, soft photolithography. Holes can be punched into the polymeric material to create inlets and outlets for buffer and sample (1605). The sheet can then be bonded onto a support platform on which a resistive microheater and temperature sensor was placed (e.g., patterned via photolithography) (1606). The graphene sensor chip can be stacked and bonded on the polymeric layer, while the functionalized graphene region faces the open sensing microchamber (1607).

FIG. 38A-E describes a method of target analyte measurement (1700) according to some embodiments. In certain embodiments, the microbeads (1702) can be functionalized with at least one type of aptamer (1704). The surface of the graphene (1701) can be functionalized with control (e.g., reagent) sample (1708) of the target analyte. The graphene surface can be functionalized with the control sample (1708) of the target analyte via a linker (1709). In certain embodiments, the linker can be 1-pyrenebutanoic acid succinimidyl ester. The linkers and aptamers are discussed in further detail below.

In certain embodiments, the device can initially be rinsed with buffer (e.g., about 10 µl/min), and the sensing microchamber (e.g., 1506) can be filled with a buffer solution to measure a reference signal ($I_{ds}$,ref). In certain embodiments, a sample solution containing the target analyte (1703) can be introduced into the enrichment microchamber (e.g., 1505). In certain embodiments, the sample solution can be introduced into the enrichment microchamber using a syringe, syringe pump, or peristaltic pump. In certain embodiments, the enrichment microchamber can be maintained between about 25° C. to about 60° C. using a temperature control unit (e.g., 1507a) an integrated microheater and a temperature controlled sensor) integrated on the support platform (e.g., 1517). In certain embodiments, the enrichment microchamber can be maintained at about 37° C. During this stage, the target analyte (1703) can be selectively captured by an aptamer (1704) immobilized on a microbead (1702) surface, and can be enriched by continuous sample infusion into the device.

Following the enrichment, the chamber can be rinsed with a buffer solution (e.g., about 10 µl/min) to remove the impurities (1706) at the same temperature the enrichment microchamber is held at following the introduction of the sample. In certain embodiments, the buffer enters the buffer/sample inlet (e.g., 1518) and passes out the waste outlet (e.g., 1519). In certain embodiments, the sample outlet is closed so that the waste goes through the waste outlet. For example, the sample outlet tube can be clamped or closed by other mechanical means.

After the removal of nonspecifically adsorbed target analyte, molecules, and impurities (1706), the enriched target analytes can be released at an elevated temperature and eluted with free aptamers (1707), causing isocratic elution of target analytes (1703) with the free aptamer (1707). The waste outlet can be closed, a plug (i.e., a small volume of solution, e.g., 4-75 µl). of the free aptamer (1707) solution (i.e., an aptamer solution unattached to any support) can be flowed through the enrichment microchamber at an elevated temperature. The aptamer solution can be at a concentration of about 5 nM to about 50 nM, about 10 nM to about 45 nM, about, about 15 nM to about 40 nM, about 20 nM to about 35 nM, or about 25 nM to about 30 nM.

In certain embodiments, the aptamer solution can be at a concentration of about 25 nM. In certain embodiments, the amount of aptamer solution can be about 5 µl to about 15 µl or about 7.5 µm to about 12.5 µl. The flow rate of the aptamer solution can be about 10 µl. The flow rate of the aptamer solution can be about 5 µl/min to about 15 µl/min, or about 7.5 µm/min to about 12.5 µl/min. The flow rate of the aptamer solution can be about 10 µl/min. The enrichment microchamber can be maintained at a temperature of about 25° C. to about 60° C. while the aptamer solution is introduced. The enrichment microchamber can be maintained at a temperature of about 55° C. while the aptamer solution is introduced.

The mixture of eluted sample target analytes (1703) and the free aptamer (1707) can then be transferred to the sensing microchamber (e.g., 1506). The sensing microchamber can be kept at the same temperature as the enrichment chamber when the sample was first introduced. The sensing microchamber can be maintained between about 25° C. to about 60° C. using a temperature control unit (e.g., 1507*b*) an integrated microheater and a temperature controlled sensor) integrated on the support platform (e.g., 1517). The sensing microchamber can be maintained at about 37° C.

In certain embodiments, the sample can be continuously infused. The sample can be continuously infused for at least about 20 minutes, at least about 30 minutes, at least about 40 minutes, at least about 50 minutes, at least about 60 minutes, at least about 70 minutes, at least about 80 minutes, at least about 90 minutes, at least about 100 minutes, at least about 110 minutes, at least about 120 minutes, at least about 130 minutes, at least about 140 minutes, at least about 150 minutes, or at least about 160 minutes. The sample can be continuously infused for at least 120 minutes. In alternative embodiments, the sample can be continuously infused for about 30 minutes to about 160 minutes, about 40 minutes to about 150 minutes, about 50 minutes to about 140 minutes, about 60 minutes to about 130 minutes, about 70 minutes to about 120 minutes, about 80 minutes to about 110 minutes, or about 90 minutes to about 100 minutes.

In certain embodiments, the binding of the free aptamers to the control target analyte immobilized on the graphene surface changes the charge density on the nanosensor surface, inducing changes in the carrier concentration of the nanosensor. In certain embodiments, the measurement circuit can use a DC power supply (e.g., E3631A, Agilent) to provide the drain voltage $V_{ds}$, a function generator (e.g., 33220A, Agilent) to supply the gate voltage $V_{gs}$, and a digit multimeter (e.g., 34410A, Agilent) to measure the drain current ($I_{ds}$). During the electrical measurement, $I_{ds}$ values (at fixed $V_{gs}$ and $V_{ds}$) can be automatically collected once per second for a determined period.

Aptamers

In certain embodiments of the disclosed subject matter, the nanosensor can be used to determine the level of a target analyte in the body, for example small organics, peptides, proteins, cells, tissues, or the like. In certain embodiments, the aptamers that identify the target analyte can be a stable single-stranded oligonucleotide (e.g., DNA, RNA, Xeno Nucleic Acid (XNA)) or peptide that binds to a specific target analyte.

Oligonucleotide aptamers can be nucleic acid species that have been engineered through repeated rounds of in vitro selection or SELEX (systematic evolution of ligands by exponential enrichment) to bind to various molecular targets.

Peptide aptamers can include a short variable peptide domain. In certain embodiments, the variable loop length can be typically composed of ten to twenty amino acids, and the scaffold can be any protein which has good solubility and stability properties. The peptide domain can be attached at both ends to a protein scaffold. The double structural constraint can increase the binding affinity of the peptide aptamer. The double structural constraint can increase the binding affinity of the peptide aptamer to nM range. Peptide aptamer selection can be made using different systems. For example, peptide aptamer selection can occur by, but not limited to, yeast two-hybrid system, selection and combinatorial peptide libraries constructed by phage display and other surface display technologies such as mRNA display, ribosome display, bacterial display and yeast display. Peptide aptamers can also include affimers, which are small, stable proteins engineered to display peptide loops which provides a high affinity binding surface for specific target analytes. In certain embodiments, the affimers can be low molecular weight (e.g., 12-14 kDa).

The binding between the aptamer and the analyte of interest can be irreversible or reversible. In certain embodiments, the aptamer binds reversibly to the target analyte. For example, the binding and dissociation between the target analyte and the aptamer can be an equilibrium phenomenon driven by the concentration of the analyte in the sample and/or conducting channel. The amount of the analyte bound with the aptamer depends on the concentration of the analyte in the sample and/or conducting channel.

In certain embodiments, the aptamer can be conjugated to a substance that can immobilize the aptamers on the graphene sensor and/or microbead surface (i.e., functionalized surface (e.g., graphene sensor and/or microbead).

In certain embodiments, the aptamers can be irreversibly attached to graphene with strength comparable to a covalent attachment. The linker can be a pyrene-terminated agent. The pyrene-terminated agent can be 1-pyrenebutanoic acid succinimidyl ester ("PASE"). A pyrene-terminated agent can be synthesized that can irreversibly attached to graphene using a sticky point for π-π stacking interactions without disrupting the graphene's conjugation or altering its electronic properties. The amino group-terminated aptamer can be directly attached to PASE by forming amide bond.

In certain embodiments, the aptamers can be irreversibly attached to microbead. For example, the attachment can occur using interactions between avidin-biotin or NHS ester-amine.

In certain embodiments, the nanosensor can be serially functionalized with a polymer and aptamer. The polymer can minimize the non-specific adsorption of background molecules onto the graphene. In certain embodiments, the nanosensor can have a nanolayer of polymer, and, the polymer can be polyethlene glycol ("PEG"). The PEG molecule can have a molecular mass below about 2000. In certain embodiments, the PEG molecule can have a molecular mass between about 1000 to about 2000. In certain embodiments, the PEG molecule can have a molecular mass between about 1000 to about 1500, about 1100 to about 1400, or about 1200 to about 1300. In certain embodiments, the PEG molecule can have a molecular mass between about 1500 to about 2000, about 1600 to about 1900, or about 1700 to about 1800. In certain embodiments, the PEG can be linear. In certain embodiments the PEG can be branched. In certain embodiments, the polymer can be conjugated to a linker on one end of the polymer and the aptamer to the other end of the polymer. The linkage for both can be formed by amide bonds.

In certain embodiments, in order to screen out effects not caused by the target analyte, for example, environmental factors such as temperature or other analytes, the reference chamber can include a graphene sensor that is functionalized with the linker and/or linker and polymer without the aptamer (the reference linker). The reference linker does not bind with the target analyte. In certain embodiments, the reference linker can be the same linker and/or linker and polymer used to functionalize the graphene support. Also, the reference linker could not bind or react specifically with any other substance in the sample. The reference linker and polymer could, however, respond similarly to non-target analytes and environmental conditions.

In certain embodiments, in order to screen out effects not caused by the target analyte, control testing can be carried out with a control molecule (i.e., a molecule that is not the target analyte). The graphene nanosensor can be exposed to samples spiked with various concentrations of the control molecule. The transfer characteristics can be examined to see if there is a shift introduced by non-specific binding of control molecules to the graphene surface.

Additional aspects and embodiments of the disclosed subject matter are illustrated in the following examples, which are provided for better understanding of the disclosed subject matter and not limitation.

Example 14. An Aptameric Graphene Nanosensor for Analyte Detection

Illustrated herein is an aptameric graphene nanosensor that can allow accurate detection of a target analyte (e.g., 1409). Presented is an aptameric graphene field-effect transistor ("GFET") nanosensor for sensitive and label-free detection of biomarkers in serum. The graphene nanosensor was serially functionalized with a polyethylene glycol ("PEG") nanolayer and an aptamer for specific detection of a target analyte and effective rejection of background molecules.

This example presents a graphene nanosensor for the detection of immunoglobulin E ("IgE") as a representative analyte. IgE can be an antibody that plays a role in mammalian immune defense eliciting protective response including local inflammation, itching, and mucus production. The PEG reduced nonspecific adsorption of serum background molecules onto graphene. The binding of IgE with the aptamer on the surface induced changes in the carrier density and mobility in the bulk of the graphene, generating a detectable signal. Results demonstrated the specific IgE detection in serum in a physiologically relevant range of 50 pM to 35 nM. Hence this nanosensor can be utilized in clinical diagnostics.

An example graphene nanosensor (e.g., 1100) was configured as an electrolyte-gated FET where graphene (e.g., 1101) was the conducting channel, formed between drain (e.g., 1103) and source electrodes (e.g., 1102) on the $SiO_2$ substrate platform (e.g., 1104) (FIG. 32A-Biii). Pyrene group terminated 1-pyrenebutanoic acid succinimidyl ester ("PASE") (e.g., 1105b)) was attached to graphene (e.g., 1101a) via π-π stacking. Then, PEG (e.g., 1105c) was conjugated to PASE (e.g., 1105b), and the aptamer (e.g., 1105a) to the free end of PEG (e.g., 1105c), both by forming amide bonds. The analyte sample (e.g., 106) was held above the PEG (e.g., 1105c) and aptamer (e.g., 1105a) modified graphene (e.g., 1101a) in a polydimethylsiloxane ("PDMS") well (e.g., 1107), and an Ag/AgCl wire was inserted to the solution as a gate electrode (e.g., 1108). In this embodiment, an electrical double layer ("EDL") was formed at the interface of the graphene and solution serving as the gate dielectric layer.

During operation, the modified graphene nanosensor (FIG. 32b) was incubated in serum (e.g., 1106) containing IgE (e.g., 1109) (FIG. 32b(ii)). After removal of the serum followed with buffer washes (FIG. 32b(iii)), the IgE was purified from serum by the anti-IgE aptamer (e.g., 105a) while the functionalized PEG (e.g., 1105c) drastically reduces the nonspecific adsorption of background molecules to the graphene surface (e.g., 1101a). A bias drain-source voltage ($V_{ds}$) applied between the drain (e.g., 1103) and source (e.g., 1102) s generated a drain-source current ($I_{ds}$) through the graphene channel, and the $I_{ds}$ was controlled by the applied gate voltage ($V_g$). This yielded the transfer characteristics of the GFET (i.e., the functional dependence of $I_{ds}$ on $V_g$). When the IgE (e.g., 1109) in a serum sample (e.g., 1106) was captured by the anti-IgE aptamer (e.g., 1105a), the charged IgE altered the carrier concentration of the graphene (e.g., 1101), and thus induced a shift of the Dirac point ($V_{Dirac}$), the voltage at which the $I_{ds}$ reaches its minimum.

An example device was fabricated using micro and nano-fabrication techniques on an oxidized silicon wafer. After cleaning by piranha, a layer of 5/45 nm Cr/Au was deposited using thermal evaporation (e.g., 1301). A layer of photoresist was then spin-coated on top of Au layer (e.g., 1302) and baked (e.g., 1303) at 115° C. for 1 min. Photolithography was used to pattern the source and drain electrodes (e.g., 1304), and the wafer was then developed (e.g., 1305) and etched in gold (e.g., 1306) and chrome etchant (e.g., 1307) sequentially. Graphene was synthesized via chemical vapor deposition ("CVD") substrate (see Example 15 for an example protocol) and was transferred onto the to connect the source and drain electrodes (FIGS. 32a, 32b, and 34) (e.g., 1308).

To achieve noncovalent functionalization of the graphene surface (e.g., 400), the GFET was immersed for 2 hours at room temperature in a dimethylformamide ("DMF") solution of 5 mM 1-pyrenebutanoic acid succinimidyl ester ("PASE"), which serves as a linker (e.g., 1401). After rinsing thoroughly with ethanol followed by phosphate buffered saline ("PBS") buffer (e.g., 1402), the graphene sensor was immersed in a 1 mg/mL solution of PEG (MW: 2,000) in PBS solution for 12 hours at room temperature (e.g., 404). The mixture of 1-ethyl-3-(3-dimethylaminepropyl) carbodiimide hydrochloride (EDC.HCl) and N-hydroxysulfosuccinimide ("NHS") at pH=6 in PBS solution was used to activate carboxylic group at the free end of the PEG for 1 hour (e.g., 1405). Finally, a solution of IgE specific aptamer in PBS (concentration: 1 μM) was added to the channel of GFET for 12 hours at room temperature (e.g., 1406). A rinse is applied between each procedure.

A PDMS well (~10 L in volume) was placed above the graphene sensing region (e.g., 107) that could be filled with a serum sample. An Ag/AgCl wire was inserted into the solution to apply the gate voltage (e.g., 1108).

In testing, serum samples with different IgE concentrations were introduced into the PDMS well (e.g., 1107) for 5 minutes and then washed with PBS buffer, and the transfer characteristics of graphene then were measured in buffer by sweeping the gate voltage.

The graphene was verified to be a single layer via Raman spectroscope (FIG. 39), where a G band at 1580 cm$^{-1}$ and 2D band at 2685 cm$^{-1}$ in Raman spectrum are characteristics of single-layer graphene.

To characterize the serial functionalization of the graphene surface with PEG and the IgE-specific aptamer, the modified graphene was exposed to a fluorescently labeled single-strand DNA probe that was complementary to the aptamer. Negligible fluorescence was observed on the PEG functionalized graphene while a strong fluorescence signal was observed on the aptamer and PEG modified graphene (FIG. 40), indicating that the PEG and aptamer were successfully immobilized on graphene surface.

The nonspecific adsorption of background molecules to graphene was observed by measuring the transfer characteristics of the bare graphene in buffer before and after the serum incubation. After incubation of the bare graphene in serum, the Dirac point $V_{Dirac}$ shifted to negative gate voltage by 50 mV, which can be caused by the n-doping of the background molecule adsorption to graphene surface. In contrast, the PEG modified graphene did not exhibit appreciable shift of $V_{Dirac}$ after serum incubation. This supports that the nonspecific adsorption was inhibited by the PEG nanolayer (FIG. 41A-B), which was attributed to the improved hydrophilicity and water solubility of graphene by the grafted PEG.

To investigate the response of the graphene nanosensor at varying IgE concentrations, the nanosenor was incubated in serum samples with various IgE concentrations, and the transfer characteristics were measured. The $V_{Dirac}$ was observed to consistently shift toward the negative gate voltage from 101 mV to 85 mV as the IgE concentration increased from 50 pM to 35 nM (FIG. 42 and FIG. 43). The IgE is positively charged based on the IgE concentration dependent transfer characteristics. The IgE concentration dependent transfer characteristics can be illustrated by the p-type behavior of the graphene in the FET structure. Graphene is known as a p-type semiconductor with holes as the majority of carrier, such that the charged IgE protein captured by the IgE specific aptamer screens the graphene surface and lowers the carrier concentration in the bulk of graphene and hence reduce the conductance, suggesting n-type doing was induced in graphene. The transconductance was found to be approximately constant regardless of IgE concentrations implying the constant carrier mobility. Therefore, electrostatic interaction was believed to be the dominating effect, otherwise the carrier mobility would be significantly altered. A higher IgE concentration leads to a greater decrease of the carrier concentration and conductance of the graphene (inset in FIG. 11A-B), as described by the transfer characteristics equation (1).

$$I_{ds}=\mu(W/L)CV_{ds}(V_{gs}-V_{Dirac}) \quad (11)$$

where C is the top-gate capacitance per unit area, is the carrier mobility, W and L are respectively the width and length of the graphene channel.

To exclude the possibility of nonspecific binding and false signals, control testing was carried out with a control molecule, immunoglobulin G (IgG). The graphene nanosensor was exposed to samples spiked with various IgG concentrations. The transfer characteristic curves showed negligible shifts (FIG. 44), which demonstrated the specific capture of the IgE in human serum and the capability of preventing nonspecific adsorption of the grafted PEG nanolayer.

Example 15. Construction of CVD Graphene

CVD graphene (11401) was synthesized by heating annealed Cu foil (11402) in a quartz tubing furnace (FIG. 45A-B). The Cu foil (11402) was first sharply heated to 1000° C. in Argon (Ar) environment (200 mTorr), and annealed in hydrogen (H2) environment (10 mTorr). The mixture of methane ($CH_4$) and $H_2$ were then introduced and allowed to react for 18 min ($CH_4$: 170 mTorr, Hz: 10 mTorr), after which the sample was cooled down to room temperature in Ar flow at 200 mTorr and then retrieved from the tube. After graphene growth, 500 nm PMMA (11403) was spin coated on top for protection and a PDMS stamp (11405) and glass slide (11404) was attached by pressing. Cu (11402) was removed by wet etching.

Graphene (11401) was transferred onto the substrate (11406) at 170° C. (FIG. 45*b*) to realize the graphene conducting channel stretching over drain/source electrodes. After the protective PMMA layer (11403) on graphene surface was dissolved by acetone, AFM (XE-100, Park System) and Raman spectroscopy (Renishaw, 532 nm laser) were used to verify the single-layer graphene sheet (FIG. 46A-C).

Example 16. A Microfluidic Aptasensor Graphene Nanosensor with Integrated Specific Enrichment Illustrated herein is an aptameric graphene nanosensor that can allow accurate detection of a target analyte (e.g., 1500).

This example presents an integrated microfluidic aptasensor which combined aptamer-based specific enrichment and conductance-based graphene nanosensing, allowing detection of a low charged and small biomolecule with high sensitivity. An aptamer specific to a target analyte was immobilized on microbeads for solid phase-based selective enrichment and isocratic elution of the analyte. A FET configuration was used to measure changes in graphene conductance, which were used to determine the analyte concentration. Microfluidic integration of enrichment and sensing on a single chip eliminates the need for off-chip sample handling, thus minimizing potential sample contamination or loss.

For demonstration, arginine vasopressin (AVP), a small peptide and a clinically important biomarker for septic and hemorrhagic shocks, was chosen as a target analyte. Results discussed below (e.g. FIG. 51) show that the integrated aptasensor is capable of detecting label-free AVP at clinically relevant low concentrations (1-500 pM). Hence this nanosensor can be utilized in clinical diagnostics.

An example graphene nanosensor of a FET configuration is shown in FIG. 36A-C. The integrated microdevice consisted of an enrichment microchamber (height: 200 volume: 2.5 µl), a graphene-based sensing microchamber (height: 1 mm, volume: ~5 µl) combined with a graphene nanosensor, three temperature control units (Cr/Au resistive microheater and temperature sensor), and a flow gate connected to a serpentine channel (width: 500 height: 20 µm) for sample transfer to the sensing microchamber. A weir structure (height: 20 µm) in the enrichment microchamber retained microbeads (diameter: 50 to 80 µm) within the chamber during the selective enrichment process. Three sets of a resistive heater and a temperature sensor separately controlled temperatures inside two microchambers and the serpentine channel for forming or disrupting aptamer-AVP complexes.

The source and drain electrodes were connected by graphene which served as a conducting channel. A voltage was applied to the gate electrode forming a gate voltage ($V_{gs}$) through a sample solution. In this FET configuration, the electrical conductance through graphene, which depends on the charge on the graphene surface, was measured from the drain current ($I_{ds}$) at a fixed drain voltage ($V_{ds}$).

The microfluidic device was fabricated as follows. Graphene was synthesized via chemical vapor deposition (see Example 15), and transferred onto gold electrodes that were fabricated on a silicon dioxide-coated silicon substrate. The graphene surface was then functionalized with AVP by incubating in 1-pyrenebutanoic acid succinimidyl ester (PASE linker, 2 mM) solution for 1 hr and AVP solution (1 µM) for 4.5 hrs, sequentially. A PDMS sheet defining microchambers and channels was fabricated via soft lithography, followed by punching through-holes which were used as inlet/outlet ports and an open chamber. The sheet was then bonded onto a glass substrate on which a resistive microheater and temperature sensor was patterned via photolithography. The graphene sensor chip was finally stacked and bonded on the PDMS layer, while the AVP-functionalized graphene region was included within the open sensing microchamber.

The principle of AVP detection in the device is schematically shown in FIG. 38A-E. AVP molecules in a sample ("sample AVP") were selectively captured by an aptamer immobilized on microbead surfaces at 37° C. (FIG. 38a), and were enriched by continuous sample infusion into the device. After removal of nonspecifically adsorbed AVP molecules and impurities through buffer washing (FIG. 38b), the enriched AVP molecules were released at an elevated temperature (55° C.) and eluted with solution-borne aptamer molecules ("free aptamer"), causing isocratic elution of AVP with the free aptamer (FIG. 38c). The mixture of the free aptamer and released sample AVP was incubated with graphene functionalized with standard AVP (FIG. 38d), inducing the binding of the free aptamer to the standard AVP on graphene via competitive binding (FIG. 38e), thus changing the graphene conductance.

The device was initially rinsed with buffer (10 µl/min), and the sensing microchamber was filled with a buffer solution to measure a reference signal ($I_{ds,ref}$). A sample solution (10 µl/min for 2 hrs) prepared in buffer with varying AVP concentrations was continuously introduced into the enrichment microchamber using a syringe pump (KD210P, KD Scientific Inc.) while the chamber was maintained at 37° C. using a temperature control unit (an integrated microheater and a temperature sensor controlled by LabVIEW) integrated on the bottom glass substrate. Following the enrichment, the chamber was thoroughly rinsed with a buffer solution (10 µl/min) at 37° C. After the waste outlet was closed, a plug of the free aptamer solution at 25 nM was flowed through (10 µl at 10 µl/min) the enrichment microchamber at an elevated temperature, 55° C. The mixture of eluted sample AVP and the free aptamer was then transferred to the sensing microchamber whose temperature was kept at 37° C.

The measurement circuit used a DC power supply (E3631A, Agilent) to provide the drain voltage $V_{ds}$, a function generator (33220A, Agilent) to supply the gate voltage $V_{gs}$, and a digit multimeter (34410A, Agilent) to measure the drain current ($I_{ds}$). During the electrical measurement, $I_{ds}$ values (at fixed $V_{gs}$ and $V_{ds}$) were automatically collected once per second for a determined period through a PC-based Lab VIEW.

The aptamer binding-induced change in graphene conductance was characterized using the graphene nanosensor. A free aptamer solution at different concentrations in the range of 0-1000 nM was incubated with the graphene nanosensor until $I_{ds}$ reached a saturated level (FIG. 47). The magnitude of the conductance difference, $\delta I_{ds}=|I_{ds}-I_{ds,ref}|$, was found to increase with the free aptamer concentration and saturate above 100 nM, indicating that the increase of surface charge arises from the affinity binding of charged nucleic acid aptamer molecules to standard AVP on the graphene surface. Least square fitting of a monovalent binding model to the test data yielded a dissociation constant ($K_d$) of 16.7 nM for aptamer-AVP binding, approximately 10 times higher than the value obtained in a reported solution (1.7 nM (*Prot. Natl. Acad. Sci.*, vol. 103, pp. 5173-5178)), which can be attributed to the restriction of configurational freedom of surface-immobilized AVP, which substantially reduces their binding kinetics.

The nanosensor was then tested with standard mixtures of the free aptamer at a fixed concentration (25 nM) and sample AVP at a varying concentration (cAVP, 1-100 nM). Results showed that $\delta I_{ds}$ decreased with increasing cAVP in the range of 1-100 nM, which is attributed to a higher AVP concentration in a standard mixture causes a higher aptamer occupancy, which impeded the aptamer binding to surface-immobilized standard AVP (FIG. 17). However, no appreciable variation in $\delta I_{ds}$ with varying cAVP was observed below 1 nM (data not shown), necessitating the enrichment of sample AVP prior to graphene nanosensing to achieve the AVP detection in the low picomolar range, required in clinical settings.

The aptamer-based selective enrichment of AVP was characterized on microbead surfaces via fluorescence measurements. A TAMRA (as a fluorophore)-labeled AVP (TVP) solution at 100 pM was continuously infused into the enrichment chamber (10 µl/min) while the chamber temperature was maintained at 37° C., and the fluorescence intensity of the bead surface was measured every 15 min. It was observed that mean fluorescence intensities increased over time and saturated after 1.5 hr (FIG. 49), suggesting that continuous sample infusion for more than 1.5 hr was needed to attain sufficient analyte enrichment. The thermally activated release of captured AVP molecules was also tested by flushing beads with a free aptamer solution at 55° C. The fluorescence intensity was quickly (<1 min) dropped down to the baseline, indicating that enriched sample AVP molecules were released from aptamer at 55° C. which disrupts aptamer-AVP complexes. This temperature-dependent behavior of aptamer-AVP binding enables isocratic elution of the analyte, allowing subsequent graphene nanosensing. To verify the specificity of aptamer-based enrichment, integrated devices were tested with and without aptamer on microbead surfaces for AVP detection. Devices with bare beads produced higher $\delta I_{ds}$ values than those with aptamer-functionalized beads (FIG. 50) at 100 pM AVP. This indicates that the sample AVP was significantly enriched by aptamer-based specific recognition on the bead surface, thus resulting in the higher sample AVP concentration in a mixture.

Detection of AVP was tested at physiologically relevant picomolar concentrations (1-500 pM) using the integrated device. To account for variability caused by device-to-device variation of the graphene nanosensor, δIds was normalized with respect to $\delta I_{ds}$ max, the maximum conductance change of an individual graphene nanosensor. Results showed that $\delta I_{ds}$ decreased with increasing cAVP (FIG. 51), implying that a higher cAVP results in a higher aptamer occupancy in the mixture, thus less free aptamer molecules can bind to standard AVP on graphene. The results also confirmed the effectiveness of aptamer-based selective enrichment by demonstrating the picomolar detection that was difficult to attain without the enrichment process. It can thus be concluded that this approach is capable of quantitatively detecting AVP at picomolar levels, confirming the potential of the device as a quantitative AVP assay in clinical diagnostics. It was speculated that the large error bars could arise from a variation of microbead packing density in the enrichment chamber between devices.

The presently disclosed subject matter further provides an affinity-based nanosensor. As disclosed herein, affinity binding is employed for monitoring and measuring low-charge and/or low-molecular-weight analytes. Affinity binding can be specific and reversible. In other words, affinity binding can be specific when analytes or target molecules bind with analyte-specific, or target molecule-specific receptors, which do not bind with interferents that can also come into contact with such receptor. Additionally, or alternatively, affinity binding can be reversible when the analytes and/or target molecules can be released from the receptor, as depicted in exemplary FIG. 52. Such reversible affinity binding can avoid consumption of the analytes and/or target molecule and result in low drift, stable and accurate measurement. For example, and without limitation, the affinity interaction of a glucose responsive polymer (receptor), such as boronic acid, with glucose (analyte), can eliminate interference of electroactive species when used in MEMS sensing technology.

In one aspect of the presently disclosed subject matter, a graphene-based nanosensor for affinity-based detection of low-charge molecules is provided. A low-charge molecule can be a molecule, or analyte, that is substantially uncharged, such as, for example, glucose and other sugars. Additionally, or alternatively, the graphene-based nanosensor herein disclosed can accomplish affinity-based detection of low-molecular-weight molecules. A low-molecular-weight molecule, or analyte, can be, for example and without limitation, a molecule or organic compound that can regulate a biological process with a size on the order of 10-9 m, such as glucose. By way of example, and not limitation, the nanosensor can be configured as a solution-gated graphene-based field effect transistor (GFET), as depicted in exemplary FIGS. 2A-2B. A solution-gated GFET can detect analytes by transducing the binding of such analytes at the graphene surface to a change in current-voltage relationships between source and drain electrodes. The graphene 2101 can be the conducting channel, formed between the two electrodes, representing the source 2102 and the drain 2103, on an insulating substrate 2104, as illustrated in exemplary FIGS. 53A-53B. A layer of synthetic polymer, such as a glucose responsive polymer, including for example, a boronic acid attached to pyrene, can be coupled to the graphene surface via π-π stacking interactions at 2105. Such π-π stacking interactions are generally depicted in exemplary FIG. 54. A conducting material 2107, such as a silver wire, can be inserted within the microchannel 2106 above the functionalized graphene to serve as the gate electrode 2107 of the GFET described herein. The microchannel 106 can provide a path for a solution containing the target molecules and/or analytes to come into contact with immobilized glucose responsive polymer 2105.

During operation, a voltage can be applied between the drain 2103 and source 2102 electrodes to generate a current in the graphene that can be measured. A bias voltage can be applied to the gate electrode 2107. Further to the above, and as disclosed herein, when no voltage is applied to the gate electrode 2107, the resistance along the graphene microchannel 2106 can be about zero. However, when a bias voltage is applied to the gate electrode, the resistance within the microchannel 2106 can increase, and can result in a functional dependence of the drain-source current on the gate electrode voltage, which can represent the transfer characteristics of the GFET. Thus, the transfer characteristics of the GFET can be affected by glucose, or other target molecule and/or analyte, contacting and binding with the glucose-responsive polymer in the microchannel, which can be measured to determine the concentration of glucose or other target molecule and/or analyte.

For example, and without limitation, upon contacting the graphene-functionalized microchannel 2106, analytes can cause detectable changes in the electrical properties of the graphene as a result of the binding of boronic acid moieties of the polymer in FIGS. 54A-54B. Such polymer-glucose binding can change the position of the Dirac point, or the value of the gate voltage at which charge carriers neutralize and the drain-source current achieves its minimum. Additionally, or alternatively, the carrier density of the solution can vary as a result of the electron exchanges between the graphene and the target solution. For example, and not limitation, cyclic esters of boronic acid can form as a result of the binding of boronic acid groups to glucose molecules, which causes an overall ionization equilibrium shift from neutral/insoluble boronic acid moieties to anionic/hydrophilic boronate (see, e.g., FIG. 64). Thus, the charge density in the solution can change, which can in turn change the carrier density and alter the Fermi level of the graphene. Example results disclosed herein demonstrate that the detection of glucose in a concentration range of 0 to 200 mg/dL can be measured with a sensitivity of approximately 2.5 mV/(mg/dL), indicating a potential for blood glucose monitoring and control in diabetes care.

Additionally, and further to the above, due to its vanishing bandgap and high mobility, the bipolar transfer characteristics of graphene can exhibit definitive shifts upon glucose-boronic acid binding. Such shifts can reflect affinity binding-induced charge transfer to graphene, or changes in the electrostatic potential in the immediate proximity of the graphene, thereby allowing for insights into the underlying physiochemical mechanisms for affinity glucose recognition on the nanomaterial. The small size of the graphene as the transduction element can allow miniaturization of the sensor dimensions.

Additionally, and further to the above, the polymer functionalization of the graphene, as illustrated in exemplary FIGS. 53A-53B, or in other words, the coupling of graphene with boronic acid via stable chemical bonding, such as for example and without limitation, via π-π stacking interactions, can reduce the need for mechanical movable structures or physical barriers such as semipermeable membranes commonly used in existing affinity glucose sensors. Such techniques and configurations of the presently disclosed subject matter therefore simplify the device design and can enable a consistent, rapidly responsive measurement for noninvasive glucose monitoring. For example, the presently disclosed subject matter can enable wearable glucose monitoring devices to be realized, such as, in one non-limiting illustration, by integrating such sensors with contact lenses to detect glucose concentration in tears.

In another aspect of the disclosed subject matter, an affinity nanosensor can measure the concentration of low-charge target molecules or analytes and/or low-molecular-weight target molecules or analytes, such as glucose, via the dielectric response of a hydrogel embedded in a MEMS capacitive transducer. Such techniques can accomplish detection and, additionally or alternatively, monitoring of an analyte by transducing the binding of the analyte with receptors, such as functional groups, in the hydrogel to changes in the dielectric properties of the hydrogel. In this manner, for example, changes in the dielectric properties of the hydrogel can be measured using a MEMS capacitive transducer. The hydrogel-based affinity nanosensor can eliminate the irreversible consumption of the target molecules as well as the interference of electroactive species, and provide stable, nontoxic material amiable for implantation.

For example, and without limitation, a hydrogel can be directly immobilized onto the surface of the transducer via in situ polymerization and can be stable over time, thereby reducing the use of a semipermeable membrane, or other mechanical barriers and moving parts otherwise required to hold glucose sensitive material, that can be found in existing sensors, including existing CGM (continuous glucose monitoring) sensors, which often results in device complexity, among other drawbacks. Further, the hydrogel-based nanosensor can employ non-reactive equilibrium binding between glucose and the synthetic hydrogel, and can avoid irreversible glucose consumption.

Additionally, and further to the above, a synthetic hydrogel-based affinity glucose sensor and a MEMS differential dielectric transducer can be integrated to create a novel, miniaturized affinity CGM (continuous glucose monitoring) device with high levels of stability and accuracy, as depicted in exemplary FIGS. 68A-68B. As herein disclosed, the hydrogel 2501 can be disposed between a first electrode 2502 and a second electrode 2503, and can be synthetically prepared, non-toxic and polymerized in situ in the device. Thus, the hydrogel and electrodes can represent, for example and without limitation, a dielectric disposed between two capacitor plates and represented by an effective capacitance and an effective resistance. Reversible affinity binding of glucose 2504 with a boronic acid group, or other suitable glucose responsive polymer, such as PHEAA-ran¬-PAAPBA, 2505 in the hydrogel 2501 can change the dielectric properties of the hydrogel 2501, such as for example, the permittivity of the hydrogel. The permittivity of the hydrogel can represent the ability of the hydrogel to store electrical energy in an electric field (e.g., effective capacitance). The permittivity can then be measured using a MEMS capacitive transducer 2506 to determine glucose concentration, or concentration of the target molecule 2504.

Example results herein disclosed demonstrate that in a practical glucose concentration range such as for example 0-500 mg/dL and with a resolution of 0.35 mg/dL or better, the hydrogel-based affinity nanosensor of the presently disclosed subject matter can exhibit a repeatable and reversible response, and can be useful for CGM (continuing glucose monitoring).

Further details of device structure, fabrication, and operation procedures of the disclosed subject matter can be found in the following Examples, which are provided for illustration purpose only, and not for limitation.

Example 17

This Example demonstrates a graphene-based affinity glucose nanosensor configured using the above-described techniques. Specifically, a synthetic polymer-functionalized graphene nanosensor for affinity-based, label-free detection of low-charge, low-molecular-weight molecules was configured. As disclosed herein, the graphene is functionalized with a synthetic polymer monolayer derivatized with a boronic acid group, which is illustrated by way of example and without limitation in FIGS. 53A-53B. The synthetic polymer monolayer can thus exhibit reversible complexation with glucose to generate a detectable signal. For example and without limitation, the binding of the polymer monolayer with glucose on the graphene surface disposed between source and drain electrodes, as shown in exemplary FIGS. 53A-53B, can induce changes in the carrier density and mobility in the bulk of the graphene, thereby offering a high detection sensitivity of the glucose. Similar sensitivity can be obtained of other like analytes and/or target molecules. The small size of the graphene as the transduction element in the sensor of the instant Example allows miniaturization of the sensor dimensions. Moreover, the polymer functionalization of the graphene can reduce the need for physical barriers such as semipermeable membranes commonly used in existing sensors, thereby simplifying the device design and enabling rapidly responsive measurements for reliable glucose monitoring.

Devices of Example 17 can be configured as solution-gated graphene-based field effect transistors (GFET) whereby the graphene can be the conducting channel, formed between two gold electrodes (i.e., a source electrode and a drain electrode) on an insulating substrate surface, as shown in exemplary FIGS. 53A-53B. In particular, and by way of example without limitation, the monolayer of the synthetic glucose responsive polymer can be pyrene-terminated poly(3-acrylamidophenylboronic acid) (py-PAPBA). The py-PAPBA can be attached to the graphene surface via π-π stacking interactions depicted in exemplary FIG. 54. A target solution, such as a glucose solution, in phosphate buffered saline (PBS) can be held directly above the polymer-functionalized graphene in a polydimethylsiloxane (PDMS) microchannel, with an Ag/AgCl electrode inserted into the solution to serve as a gate electrode. In this manner, an electrical double layer (EDL) can form at the interface of the graphene and solution, and can serve as the gate dielectric layer.

During operation, under the control of a voltage applied between the gate and source electrodes (VGS), a bias voltage applied between the drain and source electrodes (VDS) can generate a current through the graphene (drain-source current, IDS) that can be measured. This yields transfer characteristics of the GFET, i.e., the functional dependence of IDS on VGS, and can allow glucose concentration to be determined due to the binding of boronic acid moieties of the polymer PAPBA, which changes the electrical properties of the graphene.

For example and without limitation, the polymer-glucose binding can change the position of the Dirac point (VGS, Dirac), or, in other words, the value of the gate voltage at which the charge carriers neutralize and the drain-source current, ID, achieves its minimum. Cyclic esters of boronic acid can form as a result of the binding of boronic acid groups to glucose molecules, which causes the overall ionization equilibrium to shift from neutral/insoluble boronic acid moieties to anionic/hydrophilic boronate. Thus, the carrier density can vary because of the electron exchanges between the graphene and the solution when the charge density in the solution changes. This can alter the Fermi level of the graphene, thereby shifting the Dirac point position.

Additionally, and further to the above, the polymer-glucose binding can also change the transconductance, gm, e.g., the drain-source current change rate with respect to the gate voltage (∂IDS/∂VGS), in the linear region of the GFET transfer characteristics. The charged polymer molecules on the graphene surface can be considered charged impurities, and induce electron scattering that can degrade the carrier mobility, μ, of the graphene. For example, and without limitation, this can decrease the transconductance according to:

$$\mu = [L(WC\_g\ V\_DS)]^{-1} g\_m \quad (12)$$

where W and L are respectively the width and length of the graphene conducting channel, and Cg is the gate capacitance per unit area.

As disclosed herein and further to the above, the graphene-based low-molecular-weight affinity nanosensor of Example 17 was fabricated using micro and nanofabrication methods on an oxidized silicon wafer, as illustrated in FIGS. 4A-4B. Other known fabrication techniques are also contemplated by the presently disclosed subject matter. After cleaning by piranha, or other suitable cleansing mixtures and/or protocols to remove metals and organic contamination, a layer of 5/45 nm Cr/Au can be deposited using thermal evaporation. A layer of photoresist can then be spin-coated on top of an Au layer and baked at 115° C. for 1 minute. Other suitable bake temperatures and times are within the contemplated scope of Example 17. Photolithography can then be used to pattern the gate electrode, and the wafer can then be developed and etched in gold and chrome etchant sequentially. Graphene synthesized via chemical vapor deposition (CVD) on a copper sheet can be transferred onto the substrate following an established protocol to cover the source and drain electrodes, as depicted in exemplary FIG. 56.

Next, to perform PAPBA polymer functionalization in accordance with Example 17, the graphene and the underlying substrate can be immersed in a solution of pyrene-terminated polymer (py-PAPBA/methanol 3% w/v) for 4 hours at room temperature, and then washed thoroughly using methanol. Other suitable immersion times and temperatures are within the contemplated scope of Example 17. During testing of the nanosensor, described in additional detail below, glucose solution can be placed directly above the graphene and held in a PDMS open microchannel (~2.5 μL in volume), which can be fabricated using soft lithography and reversibly bonded to the sensor device. An Ag/AgCl reference electrode 2107 can be inserted into the solution above the graphene 2101 to serve as the gate electrode for application of a gate voltage, as depicted in exemplary FIG. 57.

Raman spectroscopy can be used to test the sensor of the instant Example. Other techniques for observing and/or determining like molecular characteristics can also be employed to test the nanosensor of the presently disclosed subject matter. As illustrated by way of example and without limitation in FIG. 68A-B, Raman spectroscopy verified that single-layer graphene was used in the device. The G band at approximately 1580 cm-1 in the Raman spectrum, characteristic of the planar geometry of sp2 bonded carbon, indicated that the material was graphene. Moreover, the sharp and symmetric 2D band at approximately 2685 cm-1 indicated that the graphene consisted of a single layer of carbon atoms.

Polymer functionalization of the graphene was verified using Atomic Force Microscope (AFM) imaging. As shown in the exemplary AFM images of FIGS. 59A-59B, there was an increase (~10 nm) in the apparent height of the graphene sheet, suggesting the successful grafting of the polymer molecules. The polymer functionalization of the graphene of the sensor in the instant Example was also verified by measurement of the GFET (graphene-FET) transfer characteristics. For example and without limitation, the shape of the IDS-VGS curve was similar before and after the functionalization protocol, while the Dirac point position, VGS, Dirac, was found to have shifted from 0.22 V to 0.18 V, as depicted in exemplary FIG. 60. The lack of change in shape of the IDS-VGS curve suggested that changes in the carrier mobility in the graphene were insignificant. Such results are consistent with the polymer, and in particular the boronic acid moieties, being electrically neutral such as would cause little electron scattering to change the graphene's carrier mobility. The shift in VGS,Dirac can be attributed to n-doping (i.e., electron doping) of the graphene, and was consistent with the surface-attached polymer inducing electron transfer from the solution to the graphene. It can therefore be concluded that the graphene successfully functionalized with the PAPBA polymer in the instant Example.

Testing of the graphene's transfer characteristics at varying glucose concentrations (e.g., 0 mg/dL, 50 mg/dL, 100 mg/dL, and 200 mg/dL) revealed that the transfer characteristics changed consistently as the binding of glucose to the boronic acid shifted the electrically neutral boronic acid groups to anionic boronate esters, as depicted herein at reference nos. φ1-φ4 in exemplary FIG. 61. In response to increases in the glucose concentration in Example 17, the Dirac point position, VGS,Dirac, shifted to higher gate voltages with a sensitivity of approximately 2.5 mV/(mg/dL), while the IDS-VGS curve broadened in shape. The shift in VGS,Dirac indicated that the graphene was p-doped, or hole-doped, which can be attributed to changes in the amount of electric charge on the EDL gate capacitor due to the formation of anionic boronate esters. The broadening of the transfer characteristic curve reflected a decrease in transconductance from 100 to 20 μS. According to Equation (1), this can correspond to a decrease in the carrier mobility as a consequence of the polymer-glucose binding, as the negatively charged boronate esters, in the role of charged impurities, can cause electron scattering. The influence of potential contributors or interferents other than polymer-glucose binding was also tested in Example 17. Control measurements were performed on pristine graphene that was not functionalized with the PAPBA polymer. It was observed that neither the Dirac point position nor the transconductance changed as the glucose concentration was varied from 60 to 200 mg/dL, as depicted in exemplary FIG. 62, indicating that when not functionalized with the PAPBA polymer, there is a negligible response of the graphene to glucose concentration changes. Thus, the response of the polymer-functionalized nanosensor to the changes in glucose concentration resulted from the glucose-polymer binding of the presently disclosed subject matter.

Example 18

This Example demonstrates a graphene-based affinity glucose sensor configured using the above-described techniques. Specifically, an atomically thin graphene-based affinity glucose nanosensor was configured as a solution-gated graphene field effect transistor (GFET), as illustrated in exemplary FIGS. 53A-53B. The graphene, serving in Example 18 as the conducting channel, was functionalized with pyrene-1-boronic acid (PBA) via π-π stacking interactions, as shown by way of example and not limitation in FIG. 63. The sensor was fabricated using known micro and nanofabrication techniques. A polydimethylsiloxane (PDMS)-based open well (~20 μL) was bonded to the substrate, and glucose solution was placed into the well. An Ag/AgCl reference electrode, mounted on a three-axis positioner, was inserted into the solution to serve as the gate electrode. An electrical double layer (EDL) formed at the interface of the graphene and solution served as the gate capacitor. Binding of glucose and the boronic acid formed a glucose-boronate ester complex, as shown in exemplary FIG. 64, inducing changes in the electric conductance of the graphene, which was measured to determine the glucose concentration.

Because the capacitance of the double layer can be influenced by the solution composition in a solution-gated FET, prior to any chemical functionalization of the graphene, the fluctuations of the EDL capacitance that can be attributed to changes in the glucose concentration were examined in the instant Example. For example, and without limitation, glucose was dissolved in phosphate buffered solution (pH 7.4) to obtain desired concentrations (2 μM to 25 mM). The same solutions were used in all of the subsequent tests of the instant Example for purpose of consistency, and not limitation. Without any chemical functionalization of graphene, the transfer characteristics (source-drain current IDS as a function of gate voltage VGS) measured at the different glucose concentrations were approximately identical, as depicted in exemplary FIG. 65A. The results suggested that glucose, at the selected concentration range, did not either interact with graphene or vary the capacitance of the EDL.

As herein disclosed, and further to the above, the nanosensor of Example 18 was then immersed in PBA (pyrene-1-boronic acid) solution for 4 hours at room temperature, followed by sequentially rinsing in acetonitrile, isopropanol and deionized water to remove free PBA. Prior to chemical functionalization, in the Raman spectrum of the graphene, depicted in exemplary FIG. 65B, at the channel region, the ratio of the intensity of the 2D band to the G band (I2D/IG) was 2.5, and the full width at half maximum (FWHM) of the 2D band was ~27 from Lorentz fitting, both of which are evidence of monolayer graphene in addition to the color contrast observed under microscope shown in exemplary FIG. 56. The Raman spectrum of the PBA solution-rinsed graphene exhibited signature peaks of BOH bending (1286 cm-1), B-O stretching (1378 cm-1), and G-band splitting (1574, 1595, 1613 cm-1) due to the graphene-pyrene π-π stacking interaction. Also, the 2D band was measured as shifting to a higher wavenumber (from 2685 to 2692 cm-1), which was considered as a result of chemical doping. The measured transfer characteristics, depicted in FIG. 65A, also verified the chemically induced p-type doping, represented by the increase of the neutral point voltage VNP (the gate voltage at which IDS attains its minimum) from 0.33 V to 0.575 V. These observed characteristics of the boronic acid as well as the graphene-pyrene interaction confirm that the PBA molecules successfully immobilize on the graphene.

After functionalization, it was confirmed that replenishment of sample solution to the nanosensor did not interrupt the pyrene-graphene coupling. As depicted in exemplary FIG. 66, the nanosensor of Example 18 was then tested by exposure to glucose solution at different concentrations. The transfer characteristics curve was found to shift to the left. For example, and with reference again to exemplary FIG. 66, the shift was approximately 0.115 V as the glucose concentration increased from 0 to 25 mM. This suggests that the binding of glucose and boronic acid generated n-type doping to graphene. As the estimated transconductance (i.e., the slope of linear sections of the transfer characteristics curve) did not change significantly, the carrier mobility of the graphene was believed to be approximately constant. Rather, changes in the carrier concentration of graphene was considered the main contributor to the observed shift of VNP. Measurements using butyric-acid functionalized graphene were also performed to serve as control. Variations in the source-drain current IDS with the glucose concentration at a fixed gate voltage VGS were also examined. It was observed that IDS decreased monotonically with glucose concentration when VGS was lower than the neutral point voltage VNP, and this trend was reversed when VGS >VNP, as depicted in FIG. 66, which can be attributed to the shift of the transfer characteristics. Using this observed dependence of IDS on the glucose concentration, it can be estimated that, with a noise level of approximately 17 nA for IDS, the resolution of the nanosensors for glucose measurements herein described in Example 18 was approximately 0.46 μM, appropriate for monitoring glucose in human bodily fluids, such as for example, saliva and tears.

Additionally, the change of VNP before and after PBA functionalization, denoted herein as ΔVNP,B, and the further changes of VNP after the graphene was exposed to glucose, denoted herein as ΔVNP,G, were further studied. As herein disclosed, ΔVNP,B=ΔVNP,B −ΔVNP,P, and ΔVNP,G=ΔVNP,B −ΔVNP,G, where ΔVNP,P and the ΔVNP,B are the neutral point voltages measured in fresh buffer for pristine graphene and PBA-functionalized graphene, respectively; ΔVNP,G is the neutral point voltage for PBA-functionalized graphene measured in glucose solution. Both ΔVNP,B and ΔVNP,G varied from sensor to sensor, e.g., because of artifacts such as organic residue left on graphene from the fabrication process. These artifacts can cause a device-to-device disparity in chemical functionalization of graphene, and hence in the doping level at a given glucose concentration. At a given concentration, it was observed, and depicted in exemplary FIG. 66, that the ratio ΔVNP,G/ΔVNP,B did not vary significantly from sensor to sensor, with a variation of less than 6% for the three nanosensors tested in the instant Example. It can be noted that ΔVNP,B is the shift of VNP caused by functionalization of boronic acid and ΔVNP,G is by glucose-boronic acid binding, therefore ΔVNP,G/ΔVNP,B can be regarded as a measure of the fraction of boronic acid that is occupied by glucose. Since the present Example was conducted under conditions of constant temperature and pH, the fraction of boronic acid that binds to glucose is solely dependent on the glucose concentration. This suggests that $\Delta VNP,G/\Delta VNP,B$ should be a function of glucose only, and independent of the sensor or the order in which the sample solution was added. The measured dependence of this ratio on glucose concentration followed the Hill-Langmuir equation for equilibrium ligand-receptor binding. For example, and as depicted in exemplary FIG. 67, a least squares fit yielded an equilibrium dissociation constant (KD) of 38.6 µM, which is appropriate for practical glucose sensing applications.

To explain the observed p-type doping due to the attachment of PBA, depicted in FIG. 69A, it can be noted that while pyrene group is electron-rich and not expected to induce p-doping, boronic acid is electron deficient and its electron-withdrawing nature can induce p-doping in the graphene. This is supported by tests in which immobilization of electron-rich groups on graphene, such as for example, butyric acid, a carboxylic acid, can result in n-type doping in the graphene. Further, the observed n-type doping due to the boronic acid-glucose binding can be attributed to an increase in the local electrostatic potential in the proximity of graphene. This electrostatic potential increase can result from the formation of boronate, which increasing the electron donating ability of boronic acid while weakening its electron-withdrawing ability.

In the instant Example, a graphene-based nanosensor for affinity-based detection of low-charge, low-molecular-weight molecules and/or analytes, such as glucose, was configured and tested. Similar analytes are within the scope of Example 18, as well as the other Examples of the presently disclosed subject matter. The nanosensor of Example 18 employed a GFET (graphene field-effect transistor) in which graphene was functionalized with boronic acid groups for glucose recognition. The boronic acid was attached to the graphene via the interaction between graphene and pyrene groups, thereby allowing sensitive detection of electrically neutral glucose molecules. Testing results from Example 18 demonstrate that the nanosensor herein disclosed can measure glucose in a practically relevant range of 2 µM to 25 mM, with a resolution of 0.46 µM. The observed shifts of the transfer characteristics strongly indicate that recognition of glucose can result from the formation of glucose-boronate ester, which can reduce the boronic acid-induced p-type doping in the graphene. For practical clinical applications, the nanosensor of Example 18, representative of the presently disclosed subject matter, without limitation, can be highly miniaturized without the use of mechanical moving parts or physical barriers, and thus of practical utility in glucose monitoring applications.

In addition to the embodiments of Examples 17 and 18, it is contemplated that graphene modified using other attachment groups, such as for example and without limitation, 9-anthracene-boronic acid, instead of PBA, can obtain consistent results.

Example 19

This Example demonstrates a hydrogel-based affinity glucose nanosensor configured using the above-described techniques. Specifically, the MEMS affinity of the instant Example can include a sensor chip integrated with a hydrogel of a synthetic copolymer 505, such as, for example and without limitation, poly(N-hydroxyethyl acrylamide-ran-¬3-acrylamidophenylboronic acid) (PHEAA-ran-PAAPBA), as depicted in exemplary FIG. 68A-68B. The sensor chip can further include coplanar electrodes 2502, 2503 for impedance sensing, and a thermistor sensor 2507 for closed-loop temperature control, as depicted in exemplary FIG. 69. Glucose can bind reversibly to phenylboronic acid moieties to form strong cyclic boronate ester bonds, which can induce changes in the hydrogel's dielectric properties. Such changes in the dielectric properties of the hydrogel can be measured to determine the glucose concentration, or other such target molecule or analyte.

To fabricate the MEMS affinity nanosensor herein disclosed in Example 19, reference can be made to exemplary FIGS. 70A-70C. With reference to FIG. 70A, for example and without limitation, a chrome (Cr)/gold (Au) film (5/50 nm) can be deposited on a SiO2 substrate by thermal evaporation and patterned to form the coplanar electrodes (502, 503) (1 mm×1 mm) and thermistor sensor 2507 as in exemplary FIGS. 70B-71A. The hydrogel 2501 can be synthesized in situ on the sensor, as shown in exemplary FIGS. 70C-71B. A mixed prepolymer solution containing hydrogel components (AAPBA, HEAA, TEGDA, and AAPH) can be spin-coated on the sensor chip and allowed to gelate in situ and covalently attach to the substrate at 70° C., or other suitable temperature.

During testing of the sensor herein disclosed in Example 3, the sensor was immersed in glucose solution. The device was connected to an impedance/voltage transformation circuit 2701 driven by sinusoidal input from a function generator 2702, such as for example and without limitation, an Agilent 33220A, and as shown in exemplary FIGS. 71C-71D. Other such suitable function generators are within the scope of the presently disclosed subject matter. The sinusoidal input from the function generator 2702 imposed an AC field between the electrodes (2502, 2503), which caused permittivity to be manifested in hydrogel polarization. Such tests were conducted at frequencies below 100 kHz allowed by a lock-in amplifier 2703 used to detect the amplitude and phase shift of the output voltage from the circuit.

First, in testing the sensor of Example 19, the sensor's hydrogel thickness was characterized using vertical scanning interference microscopy. Other suitable methods and techniques can be used to characterize hydrogel thickness. Next, the sensor's frequency-dependent effective capacitance and effective resistance at selected glucose concentrations were tested. Further, the sensor's time response to changes in glucose concentration within 40-300 mg/dL was assessed to demonstrate the potential of the sensor for realizing real-time monitoring of glucose concentrations. Finally, the output of the sensor under physiologically relevant ranges of glucose, such as, for example and without limitation, 0-500 mg/dL, was tested to evaluate the repeatability of the device for stable CGM (continuous glucose monitoring) applications.

The frequency responses of the nanosensor of Example 19, with an 8-µm hydrogel was tested at varying bias voltage frequency, denoted herein as f, and ranging from 5-90 kHz, and glucose concentration, denoted herein as cglucose, and ranging from 40-300 mg/dL. At a given cglucose in the instant Example, the effective capacitance (C) and resistance (R) both decreased with frequency as a result of the hydrogel's dielectric relaxation, as illustrated by way of example and not limitation in FIGS. 72A-72B. At all frequencies tested in Example 19, C and R both increased with glucose concentrations. Thus, the frequency-dependent sensor response suggests that glucose-induced dielectric change at a fixed excitation frequency can be measured. In response to such changes in cglucose within 40-300 mg/dL, the effective capacitance of the sensor at a given f (e.g., 30 kHz) rapidly reached steady state, for example, within 22 seconds, as depicted in exemplary FIG. 73. Also at f=30 kHz, C and R both increased monotonically with cglucose in the range of 0-500 mg/dL, as depicted in exemplary FIGS. 74A-74B. This trend indicates that the hydrogel-glucose binding of the presently disclosed subject matter influences the polarization behavior of the hydrogel. For example and without limitation, a number of polarization mechanisms such as dipole reorientation, ionic polarization, interfacial polarization, and counter ion diffusion, can combine to contribute to the glucose-dependent impedance change of the nanosensor herein disclosed. The sensor's glucose measurement resolution was determined to be 0.47 mg/dL (for capacitance) and 0.27 mg/dL (for resistance).

In the instant Example, the sensor can be used for CGM monitoring. The sensor can include coplanar electrodes and small hydrogel thickness. Additionally, the sensor disclosed herein permits repeatable and rapid measurements of glucose concentration. The effective capacitance (C) and effective resistance (R) both increasing monotonically with glucose concentration (cglucose) in clinically relevant glucose concentrations of 0-500 mg/dL, also demonstrating the applicability of such sensors for ISF (interstitial fluid) glucose monitoring.

Example 20

This Example provides a hydrogel-based affinity sensor configured using the above-described techniques. Specifically, a MEMS affinity nanosensor can utilize a synthetic glucose-sensitive hydrogel, which can be constructed, for example and without limitation, by N-3-acrylamidophenylboronic acid (AAPBA) glucose-binding motifs, and acryl N-Hydroxyethyl acrylamide (HEAA) with a tunable hydrophilicity, and which uses tetraethyleneglycol diacrylate (TEGDA) as the cross-linker 508 and 2,2'-Azobis (2-methylpropionamidine) dihydrochloride (AAPH) as the free radical polymerization initiator. In the instant Example, when glucose 2504 binds reversibly to the phenylboronic acid moieties in the AAPBA segments to form strong cyclic boronate ester bonds, a change in the dielectric properties of the hydrogel 2501 occurs and can be measured to determine the glucose concentration.

By way of example, and not limitation, the dielectric properties of the hydrogel can be represented by the complex permittivity:

$$\varepsilon^{\wedge *}=\varepsilon^{\wedge \prime}-i\varepsilon^{\wedge \prime\prime} \quad (13)$$

where the real permittivity $\varepsilon'$ represents the ability of the hydrogel to store electric energy, while the imaginary permittivity $\varepsilon''$ is related to the dissipation of energy. In the instant Example, when the gap between the electrodes of a parallel-plate transducer is filled with the hydrogel, as shown in exemplary FIG. 75, the transducer can be represented by a capacitor having an effective capacitance denoted herein as Cx, and resistor having an effective resistance denoted herein as Rx, connected in series. Correspondingly, the real and imaginary parts of the complex permittivity can be related to these parameters by the following equations:

$$\varepsilon^{\wedge \prime}=C\_x/C\_0 \quad (14)$$

$$\varepsilon^{\wedge \prime\prime}=1/(\omega R\_x\, C\_0) \quad (15)$$

where C0 can be the capacitance when the electrode gap is in vacuum. The interactions of the hydrogel with glucose as disclosed herein can cause changes in the hydrogel's composition and conformation, and thus changes in its dielectric properties $\varepsilon'$ and $\varepsilon''$. Thus, the transducer of the instant Example can experience changes in its effective capacitance Cx and effective resistance Rx, which can be measured to determine glucose concentration.

Further to the above, and as disclosed herein, the transducer of the instant Example can be enabled by MEMS technology and can use a pair of parallel electrodes (2510, 2511) sandwiching the hydrogel 2501, as shown by way of example and not limitation, in FIGS. 75 and 76A-76B. The upper electrode 2510 can be perforated to allow passage of glucose molecules 2504, and can be passivated within a perforated diaphragm to avoid direct contact with the hydrogel 2501. The perforated electrode 2510 and diaphragm can be supported by microposts 2512 so that they do not collapse onto the lower electrode 2511 on the substrate. In this Example, glucose molecules 2504 can reversibly bind with the hydrogel 2501, thereby changing the hydrogel's complex permittivity. Such changes can occur in both the real and imaginary parts of the complex permittivity, which can be used to determine glucose concentration. For example, and without limitation, the real permittivity can be interrogated via measurement of the capacitance between the electrodes (2510, 2511) to determine the glucose concentration.

To fabricate the exemplary MEMS capacitive transducer of the instant Example, a chrome (Cr)/gold (Au) film (5/100 nm) can be deposited by thermal evaporation and patterned to form a lower electrode 511 (500 μm×500 μm) on a SiO2-coated wafer. The patterned gold electrode can then be passivated, for example, with Parylene (1 μm). Subsequently, a sacrificial layer (5 μm), such as for example an S1818, and an additional layer of Parylene (1.5 μm) can be deposited. Another Cr/Au (5/100 nm) film can then be patterned to form the upper electrode 2510 and passivated by another Parylene layer or like chemical vapor. An SU-8 layer can then be patterned to form a channel and anti-collapse microposts 2512 between the electrodes (2510, 2511). The Parylene diaphragm can be patterned with reactive ion etching (RIE) to form perforation holes to allow glucose permeation through one or more glucose permeation holes 510a. The sacrificial photoresist layer can then be removed with acetone to release the diaphragm. Such fabrication process is illustrated by way of example without limitation in FIGS. 77A-77B.

In the instant Example, the hydrogel can be prepared in situ in the capacitive transducer. First, a mixture of the hydrogel components (AAPBA, HEAA, TEGDA, and AAPH) in solution can be deoxygenated by nitrogen gas for 30 minutes, or other such suitable time, and then injected into the sensor, filling the gap between the parallel electrodes. The sensor can then be placed in a nitrogen environment and heated for four hours at 70° C., or other such suitable time and temperature, as shown by way of example and not limitation in FIG. 77D. The hydrogel-integrated sensor can then be rinsed with water and ethanol or other suitable washing solution to remove unreacted monomer and reagents.

The hydrogel, as herein disclosed, can be synthesize via free radical polymerization with AAPBA and HEAA monomers. An HEAA to AAPBA molar ratio can be approximately equal to 9, or approximately 10% AAPBA in all the monomers. A solution including AAPBA (1.1% w/v), HEAA (5.5% v/v), TEGDA (0.8% v/v), and AAPH (0.16% w/v) in distilled water can then be prepared for polymerization. A stock solution (0.1 M) of glucose can be prepared by dissolving D-(+)-glucose (0.9 g) in distilled water to 50 mL. In the instant Example, glucose solution at varying concentrations (40, 70, 90, 180, 300, and 500 mg/dL) can be prepared by diluting the stock solution.

During testing of the nanosensor of the instant Example, the device was placed in an acrylic test cell (2 mL in volume) filled with glucose solution, as shown in exemplary FIGS. 78A-78D. The sensor was connected to a capacitance/voltage transformation circuit 2701 driven by a sinusoidal input from a function generator 2702, such as an Agilent 33220A, which imposed an AC field on the electrodes (2510, 2511) of the device to induce a glucose concentration-dependent change in the permittivity of the hydrogel 2501. The resulting changes in the effective capacitance $C_x$ of the capacitance/voltage transformation circuit 2701 can be determined by measuring the output voltage ($U_{out}$) from a given input AC voltage ($U_{in}$). All tests of the instant Example were conducted at frequencies in a range of 1 to 100 kHz as allowed by a lock-in amplifier 2703, such as Stanford Research Systems SR844, used in output voltage measurements.

First, the sensor of the presently disclosed subject matter of the instant Example was tested to investigate its response to different glucose concentrations under bias voltages of different frequencies, as depicted in exemplary FIGS. 79A-79B. At each of a series of physiologically relevant glucose concentrations, such as for example and without limitation, 0-500 mg/dL, the effective capacitance of the sensor, and hence the permittivity of the hydrogel, decreased with increasing frequency over the entire frequency range tested, ranging from 1-100 kHz, as depicted in exemplary FIG. 79A. This trend demonstrates dielectric relaxation of the hydrogel, in which the dielectric properties of the hydrogel have a momentary delay with respect to a changing electric field. The dielectric properties of the hydrogel in an electric field can be influenced by a number of mechanisms of polarization, or in other words, can be influenced by a shift of electrical charges from their equilibrium positions under the influence of an electric field, including for example, electronic polarization, ionic polarization, dipolar polarization, counter-ion polarization, and interfacial polarization. Electronic polarization and ionic polarization can involve the distortion of electron clouds with nucleus and the stretching of atomic bonds, while counter-ion polarization and dipolar polarization reflect redistribution of ions and reorientation of electrical dipoles.

In the instant Example, at a given frequency, the effective capacitance of the hydrogel increased consistently with glucose concentration in the entire range tested of 0-500 mg/dL, which is reflected in the sensor's frequency response depicted in exemplary FIG. 79A. The response is plotted versus the glucose concentration in exemplary FIG. 79B. For example, and without limitation, at 30 kHz, the effective capacitance increased from 16.2 pH to 24.8 pF as the glucose concentration increased from 0 mg/dL to 500 mg/dL. This indicates that the binding between the hydrogel and the glucose influences the polarization of the hydrogel, which can include changes in the hydrogel's structural conformations, permanent dipole moments, elastic resistance to the dipole rearrangement in the electric field, and EDL (electric double layer) characteristics. Such effects, resulting from the configuration of the presently disclosed subject matter, combine to result in the glucose concentration dependence of the hydrogel's dielectric properties, explaining the observed variation of the device's effective capacitance with glucose concentration.

With reference to exemplary FIG. 79B, the dependence of the effective capacitance on glucose concentration is generally nonlinear over the full glucose concentration range tested (0-500 mg/dL). Thus, in practical applications, a calibration curve represented by a lookup chart, nonlinear equation, or other suitable representation, can be used to determine the glucose concentration from a measured effective capacitance value. In moderately smaller glucose concentration ranges, however, this relationship can become more linear. For example, and without limitation, the effective capacitance was approximately linear with glucose concentration from 40-300 mg/dL ($R^2=0.993$), a range that is relevant to CGM (continuous glucose monitoring) needs. In this range, a calibrated linear equation can hence be adequate for the determination of glucose concentration from measurement results.

As described herein and further to the above, the sensor was next tested by conducting tests in triplicates to examine the ability of the sensor herein disclosed to measure glucose concentrations in a repeatable manner and with adequate sensitivity, as depicted in exemplary FIG. 79B. At all glucose concentrations of the instant Example, the standard error in the effective capacitance was less than 0.91 pF (2.3%), indicating excellent repeatability. In addition, at all of the measurement frequencies used in the instant Example, the resolution and range of glucose measurement resolution were found to be appropriate for CGM. Considering, for example and without limitation, a 30 kHz frequency, the sensitivity of the sensor was approximately 15 fF(mg/dL)−1 in the glucose concentration range of 0-40 mg/dL. With a capacitance measurement resolution of 3 fF, as allowed by the measurement setup herein disclosed, the resolution for glucose concentration measurement of the sensor was correspondingly estimated to be 0.2 mg/dL. At a signal-to-noise ratio of 3, such resolution yielded a detection limit of 0.6 mg/dL, which is well below the physiologically relevant glucose concentration range (typically greater than 40 mg/dL). For glucose concentrations within 40-300 mg/dL, the sensitivity was approximately 23 fF(mg/dL)−1, corresponding to an estimated resolution of 0.12 mg/dL. At higher glucose concentrations, such as for example, 300-500 mg/dL, the nonlinear sensor response can experience a gradual declination in sensitivity and resolution (respectively to 8.4 fF(mg/dL)−1 and 0.35 mg/dL at 500 mg/dL) as an increasingly small number of binding sites remained available in the hydrogel. These sensor characteristics, appropriate for practical applications, are comparable to those of commercially available electrochemical sensors, such as for example, 1 mg/dL over a glucose concentration range from 0-400 mg/dL, or 500 mg/dL) as well as other research-stage boronic acid-based affinity sensors, such as for example, 0.3 mg/dL over a range from 0-300 mg/dL or 540 mg/dL, for CGM.

Additionally, and further to the above, the response to glucose as compared to the response of potential interferents of the hydrogel-based sensor herein disclosed was tested. For example, and without limitation, nonspecific molecules exist in ISF (interstitial fluid) and can interact with boronic acid, which is the glucose sensitive component of the hydrogel of the sensors herein disclosed. Such molecules can include fructose (~1.8 mg/dL), galactose (~1.8 mg/dL), lactate (~9 mg/dL), and ascorbic acid (~1.32 mg/dL). The hydrogel-based sensor of the presently disclosed subject matter, subjected to interaction with such molecules, resulted in a response lower than the response to glucose molecules. For example, at the same concentration of 90 mg/dL, the effective capacitance changes at 30 kHz due to fructose, galactose, lactate, and ascorbic acid was 17%, 38%, 32%, and 28%, respectively, as depicted in exemplary FIG. 80A. The effective capacitance C, of the instant Example can be calculated according to:

$$\Delta C = C - C\_0 \quad (16)$$

where C is the effective capacitance at a given glucose (or interferent) concentration, and C0 is the effective capacitance in the absence of glucose and interferents. Considering that the physiological concentrations of the potential interferents were about one order of magnitude lower than that of glucose, the sensor of the instant Example was determined to be sufficiently selective for measurements of glucose in interstitial fluid for CGM applications.

While boronic acid can bind to diol-containing molecules, the selective response of the sensor to glucose over the potential interferents can be attributed to the unique binding behavior between boronic acid and glucose. At a 1:1 ratio, boronic acid in fact binds more strongly to fructose than glucose. However, with a high concentration of boronic acid units, which is the case in the instant Example, boronic acid can bind with glucose at a 2:1 ratio. The 2:1 binding between glucose and boronic acid units can play a major role in the sensor response by causing additional crosslinking of the hydrogel that can lead to the augmentation of elastic resistance to electric field-induced dipole reorientation. The rather insignificant device response to the exemplary potential interferents (fructose, galactose, ascorbic acid, and lactate) can alternatively be attributed to a lack of the 2:1 binding mode.

To gain further insight into the principle and operation of the sensor herein disclosed, the role of boronic acid in glucose concentration was also tested. For example, and without limitation, using hydrogels with and without AAPBA content, the dependence of the effective capacitance on glucose concentration can be obtained. Such technique is illustrated by way of example and not limitation in FIG. 80B. It can be seen that when using an AAPBA-free hydrogel, the sensor can exhibit negligible changes in the effective capacitance in response to glucose concentration changes. This contrasts with the strong glucose-induced response of the sensor when it was equipped with the 10%-AAPBA hydrogel, indicating for example that boronic acid moieties in the hydrogel were responsible for the desired recognition of glucose by the sensor.

Finally, the sensor of Example 20 was tested with time-resolved glucose concentration measurements to assess its ability to track glucose concentration changes in a consistent and reversible manner. For example, and without limitation, the measured sensor output at 30 kHz varied from 16.5 pF at 0 mg/dL to 24.8 pF at 500 mg/dL, as depicted in exemplary FIG. 81. In particular, when the sensor was exposed to a glucose concentration after experiencing another sample that was either higher or lower in concentration, virtually the same effective capacitance value was consistently obtained. For example, the effective capacitance at 40 mg/dL over the two periods, from 20 to 38 minutes and from 321 to 341 minutes in this Example, were respectively 16.87 pF and 16.73 pF, agreeing within 0.8%. Similarly, the reversibility was within 3.4% and 1.3% for the measurement data at glucose concentrations of 180 and 300 mg/dL, respectively. This indicates that because the binding between glucose and boronic acid moieties in the hydrogel, the sensor possesses excellent reversibility in response to glucose concentration changes. The time constant of the response, in other words the time for the sensor to reach 63% of the steady state response, was approximately 16 minutes. This time constant was attributable to the relatively large thickness of the hydrogel (~200 µm), through which glucose molecules diffuse to interact with the capacitive transducer. As the glucose diffusion time decreases with the square of the hydrogel thickness, thinner hydrogels can be used to effectively obtain more rapid time responses.

Accordingly, a hydrogel-based affinity glucose nanosensor that measures glucose concentration through dielectric transduction was provided and tested in Example 4 of the presently disclosed subject matter. The sensor can include a pair of thin-film parallel capacitive electrodes sandwiching a synthetic hydrogel. Glucose molecules permeate into the hydrogel through electrode perforations and bind reversibly to boronic acid moieties of the hydrogel. Such binding can induce changes in the dielectric polarization behavior, and hence the complex permittivity, of the hydrogel. Thus, the effective capacitance between the electrodes, which is directly related to the real part of the complex permittivity, can be measured to determine glucose concentration. The use of an in situ polymerized hydrogel in Example 4 can simplify the design of the sensor, facilitate its miniaturization and robust operation, and can improve the tolerance of the device to biofouling, for example, when implanted subcutaneously. Testing of the sensor, herein described by way of example and not limitation, showed that the effective capacitance of the sensor, in a measurement frequency range of 1-100 kHz, responded consistently to glucose concentration changes ranging from 0 to 500 mg/dL. At a given frequency, the effective capacitance increased consistently with glucose concentration, suggesting that the affinity binding between the glucose and boronic acid moieties caused the real permittivity of the hydrogel to increase. At 30 kHz, the measurement resolution of the sensor was estimated to be 0.2, 0.12, and 0.35 mg/dL in the glucose concentration ranges of 0-40, 40-300, and 300-500 mg/dL, respectively. When subjected to time varying glucose concentration changes in the full 0-500 mg/dL range, the microsensor response was consistent and reversible. The time constant of this response was approximately 16 minutes, which can be improved by using thinner hydrogels for reduced diffusion distances.

Characterization of Biomolecules Using an Aptamer-Based Graphene Nanosensor

Another aspect of the presently disclosed subject matter provides systems and methods for characterizing biomolecules using an aptamer-based graphene nanosensor.

In some embodiments, understanding binding properties of biomolecules and their dependence on environmental conditions such as temperature and ionic strength can be of great interest to basic science studies and applied pharmacology. While successful characterization of biomolecular binding properties can be performed with traditional methods (e.g., optical, electrochemical, and electromechanical characterization), the traditional approaches for binding studies commonly either require molecular labeling groups and/or involve complex sensor structure and instrumentation. By contrast, graphene nanosensors, configured as graphene field-effect transistors (FET), can be configured for biomolecular binding studies because of high carrier mobility provided by FETs, resulting in high sensitivity to charged molecules. However, traditional graphene nanosensors are typically limited to equilibrium binding measurements.

The disclosed subject matter provides systems and methods for studying biomolecular interactions under different levels of ionic strength and temperature using a microfluidic graphene FET nanosensor, which is activated by analyte-specific aptamer for target molecule recognition. The disclosed systems and methods provide label-free, direct characterization of biomolecular binding properties with a single-step electrical readout so that the potential inaccurate transductional conversions commonly found in traditional platforms, where the binding kinetics are characterized by fluorescent intensity, resonate frequency or refractive index, can be eliminated.

FIG. 82 depicts the process of association and disassociation between aptamers and analytes. As illustrated, aptamers that are functionalized onto a substrate can be bound to analytes that are introduced (e.g, analytes can be flowed over the functionalized substrate). Over time, the analytes can dissociate from the aptamers. FIG. 83 depicts a graph illustrating aptamer-analyte interaction. As shown, the binding can increase as a function of time as the analytes are introduced to an assay and/or a surface functionalized with aptamers. With the passage of time, as the analytes dissociate, the number of bonds and/or binding decrease.

FIG. 84 depicts a diagram illustrating the aptamer-analyte interaction. As illustrated by FIG. 84, the aptamers (e.g., single strands of DNA and/or RNA) can be configured to bind to target analytes. The aptamers can be configured to bind to the target analytes with a high specificity. The aptamers can be selected to control the reversibility of the binding interaction between the aptamer and the analyte.

Figure 85E:
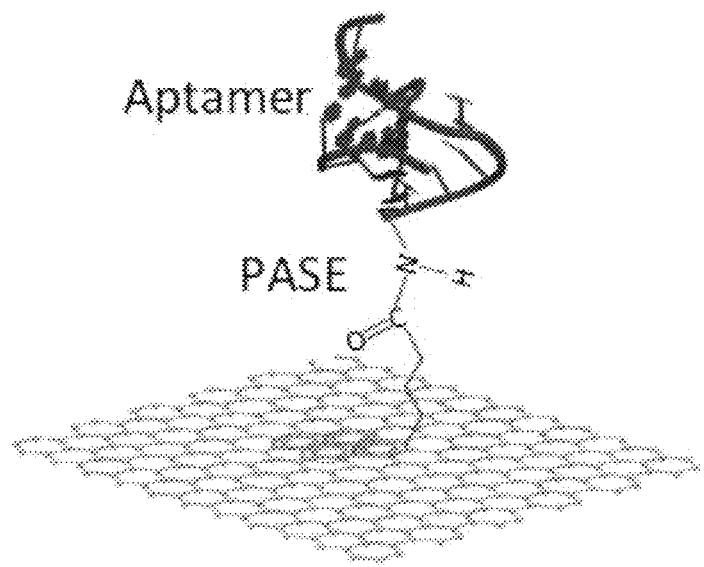

FIGS. 85A-E depict diagrams illustrating the process by which a graphene surface can be functionalized with aptamers. FIG. 85A illustrates an aptamer-modified graphene surface and/or sheet. As illustrated, multiple different aptamers can be functionalized onto the graphene surface. As illustrated in FIG. 85B, analyte that is introduced onto the aptamer-modified graphene surface can be bound to the aptamers functionalized onto the graphene surface (e.g. the surface of the graphene FET nanosensor). As illustrated in FIG. 85C, the dissociation of the aptamer-analyte complex can be initiated by introduction of binding buffer.

FIG. 85D illustrates a diagram showing in greater detail the process by which a graphene sheet is functionalized with aptamers designed to bind to the target analyte, resulting in the aptamer-modified graphene sheet illustrated in FIG. 85A. In certain embodiments, the aptamers can be irreversibly attached to graphene with strength comparable to a covalent attachment. The linker can be a pyrene-terminated agent. The pyrene-terminated agent can be 1-pyrenebutanoic acid succinimidyl ester ("PASE"). A pyrene-terminated agent can be synthesized that can irreversibly attached to graphene using a sticky point for π-π stacking interactions without disrupting the graphene's conjugation or altering its electronic properties. The amino group-terminated aptamer can be directly attached to PASE by forming amide bond. In some embodiments, a pyrene group terminated 1-pyrenebutanoic acid succinimidyl ester ("PASE") can be attached to graphene via π-π stacking. Then, a polyether compound (e.g., PEG) can be conjugated to PASE, and the aptamer can be attached to the free end of the polyether compound, both by forming amide bonds. The analyte sample can be held above the polyether compound and the aptamer modified graphene. FIG. 85E illustrates such an aptamer bound to the aptamer functionalized graphene sheet as described above.

In some embodiments, as provided by the disclosed subject matter, graphene surface can be functionalized with molecules more easily compared to gold surface-based approaches (e.g., surface plasmon resonance and quartz crystal microbalance), which require additional steps and/or a controlled environmental condition (e.g., pH). In some embodiments, the embedded temperature microsensor can be located close to the graphene sensing region of the graphene FET nanosensor to enable accurate temperature control for temperature-dependent biomolecular interaction.

FIG. 86 depicts a diagram illustrating a sensor device used to detect analytes that bind to the aptamer functionalized graphene surface. In some embodiments, the sensor device can be configured as an electrolyte-gated graphene FET with embedded gate electrode and temperature sensor. In some embodiments, a polydimethylsiloxane (PDMS) microfluidic channel 8602 can be bound to the substrate of the sensor device for analyte and buffer introduction to initiate the association and dissociation respectively. An electrical double layer (EDL) formed at the interface of the graphene 8604 and solution can function as the gate capacitor. Binding of IgE and the aptamer can result in large conformational change of the aptamer, which in turn can bring the analyte in a proximity to the graphene 8604's surface, thereby changing the electrical properties of graphene 8604 by either charging transferring or electrostatic interaction. In some embodiments, association of the analyte to the aptamers can be initiated by introducing analyte to the aptamer surface. In some embodiments, the binding of the aptamer can alter the conductance of the graphene 8604. In some embodiments, dissociation of the analyte from the aptamers can be initiated by introducing the buffer to the aptamer surface. The time-resolved change of electrical properties can be measured to monitor their binding process.

In some embodiments, binding properties of biomolecules (e.g., analytes) and their dependence on ionic strength and temperature can be characterized using a microfluidic aptameric graphene field-effect transistor (FET) nanosensor. Aptamer-immobilized graphene can be used to recognize target molecules, and the resulting changes in graphene conductance can be measured to study the binding kinetics of biomolecules. Binding properties of aptamer-protein interactions at different ionic strength and temperature can be investigated, yielding insight into the pharmacologic basis of biomolecular recognition. As illustrated by FIG. 86, the nanosensor can be configured as an electrolyte-gated graphene FET where graphene is the conducting channel, formed between drain electrode 8610 and source electrode 8606 on the SiO2 substrate, with an embedded gate electrode 8608. A drain voltage ($V_{ds}$) and/or a current source ($I_{ds}$) can be applied to the drain electrode 8610 through a probe 8614 in contact with the drain electrode 8610 while the source electrode 8606 can be grounded (e.g., by placing the source electrode 8606 in contact with a probe that is grounded electrically. The gate electrode 8608 can be embedded on the chip. A gate voltage (Vgs) can be applied to the gate electrode 8608 through a probe in contact with the gate electrode 8608.

In some embodiments, a microfluidic channel 8602 can be bound to the chip to introduce the analyte and buffer. Pyrene group terminated 1-pyrenebutanoic acid succinimidyl ester (PASE) can be coupled to graphene via—stacking, and a D17.4 aptamer can be attached to the free end of PASE by forming an amide bond. When exposed to the target analyte, captured IgE by the aptamer varies carrier concentration in the graphene 8604, yielding detectable signal. A polydimethylsiloxane (PDMS) microfluidic channel 8602 can be bound to the substrate for analyte and buffer introduction to initiate the association and dissociation. Materials such as analyte and buffers can be flowed into the microfluidic channel 8602 through inlet ports 8612 and can flow out of the microfluidic channel 8602 through outlet port 8616. An on-chip temperature sensor and a Peltier module can be used for the closed-looped temperature control. The Peltier module can be a solid-state active heat pump configured to transfer heat from one side of the module to the other side, with consumption of electrical energy, depending on the direction of the current.

In some embodiments, the graphene FET nanosensor device can include an on-chip gate electrode 8608 to eliminate the use of cumbersome external wire electrodes, allowing transition-state thermodynamic parameters to be determined simultaneously in an integrated, miniaturized manner. At the same time, the disclosed graphene FET nanosensor device can facilitate a binding study of the analytes at different ionic strength and temperatures by simply normalizing the yielded signal to fraction of aptamer bound, even though the graphene is sensitive to environment conditions. Accordingly, the disclosed systems and methods for characterizing biomolecule interaction can be robust for binding studies under different circumstances.

The disclosed nanosensor can provide for label-free, direct characterization of biomolecular binding properties with one-step electrical readout so that the potential inaccurate transductional conversions commonly found in traditional platforms, where the binding kinetics are characterized by fluorescent intensity, resonate frequency or refractive index, can be eliminated. In addition, the graphene surface can be much easier to functionalize with molecules compared with gold surface-based approaches (e.g., Surface plasmon resonance and Quartz Crystal Microbalance), which require more steps and controlled environmental condition such as pH. The disclosed nanosensor device can employ a graphene FET that enables the binding assays in a label-free manner to minimize inaccuracy in binding characterization. Label-free characterization with graphene's high sensitivity to charged molecules can provide accurate quantification of biomolecular interaction. The disclosed nanosensor device, which integrates the graphene FET and microfluidic system, can greatly miniaturize the system for binding assays.

FIGS. 87A-C depict diagrams illustrating different aspects of the fabricated sensor device of FIG. 86. FIG. 87A illustrates the graphene channel of the graphene FET device used in the disclosed nanosensor device, formed between the drain and source electrodes. FIG. 87B illustrates a micrograph of the sensing region of the graphene FET device. As illustrated by FIG. 87B, the gate electrode 8702 and temperature sensor 8704 can be embedded on the chip. FIG. 87C illustrates the packaged nanosensor device.

In some embodiments, the disclosed nanosensor device can be fabricated using microfabrication and/or nanofabrication techniques on an oxidized silicon wafer. In some embodiments, thermal assisted bilayer lift-off process can be used to fabricate the electrodes. In an exemplary embodiment, after cleaning by piranha, two layers of photoresist with different reflow temperature can be spin-coated on top of substrate. In some embodiments, the source, drain and gate electrodes can be patterned through photolithography. In an exemplary embodiment, after photolithographic patterning of electrodes, a layer of 5/45 nm Cr/Au can be deposited using thermal evaporation, and the remaining resist can be completely removed by immersing the whole wafer in the remover PG. In an exemplary embodiment, the graphene synthesized via chemical vapor deposition (CVD) can be transferred onto the substrate to connect the source and drain electrodes as illustrated in FIG. 87B.

In an exemplary embodiment, to achieve noncovalent functionalization of graphene surface, the graphene FET can be immersed for 2 hours at room temperature in a dimethylformamide (DMF) solution of 5 mM 1-pyrenebutanoic acid succinimidyl ester (PASE), which can serve as a linker. After rinsing thoroughly with ethanol, phosphate buffered saline (PBS) buffer and deionized water, the graphene sensor can be immersed in a solution of D17.4 aptamer in PBS (e.g., 1 µM concentration) for 12 hours at room temperature.

In some embodiments, the utility of the disclosed graphene nanosensor device can be illustrated by characterizing the kinetics of the binding between the Immunoglobulin E (IgE) and its specific aptamer (D17.4) as a representative at different $Na^+$ and $Mg^{2+}$ ionic strength, and energetics at varying temperatures, yielding insight into the pharmacologic basis of biomolecular recognition.

In some embodiments, during the operation, the association of analytes to aptamers functionalized on the graphene surface can be initiated by introducing the analyte, and dissociation can be induced by switching to buffer when the association reached equilibrium state. In an exemplary embodiment, a binding buffer containing 2.9 mM $Na_2HPO_4$, 1 mM $KH_2PO_4$ with different salts ionic strength can be prepared to study the ion-dependent binding kinetics.

In some embodiments, temperature-dependent biomolecular interactions can be investigated by measuring the response of graphene nanosensor to the interaction of IgE-D17.4 at different temperature. Temperature control enabled by the on-chip temperature sensor and a Peltier module can be achieved by a PID control system. In an exemplary embodiment, IgE at 5 nM concentration in the buffer can be prepared. Both the IgE and buffer at 5 µL/min can be introduced into the microfluidic chamber throughout the measurement. Source-drain current (i.e., Ids) at an appropriate fixed gate voltage Vgs can be measured throughout the experiments to monitor the association and dissociation events.

FIG. 88 depicts a graph illustrating Raman spectrum measurements of a single-layer graphene flake used in the sensor device. As illustrated by FIG. 88, the graphene was verified to be a single layer via Raman spectroscope. For example, the Raman spectrum measurements of the graphene flake indicates a G band at 1580 $cm^{-1}$ and 2D band at 2685 $cm^{-1}$ in the Raman spectrum, which are signature characteristics of single-layer graphene.

FIGS. 89A-B depict surface morphology images illustrating the surface of the graphene before and after the graphene surface is functionalized with aptamers. As illustrated by FIG. 89A illustrating the surface of the graphene before the graphene surface is functionalized with aptamers, the graphene surface is relatively flat. FIG. 89B illustrates the surface of the graphene after the graphene surface is functionalized with aptamers. As illustrated by FIG. 89B, the graphene surface is considerably uneven by the introduction of the aptamers bound to the graphene surface.

FIG. 90 depicts a graph characterizing the graphene surface functionalization. Transport characteristics can be measured at completion of every functionalization step. FIG. 90 illustrates the functionalization of the PASE and aptamer induced p-doping and n-doping respectively to the bare graphene. FIG. 90 shows the response in the source drain current (Ids) with respect to modulation in the gate source voltage (Vgs). As shown in FIG. 90, the surface functionalization can be validated by measuring the transport characteristics of graphene channel at completion of PASE and aptamer functionalization respectively. According to FIG. 90, the obtained results showed good agreement with the reported results.

FIGS. 91A-B depict graphs illustrating association and disassociation profiles of the aptamer interaction at different levels of $Mg^{2+}$ (i.e., 1 mM, 20 mM, and 40 mM of $Mg^{2+}$). FIG. 91A illustrates the association profile of IgE-D17.4 aptamer interaction at various Mg²⁺ concentrations (i.e., 1 mM, 20 mM, and 40 mM of Mg²⁺ in the buffer containing 2.9 mM Na$_2$HPO$_4$, 1 mM KH$_2$PO$_4$, and 155 mM NaCl). FIG. 91B illustrates the disassociation profile of IgE-D17.4 aptamer interaction at various Mg²⁺ concentrations (i.e., 1 mM, 20 mM, and 40 mM of Mg²⁺ in the buffer containing 2.9 mM Na$_2$HPO$_4$, 1 mM KH$_2$PO$_4$, and 155 mM NaCl).

FIGS. 92A-B depict graphs illustrating association and disassociation profiles of the aptamer interaction at different levels of Nat (i.e., 155 mM, 300 mM, and 450 mM of Na⁺). FIG. 92A illustrates the association profile of IgE-D17.4 aptamer interaction at various Na⁺ concentrations (i.e., 155 mM, 300 mM, and 450 mM of Na⁺ in the buffer containing 2.9 mM Na$_2$HPO$_4$, 1 mM KH$_2$PO$_4$, and 1 mM MgCl$_2$). FIG. 92B illustrates the disassociation profile of IgE-D17.4 aptamer interaction at various Mg²⁺ concentrations (i.e., 1 mM, 20 mM, and 40 mM of Mg²⁺ in the buffer containing 2.9 mM Na$_2$HPO$_4$, 1 mM KH$_2$PO$_4$, and 1 mM MgCl$_2$).

The results of studies illustrated in FIGS. 91A-B and FIGS. 92A-B investigating the binding kinetics at different ionic strength of Na+ and Mg²+ indicate that both association and dissociation can be enhanced by increasing the level of salt ions. The presence of salt ions can pre-fold the conformational structure of aptamer through electrostatic interaction with backbone of DNA strand, thereby favoring the target analyte recognition during association. On the other hand, salt ions can also decrease the conformational flexibility of aptamer in the dissociation period, resulting in decreased target analyte recognition capability.

FIG. 93 depicts a graph illustrating the disassociation profiles of the aptamer interaction at varying temperatures. Dissociation of IgE-aptamer complex was studied at various temperatures 10° C., 20° C., 25° C., and 30° C. to understand the effect of temperature on IgE-D17.4 interactions. As illustrated in FIG. 93, the temperature-dependent dissociation profiles showed the decrease in affinity with increasing temperature, which can be attributed to the progressive destabilization of aptamer structure.

FIG. 94 depicts a graph illustrating an Arrhenius plot for disassociation of aptamers as a function of temperature further illustrating the effect of temperature of binding kinetics shown in FIG. 93.

FIG. 95 depicts a temperature map illustrating the temperature distribution in the channel of the sensor device. The temperature map of FIG. 95 was generated as a result of a simulation that was carried out to demonstrate the thermal distribution inside the chamber at 10° C. As illustrated by FIG. 95, the simulation showed good uniformity for IgE-D17.4 interactions.

In some embodiments, the specific recognition of aptamers and target molecules can induce changes in the conductance of graphene, which can be measured to monitor the association and dissociation between aptamers and target molecules. Binding kinetics of IgE-D17.4 and its dependence on salt, ionic strength, and temperature, can demonstrate the capability of the disclosed graphene nanosensor to characterize the biomolecular interaction at different environmental conditions.

The foregoing merely illustrates the principles of the disclosed subject matter. Various modifications and alterations to the described embodiments will be apparent to those skilled in the art in view of the inventors' teachings herein. Features of existing methods can be integrated into the methods of the exemplary embodiments of the disclosed subject matter or a similar method. It will thus be appreciated that those skilled in the art will be able to devise numerous methods which, although not explicitly shown or described herein, embody the principles of the disclosed subject matter and are thus within its spirit and scope.

Various publications, patents and patent application are cited herein, the contents of which are hereby incorporated by reference in their entireties.

Example 21. Real-Time Monitoring of Insulin Using a Graphene Field-Effect Transistor Aptameric Nanosensor This example illustrates methods and systems for real-time, label free and specific monitoring using a field-effect transistor, whose graphene-based channel is functionalized with a guanine-rich IGA3 aptamer.

Materials and Method

The nanosensor was configured as a graphene-based FET (FIG. 96A). The electrical double layer at the interface of the graphene and electrolytes serves as a gate dielectric. A drain-source bias Vds generates a current Ids through the graphene channel, as a function of applied gate voltage Vg.

Detection of insulin was allowed by the structural change of the insulin-specific aptamer (IGA3) when interacting with insulin (FIG. 97). IGA3 is a guanine-rich oligonucleotide strand, in which G-quartet planes can form via Hoogsteen base pairing, consisting of four hydrogen-bonded guanine bases. G-quadruplexes can then be generated by stacking of two or more G-quartet structures. These structural changes of the aptamer in the close vicinity of graphene cause disturbances to the charge carriers in graphene and result in detectable changes in the measured Ids.

Chemical vapor deposition graphene was grown on an annealed copper (Cu) foil (99.9%, 25 μm thick). Polydimethylsi-loxane (PDMS, SYLGARD-184) was used for the PDMS chamber. 1-Pyrenebutanoic acid succinimidyl ester (PASE), phosphate buffered saline (PBS), human insulin, human glucagon, and human somatostatin were used. Insulin-specific aptamer (IGA3, sequence 5'-NH2-GGT GGT GGG GGT TGG TAG GGT GTC TTC-3' (SEQ ID NO: 1) was synthesized and purified by Integrated DNA Technologies.

Graphene was transferred onto 285 nm SiO2/Si substrate. Gate, drain, and source electrodes (Cr/Au) were subsequently fabricated using E-beam evaporation and lift-off techniques. The graphene was then patterned to define the conducting channel using photolithography and oxygen plasma etching.

The graphene channel was then biochemically functionalized. PASE was noncovalently coupled to graphene via π-π interaction, after which the IGA3 aptamer was immobilized on the surface via the reaction of an amine group on the aptamer with the N-hydroxysuccinimide ester on PASE.

For the GFET-based electrical measurements, both the drain and gate voltages were supplied by digital sourcemeters and the current Ids was simultaneously measured using a custom-designed Lab VIEW program.

Results and Discussion

To examine the inertness of graphene to insulin, measurements were carried out by exposing the nanosensor to insulin solutions without prior biochemical functionalization of graphene (FIG. 98A). Because of insulin's characteristics (e.g., molecular weight of insulin and concentration), insulin is not adsorbed to bare graphene in a few minutes (<10 min) or the adsorption does not introduce significant variation in the graphene conductivity. Therefore, graphene is appropriate for insulin detection.

Characterization of the functionalization of PASE and the aptamer was performed. The coupling of PASE to graphene was found to increase VDirac from 58.5 to 181 mV (FIG. 98B), suggesting that PASE introduced strong p-type doping in graphene. The G-band splitting (1590 and 1621 cm-1) observed in the Raman spectra further confirmed the coupling of graphene and the pyrene groups on PASE (FIG. 98C). After treatment of the IGA3 aptamer, VDirac was decreased by 31 mV, to a value of 150 mV (FIG. 98B). The thickness of the graphene channel was measured by atomic force microscopy (AFM) and was found to have increased from 0.9 to 3.4 nm (FIGS. 98D and 98E). Therefore, it was concluded that the aptamer was immobilized on the graphene surface.

The nanosensor insulin measuring capabilities were subsequently tested in PBS buffer. Insulin solutions of increasing concentrations from 100 pM to 1 M were sequentially introduced to the PDMS chamber of the nanosensor. The binding of insulin to the IGA3 aptamer was allowed to reach equilibrium before the replenishment of sample solutions. After exposure to insulin, the measured VDirac decreased significantly, at a rate of −0.075 mV/pM within physiologically relevant insulin levels (FIG. 99A), indicating that binding of insulin to the IGA3 aptamer generated n-type doping to graphene.

It was observed that the transconductance of both hole and electron conduction branches remained constant, at 40.476±0.686 S. Given that the ionic strength of the buffer did not change, the double layer capacitance was also deemed unchanged. Therefore, the carrier mobility was not expected to be varied significantly by the insulin-aptamer binding. Instead, the left shift of VDirac clearly suggested that more electrons (n-type carrier) were doped into graphene upon the interaction of insulin to the IGA3 aptamer. Typically, the detection of large biomarkers, such as proteins, using a solution-gated GFET is based on the electrostatic gating effect generated by the charged biomarkers on graphene. Under these circumstances, the charges induced in graphene were opposite to and hence in balance with the charges carried by the target molecules. In the experiments, while the insulin, whose isoelectric point (PI) is 5.8, was weakly and negatively charged at pH 7.4, n-type doping was generated in graphene upon binding of insulin to the IGA3 aptamer. Thus, the increase in the electron (n-type carrier) concentration in graphene was not considered as a result of the electrostatic gating effect but could be attributed to the direct charge transfer to graphene, from either insulin or the deformed IGA3 aptamer. Note that in the absence of insulin, the guanine-rich IGA3 was mostly unfolded in the solution while G-quartet structure could have formed as a result of Hoogsteen base pairing. Upon capture of insulin, the existing G-quartet structures can switch to stable, compact parallel or antiparallel G-quadruplex structures. These conformational changes brought the electron-rich aromatic nucleotide strands and insulin to the close proximity of the graphene surface, resulting in the direct binding of nucleotide or aromatic amino acids in insulin with the graphene surface and making electrons from either insulin or the deformed IGA3 aptamer more likely to be directly transferred into graphene through the π-π stacking interactions between them and generating n-type doping to graphene. This physical process has also been observed in the immobilization of DNA on carbon nanotubes and graphene oxide sheets and possibly serves as the underlying mechanism that allows us to measure the insulin levels.

The binding of insulin and aptamer was allowed to reach equilibrium for 10 min before the replenishment of higher concentration insulin solution. Thus, the dipping time of graphene in solutions was increased with the ongoing experiment. The slight decrease in the minimum of Ids (Ids,min) in the transfer characteristic curve, observed in FIG. 99A was considered as a result of the increase in the ionic strength caused by the evaporation of PBS buffer (150 mM NaCl) with increasing dipping time. This is supported by control experiments in which Ids,min was observed to decrease from 2.03 to 1.85 A with increasing dipping time and increasing concentrations of insulin (diluted in PBS buffer) from 0 to 1M (FIG. 98A) and also in agreement with experimental observations reported by others.

Further, the equilibrium dissociation constant (KD) for the IGA3 aptamer and insulin with different VDirac at corresponding insulin concentrations was evaluated using the aptamer-functionalized GFETs. As shown in FIG. 99A, the VDirac of transfer curves shifted to the left with a stepwise increase in the insulin concentration. The change in VDirac, denoted as ΔVDirac, is plotted as a function of insulin concentrations with error bars obtained from three different devices (FIG. 99B). It can be seen that ΔVDirac sharply increased with increasing insulin concentrations from 100 pM to 50 nM and then gradually became saturated above 350 nM. Using this result, the binding of IGA3 aptamer with insulin on the graphene channel can be described by the Hill-Langmuir equation:

$$\Delta VDirac = \frac{\Delta VDirac, \max C_{Ins}}{KD + C_{INS}} \quad (17)$$

where ΔVDirac,max and CINS are the saturated change of the VDirac and the concentration of insulin, respectively. KD is estimated to be 35 nM from the fitted curve shown in FIG. 99B (dash curve), indicating a high affinity between IGA3 aptamer and insulin.

Time-resolved measurements of insulin were performed on the nanosensor with fixed drain-source bias Vds=50 mV and gate bias Vg=−50 mV (FIG. 100A). With increasing insulin concentrations from 100 pM to 1 M, the measured Ids monotonically decreased from 8.09 to 7.16 A (FIG. 100B). The binding of insulin with the monolayer IGA3 aptamer reached equilibrium within 260 s (FIG. 100C), appropriate for real-time monitoring of insulin levels. With a noise level of 8.66 nA, the limit of detection (LOD) was estimated to be 35 pM, which was improved from existing techniques (Table 1).

TABLE 1

Comparison of the response characteristics of the nanosensor and other detection methods.

| Detection method | LOD |
| --- | --- |
| Peroxidase activity | 1000 nM |
| Fluorescence quenching | 500 nM |
| High-performance liquid chromatography | 258.3 nM |
| Oxidation with carbon electrodes | 30 nM |
| Gold electrode-based electrochemical method | 10 nM |
| Photoluminescence transduction | 10 nM |
| Carbon nanotube-based electrochemical method | 1.34 nM |
| Graphene-based aptameric nanosensor | 35 pM |

To examine the specificity of the nanosensor to insulin over other related analogues that might interfere with the detection of insulin, glucagon and somatostatin, which were secreted by the pancreatic islet alpha and delta cells, respectively, were evaluated as negative control analytes. This is because glucagon [molecular weight (MW): 3.5 kD, PI: 6.2], promoting glucose storage by the liver and together with somatostatin (MW: 1.63 kD, PI: 5.6) regulating the secretion of insulin, share similar physical properties with insulin, which can affect the sensing performance.

The functionalized graphene nanosensor was first exposed to somatostatin solutions prior to the introduction of insulin. The change in Ids, denoted as ΔIds, was recorded throughout the experiment and compared as the response of the aptameric nanosensor to the given solutions. To minimize errors caused by device-to-device nonuniformity, the time-resolved selective response as the ratio of ΔIds to ΔIds,max (the maximum value of ΔIds) was calculated:

$$\Delta Ids = Ids - Ids, PBS \quad (18)$$

where Ids,PBS is the Ids measured in fresh PBS buffer. With exposure to somatostatin solutions at given levels, the value of ΔIds/ΔIds,max was limited to less than 0.192, indicating that the aptameric nanosensor almost did not respond to the somatostatin solution at tested concentrations. On the contrary, the calculated ΔIds/ΔIds,max value increased and reached 1.0 at 1 M insulin with stepwise increments in the insulin concentration (FIG. 101A).

Additionally, a similar real-time monitoring control experiment was conducted with glucagon (FIG. 107). The selective responses of the graphene aptameric nanosensor to different concentrations of glucagon, somatostatin, and insulin are shown in FIG. 101B. Here, ΔIds,S(C)=Ids,S(C)−Ids,PBS, where Ids,S(C) is the Ids measured at the binding equilibrium for given solutions (insulin/glucagon/somatostatin) at representative tested concentrations. The measured current did not show a significant variation (<1.3%) in the presence of glucagon or somatostatin at concentrations lower than 1 μM, when compared to the response (8.5%) in the presence of equivalent concentrations of insulin alone. These results indicated the ability of the graphene nanosensor to detect insulin with a high selectivity, which was achieved by using the IGA3 aptamer with a sequence that was specific for insulin.

In view of the potential use of the disclosed nanosensor for monitoring of insulin secretion from pancreatic islet beta cells, the validity of the graphene aptameric nanosensor for insulin detection in Krebs-Ringer bicarbonate (KRB) buffer was evaluated. Considering that various cytokines in serum can influence the glucose-stimulated insulin release assays, KRB buffer is generally used instead of serum-containing media as an islet perfusion medium.48,49 However, different from pure PBS buffer, KRB buffer contains 0.1% bovine serum albumin (BSA), which is a protein used as a nutrient in cell culture. To examine the stability of the graphene nanosensor in KRB buffer, control experiments were carried out by exposing the graphene channel to insulin solutions without biochemical functionalization. The variation in VDirac was not distinguishable with increasing concentrations of insulin (0-960 nM in KRB) (FIG. 102A). This suggested that constituents of KRB solutions (Table 2), such as BSA and carbonates, did not impact the sensing performance.

TABLE 2

Components of the base KRB buffer.

| Components | Mass (g) |
| --- | --- |
| HEPES | 5.96 |
| NaCl | 6.72 |
| NaHCO₃ | 2.02 |

TABLE 2-continued

Components of the base KRB buffer.

| Components | Mass (g) |
| --- | --- |
| KCl | 0.3728 |
| MgCl₂ 6H₂O | 0.2033 |
| BSA | 1.0 |
| CaCl₂ 2H₂O | 0.3675 |

After biofunctionalization of PASE and aptamers, the graphene channel was exposed to KRB buffer and insulin solutions of increasing concentrations from 900 pM to 405 nM. After exposure to insulin, the measured VDirac negatively and dramatically shifted by 42 mV, from 0.2 to 0.158 V (FIG. 102B), indicating that binding of insulin to IGA3 aptamer also generated n-type doping to graphene even in KRB buffer containing BSA, which was in agreement with the previous result obtained in PBS buffer. Different from the slight decrease in Ids,min, which is related to the ionic strength, observed in experiments using PBS buffer (FIG. 99A), the Ids,min was found to increase significantly with the ongoing experiment when using KRB buffer (FIG. 102b). The nonspecific binding of charged organic molecules, such as BSA, on the graphene surface is likely to play the dominant role in the observed increase of Ids,min. This was supported by the reported experiment, in which the graphene conductance was found to increase slightly with exposure to 100 nM BSA (diluted in PBS buffer) for more than 10 min. In control experiments (FIG. 102A), the Ids,min was also found to increase from 0.79 to 0.83 μA with increasing dipping time and increasing concentrations of insulin (diluted in KRB buffer) from 0 to 960 nM. Thus, it can be concluded that our graphene nanosensor can be used in the monitoring of insulin secretion from pancreatic islet beta cells in vitro.

CONCLUSION

In this work, G-quadruplex conformation-switching signaling was applied as the principle for a graphene aptameric nanosensor to real-time monitor insulin. The insulin specifically binds to the surface-immobilized IGA3 aptamer, promoting and stabilizing the formations of both parallel and antiparallel G-quadruplex and subsequently varying the carrier density in the graphene channel. The resulting change in the electrical conductance of graphene was measured to determine the insulin concentration.

Experimental results indicated that the graphene nanosensor used by this approach demonstrated a distinctive ability in quantitative monitoring of insulin levels ranging from 100 pM to 1 μM with a LOD down to 35 pM. Additionally, the sensing performance and the practicability of this graphene nanosensor in KRB buffer were evaluated. Hence, this approach could be used in glucose-stimulated insulin release assays and holds the potential for timely and accurate prediction of insulin doses for type 1 diabetes (T1D) patients in clinical diagnostics.

Example 22. Fabrication of an Insulin-Specific Aptamer Functionalized Field-Effect Transistor This example illustrates methods of device fabrication, surface functionalization, and use of the functionalized field-effect transistors for sensing target molecules.

Device Fabrication Protocol

As the fabrication protocol shown in FIG. 104, the wafer (285 nm SiO2/Si) employed as the substrate of the device was cleaned successively with acetone, IPA and deionized water, then dried by N2 901. The device was fabricated via a bilayer lift-off process. Two layers of resist (sacrificial layer LOR 3A and photoresist S1811) were sequentially spin-coated on the wafer using spin coater (Spin coater WS-650-23B, Laurell) 902. The planar source, drain and gate electrodes consisting of a Cr/Au structure (5 nm/45 nm) were defined on the SiO2 surface using standard photolithography (SÜSS MA6 mask aligner, SÜSS Microtech) 903 and metal deposition (Angstrom evovac deposition system, Angstrom Engineering) techniques 904. Then the device was kept in remover PG overnight at room temperature for resist removal 905. The sample was exposure to oxygen plasma (Plasma etch system, Diener) to remove the remaining residue on the SiO2 surface. Then, the graphene was transferred for patterning 906. After patterning, the graphene was assembled with microfluid device to form GFET device.

As shown in FIG. 105, the synthesized CVD graphene was then transferred onto the substrate. To pattern the graphene sheet into a rectangle shape stretching over drain/source electrodes, the photoresist S1811 layers was spin coated on graphene surface in turn for photolithography. After exposure and the resist developing with developer AZ 300 MIF, graphene sheet in the unprotected area was etched using oxygen plasma to create the GFET unit with a regular conducting channel.

Surface Functionalization Protocol

To immobilize the aptamer onto the graphene channel, the sensor was first immersed in 5 mM PASE solution for 2 hours at room temperature and sequentially rinsed with dimethylformamide (DMF) to remove any free PASE. The device was then rinsed with PBS followed by incubation with 100 nM aptamer IGA3 solution overnight at room temperature. After rinsing with PBS, 100 mM ethanolamine was added onto the graphene channel for 1 h to deactivate and block the excess reactive groups remaining on the graphene surface. A polydimethylsiloxane (PDMS)-based open chamber (~30 µL) was used to hold sample solutions and was finally bonded to the device.

To test the successful functionalization of PASE and aptamer IGA3, the graphene channels of different devices were characterized with Raman Spectrum and AFM. The G-band splitting (1626, 1628, 1626 cm$^{-1}$, respectively) was observed in the Raman spectra (FIG. 106A, C, E), implying the PASE was coupled to graphene. Transfer characteristic curves, corresponding to different graphene functionalization procedures and displaying an ambipolar behavior with different $I_{Dirac}$ were plotted in FIGS. 106B, D, and F. The results, PASE induced p-type doping and single strand DNA aptamer induced n-type doping to graphene, were consistent with previous works, indicating the successful functionalization.

Control Experiments

As shown in FIG. 107, the real-time monitoring control experiment was also conducted with glucagon. The value of AIds/AIds, max, calculated with the time-resolved selective response, was less than 0.3. The results indicated that the graphene based aptameric nanosensor showed high specificity to insulin over glucagon.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

The invention claimed is:

1. A microdevice for monitoring a target analyte, the microdevice comprising:
   a field effect transistor comprising:
   a substrate;
   a gate electrode; and
   a microfluidic channel or a micro transducer,
   wherein the microfluidic channel or the micro transducer are formed between drain electrodes and source electrodes located on the substrate, wherein the drain electrodes and source electrodes are connected through graphene, and the graphene lies on a dielectric layer; and
   at least one aptamer functionalized on a surface of the graphene, wherein the at least one aptamer is adapted for binding to the target analyte, and wherein binding of the target analyte to the at least one aptamer alters the conductance of the graphene, wherein the at least one aptamer is attached on the surface of the graphene in the first conformation,
   wherein binding of the target analyte to the at least one aptamer causes a conformational change of the at least one aptamer from the first conformation to a second conformation, wherein a nucleotide strand of the at least one aptamer and the bound target analyte are brought into a proximity to the surface of the graphene in the second conformation; and wherein the microfluidic channel or the micro transducer is bound to the substrate for analyte and buffer introduction to initiate association and dissociation of the target analyte to the at least one aptamer.

2. The microdevice of claim 1, wherein the field effect transistor further comprises a gate capacitor comprising of an electrical double layer formed at the interface of the graphene and the solution.

3. The microdevice of claim 1, wherein the target analyte being brought into proximity to the surface of the graphene causes electrical properties of graphene to change by at least one of charge transfer and electrostatic interaction.

4. The microdevice of claim 1, further comprising at least one of an on-chip temperature sensor and a Peltier module to perform closed-looped temperature control of the microdevice.

5. The microdevice of claim 1, wherein the microdevice is configured to provide a label-free direct characterization of biomolecular binding properties with one-step electrical readout.

6. The microdevice of claim 1, wherein binding of the target analyte to the at least one aptamer causes a carrier concentration in the graphene to be altered, resulting in a detectable signal.

7. The microdevice of claim 1, wherein the at least one aptamer is functionalized on the surface of the graphene using a linker, wherein the linker is configured to be irreversibly attached to the graphene without altering electronic properties of the graphene.

8. The microdevice of claim 7, wherein the at least one aptamer is directly attached to the linker by forming an amide bond.

9. The microdevice of claim 7, wherein the linker can be coupled to the graphene via stacking, and wherein the at least one aptamer can be attached to the free end of linker by forming an amide bond.

10. The microdevice of claim 7, wherein the linker comprises 1-pyrenebutanoic acid succinimidyl ester (PASE).

11. The microdevice of claim 1, wherein the graphene comprises a single layer sheet.

12. The microdevice of claim 1, wherein the target analyte is disassociated from the at least one aptamer by introducing a buffer to the at least one aptamer.

13. The microdevice of claim 1, wherein at least one aptamer is replaced with a receptor capable of binding to a target analyte.

14. The microdevice of claim 1, wherein the conformational change of the at least one aptamer includes parallel G-quadruplex conformation and antiparallel G-quadruplex conformation.

15. The microdevice of claim 1, wherein the at least one aptamer comprises a guanine-rich IGA3 aptamer or a synthetic single-stranded DNA VR11 aptameter.

16. The microdevice of claim 10, wherein the at least one aptamer is coupled to the PASE through a reaction of an amino group of the aptamer with N-hydroxysuccinimide ester of PASE.

17. The microdevice of claim 1, wherein the microdevice is adapted for real-time detection of changes in the concentration of the target analyte.

18. The microdevice of claim 17, wherein the real-time detection is continuous over time.

19. The microdevice of claim 1, wherein the substrate of the field effect transistor comprises silicon (Si) and/or silicon dioxide ($SiO_2$).

20. The microdevice of claim 1, wherein the substrate of the field effect transistor comprises flexible materials, wherein the flexible materials comprise polyethylene terephthalate (PET) or biaxially-oriented polyethylene terephthalate (Mylar).

21. The microdevice of claim 20, wherein the microdevice maintains consistent mechanical properties through cyclic rolling, twisting, and/or stretching deformations, wherein the mechanical properties include flexibility, durability, or elasticity.

22. The microdevice of claim 20, wherein the microdevice maintains consistent electrical properties through cyclic rolling, twisting, and/or stretching deformations, wherein the electrical properties include transconductance, carrier mobility, or on/off ratio.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' NH2

<400> SEQUENCE: 1
ggtggtgggg ggggttggta gggtgtcttc                                          30

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
acagggtgt ggggacaggg gtgtgggg                                              28

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaggtggat ggggaggggg aggtgtgttt                                           30

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 ggaggggtg gggagggggc tggttgtcc                                             29
```